(12) United States Patent
Krepski et al.

(10) Patent No.: US 8,697,873 B2
(45) Date of Patent: Apr. 15, 2014

(54) AMIDE SUBSTITUTED IMIDAZOPYRIDINES, IMIDAZOQUINOLINES, AND IMIDAZONAPHTHYRIDINES

(75) Inventors: Larry R. Krepski, White Bear Lake, MN (US); Joseph F. Dellaria, Jr., Woodbury, MN (US); Daniel E. Duffy, White Bear Lake Township, MN (US); David T. Amos, St. Paul, MN (US); Bernhard M. Zimmermann, Eagan, MN (US); William H. Moser, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1910 days.

(21) Appl. No.: 10/599,159

(22) PCT Filed: Mar. 24, 2005

(86) PCT No.: PCT/US2005/009880
§ 371 (c)(1),
(2), (4) Date: Sep. 21, 2006

(87) PCT Pub. No.: WO2005/094531
PCT Pub. Date: Oct. 13, 2005

(65) Prior Publication Data
US 2007/0219196 A1    Sep. 20, 2007

Related U.S. Application Data

(60) Provisional application No. 60/555,753, filed on Mar. 24, 2004, provisional application No. 60/578,769, filed on Jun. 10, 2004.

(51) Int. Cl.
*C07D 401/02* (2006.01)
*A61K 31/437* (2006.01)

(52) U.S. Cl.
USPC ............................................. 546/80; 514/292

(58) Field of Classification Search
USPC ............................................ 546/80; 514/292
See application file for complete search history.

(56) References Cited

U.S. PATENT DOCUMENTS

| | | |
|---|---|---|
| 3,314,941 A | 4/1967 | Littell et al. |
| 3,450,693 A | 6/1969 | Suzuki et al. |
| 3,670,086 A | 6/1972 | Pryor et al. |
| 3,692,907 A | 9/1972 | Fleming et al. |
| 3,891,660 A | 6/1975 | Denzel et al. |
| 3,899,508 A | 8/1975 | Wikel |
| 3,917,624 A | 11/1975 | Abu El-Haj et al. |
| 4,006,237 A | 2/1977 | Buckle et al. |
| 4,053,588 A | 10/1977 | Konig et al. |
| 4,381,344 A | 4/1983 | Rideout et al. |
| 4,552,874 A | 11/1985 | Mardin et al. |
| 4,563,525 A | 1/1986 | Campbell, Jr. |
| 4,593,821 A | 6/1986 | Brule |
| 4,668,686 A | 5/1987 | Meanwell et al. |
| 4,689,338 A | 8/1987 | Gerster |
| 4,690,930 A | 9/1987 | Takada et al. |
| 4,698,346 A | 10/1987 | Musser et al. |
| 4,698,348 A | 10/1987 | Gerster |
| 4,753,951 A | 6/1988 | Takada et al. |
| 4,758,574 A | 7/1988 | Robertson et al. |
| 4,774,339 A | 9/1988 | Haugland et al. |
| 4,775,674 A | 10/1988 | Meanwell et al. |
| 4,800,206 A | 1/1989 | Alig et al. |
| 4,826,830 A | 5/1989 | Han et al. |
| 4,837,378 A | 6/1989 | Borgman |
| 4,880,779 A | 11/1989 | Gallaher |
| 4,904,669 A | 2/1990 | Knoll et al. |
| 4,929,624 A | 5/1990 | Gerster et al. |
| 4,988,714 A | 1/1991 | Alig et al. |
| 4,988,815 A | 1/1991 | Andre et al. |
| 5,037,986 A | 8/1991 | Gerster |
| 5,175,296 A | 12/1992 | Gerster |
| 5,187,288 A | 2/1993 | Kang et al. |
| 5,225,183 A | 7/1993 | Purewal et al. |
| 5,238,944 A | 8/1993 | Wick et al. |
| 5,248,782 A | 9/1993 | Haugland et al. |
| 5,266,575 A | 11/1993 | Gerster |
| 5,268,376 A | 12/1993 | Gester |
| 5,274,113 A | 12/1993 | Kang et al. |
| 5,342,784 A | 8/1994 | Yamada et al. |
| 5,346,905 A | 9/1994 | Gerster |
| 5,352,680 A | 10/1994 | Portoghese et al. |
| 5,352,784 A | 10/1994 | Nikolaides et al. |
| 5,367,076 A | 11/1994 | Gerster |
| 5,376,501 A | 12/1994 | Marien et al. |

(Continued)

FOREIGN PATENT DOCUMENTS

| | | |
|---|---|---|
| AU | 2004220534 A1 | 9/2004 |
| AU | 2004229478 A1 | 10/2004 |

(Continued)

OTHER PUBLICATIONS

Dorwald F. A. Side Reactions in Organic Synthesis, 2005, Wiley: VCH, Weinheim p. IX of Preface.*
Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.
Brennan et al., "Automated Bioassay of Interferons in Micro-test Plates.", *Biotechniques*, June/July 78, 1983.
Testerman et al., "Cytokine Induction by the Immunomodulators Imiquimod and S-27609.", *Journal of Leukocyte Biology*, vol. 58, pp. 365-372, Sep. 1995.
Bachman et al., "Synthesis of Substituted Quinolylamines. Derivatives of 4-Amino-7-Chloroquinoline.", *J. Org. Chem.* 15, pp. 1278-1284 (1950).
Jain et al., "Chemical and Pharmacological Investigations of Some ω-Substituted Alkylamino-3-aminopyridines.", *J. Med. Chem.*, 11, pp. 87-92 (1968).

(Continued)

*Primary Examiner* — Rita Desai

(57) ABSTRACT

Imidazopyridine, imidazoquinoline, and imidazonaphthyridine compounds having an amide substituent at the 1-position, pharmaceutical compositions containing the compounds, intermediates, and methods of making and methods of use of these compounds as immunomodulators, for modulating cytokine biosynthesis in animals and in the treatment of diseases including viral and neoplastic diseases are disclosed.

17 Claims, No Drawings

(56) References Cited

U.S. PATENT DOCUMENTS

| | | |
|---|---|---|
| 5,378,848 A | 1/1995 | Takada et al. |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Llindstrom et al. |
| 5,446,160 A | 8/1995 | Stucky et al. |
| 5,482,936 A | 1/1996 | Lindstrom |
| 5,494,916 A | 2/1996 | Lindstrom et al. |
| 5,500,228 A | 3/1996 | Lawter et al. |
| 5,525,612 A | 6/1996 | Gerster |
| 5,530,114 A | 6/1996 | Bennett et al. |
| 5,569,450 A | 10/1996 | Duan et al. |
| 5,571,819 A | 11/1996 | Sabb et al. |
| 5,578,727 A | 11/1996 | Andre et al. |
| 5,585,612 A | 12/1996 | Harp, Jr. |
| 5,602,256 A | 2/1997 | Andr e et al. |
| 5,605,899 A | 2/1997 | Gerster et al. |
| 5,612,377 A | 3/1997 | Crooks et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,731,193 A | 3/1998 | Mori et al. |
| 5,736,553 A | 4/1998 | Wick et al. |
| 5,741,908 A | 4/1998 | Gerster et al. |
| 5,741,909 A | 4/1998 | Gerster et al. |
| 5,750,134 A | 5/1998 | Scholz et al. |
| 5,756,747 A | 5/1998 | Gerster et al. |
| 5,776,432 A | 7/1998 | Schultz et al. |
| 5,780,045 A | 7/1998 | McQuinn et al. |
| 5,837,809 A | 11/1998 | Grandy et al. |
| 5,840,744 A | 11/1998 | Borgman |
| 5,854,257 A | 12/1998 | Armitage et al. |
| 5,861,268 A | 1/1999 | Tang et al. |
| 5,886,006 A | 3/1999 | Nikolaides et al. |
| 5,939,047 A | 8/1999 | Jernberg |
| 5,939,090 A | 8/1999 | Beaurline et al. |
| 5,962,479 A | 10/1999 | Chen |
| 5,962,636 A | 10/1999 | Bachmaier et al. |
| 5,977,366 A | 11/1999 | Gerster et al. |
| 6,028,076 A | 2/2000 | Hirota et al. |
| 6,039,969 A | 3/2000 | Tomai et al. |
| 6,057,371 A | 5/2000 | Glennon |
| 6,069,140 A | 5/2000 | Sessler et al. |
| 6,069,149 A | 5/2000 | Nanba et al. |
| 6,071,949 A | 6/2000 | Mulshine et al. |
| 6,077,349 A | 6/2000 | Kikuchi |
| 6,083,505 A | 7/2000 | Miller et al. |
| 6,110,929 A | 8/2000 | Gerster et al. |
| 6,113,918 A | 9/2000 | Johnson et al. |
| 6,121,323 A | 9/2000 | Merrill |
| 6,123,957 A | 9/2000 | Jernberg |
| 6,126,938 A | 10/2000 | Guy et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,294,271 B1 | 9/2001 | Sumita et al. |
| 6,303,347 B1 | 10/2001 | Johnson et al. |
| 6,309,623 B1 | 10/2001 | Weers et al. |
| 6,315,985 B1 | 11/2001 | Wu et al. |
| 6,323,200 B1 | 11/2001 | Gerster et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,348,462 B1 | 2/2002 | Gerster et al. |
| 6,365,166 B2 | 4/2002 | Beaurline et al. |
| 6,376,501 B1 | 4/2002 | Isobe et al. |
| 6,376,669 B1 | 4/2002 | Rice et al. |
| 6,387,383 B1 | 5/2002 | Dow et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,440,992 B1 | 8/2002 | Gerster et al. |
| 6,451,485 B1 | 9/2002 | James et al. |
| 6,451,810 B1 | 9/2002 | Coleman et al. |
| 6,465,654 B2 | 10/2002 | Gerster et al. |
| 6,476,000 B1 | 11/2002 | Agrawal |
| 6,486,168 B1 | 11/2002 | Skwierczynski et al. |
| 6,486,186 B2 | 11/2002 | Fowler et al. |
| 6,511,485 B2 | 1/2003 | Hirt et al. |
| 6,514,985 B1 | 2/2003 | Gerster et al. |
| 6,518,239 B1 | 2/2003 | Kuo et al. |
| 6,518,265 B1 | 2/2003 | Kato et al. |
| 6,518,280 B2 | 2/2003 | Gerster et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,582,957 B1 | 6/2003 | Turner, Jr. et al. |
| 6,610,319 B2 | 8/2003 | Tomai et al. |
| 6,627,638 B2 | 9/2003 | Gerster et al. |
| 6,627,639 B2 | 9/2003 | Stack et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,334 B2 | 1/2004 | Gerster et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,780,873 B2 | 8/2004 | Crooks et al. |
| 6,784,188 B2 | 8/2004 | Crooks et al. |
| 6,790,961 B2 | 9/2004 | Gerster et al. |
| 6,797,718 B2 | 9/2004 | Dellaria et al. |
| 6,800,624 B2 | 10/2004 | Crooks et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,855,217 B2 | 2/2005 | Suzuki |
| 6,855,350 B2 | 2/2005 | Lu |
| 6,878,719 B2 | 4/2005 | Lindstrom et al. |
| 6,888,000 B2 | 5/2005 | Crooks et al. |
| 6,894,060 B2 | 5/2005 | Slade |
| 6,894,165 B2 | 5/2005 | Gerster et al. |
| 6,897,221 B2 | 5/2005 | Crooks et al. |
| 6,900,016 B1 | 5/2005 | Venter et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,240 B2 | 9/2005 | Bauer et al. |
| 6,943,255 B2 | 9/2005 | Lindstrom et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |

(56) References Cited

U.S. PATENT DOCUMENTS

| | | |
|---|---|---|
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,253 B2 | 7/2006 | Brunner et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,544,697 B2 | 6/2009 | Hays et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 2001/0046968 A1 | 11/2001 | Zagon et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2002/0110840 A1 | 8/2002 | Tomai et al. |
| 2002/0137101 A1 | 9/2002 | Meyers |
| 2002/0173655 A1 | 11/2002 | Dellaria et al. |
| 2002/0193729 A1 | 12/2002 | Cormier et al. |
| 2003/0022302 A1 | 1/2003 | Lewis et al. |
| 2003/0044429 A1 | 3/2003 | Aderem et al. |
| 2003/0082108 A1 | 5/2003 | Mulshine et al. |
| 2003/0088102 A1 | 5/2003 | Matsubara et al. |
| 2003/0096835 A1 | 5/2003 | Crooks et al. |
| 2003/0096998 A1 | 5/2003 | Gerster et al. |
| 2003/0130299 A1 | 7/2003 | Crooks et al. |
| 2003/0133733 A1* | 7/2003 | Korhonen ............... 399/389 |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0144286 A1 | 7/2003 | Frenkel et al. |
| 2003/0158192 A1 | 8/2003 | Crooks et al. |
| 2003/0161797 A1 | 8/2003 | Miller et al. |
| 2003/0172391 A1 | 9/2003 | Turner et al. |
| 2003/0185835 A1 | 10/2003 | Braun |
| 2003/0187016 A1 | 10/2003 | Crooks et al. |
| 2003/0199461 A1 | 10/2003 | Averett et al. |
| 2003/0199538 A1 | 10/2003 | Skwierczynski et al. |
| 2003/0212092 A1 | 11/2003 | Heppner et al. |
| 2003/0216481 A1 | 11/2003 | Jia |
| 2003/0232074 A1 | 12/2003 | Lipford et al. |
| 2003/0232763 A1 | 12/2003 | Jia |
| 2003/0232852 A1 | 12/2003 | Lindstrom et al. |
| 2004/0010007 A1 | 1/2004 | Dellaria et al. |
| 2004/0014779 A1 | 1/2004 | Gorden et al. |
| 2004/0023870 A1 | 2/2004 | Dedera et al. |
| 2004/0067975 A1 | 4/2004 | Crooks et al. |
| 2004/0072858 A1 | 4/2004 | Charles et al. |
| 2004/0076633 A1 | 4/2004 | Thomsen et al. |
| 2004/0091491 A1 | 5/2004 | Kedl et al. |
| 2004/0092545 A1 | 5/2004 | Crooks et al. |
| 2004/0097542 A1 | 5/2004 | Crooks et al. |
| 2004/0106638 A1 | 6/2004 | Lindstrom |
| 2004/0132079 A1 | 7/2004 | Gupta et al. |
| 2004/0132748 A1 | 7/2004 | Isobe et al. |
| 2004/0132766 A1 | 7/2004 | Griesgraber |
| 2004/0141950 A1 | 7/2004 | Noelle et al. |
| 2004/0147543 A1 | 7/2004 | Hays et al. |
| 2004/0157874 A1 | 8/2004 | Crooks et al. |
| 2004/0162309 A1 | 8/2004 | Gorden et al. |
| 2004/0167157 A1 | 8/2004 | Masui et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Lee et al. |
| 2004/0181130 A1 | 9/2004 | Fox et al. |
| 2004/0181211 A1 | 9/2004 | Elliott et al. |
| 2004/0191833 A1 | 9/2004 | Fink et al. |
| 2004/0192585 A1 | 9/2004 | Fox et al. |
| 2004/0197865 A1 | 10/2004 | Gupta et al. |
| 2004/0202720 A1 | 10/2004 | Wightman et al. |
| 2004/0204436 A1 | 10/2004 | Gerster et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0009858 A1 | 1/2005 | Martinez-Colon et al. |
| 2005/0032829 A1 | 2/2005 | Lindstrom et al. |
| 2005/0048072 A1 | 3/2005 | Kedl et al. |
| 2005/0054590 A1 | 3/2005 | Averett |
| 2005/0054640 A1 | 3/2005 | Griesgraber et al. |
| 2005/0054665 A1 | 3/2005 | Miller et al. |
| 2005/0059072 A1 | 3/2005 | Birmachu et al. |
| 2005/0070460 A1 | 3/2005 | Hammerbeck et al. |
| 2005/0085500 A1 | 4/2005 | Gutman et al. |
| 2005/0096259 A1 | 5/2005 | Tomai et al. |
| 2005/0119273 A1 | 6/2005 | Lipford et al. |
| 2005/0136065 A1 | 6/2005 | Valiante |
| 2005/0148620 A1 | 7/2005 | Crooks et al. |
| 2005/0158325 A1 | 7/2005 | Hammerbeck et al. |
| 2005/0165236 A1 | 7/2005 | Colombo et al. |
| 2005/0171072 A1 | 8/2005 | Tomai et al. |
| 2005/0226878 A1 | 10/2005 | Tomai et al. |
| 2005/0234088 A1 | 10/2005 | Griesgraber |
| 2005/0239733 A1 | 10/2005 | Jurk et al. |
| 2005/0239735 A1 | 10/2005 | Miller et al. |
| 2005/0245562 A1 | 11/2005 | Garcia-Echeverria et al. |
| 2005/0267145 A1 | 12/2005 | Merrill et al. |
| 2005/0281813 A1 | 12/2005 | Dedera et al. |
| 2006/0009482 A1 | 1/2006 | Tomai et al. |
| 2006/0100229 A1 | 5/2006 | Hays et al. |
| 2006/0106052 A1 | 5/2006 | Crooks et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1* | 5/2007 | Krepski et al. ............... 514/218 |
| 2007/0155767 A1 | 7/2007 | Radmer et al. |
| 2007/0167476 A1 | 7/2007 | Kshirsagar et al. |
| 2007/0208052 A1 | 9/2007 | Prince et al. |
| 2007/0213356 A1 | 9/2007 | Merrill et al. |
| 2007/0219228 A1 | 9/2007 | Niwas et al. |
| 2007/0259881 A1 | 11/2007 | Dellaria et al. |
| 2007/0259907 A1 | 11/2007 | Prince |
| 2007/0287725 A1 | 12/2007 | Miser et al. |
| 2007/0292456 A1* | 12/2007 | Hammerbeck et al. .... 424/278.1 |
| 2008/0015184 A1 | 1/2008 | Kshirsagar et al. |
| 2008/0070907 A1 | 3/2008 | Griesgraber et al. |
| 2008/0085895 A1 | 4/2008 | Griesgraber et al. |
| 2008/0114019 A1 | 5/2008 | Kshirsagar et al. |
| 2008/0119508 A1 | 5/2008 | Slade et al. |
| 2008/0207674 A1 | 8/2008 | Stoesz et al. |
| 2008/0269192 A1 | 10/2008 | Griesgraber et al. |
| 2008/0306252 A1 | 12/2008 | Crooks et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0018122 A1 | 1/2009 | Lindstrom et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0042925 A1 | 2/2009 | Kshirsagar et al. |
| 2009/0062272 A1 | 3/2009 | Bonk et al. |
| 2009/0062328 A1 | 3/2009 | Kshirsagar et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |

(56) References Cited

U.S. PATENT DOCUMENTS

| | | |
|---|---|---|
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0163532 A1* | 6/2009 | Perman et al. ............... 514/293 |
| 2009/0163533 A1 | 6/2009 | Hays et al. |
| 2009/0176821 A1 | 7/2009 | Kshirsagar et al. |
| 2009/0240055 A1 | 9/2009 | Krepski et al. |
| 2009/0253695 A1 | 10/2009 | Kshirsagar et al. |
| 2009/0270443 A1 | 10/2009 | Stoermer et al. |
| 2009/0318435 A1 | 12/2009 | Hays et al. |
| 2010/0113565 A1 | 5/2010 | Gorden et al. |

FOREIGN PATENT DOCUMENTS

| | | |
|---|---|---|
| AU | 2004264336 A1 | 2/2005 |
| AU | 2004268625 A1 | 3/2005 |
| AU | 2002239547 B2 | 11/2006 |
| CA | 2044087 A1 | 12/1991 |
| CA | 2158996 A1 | 10/1994 |
| CN | 1354663 A | 6/2002 |
| EP | 0 145 340 A2 | 6/1985 |
| EP | 0 223 420 A1 | 5/1987 |
| EP | 0 310 950 A1 | 4/1989 |
| EP | 0 385 630 A2 | 9/1990 |
| EP | 0 389 302 A1 | 9/1990 |
| EP | 0 394 026 | 10/1990 |
| EP | 0 425 306 A2 | 5/1991 |
| EP | 0 510 260 A2 | 10/1992 |
| EP | 0 645 389 A1 | 3/1995 |
| EP | 0 778 277 A1 | 6/1997 |
| EP | 0 894 797 A1 | 2/1999 |
| EP | 1 082 960 A2 | 3/2001 |
| EP | 1 097 709 A2 | 5/2001 |
| EP | 1 104 764 | 6/2001 |
| EP | 1 145 340 A2 | 10/2001 |
| EP | 1 256 582 A1 | 11/2002 |
| EP | 1 341 791 A2 | 9/2003 |
| EP | 1 495 758 A2 | 1/2005 |
| HU | 34479 A2 | 3/1985 |
| HU | 210051 A2 | 6/1991 |
| HU | 218950 A2 | 9/1995 |
| IL | 73534 A | 12/1990 |
| JP | 53050197 A | 5/1978 |
| JP | 63010787 A | 1/1988 |
| JP | 4066571 A | 3/1992 |
| JP | 4327587 A | 11/1992 |
| JP | 5286973 A | 11/1993 |
| JP | 9-208584 | 8/1997 |
| JP | 11-080156 A | 3/1999 |
| JP | 11-222432 | 8/1999 |
| JP | 2000-247884 | 9/2000 |
| NZ | 545412 A | 12/2008 |
| RU | 2076105 C1 | 3/1997 |
| RU | 2127273 C1 | 3/1999 |
| RU | 2221798 C2 | 1/2004 |
| WO | WO-91/06682 A1 | 5/1991 |
| WO | WO-92/06093 A1 | 4/1992 |
| WO | WO-92/15581 A1 | 9/1992 |
| WO | WO-92/15582 A1 | 9/1992 |
| WO | WO-93/05042 A1 | 3/1993 |
| WO | WO-93/09119 A1 | 5/1993 |
| WO | WO-93/20847 A1 | 10/1993 |
| WO | WO-94/10171 A1 | 5/1994 |
| WO | WO-95/02597 A1 | 1/1995 |
| WO | WO-95/02598 A1 | 1/1995 |
| WO | WO-96/11199 A1 | 4/1996 |
| WO | WO-96/21663 A1 | 7/1996 |
| WO | WO-97/48703 A1 | 12/1997 |
| WO | WO-97/48704 A1 | 12/1997 |
| WO | WO-98/17279 A1 | 4/1998 |
| WO | WO-98/30562 A1 | 7/1998 |
| WO | WO-98/48805 A1 | 11/1998 |
| WO | WO-98/50547 A2 | 11/1998 |
| WO | WO-98/54226 A1 | 12/1998 |
| WO | WO-99/18105 A1 | 4/1999 |
| WO | WO-99/29693 A1 | 6/1999 |
| WO | WO-00/06577 A1 | 2/2000 |
| WO | WO-00/09506 A1 | 2/2000 |
| WO | WO-00/19987 A1 | 4/2000 |
| WO | WO-00/40228 A2 | 7/2000 |
| WO | WO-00/47719 A2 | 8/2000 |
| WO | WO-00/75304 A1 | 12/2000 |
| WO | WO-00/76505 A1 | 12/2000 |
| WO | WO-00/76518 A1 | 12/2000 |
| WO | WO-00/76519 A1 | 12/2000 |
| WO | WO-01/34709 A1 | 5/2001 |
| WO | WO-01/51486 A2 | 7/2001 |
| WO | WO-01/55439 A1 | 8/2001 |
| WO | WO-01/58900 A1 | 8/2001 |
| WO | WO-01/74343 A2 | 10/2001 |
| WO | WO-01/74821 A1 | 10/2001 |
| WO | WO-02/07725 A1 | 1/2002 |
| WO | WO-02/22809 A2 | 3/2002 |
| WO | WO-02/24225 A1 | 3/2002 |
| WO | WO 02/36592 | 5/2002 |
| WO | WO-02/46188 A2 | 6/2002 |
| WO | WO-02/46189 A2 | 6/2002 |
| WO | WO-02/46190 A2 | 6/2002 |
| WO | WO-02/46191 A2 | 6/2002 |
| WO | WO-02/46192 A2 | 6/2002 |
| WO | WO-02/46193 A2 | 6/2002 |
| WO | WO-02/46194 A2 | 6/2002 |
| WO | WO-02/46749 A2 | 6/2002 |
| WO | WO-02/085905 A1 | 10/2002 |
| WO | WO-02/102377 A1 | 12/2002 |
| WO | WO-03/008421 A1 | 1/2003 |
| WO | WO-03/009852 A1 | 2/2003 |
| WO | WO-03/020889 A2 | 3/2003 |
| WO | WO-03/043572 A2 | 5/2003 |
| WO | WO-03/045391 A1 | 6/2003 |
| WO | WO-03/045494 A2 | 6/2003 |
| WO | WO-03/045929 A1 | 6/2003 |
| WO | WO-03/050117 A1 | 6/2003 |
| WO | WO-03/050118 A1 | 6/2003 |
| WO | WO-03/050119 A2 | 6/2003 |
| WO | WO-03/050121 A1 | 6/2003 |
| WO | WO-03/077944 A1 | 9/2003 |
| WO | WO-03/080114 A2 | 10/2003 |
| WO | WO-03/086280 A2 | 10/2003 |
| WO | WO-03/086350 A1 | 10/2003 |
| WO | WO-03/089602 A2 | 10/2003 |
| WO | WO-03/097641 A1 | 11/2003 |
| WO | WO-03/101949 A2 | 12/2003 |
| WO | WO-03/103584 A2 | 12/2003 |
| WO | WO-2004/028539 A2 | 4/2004 |
| WO | WO-2004/041285 A1 | 5/2004 |
| WO | WO-2004/043913 A2 | 5/2004 |
| WO | WO-2004/053057 A2 | 6/2004 |
| WO | WO-2004/053452 A2 | 6/2004 |
| WO | WO-2004/058759 A1 | 7/2004 |
| WO | WO-2004/071459 A2 | 8/2004 |
| WO | WO-2004/075865 A2 | 9/2004 |
| WO | WO-2004/080398 A2 | 9/2004 |
| WO | WO-2004/091500 A2 | 10/2004 |
| WO | WO-2004/096144 A2 | 11/2004 |
| WO | WO-2004/110991 A2 | 12/2004 |
| WO | WO 2004/110992 A2 | 12/2004 |
| WO | WO-2005/003064 A2 | 1/2005 |
| WO | WO-2005/003065 A2 | 1/2005 |
| WO | WO-2005/016273 A2 | 2/2005 |
| WO | WO-2005/016275 A2 | 2/2005 |
| WO | WO 2005/018551 | 3/2005 |
| WO | WO 2005/018555 | 3/2005 |
| WO | WO 2005/018556 | 3/2005 |
| WO | WO 2005/020999 | 3/2005 |
| WO | WO-2005/023190 A2 | 3/2005 |
| WO | WO-2005/025614 A2 | 3/2005 |
| WO | WO-2005/029037 A2 | 3/2005 |
| WO | WO 2005/032484 | 4/2005 |
| WO | WO-2005/041891 A2 | 5/2005 |
| WO | WO 2005/048933 | 6/2005 |
| WO | WO 2005/048945 | 6/2005 |
| WO | WO-2005/049076 A1 | 6/2005 |

(56) References Cited

FOREIGN PATENT DOCUMENTS

| | | |
|---|---|---|
| WO | WO 2005/051317 | 6/2005 |
| WO | WO 2005/051324 | 6/2005 |
| WO | WO 2005/054237 | 6/2005 |
| WO | WO 2005/054238 | 6/2005 |
| WO | WO-2005/065678 A1 | 7/2005 |
| WO | WO 2005/066169 | 7/2005 |
| WO | WO 2005/066170 | 7/2005 |
| WO | WO 2005/066172 | 7/2005 |
| WO | WO-2005/067500 A2 | 7/2005 |
| WO | WO 2005/076783 | 8/2005 |
| WO | WO 2005/079195 | 9/2005 |
| WO | WO 2005/094531 | 10/2005 |
| WO | WO-2005/110013 A2 | 11/2005 |
| WO | WO 2005/123079 | 12/2005 |
| WO | WO 2005/123080 | 12/2005 |
| WO | WO 2006/009826 | 1/2006 |
| WO | WO 2006/009832 | 1/2006 |
| WO | WO 2006/026760 | 3/2006 |
| WO | WO 2006/028451 | 3/2006 |
| WO | WO 2006/028545 | 3/2006 |
| WO | WO 2006/028962 | 3/2006 |
| WO | WO 2006/029115 | 3/2006 |
| WO | WO 2006/031878 | 3/2006 |
| WO | WO 2006/038923 | 4/2006 |
| WO | WO-2006/063072 A2 | 6/2006 |
| WO | WO-2006/063152 A2 | 6/2006 |
| WO | WO 2006/065280 | 6/2006 |
| WO | WO-2006/073940 A2 | 7/2006 |
| WO | WO 2006/074003 | 7/2006 |
| WO | WO-2006/074045 A2 | 7/2006 |
| WO | WO 2006/004737 | 8/2006 |
| WO | WO 2006/083400 | 8/2006 |
| WO | WO 2006/083440 | 8/2006 |
| WO | WO-2006/084251 A2 | 8/2006 |
| WO | WO 2006/086449 | 8/2006 |
| WO | WO 2006/086633 | 8/2006 |
| WO | WO-2006/086634 A2 | 8/2006 |
| WO | WO 2006/091394 | 8/2006 |
| WO | WO 2006/091567 | 8/2006 |
| WO | WO 2006/091568 | 8/2006 |
| WO | WO 2006/091647 | 8/2006 |
| WO | WO-2006/093514 A2 | 9/2006 |
| WO | WO 2006/098852 | 9/2006 |
| WO | WO-2006/107753 A2 | 10/2006 |
| WO | WO 2006/107771 | 10/2006 |
| WO | WO 2006/107851 | 10/2006 |
| WO | WO 2006/107853 | 10/2006 |
| WO | WO 2006/121528 | 11/2006 |
| WO | WO-2006/122806 A2 | 11/2006 |
| WO | WO-2007/028129 A1 | 3/2007 |
| WO | WO-2007/030775 A2 | 3/2007 |
| WO | WO-2007/030777 A2 | 3/2007 |
| WO | WO-2007/035935 A1 | 3/2007 |
| WO | WO-2007/056112 A2 | 5/2007 |
| WO | WO-2007/062043 A1 | 5/2007 |
| WO | WO-2007/075468 A1 | 7/2007 |
| WO | WO-2007/079086 A1 | 7/2007 |
| WO | WO-2007/079146 A1 | 7/2007 |
| WO | WO-2007/079169 A2 | 7/2007 |
| WO | WO-2007/079171 A2 | 7/2007 |
| WO | WO-2007/079202 A2 | 7/2007 |
| WO | WO-2007/079203 A2 | 7/2007 |
| WO | WO-2007/092641 A2 | 8/2007 |
| WO | WO-2007/106852 A2 | 9/2007 |
| WO | WO-2007/106854 A2 | 9/2007 |
| WO | WO-2007/120121 A2 | 10/2007 |
| WO | WO-2007/143526 A2 | 12/2007 |
| WO | WO-2008/008432 A2 | 1/2008 |
| WO | WO-2008/030511 A2 | 3/2008 |
| WO | WO-2008/036312 A1 | 3/2008 |
| WO | WO-2008/045543 A1 | 4/2008 |

OTHER PUBLICATIONS

Baranov et al., "Pyrazoles, Imidazoles, and Other 5-Membered Rings.", *Chem. Abs.* 85, 94362, (1976).

Berényi et al., "Ring Transformation of Condensed Dihydro-as-triazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines.", *Bioorganic & Medicinal Chemistry*, 11, pp. 2541-2550 (2003).

International Search Report and Written Opinion for PCT/US2005/009880 mailed Nov. 15, 2005.

International Preliminary Report on Patentability for PCT/US2005/009880 issued Sep. 26, 2006.

[No Author Listed] "Comparative Tests." Filed Apr. 8, 2005 during prosecution for EP 00938205.2, EP 00950215.4 and EP 00938211.0 in the name of 3M Innovative Properties Co.

[No Author Listed] Chemical Abstracts. 1964;61(1):6060g.

[No Author Listed] Encyclopedia of Pharmaceutical Technology. 2nd Ed. Marcel Dekker, Inc. 2002:856-60.

Agrawal et al., Synthetic agonists of Toll-like receptors 7, 8 and 9. Biochem Soc Trans. Dec. 2007;35(Pt 6):1461-7.

Ahmed et al., A new rapid and simple non-radioactive assay to monitor and determine the proliferation of lymphocytes: an alternative to [3H]thymidine incorporation assay. J Immunol Methods. Apr. 15, 1994;170(2):211-24.

Akira et al., Recognition of pathogen-associated molecular patterns by TLR family. Immunol Lett. 2003;85:85-95.

Akira et al., Toll-like receptors: critical proteins linking innate and acquired immunity. Nature Immunol. 2001;2(8):675-80.

Alexopoulou et al., Recognition of double-stranded RNA and activation of NF-kappaB by Toll-like receptor 3. Nature. Oct. 18, 2001;413(6857):732-8.

Assuma et al., IL-1 and TNF Antagonists Inhibit the Inflammatory Response and Bone Loss in Experimental Periodontitis. J Immunol. 2000;160:403-09.

Au et al., Virus-mediated induction of interferon A gene requires cooperation between multiple binding factors in the interferon alpha promoter region. J Biol Chem. Nov. 15, 1993;268(32):24032-40.

Auerbach et al., Erythema nodosum following a jellyfish sting. J Emerg Med. Nov.-Dec. 1987;5(6):487-91.

Auwers, [Uber die Isomerie-Verhaltnisse in der Pyrazol-Reihe. Berichte. VI.] 1926;601-607. German.

Baffis et al., Use of interferon for prevention of hepatocellular carcinoma in cirrhotic patients with hepatitis B or hepatitis C virus infection. Ann Intern Med. Nov. 2, 1999;131(9):696-701.

Baker et al., Oral infection with *Porphyromonas gingivalis* and induced alveolar bone loss in immunocompetent and severe combined immunodeficient mice. Arch Oral Biol. Dec. 1994;39(12):1035-40.

Baldwin et al., Amino Acid Synthesis via Ring Opening of N-Sulphonyl Aziridine-2-Carboxylate Esters with Organometallic Reagents. Tetrahedron. 1993;49:6309-30.

Bártová et al., Th1 and Th2 cytokine profile in patients with early onset periodontitis and their healthy siblings. Mediators Inflamm. 2000;9(2):115-20.

Beck et al., Dental Infections and Atherosclerosis. Am Heart J. 1999;13:528-33.

Beckett et al., Configurational Studies in Synthetic Analgesics: the Synthesis of (−)-Methadone from D-(−)-Alanine. J Chem Soc. 1957;1:858-61.

Beilman et al., Experimental brown spider bite in the guinea pig: Results of treatment with dapsone or hyperbaric oxygen. J Wilderness Medicine. 1994;5:287-94.

Belikov, Abbreviated Guide to Synthetic and Natural Medications. Pharmaceutical Chemistry. Higher School. 1993;1:43-47. Russian.

Beltrami et al., Some Methylhydrazonium Salts; An Improved Synthesis of Tetramethylhydrazine. J Am Chem Soc. 1956;78:467-68.

Bernstein et al., Daily or weekly therapy with resiquimod (R-848) reduces genital recurrences in herpes simplex virus-infected guinea pigs during and after treatment. J Infect Dis. Mar. 15, 2001;183(6):844-9. Epub Feb. 13, 2001.

(56) References Cited

OTHER PUBLICATIONS

Bertino et al., Principles of Cancer Therapy. Cecil Textbook of Medicine. Goldman et al., eds. 21th Ed. W.B. Saunders Company. 2000:1:1060-74.

Beutler et al., Tumor necrosis factor in the pathogenesis of infectious diseases. Crit Care Med. Oct. 1993;21(10 Suppl):S423-35.

Beutner et al., Therapeutic response of basal cell carcinoma to the immune response modifier imiquimod 5% cream. J Am Acad Dermatol. Dec. 1999;41(6):1002-7.

Beutner et al., Treatment of genital warts with an immune-response modifier (imiquimod). J Am Acad Dermatol. Feb. 1998;38(2 Pt 1):230-9.

Binder, Acute arthropod envenomation. Incidence, clinical features and management. Med Toxicol Adverse Drug Exp. May-Jun. 1989;4(3):163-73.

Bishop et al., Molecular mechanisms of B lymphocyte activation by the immune response modifier R-848. J Immunol. Nov. 15, 2000;165(10):5552-7.

Bitterman-Deutsch et al., [Brown spider bite]. Harefuah. Sep. 1990;119(5-6):137-9. Hebrew.

Booth et al., Dapsone suppresses integrin-mediated neutrophil adherence function. J Invest Dermatol. Feb. 1992;98(2):135-40.

Borkan et al., An outbreak of venomous spider bites in a citrus grove. Am J Trop Med Hyg. Mar. 1995;52(3):228-30.

Bourke et al., The toll-like receptor repertoire of human B lymphocytes: inducible and selective expression of TLR9 and TLR10 in normal and transformed cells. Blood. Aug. 1, 2003;102(3):956-63. Epub Apr. 10, 2003.

Brants, The Distribution of Tobacco Mosaic Virus (TMV) in Excised Tomato Roots Cultivated in Vitro. Tijdschr Plantenziekten, 1962;68:198-207.

Brassard et al., Interferon-α as an immunotherapeutic protein. J Leukoc Biol. Apr. 2002;71(4):565-81.

Breathnach, Azelaic acid: potential as a general antitumoural agent. Med Hypotheses. Mar. 1999;52(3):221-6.

Broughton, Management of the brown recluse spider bite to the glans penis. Mil Med. Oct. 1996;161(10):627-9.

Buckle et al., 4-hydroxy-3-nitro-2-quinolones and related compounds as inhibitors of allergic reactions. J Med Chem. Jul. 1975;18(7):726-32.

Buisson et al., Preparation and use of (S)-O-acetyllactyl chloride (Mosandl's reagent) as a chiral derivatizing agent. Tetrahedron Assym. 1999;10:2997-3002.

Bulut et al., Cooperation of Toll-like receptor 2 and 6 for cellular activation by soluble tuberculosis factor and Borrelia burgdorferi outer surface protein A lipoprotein: role of Toll-interacting protein and IL-1 receptor signaling molecules in Toll-like receptor 2 signaling. J Immunol. Jul. 15, 2001;167(2):987-94.

Burleson, Chapter 14. Influenza Virus Host Resistance Model for Assessment of Immunostimulation, and Antiviral Compounds. Methods in Immunology. 1995;2:181-202.

Buschle et al., Interferon γ inhibits apoptotic cell death in B cell chronic lymphocytic leukemia. J Exp Med. Jan. 1, 1993;177(1):213-8.

Cai et al., Evaluation of trifluoroacetic acid as an ion-pair reagent in the separation of small ionizable molecules by reversed-phase liquid chromatography. Analytica Chmica Acta. 1999;399:249-258.

Cantell et al., IFN-γ Enhances Production of IFN-α in Human Macrophages but Not in Monocytes. J Interferon and Cytokine Res. 1996;16:461-63.

Carceller et al., Design, synthesis, and structure-activity relationship studies of novel 1-[(1-acyl-4-piperidyl)methyl]-1H-2-methylimidazo[4,5-c]pyridine derivatives as potent, orally active platelet-activating factor antagonists. J Med Chem. Jan. 19, 1996;39(2):487-93.

Carrigan et al., Synthesis and in vitro pharmacology of substituted quinoline-2,4-dicarboxylic acids as inhibitors of vesicular glutamate transport. J Med Chem. May 23, 2002;45(11):2260-76.

Catarzi et al., Tricyclic heteroaromatic systems. Pyrazolo[3,4-c]quinolin-4-ones and pyrazolo[3,4-c]quinoline-1,4-diones: synthesis and benzodiazepine receptor activity. Arch Pharm (Weinheim). Dec. 1997;330(12):383-6.

Cheson et al., National Cancer Institute-sponsored Working Group guidelines for chronic lymphocytic leukemia: revised guidelines for diagnosis and treatment. Blood. Jun. 15, 1996;87(12):4990-7.

Chuang et al., Toll-like receptor 9 mediates CpG-DNA signaling. J Leukoc Biol. Mar. 2002;71(3):538-44.

Claisen, [Uber α-Methyl-isoxazol.] Berichte. 1909;42:59-69. German.

Cohen et al., Cytokine function: a study in biologic diversity. Am J Clin Pathol. May 1996;105(5):589-98.

Cole et al., Brown recluse spider envenomation of the eyelid: an animal model. Ophthal Plast Reconstr Surg. Sep. 1995;11(3):153-64.

Colotta et al., Synthesis and structure-activity relationships of a new set of 2-arylpyrazolo[3,4-c]quinoline derivatives as adenosine receptor antagonists. J Med Chem. Aug. 10, 2000;43(16):3118-24.

Cristalli et al., Adenosine deaminase inhibitors: synthesis and structure-activity relationships of imidazole analogues of erythro-9-(2-hydroxy-3-nonyl)adenine. J Med Chem. Mar. 1991;34(3):1187-92.

Dai et al., Synthesis of a novel C2-symmetric thiourea and its application in the Pd-catalyzed cross-coupling reactions with arenediazonium salts under aerobic conditions. Org Lett. Jan. 22, 2004;6(2):221-4.

Davis, Current therapy for chronic hepatitis C. Gastroenterology. Feb. 2000;118(2 Suppl 1):S104-14.

Davis et al., Heterocyclic Syntheses with Malonyl Chloride. Part VI. 3-Substituted Pyridine Derivatives from α-Methylene-nitriles. J Chem Soc. 1962:3638-44.

Davis et al., Self-administered topical imiquimod treatment of vulvar intraepithelial neoplasia. A report of four cases. J Reprod Med. Aug. 2000;45(8):619-23.

De et al., Structure-activity relationships for antiplasmodial activity among 7-substituted 4-aminoquinolines. J Med Chem. Dec. 3, 1998;41(25):4918-26.

Debol et al., Anti-inflammatory action of dapsone: inhibition of neutrophil adherence is associated with inhibition of chemoattractant-induced signal transduction. J Leukoc Biol. Dec. 1997;62(6):827-36.

De Clerq, Synthetic interferon inducers. Top Curr Chem. 1974;52:173-208.

Decker et al., Immunostimulatory CpG-oligonucleotides cause proliferation, cytokine production, and an immunogenic phenotype in chronic lymphocytic leukemia B cells. Blood. Feb. 1, 2000;95(3):999-1006.

Decker et al., Immunostimulatory CpG-oligonucleotides induce functional high affinity IL-2 receptors on B-CLL cells: costimulation with IL-2 results in a highly immunogenic phenotype. Exp Hematol. May 2000;28(5):558-68.

Delgado, Textbook of Organic Medicinal and Pharmaceutical Chemistry, Ninth Edition, Remers, ed., 1991:30-1.

Denzel et al. Imidazo [4,5-c]- and [4,5-b]pyridines. J. Heterocyclic Chem. 1977;14:813-821.

Diaz-Arrastia et al., Clinical and molecular responses in high-grade intraepithelial neoplasia treated with topical imiquimod 5%. Clin Cancer Res. Oct. 2001;7(10):3031-3.

Di Carlo et al., Neutrophils in anti-cancer immunological strategies: old players in new games. J Hematother Stem Cell Res. Dec. 2001;10(6):739-48.

Dicken et al., Reactions at High Pressures. [3+2] Dipolar Cycloaddition of Nitrones with Vinyl Ethers. J Org Chem. 1982;47:2047-51.

Dockrell et al., Imiquimod and resiquimod as novel immunomodulators. J Antimicrob Chemother. Dec. 2001;48(6):751-5.

Douglas, Introduction to Viral Diseases. In: Cecil Textbook of Medicine. Bennet et al., eds. 20th Ed. W.B. Saunders Company. 1996:2:1739-47.

Doyle et al., Toll-like receptor 3 mediates a more potent antiviral response than Toll-like receptor 4. J Immunol. Apr. 1, 2003;170(7):3565-71.

Drexler et al., Bryostatin 1 induces differentiation of B-chronic lymphocytic leukemia cells. Blood. Oct. 1989;74(5):1747-57.

(56) References Cited

OTHER PUBLICATIONS

Dzionek et al. BDCA-2, BDCA-3, and BDCA-4: three markers for distinct subsets of dendritic cells in human peripheral blood. J Immunol. Dec. 1, 2000;165(11):6037-46.

Edwards et al., Toll-like receptor expression in murine DC subsets: lack of TLR7 expression by CD8 alpha+ DC correlates with unresponsiveness to imidazoquinolines. Eur J Immunol. Apr. 2003;33(4):827-33.

Eriks et al., Histamine H2-receptor agonists. Synthesis, in vitro pharmacology, and qualitative structure-activity relationships of substituted 4- and 5-(2-aminoethyl)thiazoles. J Med Chem. Aug. 21, 1992;35(17):3239-46.

Fecci et al., The history, evolution, and clinical use of dendritic cell-based immunization strategies in the therapy of brain tumors. J Neurooncol. Aug.-Sep. 2003;64(1-2):161-76.

Fitzgerald-Bocarsly et al., Virally-Responsive IFN-α Producing Cells in Human Blood and Tonsil Are CD11C/CD123+ Cells Identical to Precursors of Type Two Dendritic Cells (pDC2). J Interferon Cytokine Res. 1999;19(1):S117. Abstract P81.

Flo et al., Involvement of toll-like receptor (TLR) 2 and TLR4 in cell activation by mannuronic acid polymers. J Biol Chem. Sep. 20, 2002;277(38):35489-95. Epub Jun. 27, 2002.

Fonteneau et al., Human Immunodeficiency Virus Type 1 Activates Plasmacytoid Dendritic Cells and Concomitantly Induces the Bystander Maturation of Myeloid Dendritic Cells. J Virol. 2004;78(10):5223-32.

Frankel et al., The Preparation of N-Disubstituted Formamides. Tetrahedron Lett. 1959;7:5-7.

Frantz et al., Toll4 (TLR4) expression in cardiac myocytes in normal and failing myocardium. J Clin Invest. Aug. 1999;104(3):271-80.

Fu et al., Regioselective Catalytic Hydrogenation of Polycyclic Aromatic Hydocarbons under Mild conditions. J Org Chem. 1980;45:2979-803.

Fuchsberger et al., Priming Interferon-a 1 or Interferon-a 2 Enhances the Production of Both Subtypes Simultaneously. J Interferon and Cytokine Res. 1995;15:637-39.

Galose, Dapsone (diaminodiphenylsulphone DDS). Clinical Toxicology Review. 1999:21(9). 3 pages.

Gendron, Loxosceles ignali Envenomation. Am J Emerg Med. Jan. 1990;8(1):51-4.

Genevois-Borella et al., Synthesis of 1-(3-R-Amino-4-Hydroxy Butyl)thymine Acyclonucleoside. Analogs as Potential Anti-AIDS Drugs. Tetrahedron Lett. 1990;31:4879-82.

Giannini et al., Influence of the Mucosal Epithelium Microenvironment on Langerhans Cells: Implications for the Development of Squamous Intraepithelial Lesions of the Cervix. Int J Cancer. 2002;97:654-59.

Gibson et al., Cellular requirements for cytokine production in response to the immunomodulators imiquimod and S-27609. J Interferon Cytokine Res. Jun. 1995;15(6):537-45.

Gibson et al., Plasmacytoid dendritic cells produce cytokines and mature in response to the TLR7 agonists, imiquimod and resiquimod. Cell Immunol. Jul.-Aug. 2002;218(1-2):74-86.

Gitelson et al., Chronic lymphocytic leukemia-reactive T cells during disease progression and after autologous tumor cell vaccines. Clin Cancer Res. May 2003;9(5):1656-65.

Gomez et al., Intradermal anti-loxosceles Fab fragments attenuate dermonecrotic arachnidism. Acad Emerg Med. 1999;6:1195-202.

Gorden et al., Synthetic TLR agonists reveal functional differences between human TLR7 and TLR8. J Immunol. Feb. 1, 2005;174(3):1259-68.

Gordon, Pattern recognition receptors: doubling up for the innate immune response. Cell. Dec. 27, 2002;111(7):927-30.

Gunning et al., Chemoprevention by lipoxygenase and leukotriene pathway inhibitors of vinyl carbamate-induced lung tumors in mice. Cancer Res. Aug. 1, 2002;62(15):4199-201.

Gürsel et al., Differential and competitive activation of human immune cells by distinct classes of CpG oligodeoxynucleotide. J Leukoc Biol. May 2002;71(5):813-20.

Hart, Napthyridines Hydroxynaphthyridies, Journal of Chemical Society, 1956;Part III:212-4.

Hartmann et al., Rational design of new CpG oligonucleotides that combine B cell activation with high IFN-alpha induction in plasmacytoid dendritic cells. Eur J Immunol. Jun. 2003;33(6):1633-41.

Hayashi Toll-like receptors stimulate human neutrophil function. Blood. Oct. 1, 2003;102(7):2660-9. Epub Jun. 26, 2003.

Hayes et al., Regulation of Interferon Production by Human Monocytes: Requirements for Priming for Lipopolysaccharide-Induced Production. J Leukocyte Biol. 1991;50:176-81.

Heil et al., Species-specific recognition of single-stranded RNA via toll-like receptor 7 and 8. Science. Mar. 5, 2004;303(5663):1526-9. Epub Feb. 19, 2004.

Heil et al., Synthetic immunostimulatory compounds activate immune cells via TLR7 and TLR8. 33th Annual Meeting of the Deutsche Gessellschaft Mr Immunologie, Marburg 2002. Abstract C.6.

Hemmi et al., Small anti-viral compounds activate immune cells via the TLR7 MyD88-dependent signaling pathway. Nat Immunol. Feb. 2002;3(2):196-200. Epub Jan. 22, 2002.

Hobbs et al., Comparison of hyperbaric oxygen and dapsone therapy for loxosceles envenomation. Acad Emerg Med. Aug. 1996;3(8):758-61.

Hoffman et al., Conformational requirements for histamine H2-receptor inhibitors: a structure-activity study of phenylene analogues related to cimetidine and tiotidine. J Med Chem. Feb. 1983;26(2):140-4.

Hofmanová et al., Lipoxygenase inhibitors induce arrest of tumor cells in S-phase of the cell cycle. Neoplasma. 2002;49(6):362-7.

Holladay et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett. Oct. 6, 1998;8(19):2797-802.

Horng et al., The adaptor molecule TIRAP provides signaling specificity for Toll-like receptors. Nature. Nov. 21, 2002;420(6913):329-33.

Hornung et al., Quantitative Expression of Toll-Like Receptor 1-10 mRNA in Cellular Subsets of Human Peripheral Blood Mononuclear Cells and Sensitivity to CpG Oligodeoxynucleotides. Journal of Immunol. 2002;168:4531-37.

Houben-Weyl, Quinoline and Isoquinoline. Methoden der Organischen Chemie. 1980:271-79. German.

Houston et al., Potential inhibitors of S-adenosylmethionine-dependent methyltransferases. 8. Molecular dissections of carbocyclic 3-deazaadenosine as inhibitors of S-adenosylhomocysteine hydrolase. J Med Chem. Apr. 1985;28(4):467-71.

Huppatz, Systemic fungicides. The synthesis of certain pyrazole analogues of carboxin. Aust J Chem. 1983;36:135-47.

Iino et al., Treatment of Chronic Hepatitis C With High-Dose Interferon α-2b. Multicenter Study. Dig Dis Sci. 1993;38(4):612-18.

Ito et al., Interferon-alpha and interleukin-12 are induced differentially by Toll-like receptor 7 ligands in human blood dendritic cell subsets. J Exp Med. Jun. 3, 2002;195(11):1507-12.

Iwashita et al., Syntheses of Isoretronecanol and Lupinine. J Org Chem. 1982;47:230-33.

Jacobs, The Synthesis of Acetylenes. In: Organic Reactions. New York: Wiley & Sons, Inc., 1949. vol. 5. 1-78.

Jahnsen et al., Extensive recruitment of IL-3Rαhigh dendritic-cell precursors to allergic nasal mucosa during allergen challenge. Immunology Lett. 1999;69(1):123. Abstract #32.2.

Jurk et al. Human TLR7 and TLR8 independently confer responsiveness to the antiviral compound R-848. Nat Immunol. Jun. 2002;3(6):499.

Juweid, Radioimmunotherapy of B-Cell Non-Hodgkin's Lymphoma: From Clinical Trials to Clinical Practice. J Nuclear Med. 2002;43(11):1507-29.

Katritsky et al., Comprehensive Heterocyclic Chemistry: The Structure, Reactions, Synthesis and Uses of Heterocyclic Compounds. 1984;2:586-587.

(56) References Cited

OTHER PUBLICATIONS

Keating et al., Long-term follow-up of patients with chronic lymphocytic leukemia treated with fludarabine as a single agent. Blood. Jun. 1, 1993;81(11):2878-84.

Klausen et al., Two complementary methods of assessing periodontal bone level in rats. Scand J Dent Res. Dec. 1989;97(6):494-9.

Klinman, Immunotherapeutic uses of CpG oligodeoxynucleotides. Nat Rev Immunol. Apr. 2004;4(4):249-58.

Kloek et al., An improved method for the synthesis of stabilized primary enamines and imines. J Org Chem. 1978;43:1460-62.

Kloetzel, Reactions of nitroparaffins. I. Synthesis and reduction of some ò -nitrokenes. J Am Chem Soc. 1947;69:2271-2275.

Kornman, Host modulation as a therapeutic strategy in the treatment of periodontal disease. Clin Infect Dis. Mar. 1999;28(3):520-6.

Kourafalos et al., Synthesis of 7-aminopyrazolo[3,4-c]pyridine as a probe for the preparation of compounds of pharmacological interest. Heterocycles. 2002;57(12):2335-2343.

Krause et al., Autoimmune aspects of cytokine and anticytokine therapies. Am J Med. Oct. 1, 2003;115(5):390-7.

Krenitsky et al., Imidazo[4,5-c]pyridines (3-deazapurines) and their nucleosides as immunosuppressive and anti-inflammatory agents. J Med Chem. Jan. 1986;29(1):138-43.

Kurt-Jones et al., Role of toll-like receptor 2 (TLR2) in neutrophil activation: GM-CSF enhances TLR2 expression and TLR2-mediated interleukin 8 responses in neutrophils. Blood. Sep. 1, 2002;100(5):1860-8.

Lall et al., Serine and threonine beta-lactones: a new class of hepatitis A virus 3C cysteine proteinase inhibitors. J Org Chem. Mar. 8, 2002;67(5):1536-47.

Lee et al., p38 mitogen-activated protein kinase inhibitors—mechanisms and therapeutic potentials. Pharmacol Ther. 1999;82:389-97.

Lee et al., Saturated fatty acid activates but polyunsaturated fatty acid inhibits Toll-like receptor 2 dimerized with Toll-like receptor 6 or 1. J Biol Chem. Apr. 23, 2004;279(17):16971-9. Epub Feb. 13, 2004.

Lehner et al., The role of $\gamma\sigma$ cells and β-chemokines in mucosal protection against SIV infection. Immunology Lett. 1999;69:25-192. Abstract 2.1.

Levy et al., Unique efficacy of Toll-like receptor 8 agonists in activating human neonatal antigen-presenting cells. Blood. Aug. 15, 2006;108(4):1284-90. Epub Apr. 25, 2006.

Leynadier et al., Allergic reactions to North African scorpion venom evaluated by skin test and specific IgE. J Allergy Clin Immunol. Jun. 1997;99(6 Pt 1):851-3. 4 pages.

Li et al., An improved protocol for the preparation of 3-pyridyl- and some arylboronic acids. J Org Chem. Jul. 26, 2002;67(15):5394-7.

Li et al., Solubility behavior of imiquimod in alkanoic acids. Pharmaceutical Research. 1997 American Association of Pharmaceutical Scientists Annual Meeting. Poster Presentation, Boston, MA, Nov. 2-6, 1997;S475:Abstract 3029.

Li et al., Synthesis, CoMFA analysis, and receptor docking of 3,5-diacyl-2, 4-dialkylpyridine derivatives as selective A3 adenosine receptor antagonists. J Med Chem. Feb. 25, 1999;42(4):706-21.

Litt et al., Mucosal delivery of vaccine antigens displayed on the surface of *Lactococcus lactis*. Immunology Lett. 1999;69(1):61. Abstract #11.26.

Liu et al., Synthesis of halogen-substituted 3-deazaadenosine and 3-deazaguanosine analogues as potential antitumor/antiviral agents. Nucleosides Nucleotides Nucleic Acids. Dec. 2001;20(12):1975-2000.

Loesche et al., Treatment paradigms in periodontal disease. Compend Contin Educ Dent. Mar. 1997;18(3):221-6, 228-30, 232 passim; quiz 234. Review.

Luger et al., Evidence for an epidermal cytokine network. J Invest Dermatol. Dec. 1990;95(6 Suppl):100S-104S.

Luskin et al., Olefinic Derivatives of 2,4-Diamino-s-triazines. J Org Chem. 1958;23:1032-37.

Macchia et al., Synthesis and antiviral properties of 9-[(2-methyleneaminoxyethoxy)methyl]guanine derivatives as novel Acyclovir analogues. Farmaco. Feb. 2000;55(2):104-8.

Majeski et al., Action of venom from the brown recluse spider (*Loxosceles reclusa*) on human neutrophils. Toxicon. 1977;15(5):423-7.

Makarenkova et al., Identification of delta- and mu- type opioid receptors on human and murine dendritic cells. J Neuroimmunol. 2001;117:68-77.

Male et al., Introduction to the Immune System. In: Immunology. Elsevier. 2006:6-7.

Masihi, Progress on novel immunomodulatory agents for HIV-1 infection and other infectious diseases. Expert Opin Ther Patents. 2003;13(6):867-82.

Masiukiewicz et al., Scalable Syntheses of $N^{\alpha}$-Benzyloxycarbonyl-$_L$- Ornithine and of $N^{\alpha}$-(9-Fluorenylmethoxy)Carbonyl-$_L$-Ornithine. Org Prep Proced Int. 2002;34:531-37.

Mataka et al., Condensation reaction of 3,4-Dibenzoyl-1-methyl-2,5-diphenylpyrrole and -1-phenylpyrazole with methylamine derivatives affording pyrrolo [3,4-c] pyridine and 2H-pyrazolo[3,4-c]- and [4,3-c]pyridines. Journal of Heterocyclic Chemistry. 1981;18(6):1073-5.

Mathur et al., Cell-mediated immune system regulation in periodontal diseases. Crit Rev Oral Biol Med. 1997;8(1):76-89.

Maynor et al., Brown recluse spider envenomation: a prospective trial of hyperbaric oxygen therapy. Acad Emerg Med. Mar. 1997;4(3):184-92.

Mbow et al., Small molecule and biologic modulators of the immune response to hepatitis C virus. Mini Rev Med Chem. May 2006;6(5):527-31.

McCarthy et al., Opioids, opioid receptors, and the immune response. Drug & Alcohol Dependence. 2001;62:111-23.

McKennon et al., A Convenient Reduction of Amino Acids and Their Derivatives. J Org Chem. 1993;58:3568-71.

McLaughlin et al., Opioid growth factor (OGF) inhibits the progression of human squamous cell carcinoma of the head and neck transplanted into nude mice. Cancer Lett. 2003;199:209-17.

Medzhitov, Toll-Like Receptors and Innate Immunity. Nature Rev Immunol. 2001;1:135-45.

Mee et al., Stille coupling made easier—the synergic effect of copper(I) salts and the fluoride ion. Angew Chem. 2004;116:1152-56.

Merigian et al., Envenomation From the Brown Recluse Spider: Review of Mechanism and Treatment Options. Am J Ther. Oct. 1996;3(10):724-734.

Miller et al., Imiquimod applied topically: a novel immune response modifier and new class of drug. Int J Immunopharmacol. Jan. 1999;21(1):1-14.

Minakawa et al., Nucleosides and Nucleotides. 184. Synthesis and Conformational Investigation of Anti-Fixed 3-Deaza-3-halopurine Ribonucleosides. J Org Chem. 1999;64:7158-72.

Moebius et al., The mysteries of sigma receptors: new family members reveal a role in cholesterol synthesis. Trends Pharmacol Sci. Mar. 1997;18(3):67-70.

Moldoveanu et al., Poly-L-lysine as a potential mucosal adjuvant. Immunology Lett. 1999;69(1):62. Abstract #11.28.

Mollick et al., MUC1-like tandem repeat proteins are broadly immunogenic in cancer patients. Cancer Immun. Mar. 17, 2003;3:3. 17 pages.

Moody et al., Lipoxygenase inhibitors prevent lung carcinogenesis and inhibit non-small cell lung cancer growth. Exp Lung Res. Jul.-Aug. 1998;24(4):617-28.

Moraczewski et al., Using Hydrogen Bonding to Control Carbamate C-N Rotamer Equilibria. Org Chem. Oct. 16, 1998;63(21):7258-7262.

Mosbech et al., [Allergy to insect stings] Ugeskr Laeger. Oct. 28, 1991;153(44):3067-71. Danish.

Muche et al., Imiquimod treatment of cutaneous T cell lymphoma. Journal of Investigative Dermatology. Jul. 2003;121(1):0975. Joint Meeting of the European Society for Dermatologi; Miami Beach, Florida, USA. Apr. 30-May 4, 2003. Abstract 0975.

Muller et al., An improved one-pot procedure for the synthesis of alkynes from aldehydes. Synlett. 1996;6:521-522.

Mutschler et al., 9.2 Anti-infectives. In: Drug Actions: Basic Principles and Therapeutic Aspects. 1995:515-80.

(56) References Cited

OTHER PUBLICATIONS

Muzio et al., Differential expression and regulation of toll-like receptors (TLR) in human leukocytes: selective expression of TLR3 in dendritic cells. J Immunol. Jun. 1, 2000;164(11):5998-6004.
Nagarajan et al., Condensed heterotricycles: synthesis of pyrazolo[3,4-c]quinoline derivatives. Indian Journal of Chemistry. 1992;31B:316-321.
Nagase et al., Expression and function of Toll-like receptors in eosinophils: activation by Toll-like receptor 7 ligand. J Immunol. Oct. 15, 2003;171(8):3977-82.
Nanjappan et al., An efficient synthesis of some 6-substituted 4,8-diaza-3,3,9,9-tetramethylundeca-2,10-dione dioximes (propylene amine oximes, PnAOs): Ligands for 99mTc complexes used in structure distribution relationship (SDR) studies. Tetrahedron. 1994;50(29):8617-32.
Ohana et al., Differential effect of adenosine on tumor and normal cell growth: focus on the A3 adenosine receptor. Journal of Cellular Physiology. Jan. 2001;186(1):19-23. Review.
O'Mahony et al., New patient-applied therapy for anogenital warts is rated favourably by patients. Intl J Std & Aids. 2001;12:565-70.
Osol et al., Chapter 27: Structure-Activtiy Relationship and Drug Design. In: Remington's Pharmaceutical Sciences. 16th Ed. Mach Publishing. 1980:420-35.
Ottonello et al., Sulphonamides as anti-inflammatory agents: old drugs for new therapeutic strategies in neutrophilic inflammation? Clin Sci (Lond). Mar. 1995;88(3):331-6.
Ozinsky et al., The repertoire for pattern recognition of pathogens by the innate immune system is defined by cooperation between Toll-like receptors. Proc. Nat. Acad. Sci. 2000; 97(25):13766-71.
Page et al., Advances in the pathogenesis of periodontitis: summary of developments, clinical implications and future directions. Periodontol 2000. Jun. 1997;14:216-48.
Park et al., Immunotherapy Cancer Treatment. Reprinted from Supportive Cancer Care, Rosenbaum et al. 2001. Available at http://www.cancersupportivecare.com/immunotherapy.html. Last accessed Jul. 13, 2010. 3 pages.
Park et al., Sodium Dithionite Reduction of Nitroarenes Using Viologen as an Electron Phase-Transfer Catalyst. Tetrahedron Lett. 1993;34(46):7445-46.
Patel et al., The necrotic venom of the brown recluse spider induces dysregulated endothelial cell-dependent neutrophil activation. Differential induction of GM-CSF, IL-8, and E-selectin expression. J Clin Invest. Aug. 1994;94(2):631-42.
Patrick et al., Paragraph 10.3: Drug optimization: strategies in drug design. In: An Introduction to Medicinal Chemistry. Oxford: Oxford University Press. Jan. 2005. 200-218.
Pavletic et al., Outcome of allogeneic stem cell transplantation for B cell chronic lymphocytic leukemia. Bone Marrow Transplant. Apr. 2000;25(7):717-22.
Pawlas et al., Novel anionic annelation tactics for construction of fused heteroaromatic frameworks. 1. Synthesis of 4-substituted pyrazolo[3,4-c]quinolines, 9-substituted pyrazolo[3,4-c]quinolines, and 1,4-dihydrochromeno[4,3-c]pyrazoles. Org Chem. Jun. 15, 2001;66(12):4214-9.
Payvandi et al., Exogenous and Endogenous IL-10 Regulate IFN-α Production by Peripheral Blood Mononuclear Cells in Response to Viral Stimulation. J Immunol. 1998;160:5861-68.
Peschke et al., Synthesis and in vitro characterization of new growth hormone secretagogues derived from ipamorelin with dipeptidomimetic N-terminals. Eur J Med Chem. 1999;34:363-380.
Peterson et al., The opioid-cytokine connection. J Neuroimmunol. 1998;83:63-69.
Phillips et al., Therapy of brown spider envenomation: a controlled trial of hyperbaric oxygen, dapsone, and cyproheptadine. Ann Emerg Med. Mar. 1995;25(3):363-8.
Pickersgill et al., Preparation of functionalized, conformationally constrained DTPA analogues from L-or D-serine and trans-4-hydroxy-L-proline. Hydroxymethyl substituents on the central acetic acid and on the backbone. J Org Chem. Jun. 30, 2000;65(13):4048-57.
Poljakovic et al., iNOS and COX-2 immunoreactivity in the mice bladder and kidney after bacterial instillation. Immunology Lett. 1999;69(1):122. Abstract #31.5.
Powell et al., Compendium of excipients for parenteral formulations. PDA J Pharm Sci Technol. Sep.-Oct. 1998;52(5):238-311.
Prelog et al., Cycloalkeno-pyridine. Helv Chem Acta. 1945;28:1684-93. German.
Rees et al., Brown recluse spider bites. A comparison of early surgical excision versus dapsone and delayed surgical excision. Ann Surg. Nov. 1985;202(5):659-63.
Regan et al., Activation of p38 MAPK by feline infectious peritonitis virus regulates pro-inflammatory cytokine production in primary blood-derived feline mononuclear cells. Virology. Feb. 5, 2009;384(1):135-43. Epub Dec. 5, 2008.
Rhodes, Discovery of immunopotentiatory drugs: current and future strategies. Clin Exp Immunol. Dec. 2002;130(3):363-9.
Ribera et al., "Spontaneous" complete remissions in chronic lymphocytic leukemia: report of three cases and review of the literature. Blood Cells. 1987;12(2):471-79.
Ritter et al., A new reaction of nitriles; amides from alkenes and mononitriles. J Am Chem Soc. Dec. 1948;70(12):4045-8.
Rocca et al., Carbolines. Part VII. Ansidines, Convenient tools to synthesize fficien-β-carbolines. J Heterocyclic Chem. 1995;32:1171-1175.
Rocca et al., Connection between metalation and cross-coupling strategies. A new convergent route to azacarbazoles. Tetrahedron. 1993;49(1):49-64.
Rollins, Chemokines. Blood. Aug. 1, 1997;90(3):909-28. Review.
Rosenberg et al., Treatment of 283 consecutive patients with metastatic melanoma or renal cell cancer using high-dose bolus interleukin 2. JAMA. Mar. 23-30, 1994;271(12):907-13.
Rothel et al., The use of recombinant ovine IL-1beta and TNF-alpha as natural adjuvants and their physiological effects in vivo. Immunol Cell Biol. Apr. 1998;76(2):167-72.
Roy et al., QSAR of adenosine receptor antagonists II: exploring physicochemical requirements for selective binding of 2-arlypyrazolo[3,4-c] quinoline derivatives with adenosine A1 and A3 receptor subtypes. QSAR & Comb Sci. 2003;22:614-621.
Royals et al., Studies in mixed ester condensations. IV. Acylations with methyl dimethoxyacetate. J Am Chem Soc. 1956;78:4161-4164.
Rozman et al., Chronic lymphocytic leukemia. N Engl J Med. Oct. 19, 1995;333(16):1052-7.
Sakthivel et al. Direct SnAr amination of fluorinated imizazo[4,5-c]pyridine nucleosides: efficient synthesis of 3-fluoro-3-3-deazaadenosine analogs. Tetrahedron Letters. May 2005;46(22):3883-3887.
Salaun et al., TLR3 Can Directly Trigger Apoptosis in Human Cancer Cells. J of Immunology. 2006;176:4894-901.
Salemink, Uber 2-Propyl-1- Und 2-Propyl-Desaza-Adenin. Recueil. 1961;80:545-55. German
Sambhi et al., Local production of tumor necrosis factor encoded by recombinant vaccinia virus is effective in controlling viral replication in vivo. Proc Natl Acad Sci U S A. May 1, 1991;88(9):4025-9.
Sams et al., Necrotic arachnidism. J Am Acad Dermatol. Apr. 2001;44(4):561-73; quiz 573-6.
Sauder et al., Randomized, Single-Blind, Placebo-Controlled Study of Topical Application of the Immune Response Modulator Resiquimod in Healthy Adults. Antimicrobial Agents Chemo. 2003;47(12):3846-52.
Scheerlinck, Genetic adjuvants for DNA vaccines. Vaccine. Mar. 21, 2001;19(17-19):2647-56.
Scheuer et al., Application of the Ritter reaction to mesityl oxide and chalcone. J Am Chem Soc. 1957;22:674-676.
Schofield et al., Reply. Low-Dose Interferon-alpha in Chronic Myeloid Leukemia. Ann Internal Med. 1995;122(9):728-29. 1 page.
Schwandner et al., Peptidoglycan- and lipoteichoic acid-induced cell activation is mediated by toll-like receptor 2. J Biol Chem. Jun. 18, 1999;274(25):17406-9.
Seeman et al., Steric and Conformational Effects in Nicotine Chemistry. J Org Chem. 1981;46:3040-48.

(56) References Cited

OTHER PUBLICATIONS

Serrat et al., A highly efficient and straightforward stereoselective synthesis of novel chiral α-acetylenic ketones. Tetrahedron: Assymmetry. 1999;10:3417-30.
Severa et al., Sensitization to TLR7 agonist in IFN-beta-preactivated dendritic cells. J Immunol. May 15, 2007;178(10):6208-16.
Seymour et al., Cellular immunity and hypersensitivity as components of periodontal destruction. Oral Dis. Mar. 1996;2(1):96-101. Review.
Shelburne et al., Quantitation of *Bacteroids forsythus* in subgingival plaque comparison on immunoassay and quantitative polymerase chain reaction. J Microbiol Methods. 2000;39:97-107.
Sidky et al., Inhibition of murine tumor growth by an interferon-inducing imidazoquinolinamine. Cancer Res. Jul. 1, 1992;52(13):3528-33.
Siegal et al., The nature of the principal type 1 interferon-producing cells in human blood. Science. Jun. 11, 1999;284(5421):1835-7.
Sletzinger et al., The Synthesis of Isomethadone. J Am Chem Soc. 1952;74:5619-20.
Smith et al., The role of polymorphonuclear leukocytes in the lesion caused by the venom of the brown spider, *Loxosceles reclusa*. Lab Invest. Jan. 1970;22(1):90-3.
Sofina et al., C: Possibility of Predicting the Spectrum of Antitumor Effect of Drugs on the Basis of Experimental Data. Experimental evaluation of antitumor drugs in the USA and USSR and clinical correlations. NCI Monograph 55. NIH Publication No. 80-1933. 1980:76-8.
Sommer et al., Recent Findings on How Proinflammatory Cytokines Cause Pain: Peripheral Mechanisms in Inflammatory and Neuropathic Hyperalgesia. Neurosci Letts. 2004;361:184-87.
Sonogashira et al., A convenient synthesis of acetylenes: catalytic substitutions of acetylenic hydrogen with bromoalkenes, Iodoarenes, and bromopyridines. Tetrahedron Letts. 1975;50:4467-4470.
Soria et al., Effect of food on the pharmacokinetics and bioavailability of oral imiquimod relative to a subcutaneous dose. Int J Clin Pharmacol Ther. Oct. 2000;38(10):476-81.
Spaner et al., A phase I/II trial of TLR-7 agonist immunotherapy in chronic lymphocytic leukemia. Leukemia. 2010; 24:222-26.
Spaner et al., Immunomodulatory effects of Toll-like receptor-7 activation on chronic lymphocytic leukemia cells. Leukemia. Feb. 2006;20(2):286-95.
Spaner et al., Toll-like receptor agonists in the treatment of chronic lymphocytic leukemia. Leukemia. Jan. 2007;21(1):53-60. Epub Oct. 26, 2006.
Spivey et al., Configurationally stable biaryl analogues of 4-(dimethylamino)pyridine: A novel class of chiral nucleophilic catalysts. J Org Chem. 1999;64:9430-9443.
Spruance et al., Application of a topical immune response modifier, resiquimod gel, to modify the recurrence rate of recurrent genital herpes: a pilot study. J Infect Dis. Jul. 15, 2001;184(2):196-200. Epub Jun. 8, 2001.
Stack, Images in clinical medicine. *Latrodectus mactans*. N Engl J Med. Jun. 5, 1997;336(23):1649.
Stanley, Imiquimod and the imidazoquinolones: mechanism of action and therapeutic potential. Clin Exp Dermatol. Oct. 2002;27(7):571-7. Review.
Stashenko et al., Periapical inflammatory responses and their modulation. Crit Rev Oral Biol Med. 1998;9(4):498-521.
Steele et al., Lipoxygenase inhibitors as potential cancer chemopreventives. Cancer Epidemiol Biomarkers Prev. May 1999;8(5):467-83.
Steele et al., Potential use of lipoxygenase inhibitors for cancer chemoprevention. Expert Opin Investig Drugs. Sep. 2000;9(9):2121-38.
Steinmann et al., Topical imiquimod treatment of a cutaneous melanoma metastasis. J Am Acad Dermatol. Sep. 2000;43(3):555-6.
Stewart et al., Synthesis of a Carba-analog of S-Acetyl Coenzyme A,Acetonyl-dethio Coenzyme A; an Effective Inhibitor of Citrate Synthase. Liebigs Ann Chem. 2978:57-65.
Stillings et al., Substituted 1,3,4-thiadiazoles with anticonvulsant activity. 2. Aminoalkyl derivatives. J Med Chem. Nov. 1986;29(11):2280-4.
Strandtmann et al., Reaction of cyclic β-diketones with 3,4-dihydroisoquinolines and related compounds. Preparation and anticancer activity of 2-substituted 1,3-cyclohexanediones. J Med Chem. Nov. 1967;10(6):1063-5.
Stringfellow, Induction of interferon with low molecular weight compounds: fluorenone esters, ethers (tilorone), and pyrimidinones. Methods Enzymol. 1981;78(Pt A):262-84.
Ströher et al., Progress towards the treatment of Ebola haemorrhagic fever. Expert Opin Investig Drugs. Dec. 2006;15(12):1523-35.
Sugisaka et al., The Physicochemical properties of imiquimod, the first imidazoquinoline immune response modifier. Pharmaceutical Research. 1997 American Association of Pharmaceutical Scientists Annual Meeting. Poster Presentation, Boston, MA, Nov. 2-6, 1997;S475:Abstract 3030.
Surrey et al., The Synthesis of Some 3-Nitro- and 3-Amino-4-dialkylaminoalkylaminoquinoline Derivatives. J Am Chem Soc. 1951;73:2413-16.
Takeichi et al., Cytokine profiles of T-lymphocytes from gingival tissues with pathological pocketing. J Dent Res. Aug. 2000;79(8):1548-55.
Takeshita et al., Signal transduction pathways mediated by the interaction of CpG DNA with Toll-like receptor 9. Semin Immunol. Feb. 2004;16(1):17-22.
Takeuchi et al., Discrimination of bacterial lipoproteins by Toll-like receptor 6. Int Immunol. Jul. 2001;13(7):933-40.
Temple et al., Potential anticancer agents: 5-(N-substituted-aminocarbonyl)- and 5-(N-substituted-aminothiocarbonyl)-5,6,7,8-tetrahydrofolic acids. J Med Chem. Mar. 1988;31(3):697-700.
Thesing et al., [Darstellung und Eigenschaften des $\Delta^1$-Pyrrolin-$N$-oxyds.]. Chem Ber. 1959;92:1748-55. German.
Thiruvikraman et al., Synthesis and reactions of pyrazolo-[3,4-c]quinoline derivatives. Indian Journal of Chemistry. 1987;26B:695-696.
Tomai et al., Imiquimod: in vivo and in vitro characteristics and toxicology. In: Cutaneous Infection and Therapy. Aly et al., eds. Marcel Dekkar, Inc., New York. 1997:405-15.
Tomic et al., Sensitization of IL-2 Signaling through TLR-7 Enhances B Lymphoma Cell Immunogenicity. J Immunol. 2006;176:3830-39.
Tomioka et al., Asymmetric Alkylation of α-Alkyl β-Keto Esters. J Am Chem Soc. 1984;106:2718-19.
Totterman et al., Phorbol ester-induced differentiation of chronic lymphocytic leukaemia cells. Nature. Nov. 13, 1980;288(5787):176-8.
Tracy et al., Studies in the Pyridine Series. II. Synthesis of 2-Methyl-3-(β-Hydroxyethyl)pyridine and of the Pyridine Analog of Thiamine (Vitamin B2). J Org Chem. 1941;6:54-62.
Uno et al., TNF-related apoptosis-inducing ligand (TRAIL) frequently induces apoptosis in Philadelphia chromosome-positive leukemia cells. Blood. May 1, 2003;101(9):3658-67. Epub Dec. 27, 2002.
Urosevic et al., Imiquimod treatment induces expression of opioid growth factor receptor: a novel tumor antigen induced by interferon-alpha? Clin Cancer Res. Aug. 1, 2004;10(15):4959-70.
Van De Kerhof, New Immunomodulatory Drugs. In: Skin and Environment: Perception and Protection. Ring et al., eds., 10th EADV Congress, Oct. 10-14, Munich, Germany. 2001:1:343-48.
Vasilakos et al., Adjuvant Activities of Immune Response Modifier R-848: Comparison with CoG ODN. Cell Immunol. 2000;204:64-74.
Vieweg et al., Tumor vaccines: from gene therapy to dendritic cells—the emerging frontier. Urol Clin North Am. Aug. 2003;30(3):633-43.
Vilcek, The cytokines: An overview. In: The Cytokine Handbook, Fourth Ed. M. Lotze and A.W. Thompson (eds.), 2003;1:3-14.
Volhardt, 18-5. Amides: The Least-Reactive Carboxylic Acid Derivatives. Organic Chemistry. 1987:813.
Vollmer et al., Highly immunostimulatory CpG-free oligodeoxynucleotides for activation of human leukocytes. Antisense Nucleic Acid Drug Dev. Jun. 2002;12(3):165-75.

(56) References Cited

OTHER PUBLICATIONS

Wagner et al., Induction of cytokines in cynomolgus monkeys by the immune response modifiers, imiquimod, S-27609 and S-28463. Cytokine. Nov. 1997;9(11):837-45.

Wagner et al., Modulation of TH1 and TH2 Cytokine Production with the Immune Response Modifiers, R-848 and Imiguimod. Cellular Immunology. 1999;191:10-19.

Wang, Structure and Chemistry of 4-Hydroxy-6-methyl-2-pyridone. J Heterocyclic Chem. 1970;7:389-92.

Warren et al., Macrophage Growth Factor CSF-1 Stimulates Human Monocyte Production of Interferon, Tumor Necrosis Factor, and Colony Stimulating Activity. J Immunol. 1986;137(7):2281-85.

Wasserman et al., Loxoscelism and necrotic arachnidism. J Toxicol Clin Toxicol. 1983-1984;21(4-5):451-72.

Wedlock et al., Physiological effects and adjuvanticity of recombinant brushtail possum TNF-alpha. Immunol Cell Biol. Feb. 1999;77(1):28-33.

Wells, Additivity of Mutational Effects in Proteins. Biochemistry. 1990;29(37):8509-17.

Wermuth, Molecular Variations Based on Isosteric Replacements. Practice of Medicinal Chemistry.1996:203-37.

Wexler et al., Accurate identification of experimental pulmonary metastases. J Natl Cancer Inst. Apr. 1966; 36(4):641-5.

Wibaut et al., Syntheses of 3,4-Dimethylpyridine, 2,3-Dimethylpridine and 2-Methyl-3-Ethylpyridine. Rec Trav Chim. 1944;63:231-38.

Wierda et al., CD40-ligand (CD154) gene therapy for chronic lymphocytic leukemia. Blood. Nov. 1, 2000;96(9):2917-24.

Wieseler-Frank et al., Central proinflammatory cytokines and pain enhancement. Neurosignals. 2005;14(4):166-74.

Williams et al., Grignard Reactions to Chiral Oxazolidine Aldehydes. Tetrahedron. 1996;52:11673-94.

Wilson et al., Spiders and spider bites. Dermatol Clin. Apr. 1990;8(2):277-86.

Wright et al., Clinical presentation and outcome of brown recluse spider bite. Ann Emerg Med. Jul. 1997;30(1):28-32.

Wu et al., Murine B16 melanoma vaccination-induced tumor immunity: identification of specific immune cells and functions involved. J Interferon Cytokine Res. Dec. 2001;21(12):1117-27.

Yamamoto et al., Essential role for TIRAP in activation of the signalling cascade shared by TLR2 and TLR4. Nature. Nov. 21, 2002;420(6913):324-9.

Yeung-Yue et al., The management of herpes simplex virus infections. Curr Opin Infect Dis. Apr. 2002;15(2):115-22.

Yutilov et al., Synthesis and some reactions of 4-nitroimidazo[4-5-c]pyridin-2-ones. Caplus English Abstract DN 91:175261. VINITI. 1978:1193-78. Abstract Only.

Zagon et al., Immunoelectron microscopic localization of the opioid growth factor receptor (OGFr) and OGF in the cornea. Brain Res. 2003;967:37-47.

Zagon et al., Opioids and the apoptotic pathway in human cancer cells. Neuropeptides. 2003;37:79-88.

Zagon et al., The biology of the opioid growth factor receptor (OGFr). Brain Res Brain Res Rev. Feb. 2002;38(3):351-76. Review.

Zagon et al., The expression and function of the OGF-OGFr axis—a tonically active negative regulator of growth—in COS cells. Neuropeptides. Oct. 2003;37(5):290-7.

Zambon, Periodontal diseases: microbial factors. Ann Periodontol. Nov. 1996;1(1):879-925.

Zarubin et al., Theoretical Study of Antagonists and Inhibitors of Mammalian Adenosine Deaminase: I. Adenosine and Its Aza- and Deazaanalogues. Russ J Bioorg Chem. 2002;28(4):284-92.

Zhang et al., Structural features of azidopyridinyl neonicotinoid probes conferring high affinity and selectivity for mammalian alpha4beta2 and *Drosophila nicotinic* receptors. J Med Chem. Jun. 20, 2002;45(13):2832-40.

Zhu et al., Inhibition of murine dendritic cell activation by synthetic phosphorothioate oligodeoxynucleotides. J Leukoc Biol. Dec. 2002;72(6):1154-63.

Zhu et al., Inhibition of murine macrophage nitric oxide production by synthetic oligonucleotides. J Leukoc Biol. Apr. 2002;71(4):686-94.

Ziegler-Heitbrock et al., Favorable response of early stage B CLL patients to treatment with IFN-alpha 2. Blood. May 1, 1989;73(6):1426-30.

Zyryanov et al., Heterocyclization of 1-(2'-Carbethoxyphenyl)-5-Methyltetrazole. Chemistry of Heterocylic Compounds. English Edition. 1981;16(12):1286-88.

* cited by examiner

AMIDE SUBSTITUTED IMIDAZOPYRIDINES, IMIDAZOQUINOLINES, AND IMIDAZONAPHTHYRIDINES

RELATED APPLICATIONS

This application is the National Stage of International Applications No. PCT/US2005/009880, filed Mar. 24, 2005, which claims priority to U.S. Provisional Application Ser. No. 60/555,753, filed Mar. 24, 2004, and U.S. Provisional Application Ser. No. 60/578,769, filed Jun. 10, 2004, both of which are incorporated herein by reference.

BACKGROUND OF THE INVENTION

In the 1950's the 1H-imidazo[4,5-c]quinoline ring system was developed, and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers, rendering them useful in the treatment of a variety of disorders.

There continues to be interest in and a need for compounds that have the ability to modulate the immune response, by induction of cytokine biosynthesis or other mechanisms.

SUMMARY OF THE INVENTION

It has now been found that certain amide substituted imidazopyridine, imidazoquiniline, and imidazonaphthyridine compounds modulate cytokine biosynthesis. In one aspect, the present invention provides compounds of the Formula I:

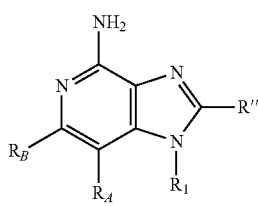

I and more specifically the following compounds of the Formulas II, III, IV, V, VI, VII, VIII, IX, X, XI, XII, and XIII:

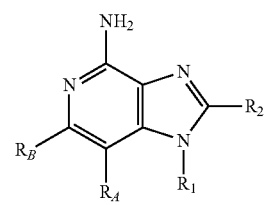

II

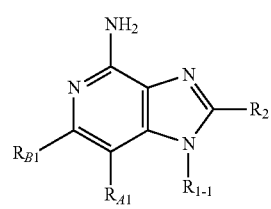

III

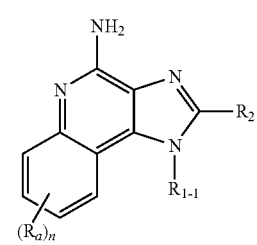

IV

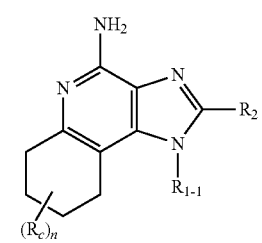

V

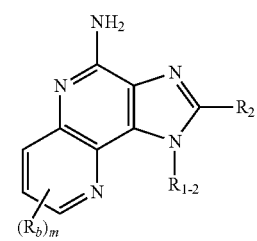

VI

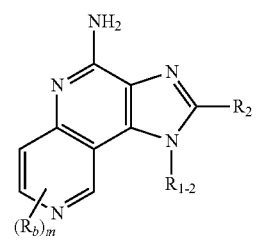

VII

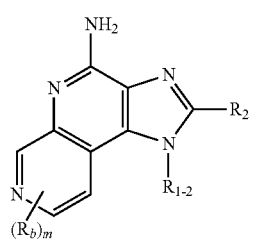

VIII

IX

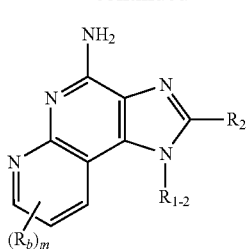

X

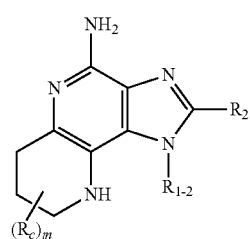

XI

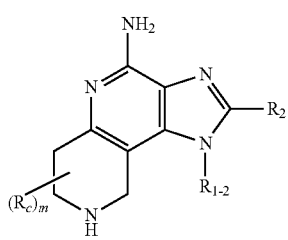

XII

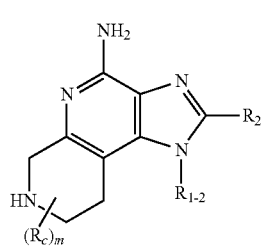

XIII

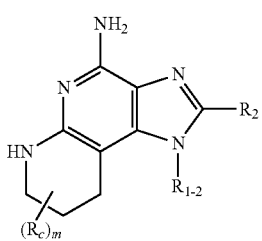

wherein $R_1$, $R_{1-1}$, $R_{1-2}$, R'', $R_2$, $R_A$, $R_B$, $R_{A1}$, $R_{B1}$, $R_a$, $R_b$, $R_c$, n, and m are as defined below; and pharmaceutically acceptable salts thereof.

The compounds of Formulas I, II, III, IV, V, VI, VII, VIII, IX, X, XI, XII, and XIII are useful, for example, as immune response modifiers (IRMs) due to their ability to modulate cytokine biosynthesis (e.g., induce the biosynthesis or production of one or more cytokines) and otherwise modulate the immune response when administered to animals. Compounds can be tested, for example, using the test procedures described in the Examples Section. Compounds can be tested for induction of cytokine biosynthesis by incubating human PBMC in a culture with the compound(s) at a concentration range of 30 to 0.014 μM and analyzing for interferon (α) or tumor necrosis factor (α) in the culture supernatant. The ability to modulate cytokine biosynthesis, for example, induce the biosynthesis of one or more cytokines, makes the compounds useful in the treatment of a variety of conditions such as viral diseases and neoplastic diseases, that are responsive to such changes in the immune response.

In another aspect, the present invention provides pharmaceutical compositions containing the immune response modifier compounds, and methods of inducing cytokine biosynthesis in animal cells, treating a viral disease in an animal, and/or treating a neoplastic disease in an animal by administering to the animal one or more compounds of the Formulas I, II, III, IV, V, VI, VII, VIII, IX, X, XI, XII, and XIII, and/or pharmaceutically acceptable salts thereof.

In another aspect, the invention provides methods of synthesizing the compounds of Formulas I, II, III, IV, V, VI, VII, VIII, IX, X, XI, XII, and XIII and intermediates useful in the synthesis of these compounds.

As used herein, "a," "an," "the," "at least one," and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive or exhaustive list.

DETAILED DESCRIPTION OF ILLUSTRATIVE EMBODIMENTS OF THE INVENTION

In one aspect, the present invention provides compounds of the Formula I:

I

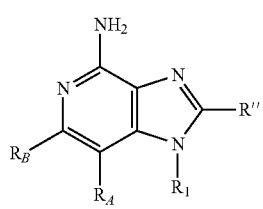

and more specifically the following compounds of the Formulas II, III, IV, V, VI, VII, VIII, IX, X, XI, XII, and XIII:

II

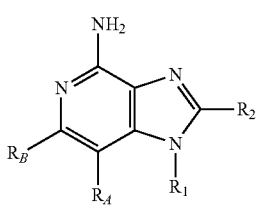

III
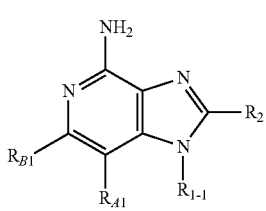
IV
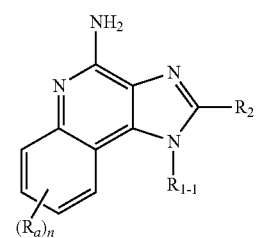
V
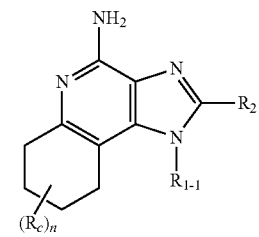
VI
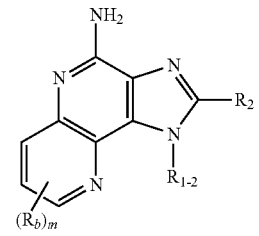
VII
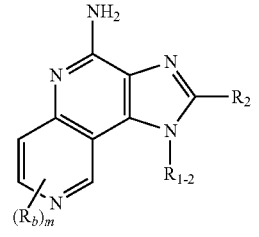
VIII
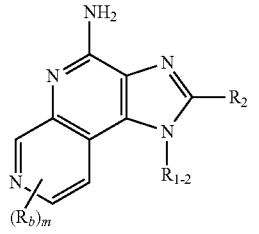
IX
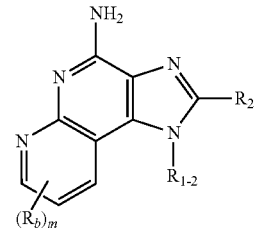
X
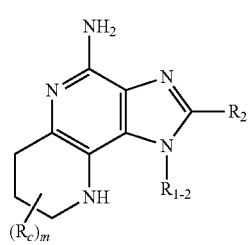
XI
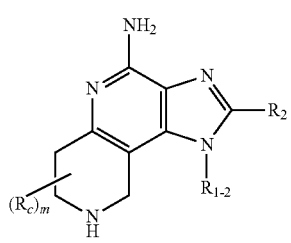
XII
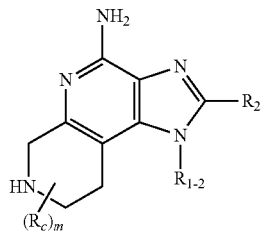
XIII
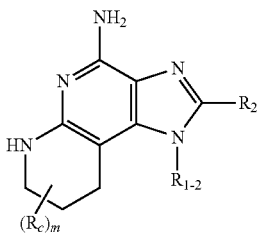
wherein $R_1$, $R_{1-1}$, $R_{1-2}$, R", $R_2$, $R_A$, $R_B$, $R_{A1}$, $R_{B1}$, $R_a$, $R_b$, $R_c$, n, and m are as defined below; and pharmaceutically acceptable salts thereof.
In one aspect, the present invention provides imidazopyridine, imidazoquinoline and imidazonaphthyridine compounds of the following Formula I:
I
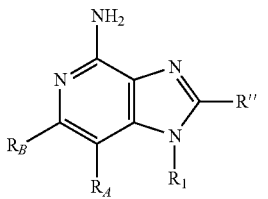

wherein:

$R_1$ is selected from the group consisting of:

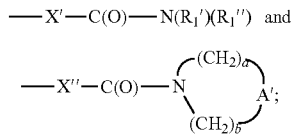

X' is selected from the group consisting of —CH($R_9$)—, —CH($R_9$)-alkylene-, and —CH($R_9$)-alkenylene-;

X" is selected from the group consisting of —CH($R_9$)—, —CH($R_9$)-alkylene-, and —CH($R_9$)-alkenylene-; wherein the alkylene and alkenylene are optionally interrupted with one or more —O— groups;

$R_1'$ and $R_1''$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
amino,
alkylamino,
dialkylamino,
arylsulfonyl, and
alkylsulfonyl;

A' is selected from the group consisting of —O—, —C(O)—, —CH$_2$—, —S(O)$_{0-2}$—, and —N(Q-$R_4$)—;

a and b are independently integers from 1 to 6 with the proviso that a+b is ≤7;

$R_A$ and $R_B$ are independently selected from the group consisting of:
hydrogen,
halogen,
alkyl,
alkenyl,
alkoxy,
alkylthio, and
—N($R_9$)$_2$;

or $R_A$ and $R_B$ taken together form either a fused aryl ring that is unsubstituted or substituted by one or more $R_a$ groups, or a fused 5 to 7 membered saturated ring that is unsubstituted or substituted by one or more $R_c$ groups;

or $R_A$ and $R_B$ taken together form a fused heteroaryl or 5 to 7 membered saturated ring containing one heteroatom selected from the group consisting of N and S, wherein the heteroaryl ring is unsubstituted or substituted by one or more $R_b$ groups, and the 5 to 7 membered saturated ring is unsubstituted or substituted by one or more $R_c$ groups;

$R_a$ is selected from the group consisting of halogen, alkyl, haloalkyl, alkoxy, and —N($R_9$)$_2$;

$R_b$ is selected from the group consisting of halogen, hydroxy, alkyl, haloalkyl, alkoxy, and —N($R_9$)$_2$;

$R_c$ is selected from the group consisting of halogen, hydroxy, alkyl, alkenyl, haloalkyl, alkoxy, alkylthio, and —N($R_9$)$_2$;

Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—;

W is selected from the group consisting of a bond, —C(O)—, and —S(O)$_2$—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, allkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, halo alkyl, halo alkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_6$ is selected from the group consisting of =O and =S;

$R_8$ is selected from the group consisting of hydrogen, alkyl, alkoxyalkylenyl, and arylalkylenyl;

$R_9$ is selected from the group consisting of hydrogen and alkyl; and

R" is hydrogen or a non-interfering substituent;

with the proviso that when $R_A$ and $R_B$ form a fused heteroaryl or 5 to 7 membered saturated ring containing one heteroatom selected from the group consisting of N and S, wherein the heteroaryl ring is unsubstituted or substituted by one or more $R_b$ groups, and the 5 to 7 membered saturated ring is unsubstituted or substituted by one or more $R_c$ groups, then $R_1$ can also be —X"—C(O)—N($R_1'$)($R_1''$);

or a pharmaceutically acceptable salt thereof.

In some embodiments, compounds or salts of Formula I induce the biosynthesis of one or more cytokines.

The present invention also provides imidazopyridine, imidazoquinoline, and imidazonaphthyridine compounds of the following Formula II:

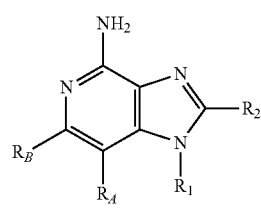

wherein:

$R_1$ is selected from the group consisting of:

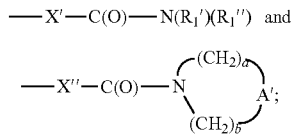

X' is selected from the group consisting of —CH($R_9$)—, —CH($R_9$)-alkylene-, and —CH($R_9$)-alkenylene-;

X" is selected from the group consisting of —CH($R_9$)—, —CH($R_9$)-alkylene-, and —CH($R_9$)-alkenylene-; wherein the alkylene and alkenylene are optionally interrupted with one or more —O— groups;

$R_1'$ and $R_1''$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
amino,
alkylamino,
dialkylamino,
arylsulfonyl, and
alkylsulfonyl;

A' is selected from the group consisting of —O—, —C(O)—, —CH$_2$—, —S(O)$_{0-2}$—, and —N(Q-$R_4$)—;

a and b are independently integers from 1 to 6 with the proviso that a+b is ≤7;

$R_A$ and $R_B$ are independently selected from the group consisting of:
hydrogen,
halogen,
alkyl,
alkenyl,
alkoxy,
alkylthio, and
—N($R_9$)$_2$;
or $R_A$ and $R_B$ taken together form either a fused aryl ring that is unsubstituted or substituted by one or more $R_a$ groups, or a fused 5 to 7 membered saturated ring that is unsubstituted or substituted by one or more $R_c$ groups;
or $R_A$ and $R_B$ taken together form a fused heteroaryl or 5 to 7 membered saturated ring containing one heteroatom selected from the group consisting of N and S, wherein the heteroaryl ring is unsubstituted or substituted by one or more $R_b$ groups, and the 5 to 7 membered saturated ring is unsubstituted or substituted by one or more $R_c$ groups;

$R_a$ is selected from the group consisting of halogen, alkyl, haloalkyl, alkoxy, and —N($R_9$)$_2$;

$R_b$ is selected from the group consisting of halogen, hydroxy, alkyl, haloalkyl, alkoxy, and —N($R_9$)$_2$;

$R_c$ is selected from the group consisting of halogen, hydroxy, alkyl, alkenyl, haloalkyl, alkoxy, alkylthio, and —N($R_9$)$_2$;

$R_2$ is selected from the group consisting of:
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;

Y is selected from the group consisting of:

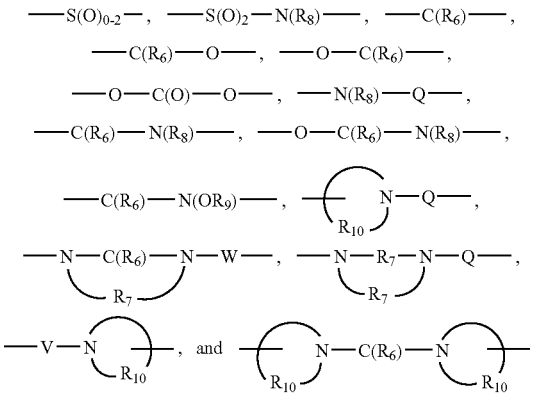

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

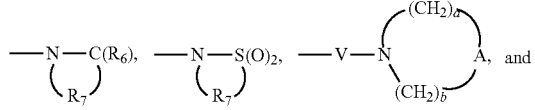

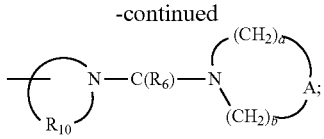

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_9$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_9$)—C(R$_6$)—, and —S(O)$_2$—; and
W is selected from the group consisting of a bond, —C(O)—, and —S(O)$_2$—;
with the proviso that when $R_A$ and $R_B$ form a fused heteroaryl or 5 to 7 membered saturated ring containing one heteroatom selected from the group consisting of N and S, wherein the heteroaryl ring is unsubstituted or substituted by one or more $R_b$ groups, and the 5 to 7 membered saturated ring is unsubstituted or substituted by one or more $R_c$ groups, then $R_1$ can also be —X″—C(O)—N((R$_1$′)(R$_1$″));
or a pharmaceutically acceptable salt thereof.

The present invention also provides imidazopyridine compounds of the following Formula III:

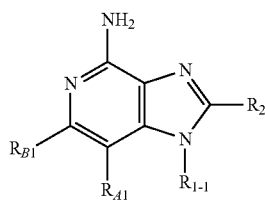

III wherein:
$R_{1-1}$ is selected from the group consisting of:

—X′—C(O)—N(R$_1$′)(R$_1$″) and

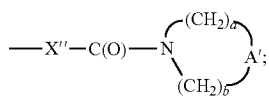

X′ is selected from the group consisting of —CH(R$_9$)—, —CH(R$_9$)-alkylene-, and —CH(R$_9$)-alkenylene-;
X″ is selected from the group consisting of —CH(R$_9$)—, —CH(R$_9$)-alkylene-, and —CH(R$_9$)-alkenylene-; wherein the alkylene and alkenylene are optionally interrupted with one or more —O— groups;
$R_1$′ and $R_1$″ are independently selected form the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
amino,
alkylamino,
dialkylamino,
arylsulfonyl, and
alkylsulfonyl;
A′ is selected from the group consisting of —O—, —C(O)—, —CH$_2$—, —S(O)$_{0-2}$—, and —N(Q-R$_4$)—;
a and b are independently integers from 1 to 6 with the proviso that a+b is ≤7;
$R_{A1}$ and $R_{B1}$ are independently selected from the group consisting of:
hydrogen,
halogen,
alkyl,
alkenyl,
alkoxy,
alkylthio, and
—N(R$_9$)$_2$;
$R_2$ is selected from the group consisting of:
—R$_4$,
—X—R$_4$,
—X—Y—R$_4$, and
—X—R$_5$;
X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;
Y is selected from the group consisting of:

—S(O)$_{0-2}$—, —S(O)$_2$—N(R$_8$)—, —C(R$_6$)—,

—C(R$_6$)—O—, —O—C(R$_6$)—,

—O—C(O)—O—, —N(R$_8$)—Q—,

—C(R$_6$)—N(R$_8$)—, —O—C(R$_6$)—N(R$_8$)—,

—C(R$_6$)—N(OR$_9$)—,

-continued

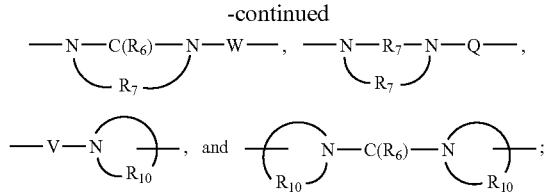

R₄ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R₅ is selected from the group consisting of:

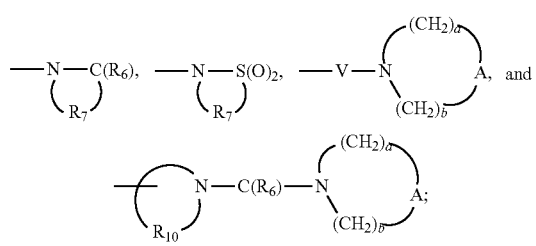

R₆ is selected from the group consisting of =O and =S;

R₇ is C₂₋₇ alkylene;

R₈ is selected from the group consisting of hydrogen, alkyl, alkoxyalkylenyl, and arylalkylenyl;

R₉ is selected from the group consisting of hydrogen and alkyl;

R₁₀ is C₃₋₈ alkylene;

A is selected from the group consisting of —O—, —C(O)—, —S(O)₀₋₂—, —CH₂—, and —N(R₄)—;

Q is selected from the group consisting of a bond, —C(R₆)—, —C(R₆)—C(R₆)—, —S(O)₂—, —C(R₆)—N(R₈)—W—, —S(O)₂—N(R₈)—, —C(R₆)—O—, and —C(R₆)—N(OR₉)—;

V is selected from the group consisting of —C(R₆)—, —O—C(R₆)—, —N(R₈)—C(R₆)—, and —S(O)₂—; and W is selected from the group consisting of a bond, —C(O)—, and —S(O)₂—; or a pharmaceutically acceptable salt thereof.

The present invention also provides imidazoquinoline compounds of the following Formula IV:

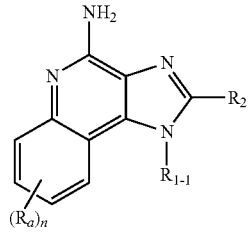

wherein:

R₁₋₁ is selected from the group consisting of:

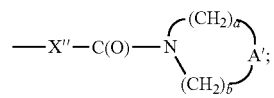

X' is selected from the group consisting of —CH(R₉)—, —CH(R₉)-alkylene-, and —CH(R₉)-alkenylene-;

X" is selected from the group consisting of —CH(R₉)—, —CH(R₉)-alkylene-, and —CH(R₉)-alkenylene-; wherein the alkylene and alkenylene are optionally interrupted with one or more —O— groups;

R₁' and R₁" are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
amino,
alkylamino,
dialkylamino,
arylsulfonyl, and
alkylsulfonyl;

A' is selected from the group consisting of —O—, —C(O)—, —CH₂—, —S(O)₀₋₂—, and —N(Q-R₄)—;

a and b are independently integers from 1 to 6 with the proviso that a+b is ≤7;

Rₐ is selected from the group consisting of halogen, alkyl, haloalkyl, alkoxy, and —N(R₉)₂;

n is an integer from 0 to 4;

$R_2$ is selected from the group consisting of:
—$R_4$,
—X—$R_4$,
—X—Y—$R_4$, and
—X—$R_5$;

X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;

Y is selected from the group consisting of:

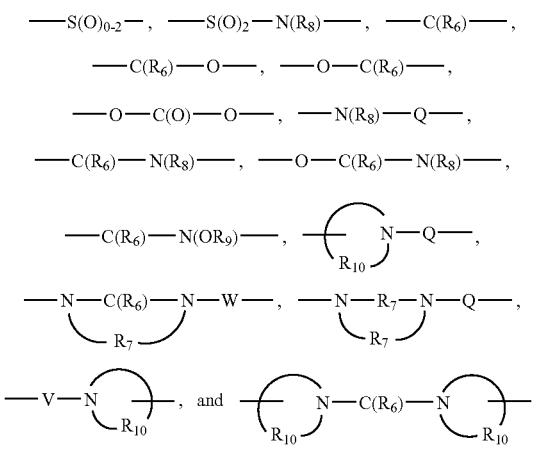

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, halo alkyl, halo alkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

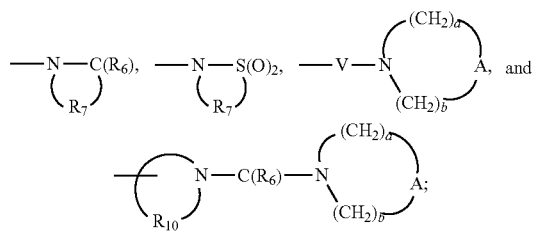

$R_6$ is selected from the group consisting of =O and =S;
$R_7$ is $C_{2-7}$ alkylene;

$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_9$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—; and
W is selected from the group consisting of a bond, —C(O)—, and —S(O)$_2$—;
or a pharmaceutically acceptable salt thereof.

The present invention also provides 6,7,8,9-tetrahydroimidazoquinoline compounds of the following Formula V:

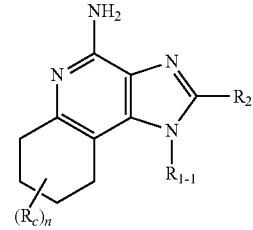

wherein:
$R_{1-1}$ is selected from the group consisting of:

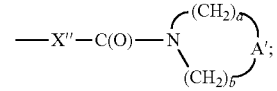

X' is selected from the group consisting of —CH(R$_9$)—, —CH(R$_9$)-alkylene-, and —CH(R$_9$)-alkenylene-;
X" is selected from the group consisting of —CH(R$_9$)—, —CH(R$_9$)-alkylene-, and —CH(R$_9$)-alkenylene-; wherein the alkylene and alkenylene are optionally interrupted with one or more —O— groups;
$R_1'$ and $R_1''$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl, alkoxy,
haloalkoxy,
halogen,
cyano,
nitro,
amino,
alkylamino,
dialkylamino,
arylsulfonyl, and
alkylsulfonyl;

A' is selected from the group consisting of —O—, —C(O)—, —CH$_2$—, —S(O)$_{0-2}$—, and —N(Q-R$_4$)—;

a and b are independently integers from 1 to 6 with the proviso that a+b is ≤7;

R$_c$ is selected from the group consisting of halogen, hydroxy, alkyl, alkenyl, haloalkyl, alkoxy, alkylthio, and —N(R$_9$)$_2$;

n is an integer from 0 to 4;

R$_2$ is selected from the group consisting of:
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;

Y is selected from the group consisting of:

—S(O)$_{0-2}$—, —S(O)$_2$—N(R$_8$)—, —C(R$_6$)—,
—C(R$_6$)—O—, —O—C(R$_6$)—,
—O—C(O)—O—, —N(R$_8$)—Q—,
—C(R$_6$)—N(R$_8$)—, —O—C(R$_6$)—N(R$_8$)—,
—C(R$_6$)—N(OR$_9$)—, [cyclic N-Q with R$_{10}$],
—N—C(R$_6$)—N—W—, —N—R$_7$—N—Q—,
       R$_7$                    R$_7$
—V—N—[ring with R$_{10}$], and [cyclic N—C(R$_6$)—N with R$_{10}$];

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

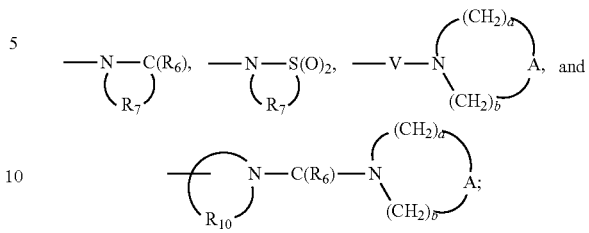

R$_6$ is selected from the group consisting of =O and =S;
R$_7$ is C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—; and W is selected from the group consisting of a bond, —C(O)—, and —S(O)$_2$—;

or a pharmaceutically acceptable salt thereof.

The present invention also provides imidazonaphthyridine compounds selected from the group consisting of the following Formulas VI, VII, VIII, and IX:

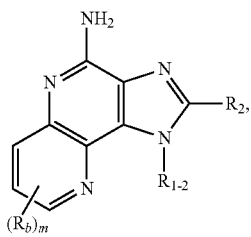

VI

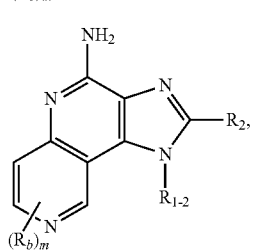

VII

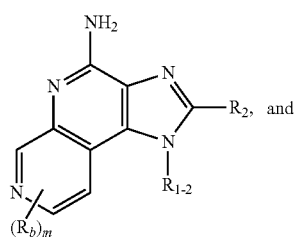

VIII

-continued

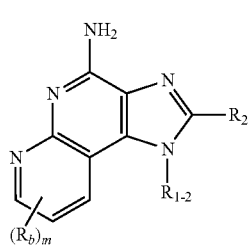

IX wherein:

$R_{1-2}$ is selected from the group consisting of:

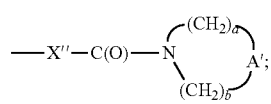

X" is selected from the group consisting of —CH($R_9$)—, —CH($R_9$)-alkylene-, and —CH($R_9$)-alkenylene-; wherein the alkylene and alkenylene are optionally interrupted with one or more —O— groups;

$R_1'$ and $R_1"$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
amino,
alkylamino,
dialkylamino,
arylsulfonyl, and
alkylsulfonyl;

A' is selected from the group consisting of —O—, —C(O)—, —CH$_2$—, —S(O)$_{0-2}$—, and —N(Q-R$_4$)—;

a and b are independently integers from 1 to 6 with the proviso that a+b is ≤7;

$R_b$ is selected from the group consisting of halogen, hydroxy, alkyl, haloalkyl, alkoxy, and —N(R$_9$)$_2$;

m is an integer from 0 to 3;

$R_2$ is selected from the group consisting of:
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;

Y is selected from the group consisting of:

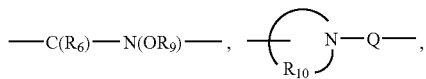
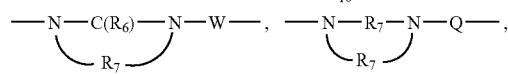
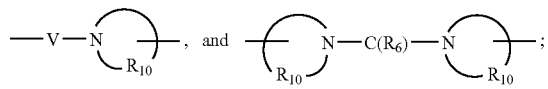

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

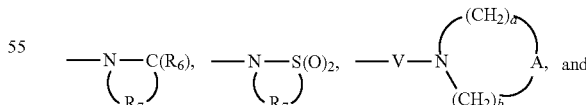
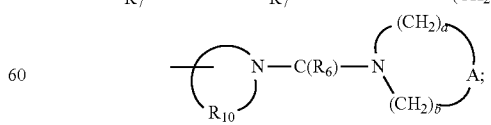

$R_6$ is selected from the group consisting of =O and =S;

$R_7$ is $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl;

$R_{10}$ is $C_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, —C(R$_6$)—N(R$_9$)—W—, —S(O)$_2$—N(R$_9$)—, —C(R$_6$)—O—, and —C(R$_6$)—N(OR$_9$)—;

V is selected from the group consisting of —C(R$_6$)—, —O—C(R$_6$)—, —N(R$_9$)—C(R$_6$)—, and —S(O)$_2$—; and W is selected from the group consisting of a bond, —C(O)—, and —S(O)$_2$—;

or a pharmaceutically acceptable salt thereof.

The present invention also provides 6,7,8,9-tetrahydroimidazonaphthyridine compounds selected from the group consisting of the following Formulas X, XI, XII, and XIII:

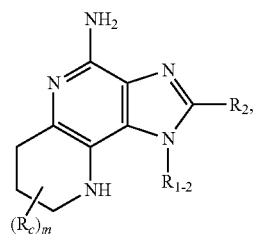

X

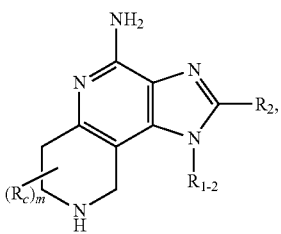

XI

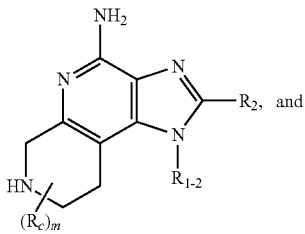

XII

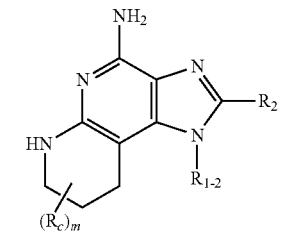

XIII wherein:

$R_{1-2}$ is selected from the group consisting of:

—X″—C(O)—N(R$_1$′)(R$_1$″) and

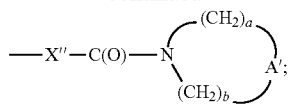

X″ is selected from the group consisting of —CH(R$_9$)—, —CH(R$_9$)-alkylene-, and —CH(R$_9$)-alkenylene-; wherein the alkylene and alkenylene are optionally interrupted with one or more —O— groups, R$_1$′ and R$_1$″ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
amino,
alkylamino,
dialkylamino,
arylsulfonyl, and
alkylsulfonyl;

A′ is selected from the group consisting of —O—, —C(O)—, —CH$_2$—, —S(O)$_{0-2}$—, and —N(Q-R$_4$)—;

a and b are independently integers from 1 to 6 with the proviso that a+b is ≤7;

R$_c$ is selected from the group consisting of halogen, hydroxy, alkyl, alkenyl, haloalkyl, alkoxy, alkylthio, and —N(R$_9$)$_2$;

m is an integer from 0 to 3;

R$_2$ is selected from the group consisting of:
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;

Y is selected from the group consisting of:

—S(O)$_{0-2}$—, —S(O)$_2$—N(R$_8$)—, —C(R$_6$)—,
—C(R$_6$)—O—, —O—C(R$_6$)—,
—O—C(O)—O—, —N(R$_8$)—Q—,

-continued

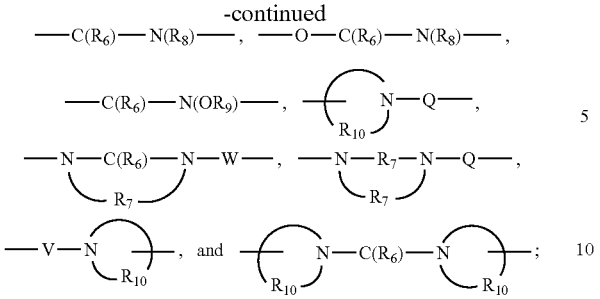

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

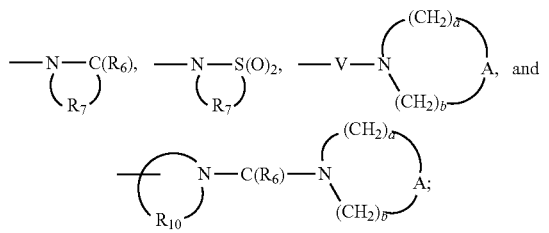

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_9$)—W—, —S(O)$_2$—N(R$_9$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—; and
W is selected from the group consisting of a bond, —C(O)—, and —S(O)$_2$—;
or a pharmaceutically acceptable salt thereof.

The present invention also provides compounds that are useful as intermediates in the synthesis of compounds of Formulas I-XIII. These intermediate compounds include those having the structural Formulas XIV, XV, and XVI described below.

The present invention provides intermediate compounds of the following Formula XIV:

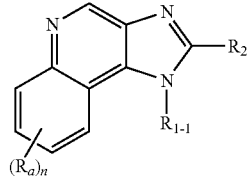

XIV wherein:
$R_{1-1}$ is selected from the group consisting of:

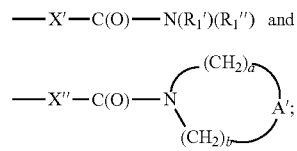

X' is selected from the group consisting of —CH(R$_9$)—, —CH(R$_9$)-alkylene-, and —CH(R$_9$)-alkenylene-;
X" is selected from the group consisting of —CH(R$_9$)—, —CH(R$_9$)-alkylene-, and —CH(R$_9$)-alkenylene-; wherein the alkylene and alkenylene are optionally interrupted with one or more —O— groups;
$R_1'$ and $R_1''$ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
amino,
alkylamino,
dialkylamino,
arylsulfonyl, and
alkylsulfonyl;
A' is selected from the group consisting of —O—, —C(O)—, —CH$_2$—, —S(O)$_{0-2}$—, and —N(Q-R$_4$)—;
a and b are independently integers from 1 to 6 with the proviso that a+b is ≤7;
$R_a$ is selected from the group consisting of halogen, alkyl, haloalkyl, alkoxy, and —N(R$_9$)$_2$;
n is an integer from 0 to 4;

R$_2$ is selected from the group consisting of:
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;

Y is selected from the group consisting of:

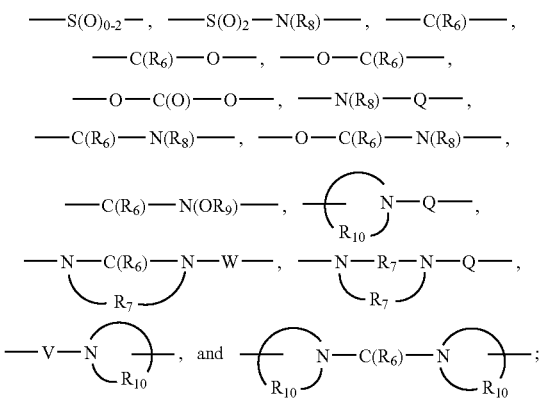

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

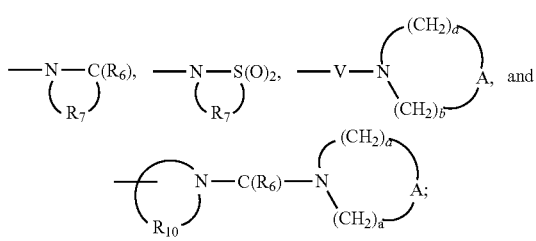

R$_6$ is selected from the group consisting of =O and =S;
R$_7$ is C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, —C(R$_6$)—N(R$_9$)—W—, —S(O)$_2$—N(R$_8$)—, —C(R$_4$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—; and W is selected from the group consisting of a bond, —C(O)—, and —S(O)$_2$—;

or a pharmaceutically acceptable salt thereof.

The present invention provides intermediate compounds of the following Formula XV:

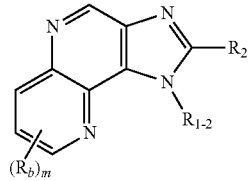

XV wherein:
R$_{1-2}$ is selected from the group consisting of:

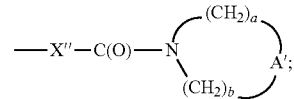

X″ is selected from the group consisting of —CH(R$_9$)—, —CH(R$_9$)-alkylene-, and —CH(R$_9$)-alkenylene-; wherein the alkylene and alkenylene are optionally interrupted with one or more —O— groups;

R$_1$' and R$_1$″ are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
amino,
alkylamino,
dialkylamino, arylsulfonyl, and
alkylsulfonyl;

A' is selected from the group consisting of —O—, —C(O)—, —CH$_2$—, —S(O)$_{0-2}$—, and —N(Q-R$_4$)—;

a and b are independently integers from 1 to 6 with the proviso that a+b is ≤7;

R$_b$ is selected from the group consisting of halogen, hydroxy, alkyl, haloalkyl, alkoxy, and —N(R$_9$)$_2$;

m is an integer from 0 to 3;

R$_2$ is selected from the group consisting of:
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;

Y is selected from the group consisting of:

—S(O)$_{0-2}$—, —S(O)$_2$—N(R$_8$)—, —C(R$_6$)—,
—C(R$_6$)—O—, —O—C(R$_6$)—,
—O—C(O)—O—, —N(R$_8$)—Q—,
—C(R$_6$)—N(R$_8$)—, —O—C(R$_6$)—N(R$_8$)—,
—C(R$_6$)—N(OR$_9$)—,

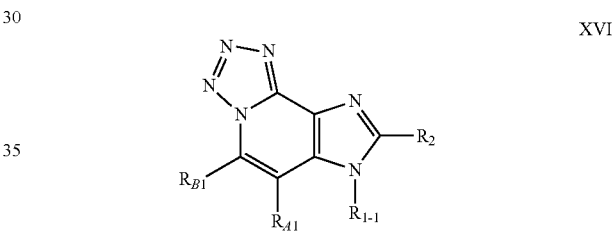

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

R$_6$ is selected from the group consisting of =O and =S;

R$_7$ is C$_{2-7}$ alkylene;

R$_8$ is selected from the group consisting of hydrogen, alkyl, alkoxyalkylenyl, and arylalkylenyl;

R$_9$ is selected from the group consisting of hydrogen and alkyl;

R$_{10}$ is C$_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—; and W is selected from the group consisting of a bond, —C(O)—, and —S(O)$_2$—;

or a pharmaceutically acceptable salt thereof.

The present invention provides intermediate compounds of the following Formula XVI:

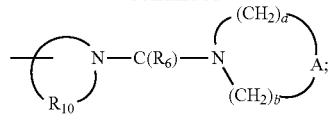

XVI wherein:

R$_{1-1}$ is selected from the group consisting of:

—X'—C(O)—N(R$_1$')(R$_1$'') and

X' is selected from the group consisting of —CH(R$_9$)—, —CH(R$_9$)-alkylene-, and —CH(R$_9$)-alkenylene-;

X'' is selected from the group consisting of —CH(R$_9$)—, —CH(R$_9$)-alkylene-, and —CH(R$_9$)-alkenylene-; wherein the alkylene and alkenylene are optionally interrupted with one or more —O— groups;

R$_1$' and R$_1$'' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxy,
alkyl,
haloalkyl,
hydroxyalkyl,
alkoxy,
haloalkoxy,
halogen,
cyano,
nitro,
amino,
alkylamino,
dialkylamino,
arylsulfonyl, and
alkylsulfonyl;

A' is selected from the group consisting of —O—, —C(O)—, —CH$_2$—, —S(O)$_{0-2}$—, and —N(Q-R$_4$)—;

a and b are independently integers from 1 to 6 with the proviso that a+b is ≤7;

R$_{A1}$ and R$_{B1}$ are independently selected from the group consisting of:
hydrogen,
halogen,
alkyl,
alkenyl,
alkoxy,
alkylthio, and
—N(R$_9$)$_2$;

R$_2$ is selected from the group consisting of:
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups;

Y is selected from the group consisting of:

—S(O)$_{0-2}$—, —S(O)$_2$—N(R$_8$)—, —C(R$_6$)—,

—C(R$_6$)—O—, —O—C(R$_6$)—,

—O—C(O)—O—, —N(R$_8$)—Q—,

—C(R$_6$)—N(R$_8$)—, —O—C(R$_6$)—N(R$_8$)—,

—C(R$_6$)—N(OR$_9$)—, ![ring with N-Q and R10],

—N—C(R$_6$)—N—W—, —N—R$_7$—N—Q—,
  R$_7$                      R$_7$

—V—N(R$_{10}$)—, and ![ring with N-C(R6)-N and R10];

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

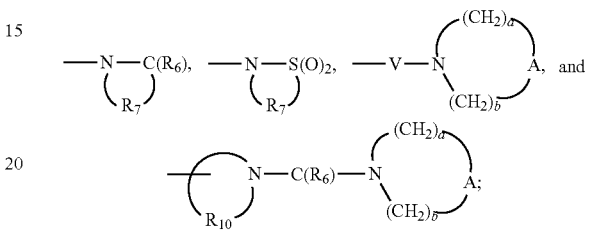

R$_6$ is selected from the group consisting of =O and =S;
R$_7$ is C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—; and W is selected from the group consisting of a bond, —C(O)—, and —S(O)$_2$—;

or a pharmaceutically acceptable salt thereof.

As used herein, the terms "alkyl," "alkenyl," "alkynyl" and the prefix "alk-" are inclusive of both straight chain and branched chain groups and of cyclic groups, i.e., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "alkenylene," and "alkynylene" are the divalent forms of the "alkyl," "alkenyl," and "alkynyl" groups defined above. The terms "alkylenyl," "alkenylenyl," and "alkynylenyl" are used when "alkylene," "alkenylene," and "alkynylene," respectively, are substituted. For example, an arylalkylenyl group comprises an "alkylene" moiety to which an aryl group is attached.

The term "haloalkyl" is inclusive of alkyl groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl The term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicyclic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one Spiro atom and three rings joined by two Spiro atoms.

The terms "arylene," "heteroarylene," and "heterocyclylene" are the divalent forms of the "aryl," and "heterocyclyl" groups defined above. Likewise, "arylenyl," "heteroarylenyl," and "heterocyclylenyl" are the divalent forms of the "aryl," "heteroaryl," and "heterocyclyl" groups defined above. For example, an alkylarylenyl group comprises an arylene moiety to which an alkyl group is attached.

Herein, "non-interfering" means that the ability of the compound or salt, which includes a non-interfering substituent, to modulate (e.g., induce) the biosynthesis of one or more cytokines is not destroyed by the non-interfering substitutent. Illustrative non-interfering R" groups include those described above for $R_2$ in Formulas II-XIV.

When a group (or substituent or variable) is present more than once in any Formula described herein, each group (or substituent or variable) is independently selected, whether explicitly stated or not. For example, for the formula —$N(R_9)_2$ each $R_9$ group is independently selected. In another example, when an A and an A' group are both present and both contain an $R_4$ group, each $R_4$ group is independently selected. In a further example, when more than one Q group is present (i.e., $R_1$ and $R_2$ each contains a Q group) and each Q group contains one or more $R_6$ groups, then each Q group is independently selected, and each $R_6$ group is independently selected.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

For any of the compounds presented herein, each one of the following variables (e.g., $R_1$, $R_{1-1}$, $R_{1-2}$, R", $R_2$, $R_4$, $R_B$, $R_{A1}$, $R_{B1}$, $R_a$, $R_b$, $R_c$, n, m, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments, $R_A$ and $R_B$ are independently selected from the group consisting of: hydrogen, halogen, alkyl, alkenyl, alkoxy, alkylthio, and —$N(R_9)_2$; or $R_A$ and $R_B$ taken together form either a fused aryl ring that is unsubstituted or substituted by one or more $R_a$ groups, or a fused 5 to 7 membered saturated ring that is unsubstituted or substituted by one or more $R_c$ groups; or $R_A$ and $R_B$ taken together form a fused heteroaryl or 5 to 7 membered saturated ring containing one heteroatom selected from the group consisting of N and S, wherein the heteroaryl ring is unsubstituted or substituted by one or more $R_b$ groups, and the 5 to 7 membered saturated ring is unsubstituted or substituted by one or more $R_c$ groups.

The term "fused aryl ring" includes fused carbocyclic aromatic rings or ring systems. Examples of fused aryl rings include benzo, naphtho, fluoreno, and indeno. In certain embodiments, the fused aryl ring is benzo.

The term "fused heteroaryl ring" includes the fused forms of 5 or 6 membered aromatic rings that contain one heteroatom selected from S and N. In certain embodiments, the fused heteroaryl ring is pyrido or thieno. In certain embodiments, the fused heteroaryl ring is pyrido. In certain of these embodiments, the pyrido ring is

wherein the highlighted bond indicates the position where the ring is fused.

The term "fused 5 to 7 membered saturated ring" includes rings which are fully saturated except for the bond where the ring is fused. In certain embodiments, the ring is a cyclohexene ring. In certain embodiments wherein one heteroatom (N or S) is present, the ring is tetrahydropyrido or dihydrothieno.

In certain embodiments, the ring is tetrahydropyrido. In certain of these embodiments, the ring is

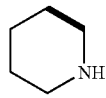

wherein the highlighted bond indicates the position where the ring is fused.

For certain embodiments, $R_{A1}$ and $R_{B1}$ are independently selected from the group consisting of: hydrogen, halogen, alkyl, alkenyl, alkoxy, alkylthio, and $-N(R_9)_2$.

For certain embodiments, $R_a$ is selected from the group consisting of: halogen, alkyl, haloalkyl, alkoxy, and $-N(R_9)_2$.

For certain embodiments, $R_b$ is selected from the group consisting of: halogen, hydroxy, alkyl, haloalkyl, alkoxy, and $-N(R_9)_2$.

For certain embodiments, $R_c$ is selected from the group consisting of: halogen, hydroxy, alkyl, alkenyl, haloalkyl, alkoxy, alkylthio, and $-N(R_9)_2$.

For certain embodiments, $R_1$ is selected from the group consisting of:

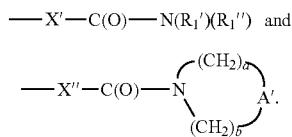

For certain embodiments, $R_1$ is

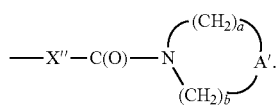

For certain embodiments $R_1$ is $-X'-C(O)-N(R_1')(R_1'')$.

For certain embodiments, when $R_A$ and Re form a fused heteroaryl or 5 to 7 membered saturated ring containing one heteroatom selected from the group consisting of N and S, wherein the heteroaryl ring is unsubstituted or substituted by one or more $R_b$ groups, and the 5 to 7 membered saturated ring is unsubstituted or substituted by one or more $R_c$ groups, then $R_1$ can also be $-X''-C(O)-N(R_1')(R_1'')$.

For certain embodiments, $R_1'$ and $R_1''$ are independently selected from the group consisting of: hydrogen, alkyl, alkenyl, aryl, arylalkylenyl, heteroaryl, heteroarylalkylenyl, heterocyclyl, heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of: hydroxy, alkyl, haloalkyl, hydroxyalkyl, alkoxy, haloalkoxy, halogen, cyano, nitro, amino, alkylamino, dialkylamino, arylsulfonyl, and alkylsulfonyl.

For certain embodiments, $R_1$ is hydrogen or $C_{1-3}$ alkyl. For certain embodiments, $R_1''$ is hydrogen. For certain embodiments, $R_1'$ and $R_1''$ are hydrogen. For certain embodiments, $R_1'$ and $R_1''$ are methyl.

For certain embodiments, $R_{1-1}$ is selected from the group consisting of:

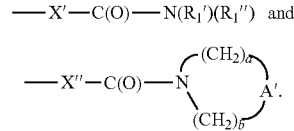

For certain embodiments, $R_{1-1}$ is

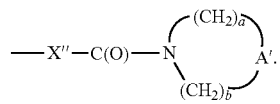

For certain embodiments, $R_{1-1}$ is $-X'-C(O)-N(R_1')(R_1'')$.

For certain embodiments, $R_{1-2}$ is selected from the group consisting of:

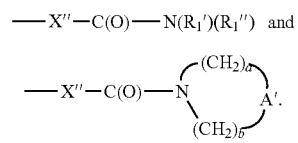

For certain embodiments, $R_{1-2}$ is

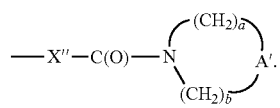

For certain embodiments, $R_{1-2}$ is $-X''-C(O)-N(R_1')(R_1'')$.

For certain embodiments, R" is hydrogen or a non-interfering substituent. For certain embodiments, R" is $R_2$.

For certain embodiments, $R_2$ is selected from the group consisting of: $-R_4$, $-X-R_4$, $-X-Y-R_4$, and $-X-R_5$. For certain embodiments, $R_2$ is hydrogen, alkoxyalkylenyl, hydroxyalkylenyl, $-R_4$, $-X-R_4$, or $-X-Y-R_4$. For certain embodiments, $R_2$ is hydrogen, alkoxyalkylenyl, $-R_4$, $-X-R_4$, or $-X-Y-R_4$. For certain embodiments, $R_2$ is hydrogen, $C_{1-4}$ alkyl, hydroxy$C_{1-4}$ alkylenyl, or $C_{1-4}$ alkyl-O-$C_{1-4}$ alkylenyl. For certain embodiments, $R_2$ is hydrogen, $C_{1-4}$ alkyl, or $C_{1-4}$ alkyl-O-$C_{1-4}$ alkylenyl. For certain embodiments, $R_2$ is hydrogen, methyl, ethyl, propyl, butyl, 2-methoxyethyl, ethoxymethyl, hydroxymethyl, or 2-hydroxyethyl. For certain embodiments, $R_2$ is hydrogen, methyl, ethyl, propyl, butyl, 2-methoxyethyl, or ethoxymethyl. For certain embodiments, $R_2$ is methyl, ethyl, propyl, butyl, 2-methoxyethyl, or ethoxymethyl.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups are unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo. In certain embodiments, $R_4$ is alkyl. In certain embodiments, $R_4$ is methyl.

For certain embodiments, $R_5$ is selected from the group consisting of:

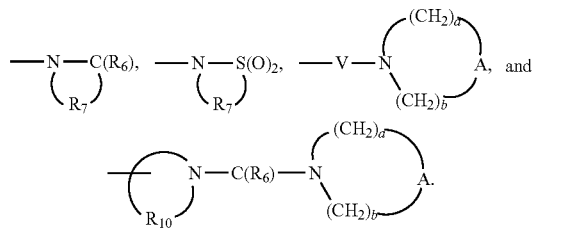

For certain embodiments, $R_6$ is selected from the group consisting of =O and =S. For certain embodiments, $R_6$ is =O.

For certain embodiments, $R_7$ is $C_{2-7}$ alkylene.

For certain embodiments, $R_8$ is selected from the group consisting of hydrogen, alkyl, alkoxyalkylenyl, and arylalkylenyl.

For certain embodiments, $R_9$ is selected from the group consisting of hydrogen and alkyl.

For certain embodiments, $R_{10}$ is $C_{3-8}$ alkylene.

For certain embodiments, A is selected from the group consisting of —O—, —C(O)—, —S(O)$_{0-2}$—, —CH$_2$—, and —N(R$_4$)—.

For certain embodiments, A' is selected from the group consisting of —O—, —C(O)—, —CH$_2$—, —S(O)$_{0-2}$—, and —N(Q-R$_4$)—. For certain embodiments, A' is —SO$_2$—, —O—, or —N(Q-R$_4$)—.

For certain embodiments, A' is —O— or —N(Q-R$_4$)—. For certain embodiments, A' is —O—. In certain embodiments, A' is —CH$_2$—.

For certain embodiments, Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_9$)—, —C(R$_6$)—O—, —C(R$_6$)—N(OR$_9$)—. For certain embodiments, Q is —C(O)—.

For certain embodiments, V is selected from the group consisting of —C(R$_6$)—, —O—C(R$_6$)—, —N(R$_8$)—C(R$_6$)—, and —S(O)$_2$—.

For certain embodiments, W is selected from the group consisting of a bond, —C(O)—, and —S(O)$_2$—.

For certain embodiments, X is selected from the group consisting of alkylene, alkenylene, alkynylene, arylene, heteroarylene, and heterocyclylene wherein the alkylene, alkenylene, and alkynylene groups are optionally interrupted or terminated by arylene, heteroarylene or heterocyclylene and optionally interrupted by one or more —O— groups. For certain embodiments, X is $C_{1-2}$ alkylene.

For certain embodiments, X' is selected from the group consisting of —CH(R$_9$)—, —CH(R$_9$)-alkylene-, and —CH(R$_9$)-alkenylene-. For certain embodiments, X' is —CH$_2$—C$_{0-10}$ alkylene-. For certain embodiments, X' is —CH$_2$—C$_{0-4}$ alkylene-. For certain embodiments, X' is —(CH$_2$)$_{1-5}$—, —CH$_2$C(CH$_3$)$_2$—, or —CH$_2$C(CH$_3$)$_2$CH$_2$—. For certain embodiments, X' is —CH$_2$—, —CH$_2$CH$_2$—, —CH$_2$CH$_2$CH$_2$—, —CH$_2$C(CH$_3$)$_2$—, —CH$_2$C(CH$_3$)$_2$CH$_2$—, or

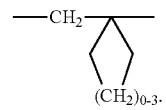

For certain embodiments, X' is —CH$_2$—, —CH$_2$CH$_2$—, —CH$_2$C(CH$_3$)$_2$—, or

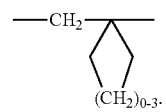

For certain embodiments, X' is —CH$_2$CH$_2$— or —CH$_2$C(CH$_3$)$_2$—.

For certain embodiments, X" is selected from the group consisting of —CH(R$_9$)—, —CH(R$_9$)-alkylene-, and —CH(R$_9$)-alkenylene-; wherein the alkylene and alkenylene are optionally interrupted with one or more —O— groups. For certain embodiments, X" is —CH$_2$—C$_{0-10}$ alkylene- or —CH$_2$—C$_{1-4}$ alkylene-O—C$_{1-4}$ alkylene-. For certain embodiments, X" is —CH$_2$—C$_{0-4}$ alkylene- or —CH$_2$—C$_{1-4}$ alkylene-O—C$_{1-4}$ alkylene-. For certain embodiments, X" is —(CH$_2$)$_{1-5}$—, —CH$_2$C(CH$_3$)$_2$—, —CH$_2$C(CH$_3$)$_2$CH$_2$—, or —(CH$_2$)$_3$—O—CH$_2$—. For certain embodiments, X" is —CH$_2$—, —CH$_2$CH$_2$—, —CH$_2$CH$_2$CH$_2$—, —CH$_2$C(CH$_3$)$_2$—, —CH$_2$C(CH$_3$)$_2$CH$_2$—, or

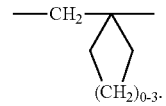

For certain embodiments, X" is —CH$_2$—, —CH$_2$CH$_2$—, —CH$_2$C(CH$_3$)$_2$—, or

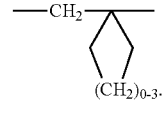

For certain embodiments, X" is —CH$_2$CH$_2$— or —CH$_2$C(CH$_3$)$_2$—.

For certain embodiments, X' or X" is —CH$_2$—, —CH$_2$CH$_2$—, —CH$_2$CH$_2$CH$_2$—, —CH$_2$C(CH$_3$)$_2$—, —CH$_2$C(CH$_3$)$_2$CH$_2$—, or

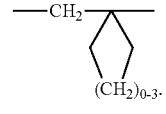

For certain embodiments, X' or X" is —CH$_2$—, —CH$_2$CH$_2$—, —CH$_2$C(CH$_3$)$_2$—, or

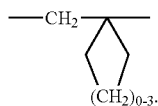

For certain embodiments, X' or X" is —CH$_2$CH$_2$— or —CH$_2$C(CH$_3$)$_2$—.

For certain embodiments, Y is selected from the group consisting of: —S(O)$_{0-2}$—, —S(O)$_2$—N(R$_8$)—, —C(R$_6$)—, —C(R$_6$)—O—, —O—C(R$_6$)—O—C(O)—O—, —N(R$_8$)-Q-, —C(R$_6$)—N(R$_8$)—, —O—C(R$_6$)—N(R$_8$)—, —C(R$_6$)—N(OR$_9$)—,

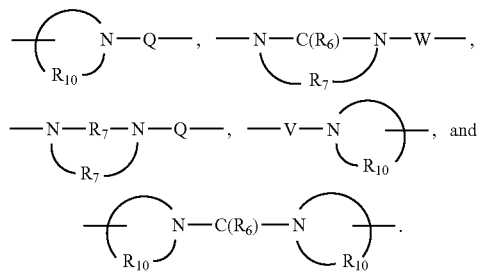

For certain embodiments, Y is —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_9$)—, —O—C(R$_6$)—N(R$_8$)—, or —C(R$_6$)—N(OR$_9$)—.

For certain embodiments, a and b are independently integers from 1 to 6 with the proviso that a+b is ≤7. For certain embodiments, a and b are independently integers from 1 to 3. For certain embodiments, a and b are independently integers from 2 to 3. For certain embodiments, a and b are each 2.

For certain embodiments, m is an integer from 0 to 3. For certain embodiments, m is 0.

For certain embodiments, n is an integer from 0 to 4. For certain embodiments, n is 0.

In some embodiments, particularly embodiments of Formulas I and II, and more particularly embodiments of Formula II, the fused aryl ring, fused heteroaryl ring, fused 5 to 7 membered saturated ring, or fused 5 to 7 membered saturated ring containing one N or S atom is unsubstituted.

In some embodiments, particularly embodiments of Formula III, R$_{A1}$ and R$_{B1}$ are methyl.

In some embodiments, particularly embodiments of Formula II, R$_1$ is

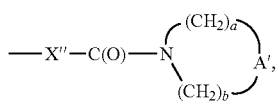

A' is —O— or —N(Q-R$_4$)—, and a and b are independently integers from 2 to 3; or A' is —CH$_2$—, and a and b are independently integers from 1 to 3.

In some embodiments, particularly embodiments of Formula II, R$_1$ is

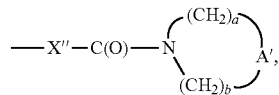

A' is —SO$_2$—, —O—, or —N(Q-R$_4$)—, and a and b are independently integers from 2 to 3; or A' is —CH$_2$—, and a and b are independently integers from 1 to 3.

In some embodiments, particularly embodiments of Formulas III, IV, and V, R$_{1-1}$ is

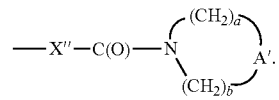

In some embodiments, particularly embodiments of Formulas III, IV, and V, R$_{1-1}$; is

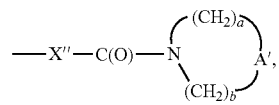

A' is —O—, and a and b are each 2.

In some embodiments, particularly embodiments of Formulas VI through XIII, and more particularly embodiments of Formulas VI through IX, R$_{1-2}$ is

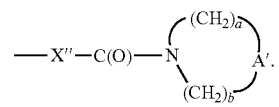

In some embodiments, particularly embodiments of Formulas VI through XIII, and more particularly embodiments of Formulas VI through IX, R$_{1-2}$ is

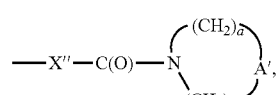

A' is —O—, and a and b are each 2.

In some embodiments, particularly embodiments of Formulas III through XIII, and more particularly embodiments of Formulas III through IX, R$_1$' is hydrogen or C$_{1-3}$ alkyl, and R$_1$" is hydrogen. In some embodiments, particularly embodiments of Formula II, R$_1$' is hydrogen or C$_{1-3}$ alkyl.

In some embodiments, particularly embodiments of Formulas III through XIII, and more particularly embodiments of Formulas III through IX, R$_1$' and R$_1$" are hydrogen. In some embodiments, particularly embodiments of Formula II, R$_1$" is hydrogen.

In some embodiments, particularly embodiments of Formulas II through XIII, and more particularly embodiments of Formulas II through IX, R$_1$' and R$_1$" are methyl.

In some embodiments, particularly embodiments of Formulas II through XIII, and more particularly embodiments of Formulas II through IX, $R_2$ is hydrogen, alkoxyalkylenyl, —$R_4$, —X—$R_4$, or —X—Y—$R_4$; X is $C_{1-2}$ alkylene; Y is —S(O)$_{0-2}$—, —S(O)$_2$—N($R_9$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, or —C($R_6$)—N(O$R_9$)—; and $R_4$ is alkyl. In some embodiments, particularly embodiments of Formulas II through XIII, and more particularly embodiments of Formulas II through IX, $R_2$ is hydrogen, $C_{1-4}$ alkyl, or $C_{1-4}$ alkyl-O—$C_{1-4}$ alkylenyl. In some embodiments, particularly embodiments of Formulas II through XIII, and more particularly embodiments of Formulas II through IX, $R_2$ is hydrogen, methyl, ethyl, propyl, butyl, 2-methoxyethyl, or ethoxymethyl.

In some embodiments, particularly embodiments of Formulas II through XIII, and more particularly embodiments of Formulas II through IX, $R_2$ is hydrogen, alkoxyalkylenyl, hydroxyalkylenyl, —$R_4$, —X—$R_4$, or —X—Y—$R_4$; X is $C_{1-2}$ alkylene; Y is —S(O)$_{0-2}$—, —S(O)$_2$—N($R_9$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, or —C($R_6$)—N(O$R_9$)—; and $R_4$ is alkyl. In some embodiments, particularly embodiments of Formulas II through XIII, and more particularly embodiments of Formulas II through IX, $R_2$ is hydrogen, $C_{1-4}$ alkyl, hydroxy$C_{1-4}$ alkylenyl, or $C_{1-4}$ alkyl-O—$C_{1-4}$ alkylenyl. In some embodiments, particularly embodiments of Formulas II through XIII, and more particularly embodiments of Formulas II through IX, $R_2$ is hydrogen, methyl, ethyl, propyl, butyl, 2-methoxyethyl, ethoxymethyl, hydroxymethyl, or 2-hydroxyethyl.

In some embodiments, particularly embodiments of Formula II, A' is —O— or —N(Q-$R_4$)—, and a and b are independently integers from 2 to 3; or A' is —CH$_2$—, and a and b are independently integers from 1 to 3.

In some embodiments, particularly embodiments of Formulas I through XIII, more particularly embodiments of Formulas I through IX, and more particularly embodiments of Formulas II through IX, A' is —SO$_2$—, —O—, or —N(Q-$R_4$)—, and a and b are independently integers from 2 to 3; or A' is —CH$_2$—, and a and b are independently integers from 1 to 3.

In some embodiments, particularly embodiments of Formulas III through XIII, and more particularly embodiments of Formulas III through IX, A' is —O—, and a and b are each 2.

In some embodiments, particularly embodiments of Formula I, X' is —CH$_2$—C$_{0-10}$ alkylene- or X" is —CH$_2$—C$_{0-10}$ alkylene- or —CH$_2$—C$_{1-4}$ alkylene-O—C$_{1-4}$ alkylene-. In some embodiments, particularly embodiments of Formulas II through V, X' is —CH$_2$—C$_{0-4}$ alkylene- or X" is —CH$_2$—C$_{0-4}$ alkylene- or —CH$_2$—C$_{1-4}$ alkylene-O—C$_{1-4}$ alkylene-.

In some embodiments, particularly embodiments of Formulas II through V, and more particularly embodiments of Formulas III through V, X' is —(CH$_2$)$_{1-5}$—, —CH$_2$C(CH$_3$)$_2$—, or —CH$_2$C(CH$_3$)$_2$CH$_2$—; or X" is —(CH$_2$)$_{1-5}$—, —CH$_2$C(CH$_3$)$_2$—, —CH$_2$C(CH$_3$)$_2$CH$_2$—, or —(CH$_2$)$_3$—O—CH$_2$—.

In some embodiments, particularly embodiments of Formulas II through V, X' or X" is —CH$_2$CH$_2$— or —CH$_2$C(CH$_3$)$_2$—.

In some embodiments, X" is —CH$_2$—C$_{0-10}$ alkylene- or —CH$_2$—C$_{1-4}$ alkylene-O—C$_{1-4}$ alkylene-. In some embodiments, particularly embodiments of Formulas VI through XIII, and more particularly embodiments of Formulas VI through IX, X" is —CH$_2$—C$_{0-4}$ alkylene- or —CH$_2$—C$_{1-4}$ alkylene-O—C$_{1-4}$ alkylene-. In some embodiments, particularly embodiments of Formulas VI through XIII, and more particularly embodiments of Formulas VI through IX, X" is —(CH$_2$)$_{1-5}$—, —CH$_2$C(CH$_3$)$_2$—, —CH$_2$C(CH$_3$)$_2$CH$_2$—, or —(CH$_2$)$_3$—O—CH$_2$—. In some embodiments, particularly embodiments of Formulas VI through XIII, and more particularly embodiments of Formulas VI through IX, X" is —CH$_2$CH$_2$— or —CH$_2$C(CH$_3$)$_2$—.

In some embodiments, particularly embodiments of Formulas I through V, more particularly embodiments of Formulas III through V, X' or X" is —CH$_2$—, —CH$_2$CH$_2$—, —CH$_2$CH$_2$CH$_2$—, —CH$_2$C(CH$_3$)$_2$—, —CH$_2$C(CH$_3$)$_2$CH$_2$—, or

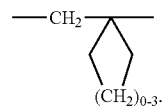

In some embodiments, particularly embodiments of Formulas I through V, more particularly embodiments of Formulas III through V, X' or X" is —CH$_2$—, —CH$_2$CH$_2$—, —CH$_2$C(CH$_3$)$_2$—, or

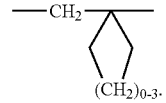

In some embodiments, particularly embodiments of Formulas VI through XIII, more particularly embodiments of Formulas VI through IX, X" is —CH$_2$—, —CH$_2$CH$_2$—, —CH$_2$CH$_2$CH$_2$—, —CH$_2$C(CH$_3$)$_2$—, —CH$_2$C(CH$_3$)$_2$CH$_2$—, or

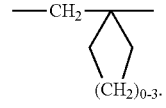

In some embodiments, particularly embodiments of Formulas VI through XIII, more particularly embodiments of Formulas VI through IX, X" is —CH$_2$—, —CH$_2$CH$_2$—, —CH$_2$C(CH$_3$)$_2$—, or

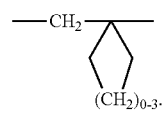

In some embodiments, particularly embodiments of Formulas VI through XIII, and more particularly embodiments of Formulas VI through IX, m is 0.

In some embodiments, particularly embodiments of Formulas IV and V, n is 0.

In some embodiments the imidazonaphthyridine compounds are of the following Formula VI:

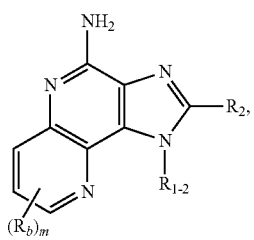

VI or a pharmaceutically acceptable salt thereof.

In some embodiments, particularly embodiments of Formula II, $R_1$ is —$CH_2CH_2C(O)NH_2$ or —$CH_2C(CH_3)_2$—$C(O)NH_2$.

In some embodiments, particularly embodiments of Formulas III through V, $R_{1-1}$ is —$CH_2CH_2C(O)NH_2$ or —$CH_2C(CH_3)_2$—$C(O)NH_2$.

In some embodiments, particularly embodiments of Formulas VI through XIII, more particularly embodiments of Formulas VI through IX, $R_{1-2}$ is —$CH_2CH_2C(O)NH_2$ or —$CH_2C(CH_3)_2$—$C(O)NH_2$.

In some embodiments, particularly embodiments of Formula II, $R_1$ is —$CH_2CH_2C(O)NH_2$ or —$CH_2C(CH_3)_2$—$C(O)NH_2$, and $R_2$ is selected from the group consisting of hydrogen, methyl, ethyl, propyl, butyl, ethoxymethyl, 2-methoxyethyl, hydroxymethyl, and 2-hydroxyethyl.

In some embodiments, particularly embodiments of Formulas III through V, $R_{1-1}$ is —$CH_2CH_2C(O)NH_2$ or —$CH_2C(CH_3)_2$—$C(O)NH_2$, and $R_2$ is selected from the group consisting of hydrogen, methyl, ethyl, propyl, butyl, ethoxymethyl, 2-methoxyethyl, hydroxymethyl, and 2-hydroxyethyl.

In some embodiments, particularly embodiments of Formulas VI through XIII, more particularly embodiments of Formulas VI through IX, $R_{1-2}$ is —$CH_2CH_2C(O)NH_2$ or —$CH_2C(CH_3)_2$—$C(O)NH_2$, and $R_2$ is selected from the group consisting of hydrogen, methyl, ethyl, propyl, butyl, ethoxymethyl, 2-methoxyethyl, hydroxymethyl, and 2-hydroxyethyl.

Preparation of the Compounds

Compounds of Formula IVa can be prepared according to Reaction Scheme I, wherein $R_a$ and n are as defined above, $X_a$ is either X' or X", and $R_{1-1a}$ and $R_{2a}$ are subsets of $R_{1-1}$ and $R_2$ as defined above that do not include those substituents that one skilled in the art would recognize as being susceptible to oxidation in step (5). These substituents include —S— and heteroaryl groups. In step (1) of Reaction Scheme I, a 4-chloro-3-nitroquinoline of Formula XX is reacted with an amino ester of the Formula $H_2N$—$X_a$—$C(O)$—$O$-alkyl or a hydrochloride salt thereof to form a compound of Formula XXI. This reaction is conveniently carried out by adding a compound of the Formula $H_2N$—$X_a$—$C(O)$—$O$-alkyl—HCl to a solution of a 4-chloro-3-nitroquinoline of Formula XX in the presence of a base such as triethylamine, potassium carbonate, or a combination thereof. The reaction is carried out in a suitable solvent, such as dichloromethane or chloroform. Compounds of the Formula $H_2N$—$X_a$—$C(O)$—$O$-alkyl—HCl can be commercially obtained or readily synthesized using conventional methods. For example, the amino ester wherein —alkyl is ethyl and $X_a$ is butylene or dodecylene can be synthesized according to the procedure of C. Temple et al., *J. Med. Chem.*, 31, pp. 697-700 (1988). Many compounds of Formula XX are known or can be prepared using known synthetic methods, see for example, U.S. Pat. Nos. 4,689,338; 5,175,296; 5,367,076; and 5,389,640; and the documents cited therein.

The resultant compound of Formula XXI can be reduced in step (2) of Reaction Scheme I using a variety of methods to provide a quinoline-3,4-diamine of Formula XXII. The reaction can be carried out by hydrogenation using a heterogeneous hydrogenation catalyst such as platinum on carbon. The hydrogenation is conveniently carried out in a Parr apparatus in a suitable solvent such as toluene or ethanol. The reaction can be carried out at ambient temperature, and the product can be isolated using conventional methods.

Alternatively step (2) can be carried out using a one- or two-phase sodium dithionite reduction The reaction is conveniently carried out using the conditions described by Park, K. K.; Oh, C. H.; and Joung, W. K.; *Tetrahedron Lett.*, 34, pp. 7445-7446 (1993) by adding sodium dithionite to a compound of Formula XXI in a mixture of dichloromethane and water at ambient temperature in the presence of potassium carbonate, ethyl viologen dibromide, ethyl viologen diiodide, or 1,1'-di-n-octyl-4,4'-bipyridinium dibromide. The product can be isolated using conventional methods.

In step (3) of Reaction Scheme I, a quinoline-3,4-diamine of Formula XXII is treated with a carboxylic acid or equivalent thereof to provide a 1H-imidazo[4,5-c]quinoline of Formula XXIII. Suitable carboxylic acid equivalents include orthoesters of Formula $R_{2a}C(O\text{-alkyl})_3$, 1,1-dialkoxyalkyl alkanoates of Formula $R_{2a}C(O\text{-alkyl})_2(O$—$C(O)\text{-alkyl})$, and acid chlorides of Formula $R_{2a}C(O)Cl$. The selection of the carboxylic acid equivalent is determined by the desired substituent at $R_{2a}$. For example, triethyl orthoformate will provide a compound where $R_{2a}$ is hydrogen, and trimethyl orthovalerate will provide a compound where $R_{2a}$ is a butyl group. The reaction is conveniently carried out by adding the carboxylic acid equivalent to a quinoline-3,4-diamine of Formula XXII in a suitable solvent such as toluene. Optionally, catalytic pyridine hydrochloride or pyridinium p-toluenesulfonate can be added. The reaction is carried out at a temperature high enough to drive off alcohol or water formed during the reaction. Conveniently, a Dean-Stark trap can be used to collect the volatiles.

Alternatively, step (3) can be carried out in two steps when an acid chloride of Formula $R_{2a}C(O)Cl$ is used as the carboxylic acid equivalent. The first step is conveniently carried out by adding the acid chloride to a solution of a quinoline-3,4-diamine of Formula XXII in a suitable solvent such as dichloromethane to afford an amide. Optionally, a tertiary amine such as triethylamine, pyridine, or 4-dimethylaminopyridine can be added. The reaction can be carried out at ambient temperature. The amide product can be isolated and optionally purified using conventional techniques before it is heated and cyclized to provide a 1H-imidazo[4,5-c]quinoline of Formula XXIII. The cyclization reaction is conveniently carried out in a solvent such as ethanol or methanol in the presence of a base such as triethylamine and may be carried out at an elevated temperature, such as the reflux temperature of the solvent. The 1H-imidazo[4,5-c]quinoline of Formula XXIII can be isolated using conventional methods.

In step (4) or steps (4a) and (4b) of Reaction Scheme I, the ester group of a 1H-imidazo[4,5-c]quinoline Formula XXIII is converted to an amide to provide a 1H-imidazo[4,5-c]quinoline of Formula XIVa. The transformation can be carried out by base-promoted hydrolysis of the ester in step (4a) to form a carboxylic acid of Formula XXIV. In step (4b), a carboxylic acid of Formula XXIV is converted to an acid chloride using conventional methods and then treated with an amine to provide an amide-substituted 1H-imidazo[4,5-c]quinoline of Formula XIVa. The base-promoted hydrolysis in step (4a) is conveniently carried out by adding sodium hydroxide to an ester-substituted 1H-imidazo[4,5-c]quinoline Formula XXIII in a suitable solvent such as ethanol. The reaction can be carried out at ambient temperature, and the product can be isolated using conventional methods. The conversion of the resulting carboxylic acid to an acid chloride is conveniently carried out by slowly adding oxalyl chloride to a solution of the carboxylic acid in a suitable solvent such as dichloromethane. The reaction can be carried out at a sub-ambient temperature, such as 0° C., or at ambient temperature. The resulting acid chloride can then be treated with an amine of Formula HN(R$_1$')(R$_1$") or

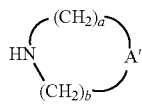

in a suitable solvent such as dichloromethane. Numerous amines of these formulas are commercially available; others can be prepared by known synthetic methods. The reaction can be run at ambient temperature, and the product of Formula XIVa or pharmaceutically acceptable salt thereof can be isolated using conventional methods.

Alternatively, step (4) can be used to convert an ester-substituted 1H-imidazo[4,5-c]quinoline of Formula XXIII to an amide of Formula XIVa in one step by treating the compound Formula XXIII with an amine of Formula HN(R$_1$')(R$_1$") or

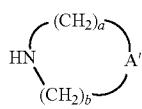

or a hydrochloride salt thereof in the presence of trimethylaluminum. The reaction is conveniently carried out by adding a solution of an ester-substituted 1H-imidazo[4,5-c]quinoline of Formula XXIII in a suitable solvent such as dichloromethane to a pre-reacted mixture of trimethylaluminum and an amine of Formula HN(R$_1$')(R$_1$") or

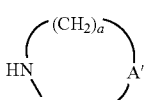

or a hydrochloride salt thereof in a suitable solvent such as dichloromethane. The reaction can then be heated at an elevated temperature, for example, the reflux temperature of the solvent. The product can be isolated using conventional methods.

Step (4) of Reaction Scheme I can also be carried out by heating an ester-substituted 1H-imidazo[4,5-c]quinoline Formula XXIII in the presence of an amine of Formula HN(R$_1$')(R$_1$") or

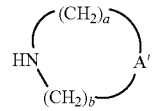

at an elevated temperature such as 90-120° C. The reaction is conveniently carried out in a high-pressure vessel and can be run neat or in a suitable solvent such as tetrahydrofuran (THF). An ester of Formula XXIII can be heated in the presence of ammonium acetate at an elevated temperature such as 110 to 140° C. to provide a compound of Formula XIVa, where R$_{1-1a}$ is —X'—C(O)—NH$_2$. The product can be isolated by conventional methods.

In step (5) of Reaction Scheme I, an amide-substituted 1H-imidazo[4,5-c]quinoline of Formula XIVa is oxidized to provide a 1H-imidazo[4,5-c]quinoline-5N-oxide of Formula XXV using a conventional oxidizing agent capable of forming N-oxides. The reaction is conveniently carried out by adding 3-chloroperoxybenzoic acid to a solution of a compound of Formula XIVa in a solvent such as dichloromethane or chloroform. The reaction can be carried out at ambient temperature, and the product can be isolated using conventional methods.

In step (6) of Reaction Scheme I, a 1H-imidazo[4,5-c]quinoline-5N-oxide of Formula XXV is aminated to provide an amide-substituted 1H-imidazo[4,5-c]quinolin-4-amine of Formula IVa, a subgenus of Formulas I, II, and IV. Step (6) can be carried out by the activation of an N-oxide of Formula XXV by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XXV in a suitable solvent such as dichloromethane or chloroform and then adding p-toluenesulfonyl chloride. The reaction can be carried out at ambient temperature. The product or pharmaceutically acceptable salt thereof can be isolated using conventional methods.

Steps (5) and (6) of Reaction Scheme I may be carried out as a one-pot procedure by adding 3-chloroperoxybenzoic acid to a solution of a compound of Formula XIVa in a solvent such as dichloromethane or chloroform and then adding ammonium hydroxide and p-toluenesulfonyl chloride without isolating the N-oxide compound of Formula XXV. The product of Formula IVa or pharmaceutically acceptable salt thereof can be isolated by conventional methods.

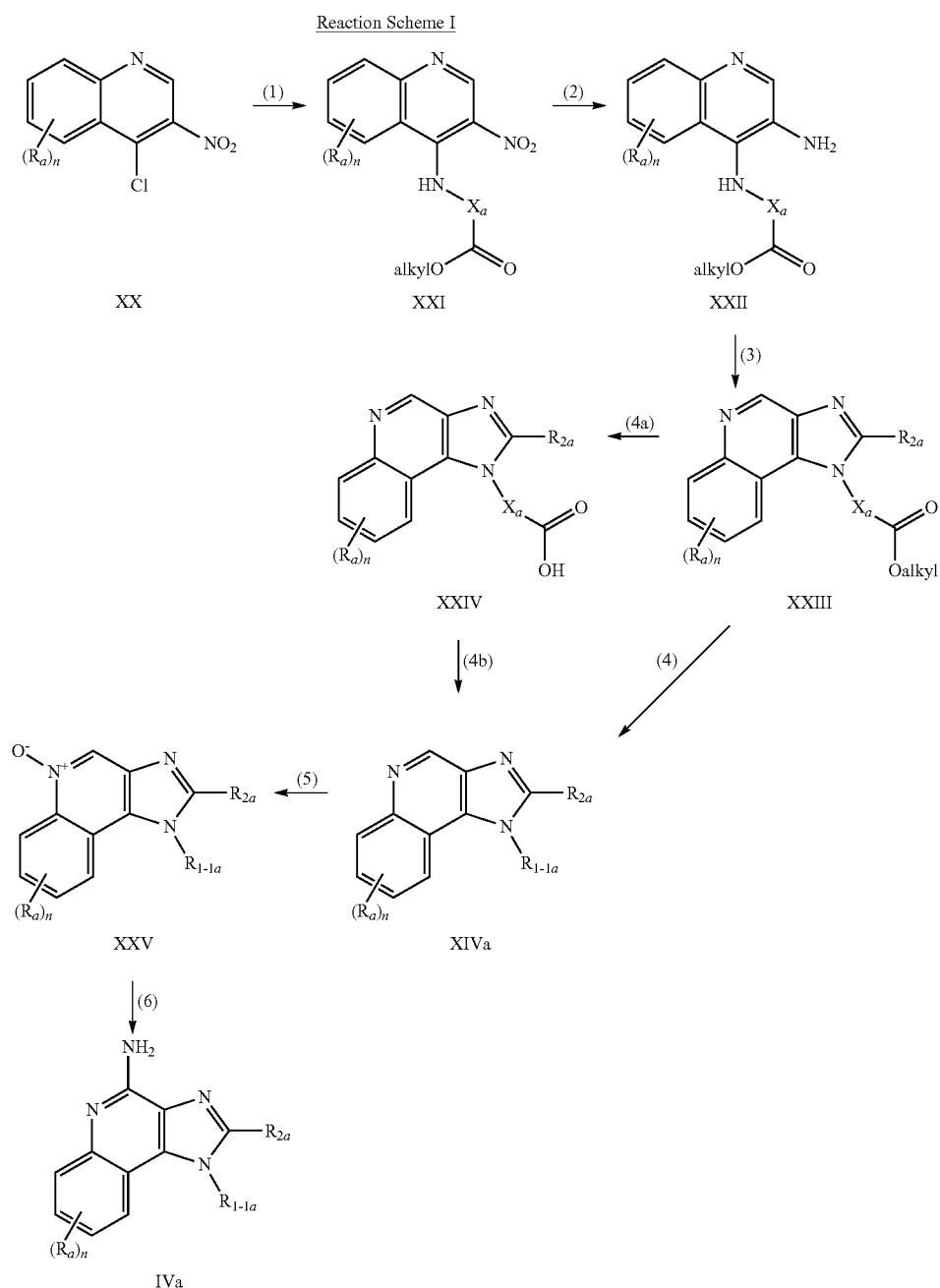

Compounds of the invention can also be prepared according to Reaction Scheme II, wherein $R_a$, $R_{2a}$, $R_{1-1}$, $X_a$, and n are as defined above. In step (1) of Reaction Scheme II, an ester-substituted 1H-imidazo[4,5-c]quinoline Formula XXIII is oxidized to an N-oxide of Formula XXVI, which is then aminated in step (2) to provide an ester-substituted 1H-imidazo[4,5-c]quinolin-4-amine Formula XXVII. Steps (1) and (2) of Reaction Scheme II can be carried out as described for steps (5) and (6) of Reaction Scheme I.

In step (3) of Reaction Scheme II, an ester-substituted 1H-imidazo[4,5-c]quinolin-4-amine Formula XXVII is heated in the presence of an amine of Formula $HN(R_1')(R_1'')$ or

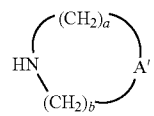

at an elevated temperature such as 90-120° C. to provide an amide-substituted 1H-imidazo[4,5-c]quinolin-4-amine Formula IVb, a subgenus of Formulas I, II, and IV. The reaction is conveniently carried out in a high-pressure vessel and can be run neat or in a suitable solvent such as THF. An ester of Formula XXVII can be heated in the presence of ammonium acetate at an elevated temperature such as 110 to 140° C. to provide a compound of Formula IVb, where $R_{1-1}$ is —$X_a$—C(O)—$NH_2$. The product or pharmaceutically acceptable salt thereof can be isolated by conventional methods.

Compounds of the invention can also be prepared according to Reaction Scheme III, wherein n is as defined above, $R_d$ is alkyl, alkoxy, or —$N(R_9)_2$ and $R_{2b}$ and $R_{1-1b}$ are subsets of $R_2$ and $R_{1-1}$ as defined above that do not include those substituents that one skilled in the art would recognize as being susceptible to reduction under the acidic hydrogenation conditions of the reaction. These susceptible groups include, for example, alkenyl, alkynyl, and aryl groups and groups bearing nitro substituents.

As shown in Reaction Scheme III, an 1H-imidazo[4,5-c]quinoline of Formula IVc can be reduced to a 6,7,8,9-tetrahydro-1H-imidazo[4,5-c]quinolin-4-amine of Formula Vb, a subgenus of Formulas I, II, and V. The reaction is conveniently carried out under heterogeneous hydrogenation conditions by adding platinum (IV) oxide to a solution of the compound of Formula IVc in trifluoroacetic acid aid placing the reaction under hydrogen pressure. The reaction can be carried out on a Parr apparatus at ambient temperature. The product or pharmaceutically acceptable salt thereof can be isolated by conventional methods.

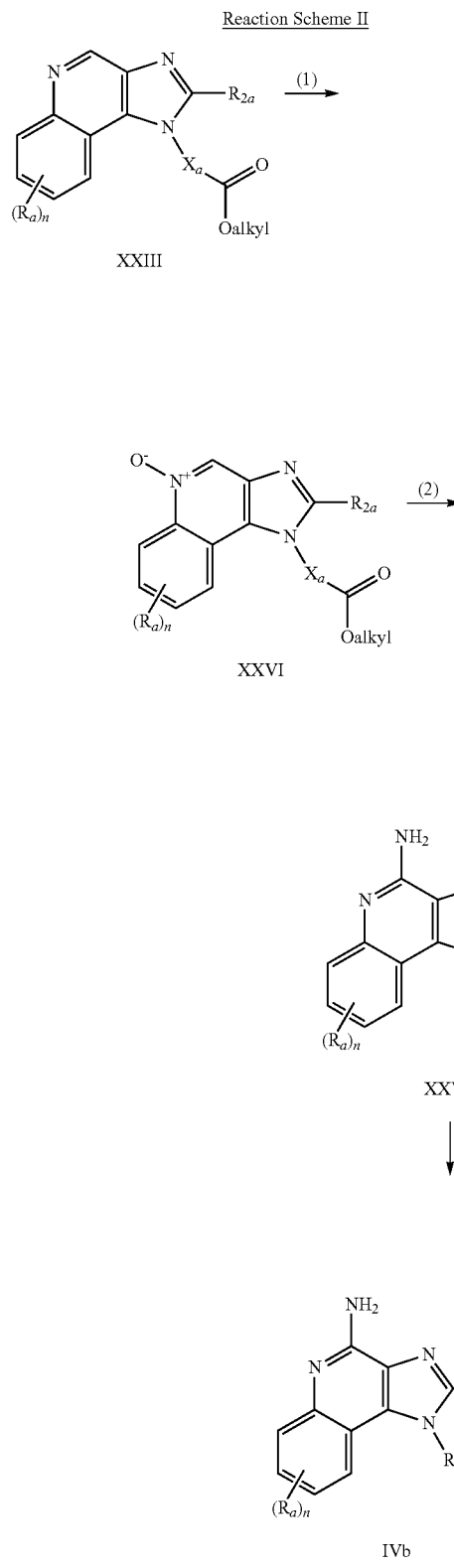

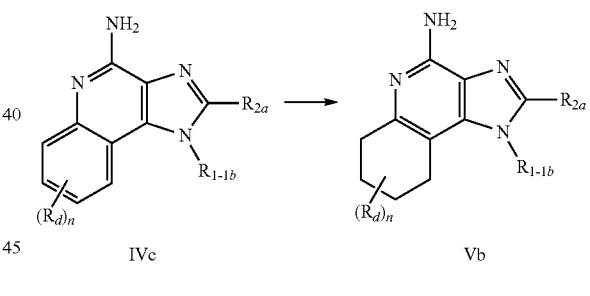

Compounds of the invention can be prepared according to Reaction Scheme IV, wherein $R_b$, X", $R_{2a}$ and m are as defined above and $R_{1-2a}$ is a subset of $R_{1-2}$ as defined above that does not include those substituents that one skilled in the art would recognize as being susceptible to oxidation in step (5). These substituents include —S— and heteroaryl groups. Reaction Scheme IV begins with a 4-chloro-3-nitro[1,5]naphthyridine of Formula XXVIII. Compounds of Formula XXVIII and their preparation are known; see, for example, U.S. Pat. No. 6,194,425 (Gerster) and U.S. Pat. No. 6,518,280 (Gerster). Steps (1) through (6) of Reaction Scheme IV can be carried out as described for the corresponding steps (1) through (6) of Reaction Scheme I to provide am amide-substituted 1H-imidazo[4,5-c][1,5]naphthyridin-4-amine of Formula VIa, a subgenus of Formulas I, II, and VI. The product or pharmaceutically acceptable salt thereof can be isolated by conventional methods.

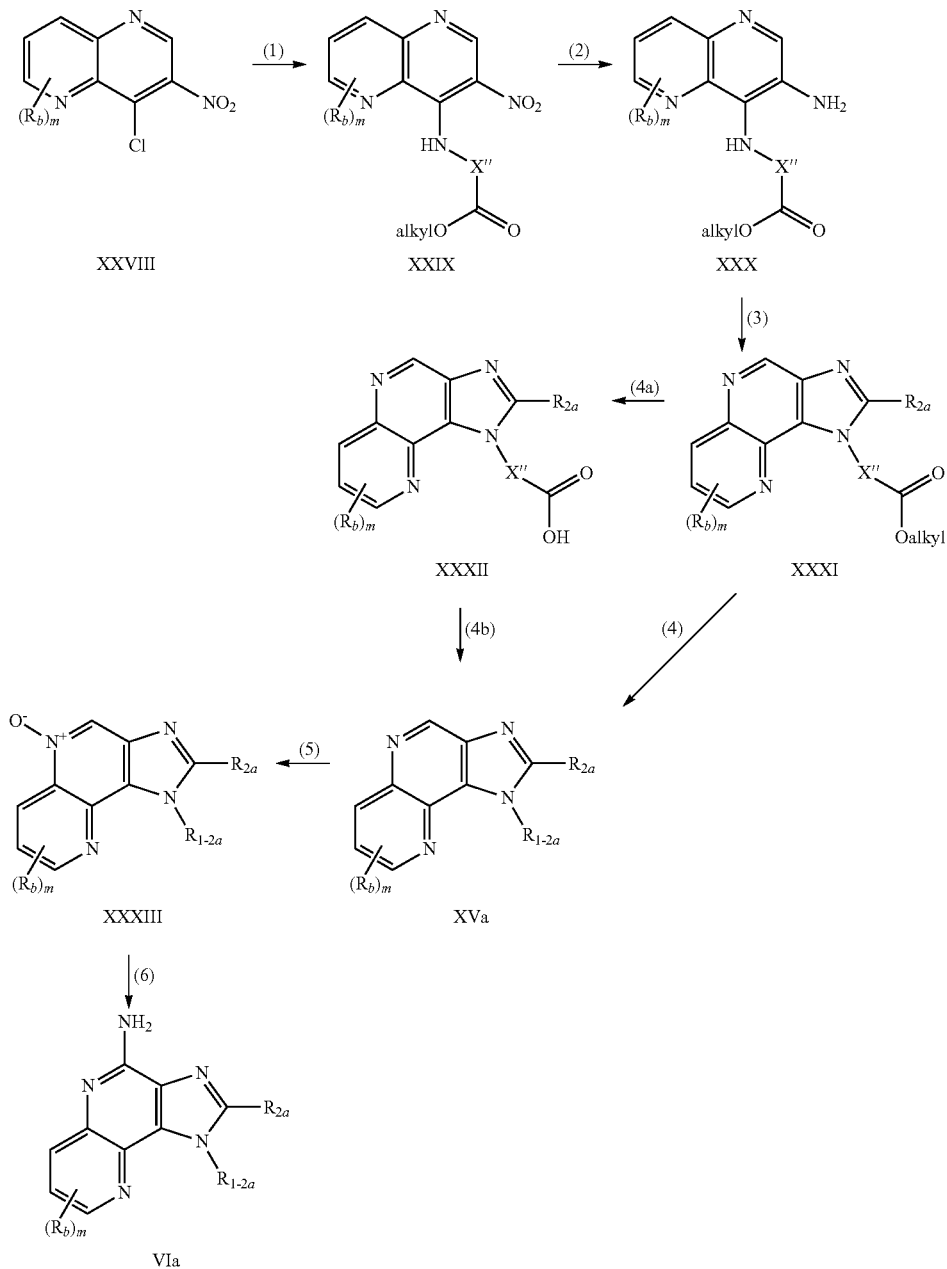

Reaction Scheme IV

For some embodiments, compounds of the invention are prepared according to Reaction Scheme V, where $R_{1-1}$, $R_2$, $R_{A1}$, $R_{B1}$, and $X_a$ are as defined above and Ph is phenyl. In step (1) of Reaction Scheme V, a 2,4-dichloro-3-nitropyridine of Formula XXXIV is reacted with an amino ester of the Formula $H_2N$—$X_a$—C(O)—O-alkyl or a hydrochloride salt thereof to form a 2-chloro-3-nitropyridine of Formula XXXV. The reaction is conveniently carried out by combining an amino ester of Formula $H_2N$—$X_a$—C(O)—O-alkyl—HCl and a 2,4-dichloro-3-nitropyridine of Formula XXXIV in the presence of a base such as triethylamine in an inert solvent such as N,N-dimethylformamide (DMF). The reaction can be carried out at ambient temperature, and the product can be isolated from the reaction mixture using conventional methods. Many 2,4-dichloro-3-nitropyridines of the Formula XXXIV are known and can be readily prepared using known synthetic methods. (See, for example, Dellaria et al, U.S. Pat. No. 6,525,064 and the references cited therein.)

In step (2) of Reaction Scheme V a 2-chloro-3-nitropyridine of Formula XXXV is reacted with an alkali metal azide to provide an 8-nitrotetrazolo[1,5-a]pyridin-7-amine of Formula XXXVI. The reaction can be carried out by combining the compound of Formula XXXV with an alkali metal azide, for example, sodium azide, in a suitable solvent such as acetonitrile/water, preferably 90/10 acetonitrile/water, in the presence of cerium III chloride, preferably cerium III chloride heptahydrate. Optionally, the reaction can be carried out with heating, for example, at the reflux temperature. Alternatively, the reaction can be carried out by combining the compound of Formula XXXV with an alkali metal azide, for example, sodium azide, in a suitable solvent such as DMF and heating, for example to about 50-60° C., optionally in the presence of ammonium chloride. The product can be isolated from the reaction mixture using conventional methods.

In step (3) of Reaction Scheme V, an 8-nitrotetrazolo[1,5-a]pyridin-7-amine of Formula XXXVI is reduced to provide a tetrazolo[1,5-a]pyridine-7,8-diamine of Formula XXXVII. The reduction can be carried out by hydrogenation using a conventional heterogeneous hydrogenation catalyst, for example, platinum on carbon or palladium on carbon. The reaction can conveniently be carried out on a Parr apparatus in a suitable solvent such as acetonitrile or ethyl acetate. The product can be isolated from the reaction mixture using conventional methods. Alternatively, the reduction can be carried out using the one- to two-phase sodium dithionite reduction described in step (2) of Reaction Scheme I.

In step (4) of Reaction Scheme V, a tetrazolo[1,5-a]pyridine-7,8-diamine of Formula XXXVII is reacted with a carboxylic acid or equivalent thereof to provide a 7H-imidazo[4,5-c]tetrazolo[1,5-a]pyridine of Formula XXXVIII. The reaction can be carried out as described in step (3) of Reaction Scheme I, and the product can be isolated from the reaction mixture using conventional methods.

In step (5) or steps (5a) and (5b) of Reaction Scheme V, the ester group of a 7H-imidazo[4,5-c]tetrazolo[1,5-a]pyridine of Formula XXXVIII is converted to an amide to provide an amide-substituted 7H-imidazo[4,5-c]tetrazolo[1,5-a]pyridine of Formula XVI. The reaction can be carried out as described in step (4) or steps (4a) and (4b) of Reaction Scheme I, and the product can be isolated by conventional methods.

In step (6) of Reaction Scheme V, the tetrazolo ring is reductively removed from a 7H-imidazo[4,5-c]tetrazolo[1,5-a]pyridine of Formula XVI to provide an amide-substituted 1H-imidazo[4,5-c]pyridin-4-amine of Formula III or a pharmaceutically acceptable salt thereof. The reaction can be carried out by reacting the 7H-imidazo[4,6-c]tetrazolo[1,5-a]pyridine of Formula XVI with hydrogen in the presence of a catalyst and an acid. The hydrogenation can be conveniently run at ambient temperature on a Parr apparatus with a suitable catalyst, such as platinum IV oxide, and a suitable acid, such as trifluoroacetic acid. The product or pharmaceutically acceptable salt thereof can be isolated from the reaction mixture using conventional methods.

Alternatively, the tetrazolo ring can be removed from a 7H-imidazo[4,5-c]tetrazolo[1,5-a]pyridine of Formula XVI as shown in step (6a) by reaction with triphenylphosphine to form an N-triphenylphosphinyl intermediate of Formula XL. The reaction with triphenylphosphine can be run in a suitable solvent such as toluene or 1,2-dichlorobenzene under an atmosphere of nitrogen with heating, for example at the reflux temperature. In step (6b) of Reaction Scheme V an N-triphenylphosphinyl intermediate of Formula XL is hydrolyzed to provide an amide-substituted 1H-imidazo[4,5-c]pyridin-4-amine of Formula III. The hydrolysis can be carried out by general methods well known to those skilled in the art, for example, by heating in a lower alkanol in the presence of an acid. The product can be isolated from the reaction mixture using conventional methods as the compound of Formula III or as a pharmaceutically acceptable salt thereof.

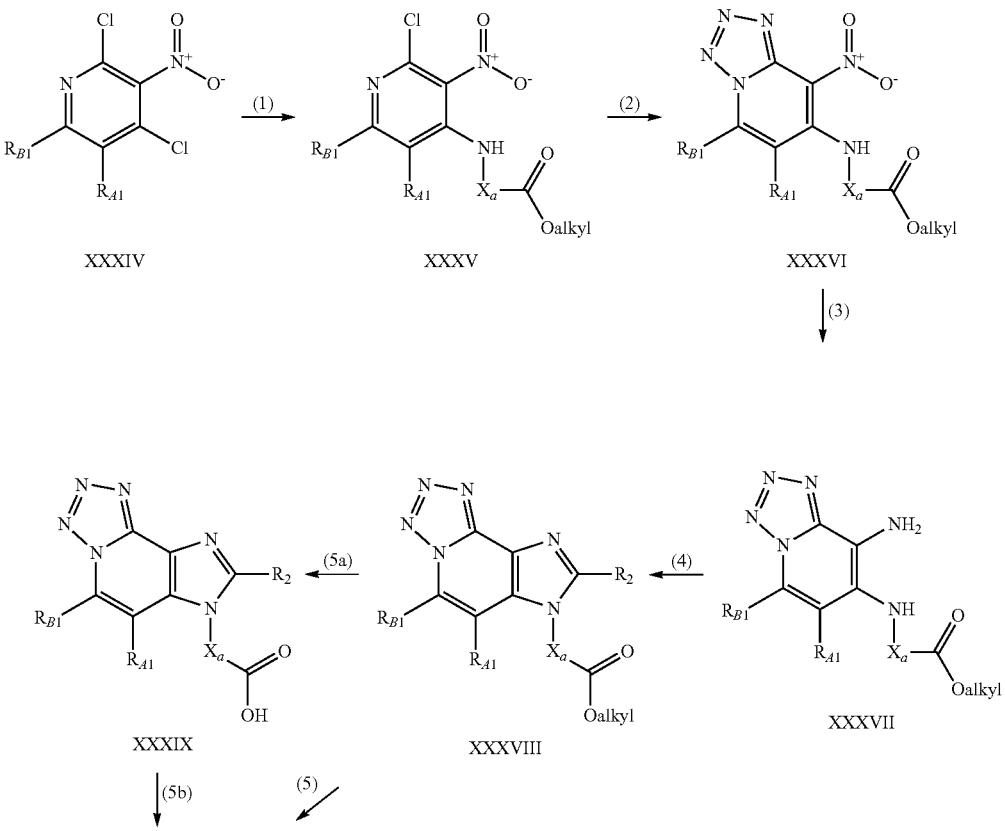

Reaction Scheme V

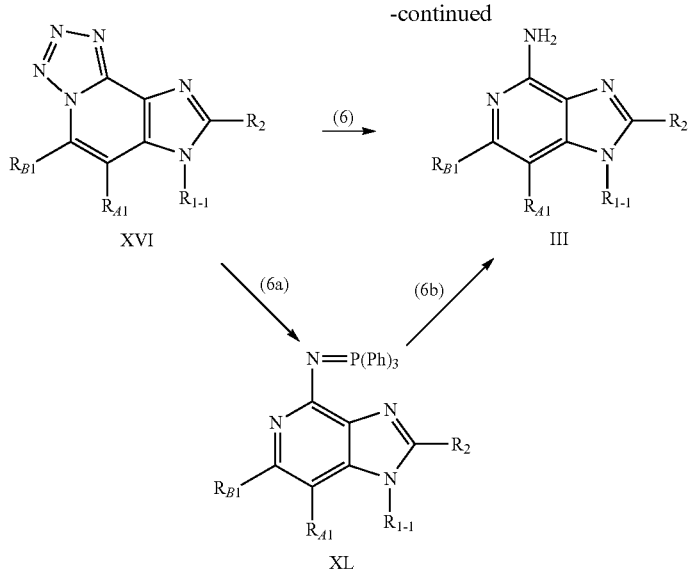

For some embodiments, naphthyridines of the invention are prepared from tetrazolo compounds of Formulas XLI and XLIV according to Reaction Scheme VI and Reaction Scheme VII, wherein $R_{1-2}$, $R_2$, $R_b$, m, and X″ are as defined above and -OTf is a trifluoromethanesulfonate group. Compounds of Formula XLI and XLIV and synthetic routes to these compounds are known; see, for example, U.S. Pat. No. 6,194,425 (Gerster) and U.S. Pat. No. 6,518,280 (Gerster).

In step (1) of Reaction Scheme VI or VII, a tetrazolonaphthyridine of Formula XLI or XLIV is reacted with an amino ester of the Formula $H_2N$—X″—C(O)—O-alkyl or a hydrochloride salt thereof to form a compound of Formula XLII or XLV. The reaction can be carried out as described in step (1) of Reaction Scheme I. An ester-substituted tetrazolonaphthyridine of Formula XLII or XLV is converted in steps (2) through (4) of Reaction Scheme VI or VII to a compound of Formula XLIII or XLVI according to the methods of steps (2), (3), and (4) or (4a) and (4b) of Reaction Scheme I. The tetrazolo group of a compound of Formula XLIII or XLVI can then be removed to provide a 1H-imidazo[4,5-c]naphthyridin-4-amine of Formula IX or VIII, which are subgenera of Formulas I and II. The removal of the tetrazolo group can be carried out as described in step (6) or steps (6a) and (6b) of Reaction Scheme V or by methods described in U.S. Pat. No. 6,194,425 (Gerster) and U.S. Pat. No. 6,518,280 (Gerster). The product or pharmaceutically acceptable salt thereof can be isolated by conventional methods.

Reaction Scheme VI

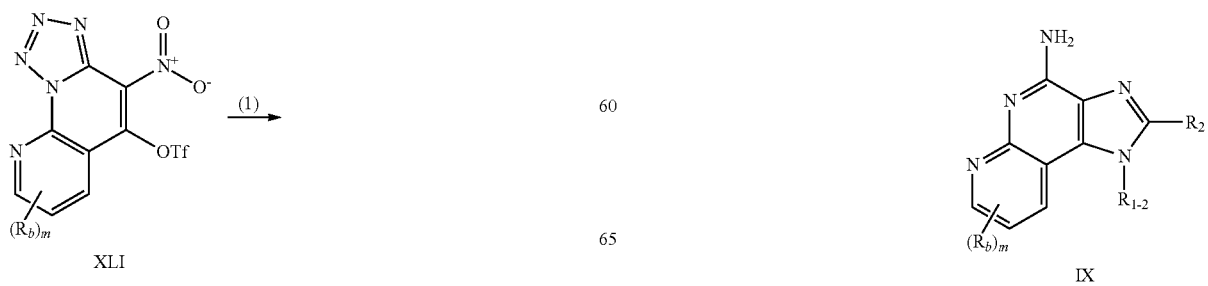

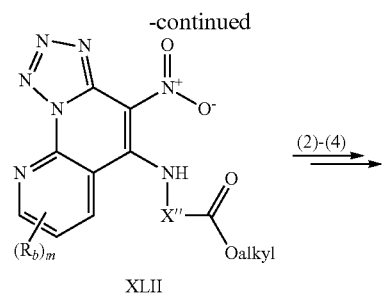

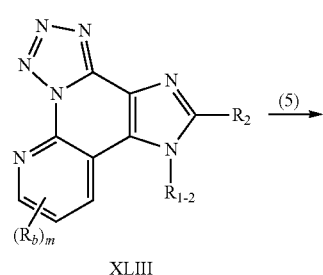

Reaction Scheme VII

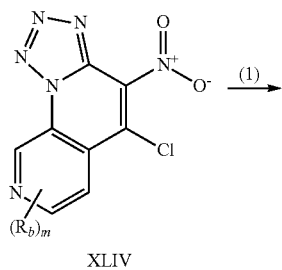

XLIV

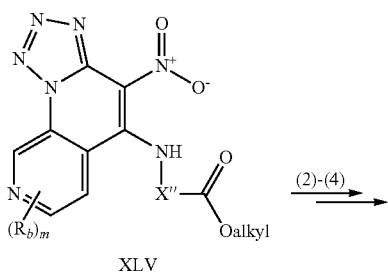

XLV

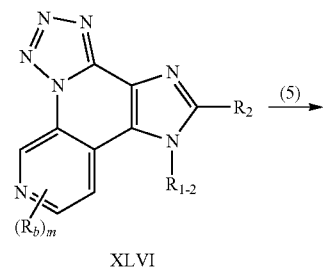

XLVI

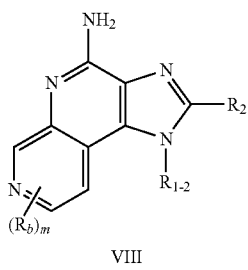

VIII

Compounds of the invention can be prepared according to Reaction Scheme VIII wherein $R_a$, $R_{1-1}$, $R_{21}$, and n are as defined above. In step (1) of Reaction Scheme VIII, a 4-chloro-3-nitroquinoline of Formula XX is reduced to provide a 3-amino-4-chloroquinoline of Formula XLVII. The reduction can be carried out using one of the methods described in step (2) of Reaction Scheme I, and the product of Formula XLVII or a salt thereof can be isolated by conventional methods. Some compounds of Formula XLVII are known. For example, 3-amino-4-chloroquinoline, 3-amino-4,5-dichloroquinoline, and 3-amino-4,7-dichloroquinoline have been prepared by Surrey et al., *Journal of the American Chemical Society*, 73, pp. 2413-2416 (1951). Compounds of Formula XLVII can also be prepared from 3-nitroquinolin-4-ols by the reduction described above followed by chlorination using conventional methods.

In step (2) of Reaction Scheme VIII, a 3-amino-4-chloroquinoline of Formula XLVII is reacted with an acid halide of Formula $R_{2a}C(O)Cl$ or $R_{2a}C(O)Br$ to provide an N-(4-chloroquinolin-3-yl) amide of Formula XLVIII. The acid halide is conveniently added to a solution of a compound of Formula XLVII in a suitable solvent such as anhydrous dichloromethane in the presence of a base such as triethylamine. The reaction can be run at a reduced temperature, for example, 0° C., or at ambient temperature. For compounds wherein $R_{2a}$ is hydrogen, the compound of Formula XLVII can be reacted with a formulating agent such as, for example, diethoxymethyl acetate. The product can be isolated by conventional methods.

In step (3) of Reaction Scheme VIII, an N-(4-chloroquinolin-3-yl) amide of Formula XLVIII is reacted with an amino ester of the Formula $H_2N$—$X_a$—$C(O)$—O-alkyl or a hydrochloride salt thereof to displace the chloro group, and the resulting intermediate is cyclized to form a 1H-imidazo[4,5-c]quinoline of Formula XXIII. The chloride displacement is conveniently carried out by combining a compound of Formula XLVIII with an amino ester of Formula $H_2N$—$X_a$—C(O)—O-alkyl. The reaction may be carried out neat at an elevated temperature such as the temperature required to melt the mixture. The reaction may also be carried out in an alcoholic solvent at the reflux temperature of the solvent. The product can be isolated and optionally purified using conventional techniques before it is heated and cyclized to provide a compound of Formula XXIII. The cyclization reaction is conveniently carried out in a solvent such as toluene, optionally in the presence of a catalyst such as pyridine hydrochloride or pyridinium p-toluenesulfonate. The cyclization may be carried out at an elevated temperature, such as the reflux temperature of the solvent. The 1H-imidazo[4,5-c]quinoline of Formula XXIII can be isolated using conventional methods. Glycine ethyl ester hydrochloride can be employed as the amino ester in this step to provide a compound wherein $X_a$ is —$CH_2$—.

In step (4) of Reaction Scheme VIII, an ester-substituted 1H-imidazo[4,5-c]quinoline of Formula XXIII is oxidized to an N-oxide of Formula XXVI, which is then aminated in step (5) to provide an ester-substituted 1H-imidazo[4,5-c]quinolin-4-amine Formula XXVII. Steps (4) and (5) of Reaction Scheme VIII can be carried out as described for steps (5) and (6) of Reaction Scheme I.

In step (6) of Reaction Scheme VIII, an ester-substituted 1H-imidazo[4,5-c]quinolin-4-amine Formula XXVII is heated in the presence of an amine or ammonium acetate according to one of the methods described in step (3) of Reaction Scheme II to provide a compound of Formula IVb. The product or a pharmaceutically acceptable salt thereof can be isolated using conventional methods.

Reaction Scheme VIII

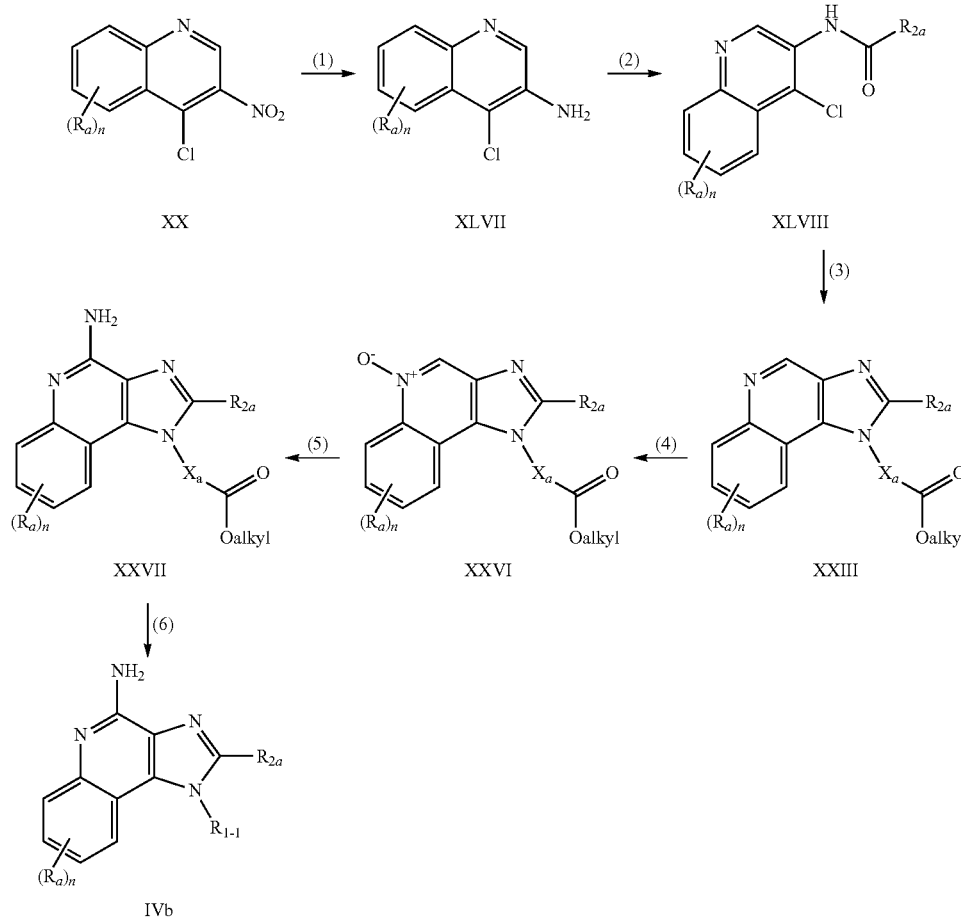

Compounds of the invention can also be prepared according to Reaction Scheme IX, wherein $R_{2b}$, $R_d$, and m are as defined above, and $R_{1-2b}$ is a subset of $R_{1-2}$ as defined above that does not include those substituents that one skilled in the art would recognize as being susceptible to reduction under the acidic hydrogenation conditions of the reaction. These susceptible groups include, for example, alkenyl, alkynyl, and aryl groups and groups bearing nitro substituents.

In Reaction Scheme IX, a 1H-imidazo[4,5-c][1,5]naphthyridin-4-amine of Formula VIb is reduced to a 6,7,8,9-tetrahydro-1H-imidazo[4,5-c][1,5]naphthyridin-4-amine of Formula Xb, a subgenus of Formulas I, II, and X. The reaction is conveniently carried out using the conditions described in Reaction Scheme III, and the product or pharmaceutically acceptable salt thereof can be isolated by conventional methods.

Reaction Scheme IX

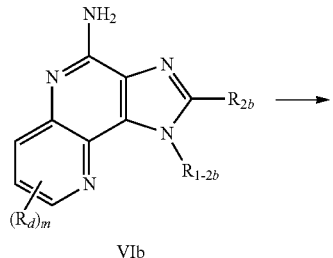

VIb

-continued

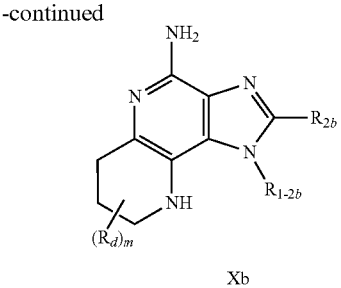

Xb

Compounds of the Formula $H_2N$—$X_a$—C(O)—O-alkyl or $H_2N$—X"—C(O)—O-alkyl in which $X_a$ or X" contains a cyclic alkyl group can be used in step (1) of Reaction Scheme I, IV, V, VI, or VII or in step (3) of Reaction Scheme VIII to prepare some compounds of the invention. These amino esters can be readily prepared in two steps from ethylcyanoacetate. In the first step, ethylcyanoacetate is combined with an alkyl dihalide, for example a dibromide of formula Br-alkylene-Br, in the presence of a base such as potassium carbonate in a suitable solvent such as acetone or DMF. The reaction can be carried out at ambient temperature or at an elevated temperature, and the product can be isolated by conventional methods. Numerous dibromides of formula Br-alkylene-Br can be obtained commercially, including, for example, 1,2-dibromoethane, 1,3-dibromopropane, 1,4-dibromobutane, and 1,5-dibromopentane. The resulting 1-cyanocycloalkanecarboxylate is then reduced to a 1-aminomethylcycloalkanecarboxylate using heterogeneous hydrogenation conditions. The reduction is conveniently carried out in the presence of acid, for example concentrated hydrochloric acid, with catalytic platinum (IV) oxide in a suitable solvent such as ethanol. The hydrogenation is conveniently carried out in a Parr apparatus, and the product can be isolated by conventional methods. When 1,2-dibromoethane, 1,3-dibromopropane, 1,4-dibromobutane, or 1,5-dibromopentane is used in the first step of this method, an amino ester of formula

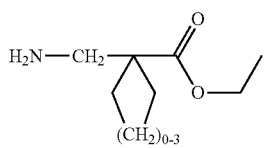

is obtained.

Synthetic transformations can be made at the $R_2$ position in many of the compounds shown in Reaction Schemes I through IX, if, for example, the carboxylic acid or equivalent thereof used in step (3) of Reaction Scheme I, IV, VI, or VII, step (4) of Reaction Scheme V, or step (2) of Reaction Scheme VIII contains a protected hydroxy or amino group. Some acid chlorides of this type are commercially available; others can be prepared by known synthetic methods. A protected hydroxy or amino group thus installed at the $R_2$ position can then be deprotected by a variety of methods well known to one of skill in the art. For example, hydroxyalkylenyl group is conveniently introduced at the $R_2$ position by the demethylation of a methoxyalkylenyl group, which can be installed by using a methoxy-substituted carboxylic acid equivalent, for example, methoxyacetyl chloride and 2-methoxypropionyl chloride, in step (3) of Reaction Scheme I. The demethylation can be carried out by treating a compound wherein $R_2$ is a methoxyalkylenyl group with boron tribromide in a suitable solvent such as dichloromethane at a sub-ambient temperature such as 0° C. The resulting hydroxy group may then be oxidized to an aldehyde or carboxylic acid or converted to a leaving group such as, for example, a chloro group using thionyl chloride or a trifluoromethanesulfonate group using trifluoromethanesulfonic anhydride. The resulting leaving group can then be displaced by a variety of nucleophiles. Sodium azide can be used as the nucleophile to install an azide group, which can then be reduced to an amino group using heterogeneous hydrogenation conditions. An amino group at the $R_2$ position can be converted to an amide, sulfonamide, sulfamide, or urea using conventional methods. A leaving group at $R_2$, such as a chloro or trifluoromethanesulfonate group, can also be displaced with a secondary amine, a substituted phenol, or a mercaptan in the presence of a base such as potassium carbonate. For examples of these and other methods used to install a variety of groups at the $R_2$ position, see U.S. Pat. No. 5,389,640 (Gerster et al.).

Some further synthetic elaborations can also be carried out at the $R_{1-1}$ or $R_{1-2}$ group in compounds prepared in Reaction Schemes I through IX. For example, the cyclic amine group added in step (4) or (4b) in Reaction Scheme I or IV may be thiomorpholine, which can be oxidized to a 1,1-dioxothiomorpholine group in step (5) of Reaction Scheme I or IV using an excess of the oxidizing agent. Step (6) of Reaction Scheme I or IV may then be carried out to provide a compound of Formula IVa or VIa, wherein $R_{1-1}$ or $R_{1-2}$ is

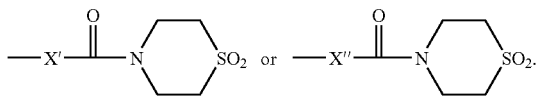

The amination reaction shown in step (6) of Reaction Scheme I or IV, step (2) of Reaction Scheme II, or step (5) of Reaction Scheme VIII can be carried out by an alternative to the method described in step (6) of Reaction Scheme I. The reaction can be carried out by treating a 5N-oxide of Formula XXV, XXVI, or XXXIII with trichloroacetyl isocyanate followed by hydrolysis of the resulting intermediate to provide a compound of Formula IVa, XXVII, or VIa, respectively. The reaction is conveniently carried out in two steps by (i) adding trichloroacetyl isocyanate to a solution of a 5N-oxide in a solvent such as dichloromethane and stirring at ambient temperature to provide an isolable amide intermediate. In step (ii), a solution of the intermediate in methanol is treated with a base such as sodium methoxide or ammonium hydroxide at ambient temperature. The product or pharmaceutically acceptable salt thereof can be isolated using conventional methods.

Compounds of the invention can also be prepared using variations of the synthetic routes shown in Reaction Schemes I through IX that would be apparent to one of skill in the art. For example, the synthetic route shown in Reaction Scheme VIII for the preparation of 1H-imidazo[4,5-c]quinolines can be used to prepare 1H-imidazo[4,5-c][1,5]naphthyridines by starting with a 4-chloro-3-nitro[1,5]naphthyridine of Formula XXVIII in lieu of the 4-chloro-3-nitroquinoline of Formula XX. Compounds of the invention can also be prepared using the synthetic routes described in the EXAMPLES below.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as, for example, cytokine induction, immunomodulation, antitumor activity, and/or antiviral activity. Although the exact amount of active compound or salt used in a pharmaceutical composition of the invention will vary according to factors known to those of skill in the art such as, for example, the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (µg/kg) to about 5 mg/kg, of the compound or salt to the subject. A variety of dosage forms may be used, such as tablets, lozenges, capsules, parenteral formulations, syrups, creams, ointments, gels, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including, for example, additional immune response modifiers, antivirals, antibiotics, antibodies, proteins, peptides, oligonucleotides, etc.

Compounds or salts of the invention have been shown to induce the production of certain cytokines in experiments performed according to the test set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-α (IFN-α) and/or tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, one aspect of the invention provides a method of inducing cytokine biosynthesis in an animal. Generally, the method includes administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which compounds or salts identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such chlamydia, fungal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, compounds or salts of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts of the present invention may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

EXAMPLES

Objects and advantages of this invention are further illustrated by the following examples, but the particular materials and amounts thereof recited in these examples, as well as other conditions and details, should not be construed to unduly limit this invention.

Example 1

1-(4-Morpholin-4-yl-4-oxobutyl)-2-propyl-1H-imidazo[4,5-c]quinolin-4-amine

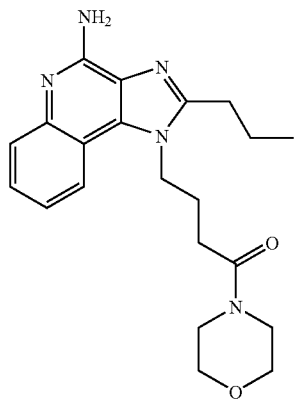 [SMILES: CCCc1nc2c(N)nc3ccccc3c2n1CCCC(=O)N1CCOCC1]

Part A

Ethanol (500 mL) was cooled to 0° C., and thionyl chloride (85 mL, 1.2 mol) was added dropwise with stirring. The reaction was stirred for one hour at 0° C., and solid 4-aminobutyric acid (100 g, 0.97 mol) was then added. After ten minutes of stirring, the reaction was allowed to warm to ambient temperature and stirred for two hours. The reaction was then allowed to stand at ambient temperature overnight. The ethanol was removed under reduced pressure, and the solid residue was dissolved in ethyl acetate. After one hour, the solution was cooled to 0° C., and a precipitate formed. The precipitate was isolated by filtration and washed with diethyl ether (300 mL) to provide 126.6 g of ethyl 4-aminobutyrate hydrochloride as a white solid. A precipitate formed in the filtrate and was isolated by filtration to provide 19.1 g of ethyl 4-aminobutyrate hydrochloride as a white solid.

Part B

Triethylamine (50.0 mL, 358 mmol) and potassium carbonate (40 g, 290 mmol) were added to a solution of 4-chloro-3-nitroquinoline (49.6 g, 238 mmol) in tetrahydrofuran (THF) (100 mL) and chloroform (250 mL). Ethyl 4-aminobutyrate hydrochloride (43.8 g, 262 mmol) was added in portions over a period of five minutes during which time an ice bath was used to cool the reaction. The reaction was stirred with cooling for 30 minutes, allowed to warm to ambient temperature, and stirred overnight. An analysis by thin layer chromatography (TLC) indicated the presence of 4-chloro-3-nitroquinoline. Additional ethyl 4-aminobutyrate hydrochloride (8.0 g, 48 mmol) was added, and the reaction was stirred at ambient temperature for one hour and then heated at reflux for two hours. Additional triethylamine (20 mL) was added, and the reaction was heated at reflux for one hour, cooled to ambient temperature, washed with water (3×100 mL), dried over potassium carbonate, filtered, and concentrated under reduced pressure to provide 63.8 g of ethyl 4-(3-nitroquinolin-4-ylamino)butyrate as a yellow solid.

Part C

A mixture of ethyl 4-(3-nitroquinolin-4-ylamino)butyrate (20.0 g, 65.9 mmol), 10% palladium on carbon (0.50 g), and ethanol (250 ml) was added to a Parr vessel, and the reaction was placed under hydrogen pressure (43 psi, 3.0×10⁵ Pa) for 3.5 hours. The pressure decreased to 31 psi (2.1×10⁵ Pa) during the reaction. The reaction mixture was filtered through a layer of CELITE filter agent, and the filtrate was concentrated under reduced pressure.

Part D

Trimethyl orthobutyrate (10.4 g, 70.2 mmol) and pyridinium p-toluenesulfonate (0.25 g, 1.0 mmol) were added to a solution of the material from Part C in toluene (350 mL), and the reaction was heated at reflux under a Dean-Stark trap for three hours while the distillate was periodically removed. The toluene was removed under reduced pressure, and the residue was stirred with 70:30 hexanes:ethyl acetate (75 mL). Additional hexane (50 mL) was added to form a precipitate. The supernatant liquid was decanted away to afford 6.75 g of a brown solid, which was mixed with 2.08 g of material from another run. The crude product was then purified by column chromatography on silica gel (eluting with 95:5 dichloromethane:methanol) to provide 14.2 g of ethyl 4-(2-propyl-1H-imidazo[4,5-c]quinolin-1-yl)butanoate as an oil that crystallized upon standing.

Part E

Trimethylaluminum (available as a 2 M solution in toluene, 15.5 mL, 31.0 mmol) was added dropwise with stirring to a solution of morpholine (2.7 mL, 31 mmol) in dichloromethane (75 mL) at ambient temperature. After 20 minutes, a solution of ethyl 4-(2-propyl-1H-imidazo[4,5-c]quinolin-1-yl)butanoate (5.0 g, 15 mmol) in dichloromethane (15 mL) was added dropwise. The reaction was then heated at reflux for three days. An analysis by high-performance liquid chromatography (HPLC) indicated the presence of starting material, and additional morpholine (0.2 mL) was adder. The reaction was heated at reflux for three hours and then allowed to stand at room temperature over three days. Hydrochloric acid (4 mL of 10%) was slowly added followed by saturated aqueous sodium bicarbonate (8 mL). The organic layer was decanted away from solids formed during the reaction. The solids were extracted with dichloromethane (2×50 mL), and the combined organic fractions were washed with 5% aqueous sodium hydroxide (35 mL) and saturated aqueous sodium bicarbonate (35 mL), dried over potassium carbonate, filtered, and concentrated under reduced pressure to provide a light yellow solid.

Part F

3-Chloroperoxybenzoic acid (mCPBA) (available as 77% pure material, 8.5 g, 38 mmol) was added in portions over a period of two minutes to a solution of the material from Part E in dichloromethane (100 mL), and the reaction was stirred for 45 minutes at ambient temperature and then washed with 5% aqueous sodium hydroxide (2×35 mL) and water (25 mL). Concentrated ammonium hydroxide (100 mL of 29%) and p-toluenesulfonyl chloride (4.9 g, 26 mmol) were then sequentially added with vigorous stirring, and the reaction was stirred for 30 minutes. The aqueous layer was separated and extracted with dichloromethane (4×50 mL). The combined organic fractions were washed with 5% aqueous sodium hydroxide solution (2×50 mL), dried over potassium carbonate, filtered, and concentrated under reduced pressure. The residue was recrystallized twice from acetonitrile (15 mL) and methanol (4 mL) to provide 0.96 g of a light orange solid. A portion was dried overnight in a vacuum oven to provide 1-(4-morpholin-4-yl-4-oxobutyl)-2-propyl-1H-imidazo[4,5-c]quinolin-4-amine as a light yellow needles, mp 200-202° C.

Anal. Calcd for $C_{21}H_{27}N_5O_2$: C, 66.12; H, 7.13; N, 18.36. Found: C, 65.86; H, 7.39; N, 18.21.

Example 2

4-(4-Amino-2-propyl-1H-imidazo[4,5-c]quinolin-1-yl)-N-propylbutanamide

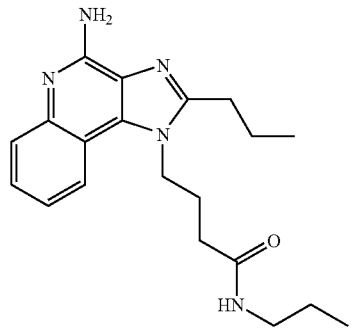 [SMILES: CCCNC(=O)CCCn1c(CCC)nc2c(N)nc3ccccc3c21]

Part A

A solution of n-propylamine (3.0 mL, 36 mmol) in dichloromethane (75 mL) was cooled to 0° C.; trimethylaluminum (available as a 2 M solution in toluene, 18 mL, 36 mmol) was added dropwise with stirring over a period of three minutes. The reaction was stirred for one hour at 0° C. and 30 minutes at ambient temperature. A solution of ethyl 4-(2-propyl-1H-imidazo[4,5-c]quinolin-1-yl)butanoate (5.80 g, 17.8 mmol, prepared as described in Parts A-D of Example 1) in dichloromethane (30 mL) was added, and the reaction was then heated at reflux for three days. The work-up procedure described in Part E of Example 1 was followed to provide N-propyl-4-(2-propyl-1H-imidazo[4,5-c]quinolin-1-yl)butanamide as a brown oil.

Part B

N-Propyl-4-(2-propyl-1H-imidazo[4,5-c]quinolin-1-yl)butanamide (5.6 g, 15 mmol) was treated with mCPBA (8.5 g, 38 mmol), concentrated ammonium hydroxide (100 mL), and p-toluenesulfonyl chloride (4.9 g, 26 mmol) according to the method described in Part F of Example 1. The crude product was dissolved in hot toluene (25 mL) and dichloromethane. A precipitate slowly formed, was isolated by filtration, and was washed with toluene (15 mL). The solid was recrystallized twice from 4:1 methanol:water (25 mL), and the crystals were heated at reflux in chloroform in the presence of charcoal (1 g). The mixture was filtered through a layer of CELITE filter agent, and the filtrate was concentrated under reduced pressure. The residue was recrystallized twice from methanol:water and twice from toluene (15 mL) and dried overnight in a vacuum even to provide 0.74 g of 4-(4-amino-2-propyl-1H-imidazo[4,5-c]quinolin-1-yl)-N-propylbutanamide as a grey solid, mp 161-163° C.

Anal. Calcd for $C_{20}H_{27}N_5O$: C, 67.96; H, 7.70; N, 19.81. Found: C, 67.64; H, 7.92; N, 19.83.

Example 3

4-(4-Amino-2-propyl-1H-imidazo[4,5-c]quinolin-1-yl)-N-methylbutanamide

Part A

A suspension of 4-chloro-3-nitroquinoline (75.0 g, 0.360 mol) in chloroform (400 mL) was cooled to 0° C.; triethylamine (75 mL, 0.54 mol) was added. Ethyl 4-aminobutyrate hydrochloride (66.0 g, 0.390 mol), prepared as described in Part A of Example 1, was added in portions over a period of five minutes. The reaction was stirred at 0° C. for 1 hour, allowed to warm to ambient temperature, and stirred overnight. An analysis by thin layer chromatography (TLC) indicated the presence of 4-chloro-3-nitroquinoline. Additional triethylamine (15 mL) was added, and the reaction was stirred for one hour. Additional ethyl 4-aminobutyrate hydrochloride (10.0 g) was added, and the reaction was heated at reflux for five hours. Additional triethylamine (22 mL) was added, and the reaction was stirred overnight at ambient temperature and heated at reflux for one hour. An analysis by TLC indicated the reaction was complete. The reaction was cooled to ambient temperature and washed with water (5×400 mL), and the resulting solution was used in Part B.

Part B

Chloroform was added to the material from Part A to provide a volume of 750 mL. Water (600 mL), potassium carbonate (80 g, 0.6 mol), and 1,1'-di-n-octyl-4,4'-bipyridinium dibromide (0.50 g, 0.92 mmol) were added. Sodium hydrosulfite (available as 85% pure material, 120 g, 0.68 mol) was then added in portions over a period of one hour, and the reaction was stirred at ambient temperature for three days. The reaction was not complete as evidenced by an HPLC analysis. Additional sodium hydrosulfite (20 g), potassium carbonate (20 g), and 1,1'-di-n-octyl-4,4'-bipyridinium dibromide (0.25 g) were added, and the reaction was stirred for three hours. Additional sodium hydrosulfite (20 g), potassium carbonate (20 g), and water (200 mL) were added, and the reaction was stirred overnight. Additional sodium hydrosulfite (5 g) and potassium carbonate (5 g) were added, and the reaction was stirred for three hours. Additional sodium hydrosulfite (5 g) was added, and the reaction was stirred for two hours. An analysis by TLC indicated the reaction was complete. The organic layer was separated and washed with water (5×200 mL), dried over potassium carbonate, and concentrated under reduced pressure to provide 97.4 g of ethyl 4-[(3-aminoquinolin-4-yl)amino]butanoate as a dark oil.

Part C

A solution of ethyl 4-[(3-aminoquinolin-4-yl)amino]butanoate (72.0 g, 263 mmol) in toluene (700 mL) was heated at reflux for 10 minutes and then cooled slightly. Trimethyl orthobutyrate (42 g, 280 mmol) and pyridinium p-toluenesulfonate (1.0 g, 4.0 mmol) were added, and the reaction was heated at reflux under a Dean-Stark trap for two hours while the distillate was periodically removed. The reaction was then stirred overnight at ambient temperature. Charcoal (5 g) was added, and the resulting mixture was heated at reflux for three hours and then filtered through a layer of CELITE filter agent. The filtrate was concentrated under reduced pressure to provide an oil that crystallized upon standing. The solid was dissolved in hot methanol (125 mL), and water (50 mL) was added. After one hour, the mixture was cooled in an ice bath to form a precipitate. The precipitate was isolated by filtration and dissolved in dichloromethane. A layer of water was present and was removed. The remaining solution was dried over potassium carbonate, filtered, and concentrated under reduced pressure to provide 53.2 g of ethyl 4-(2-propyl-1H-imidazo[4,5-c]quinolin-1-yl)butanoate.

Part D

A mixture of ethyl 4-(2-propyl-1H-imidazo[4,5-c]quinolin-1-yl)butanoate (2.0 g, 6.1 mmol), THF (10 mL), and methylamine (available as a 40% solution in water, 4 mL, 52 mmol) was sealed in a high-pressure vessel and heated at 70° C. overnight. An analysis by TLC indicated the presence of starting material, and the reaction was sealed and heated at 80° C. for nine hours. The solvent was removed under reduced pressure, and the residue was dissolved in dichloromethane (100 mL). The resulting solution was washed with 5% aqueous sodium hydroxide (2×25 mL), dried over potassium carbonate, filtered, and concentrated under reduced pressure to provide 1.83 g of N-methyl-4-(2-propyl-1H-imidazo[4,5-c]quinolin-1-yl)butanamide.

Part E mCPBA (3.3 g, 15 mmol) was added to a solution of N-methyl-4-(2-propyl-1H-imidazo[4,5-c]quinolin-1-yl)butanamide (1.83 g, 5.90 mmol) in chloroform (75 mL), and the reaction was stirred for 1.5 hours at ambient temperature. Concentrated ammonium hydroxide (75 mL of 29%) and p-toluenesulfonyl chloride (1.7 g, 8.9 mmol) were then sequentially added with stirring, and the reaction was stirred for 45 minutes. The aqueous layer was separated and extracted with chloroform (1×50 mL). The combined organic fractions were washed with 5% aqueous sodium hydroxide solution (2×50 mL), dried over potassium carbonate, filtered, and concentrated under reduced pressure. The residue was recrystallized from a mixture of toluene (20 mL) and methanol (4 mL) and then recrystallized three times from 5:1 methanol:water (18 mL) and dried overnight in a vacuum oven at 80° C. During the recrystallization, the product was mixed with material from another run to provide 0.720 g of 4-(4-amino-2-propyl-1H-imidazo[4,5-c]quinolin-1-yl)-N-methylbutanamide as a tan solid, hp 177-179° C.

Anal. Calcd for $C_{18}H_{23}N_5O \cdot 0.19H_2O$: C, 65.75; H, 7.17; N, 21.30. Found: C, 65.91; H, 7.35; N, 21.32.

Example 4

4-(4-Amino-2-propyl-1H-imidazo[4,5-c]quinolin-1-yl)butanamide

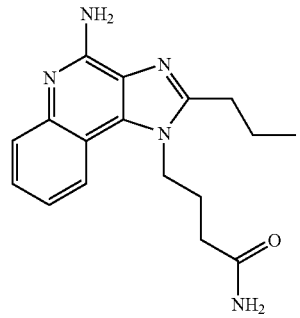 [SMILES: CCCc1nc2c(N)nc3ccccc3c2n1CCCC(N)=O]

Part A

A solution of ethyl 4-[(3-aminoquinolin-4-yl)amino]butanoate (49.7 g, 182 mmol, prepared as described in Parts A and B of Example 3) in toluene (500 mL) was heated at reflux for 10 minutes and then cooled slightly. Trimethyl orthobutyrate (29.0 g, 197 mmol) and pyridinium p-toluenesulfonate (0.70 g, 2.8 mmol) were added, and the reaction was heated at reflux under a Dean-Stark trap for 1.5 hours while the distillate was periodically removed. The reaction was allowed to stand overnight at ambient temperature. The toluene was removed under reduced pressure; chloroform (500 mL) and charcoal (4 g) were sequentially added. The resulting mixture was heated at reflux for one hour and then filtered through a layer of CELITE filter agent. The filtrate was washed with saturated aqueous sodium bicarbonate (100 mL), dried over potassium sulfate, filtered, and concentrated under reduced pressure to provide 49.4 g of ethyl 4-(2-propyl-1H-imidazo[4,5-c]quinolin-1-yl)butanoate as a dark oil.

Part B

Concentrated ammonium hydroxide (8.0 mL of 29%) was added to a solution of ethyl 4-(2-propyl-1H-imidazo[4,5-c]quinolin-1-yl)butanoate (5.1 g, 16 mmol) in 2-methyltetrahydrofuran (10 mL), and the mixture was heated overnight in a sealed high-pressure vessel at 80° C. An analysis by liquid chromatography/mass spectrometry (LC/MS) indicated the reaction was incomplete. The solvents were evaporated under a stream of nitrogen, and ammonium acetate (10 g) was added. The vessel was sealed and heated overnight at 135° C. The reaction was allowed to cool to ambient temperature, and water (50 mL) was added. The mixture was filtered, and the filtrate was washed with saturated aqueous sodium bicarbonate (25 mL), dried over potassium carbonate, filtered, and concentrated under reduced pressure to provide 2.95 g of 4-(2-propyl-1H-imidazo[4,5-c]quinolin-1-yl)butanamide as a light brown solid.

Part C 4-(2-Propyl-1H-imidazo[4,5-c]quinolin-1-yl)butanamide (2.90 g, 9.78 mmol) was treated with mCPBA (5.5 g, 25 mmol), concentrated ammonium hydroxide (100 mL of 29%), and p-toluenesulfonyl chloride (2.80 g, 14.7 mmol) according to the method described in Part E of Example 3. After the reaction solution was dried with potassium carbonate, it was decanted, and charcoal (2 g) was added. The mixture was heated at reflux for two hours, filtered through a layer of CELITE filter agent, and concentrated under reduced pressure. The crude solid was purified by column chromatography on silica gel (eluting with 90:10 dichloromethane:methanol) and combined with material from another run. The solid was recrystallized from 5:1 toluene:methanol (18 mL), dried overnight in a vacuum oven, recrystallized from ethanol:water, and dried overnight in a vacuum oven to provide 4-(4-amino-2-propyl-1H-imidazo[4,5-c]quinolin-1-yl)butanamide as a tan solid, mp 249-251° C.

Anal. Calcd for $C_{17}H_{21}N_5O$: C, 65.57; H, 6.80; N, 22.49. Found: C, 65.24; H, 6.79; N, 22.16.

Example 5

2-(Ethoxymethyl)-1-(4-morpholin-4-yl-4-oxobutyl)-1H-imidazo[4,5-c]quinolin-4-amine

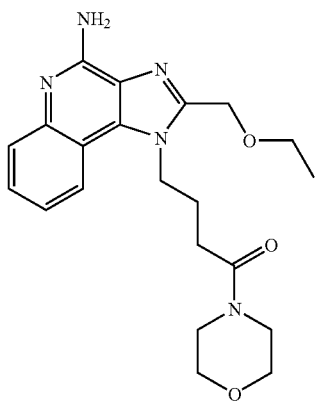 [SMILES: CCOCc1nc2c(N)nc3ccccc3c2n1CCCC(=O)N1CCOCC1]

Part A

A suspension of 4-chloro-3-nitroquinoline (40.0 g, 0.192 mol) in chloroform (250 mL) was cooled to 0° C.; triethylamine (75 mL, 0.54 mol) was added. Ethyl 4-aminobutyrate hydrochloride (35.0 g, 0.210 mol), prepared as described in Part A of Example 1, was added in portions over a period of two minutes. The reaction was stirred at 0° C. for 15 minutes, allowed to warm to ambient temperature, and stirred overnight. The reaction was heated at reflux for 15 minutes, and then chloroform (200 mL) was added. The resulting solution was washed with water (5×150 mL) and then used in Part B.

Part B

Water (400 mL), potassium carbonate (105 g, 0.760 mol), ethyl viologen dibromide (0.50 g, 1.3 mmol), and sodium hydrosulfite (115 g, 0.660 mol) were sequentially added to the solution from Part A. The reaction was stirred at ambient temperature for three days. The organic layer was separated and washed with water (3×200 mL), dried over potassium carbonate, and concentrated under reduced pressure to provide 48.4 g of ethyl 4-[(3-aminoquinolin-4-yl)amino]butanoate as an orange oil.

Part C

A solution of ethoxyacetyl chloride (6.61 g, 54.0 mmol) in dichloromethane (10 mL) was added dropwise to a solution of ethyl 4-[(3-aminoquinolin-4-yl)amino]butanoate (11.8 g, 43.2 mmol) in dichloromethane (150 mL). The reaction was stirred for 30 minutes and then concentrated under reduced pressure. Triethylamine (16.7 g, 165 mmol) and ethanol (150 mL) were added, and the resulting solution was heated at reflux for four hours. The solvent was removed under reduced pressure. Dichloromethane (75 mL) was added, and the resulting solution was washed sequentially with water (3×75 mL) and saturated aqueous sodium bicarbonate (75 mL), dried over potassium carbonate, filtered, and concentrated under reduced pressure to provide 12.5 g of ethyl 4-[2-(ethoxymethyl)-1H-imidazo[4,5-c]quinolin-1-yl]butanoate as a dark oil.

Part D

Ethyl 4-[2-(ethoxymethyl)-1H-imidazo[4,5-c]quinolin-1-yl]butanoate (6.25 g, 18.3 mmol) and morpholine (16.0 g, 184 mmol) were sealed and heated in a high-pressure vessel at 130° C. overnight. An analysis by TLC indicated the reaction was incomplete. Pyridinium p-toluenesulfonate (100 mg) was added, and the reaction was heated for three days at 105° C. and for one day at 125° C. The solution was allowed to cool and then poured into water (100 mL). The resulting solution was extracted with dichloromethane (3×75 mL), and the combined extracts were dried over potassium carbonate, filtered, and concentrated under reduced pressure. The residue was mixed with ethyl acetate (50 mL) and hexane (200 mL) and sonicated. The solvent was decanted away to afford 6.9 g of 2-(ethoxymethyl)-1-(4-morpholin-4-yl-4-oxobutyl)-1H-imidazo[4,5-c]quinoline as an oil.

Part E 2-(Ethoxymethyl)-1-(4-morpholin-4-yl-4-oxobutyl)-1H-imidazo[4,5-c]quinoline (6.9 g, 18 mmol) was treated with mCPBA (7.9 g, 35 mmol), concentrated ammonium hydroxide (50 mL of 29%), and p-toluenesulfonyl chloride (6.0 g, 32 mmol) according to a modification of the method described in Part E of Example 3. The mCPBA addition was carried out at 0° C., and the reaction was carried out in dichloromethane (150 mL). The crude product was triturated with 2:1 ethyl acetate:hexane (15 mL), and the resulting solid was isolated by filtration, washed with 30:70 ethyl acetate:hexane, recrystallized twice from methanol:water, and dried overnight in a vacuum oven at 70° C. to provide 2-(ethoxymethyl)-1-(4- morpholin-4-yl-4-oxobutyl)-1H-imidazo[4,5-c]quinolin-4-amine as yellow crystals, mp 201-203° C.

Anal. Calcd for $C_{21}H_{27}N_5O_3$: C, 63.46; H, 6.85; N, 17.62. Found: C, 63.24; H, 6.84; N, 17.54.

Example 6

1-(6-Morpholin-4-yl-6-oxohexyl)-2-propyl-1H-imidazo[4,5-c]quinolin-4-amine

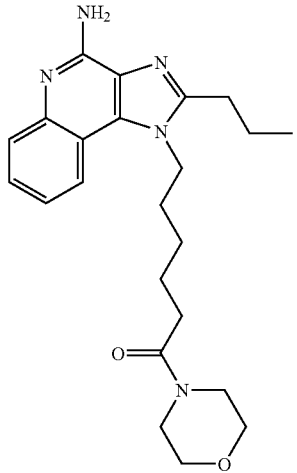 [SMILES: CCCc1nc2c(N)nc3ccccc3c2n1CCCCCC(=O)N1CCOCC1]

Part A

Anhydrous ethanol (400 mL) was cooled to −78° C., and thionyl chloride (63.34 mL, 868.4 mmol) was added. The reaction was stirred for one hour at −78° C., and solid 6-aminocaproic acid (100.0 g, 723.7 mmol) was then added. The reaction was allowed to warm to ambient temperature slowly, stirred overnight, and then concentrated under reduced pressure. The residue was recrystallized from ethyl acetate:diethyl ether to provide 137 g of ethyl 6-aminocaproate hydrochloride as a white solid.

Part B

Potassium carbonate (6.62 g, 47.9 mmol) and triethylamine (16.7 mL, 0.120 mol) were sequentially added with stirring to a solution of 4-chloro-3-nitroquinoline (10.0 g, 47.9 mmol) in chloroform (200 mL). After 15 minutes, ethyl 6-aminocaproate hydrochloride (11.23 g, 57.52 mmol) was slowly added, and the reaction was stirred for two hours; washed sequentially with water (200 mL), saturated aqueous sodium bicarbonate, and brine; dried over magnesium sulfate; filtered; concentrated under reduced pressure; and used in Part C without purification.

Part C

The material from Part B was hydrogenated according to the method described in Part C of Example 1 to provide 15.0 g of ethyl 6-[(3-aminoquinolin-4-yl)amino]hexanoate.

Part D

Trimethyl orthobutyrate (15.0 g, 49.8 mmol) and pyridinium p-toluenesulfonate (0.20 g, 0.80 mmol) were added to a solution ethyl 6-[(3-aminoquinolin-4-yl)amino]hexanoate (15.0 g, 49.8 mmol) in toluene (400 mL), and the reaction was heated at reflux under a Dean-Stark trap for 4.5 hours while the distillate was periodically removed. The reaction was allowed to cool to ambient temperature, washed sequentially with saturated aqueous sodium bicarbonate and brine, dried over magnesium sulfate, filtered, and concentrated under reduced pressure to provide ethyl 6-(2-propyl-1H-imidazo[4,5-c]quinolin-1-yl)hexanoate, which was used without purification.

Part E

A solution of sodium hydroxide (4.35 g, 109 mmol) in water (50 mL) was added to a solution of the material from Part D in ethanol (100 mL), and the reaction was stirred at ambient temperature for three hours. Additional sodium hydroxide (2.2 g, 55 mmol) was added, and the reaction was stirred for an additional hour and then concentrated under reduced pressure. The residue was diluted with water (100 mL) and adjusted to pH 5 with the addition of 10% hydrochloric acid. The mixture was extracted three times with chloroform, and the combined extracts were dried over magnesium sulfate, filtered, and concentrated under reduced pressure to provide 12.4 g of 6-(2-propyl-1H-imidazo[4,5-c]quinolin-1-yl)hexanoic acid.

Part F

A solution of 6-(2-propyl-1H-imidazo[4,5-c]quinolin-1-yl)hexanoic acid (3.0 g, 9.2 mmol) in anhydrous dichloromethane (50 mL) was cooled to 0° C. Oxalyl chloride (1.44 mL, 16.6 mmol) was added dropwise over a period of 15 minutes. The resulting solution was allowed to warm to ambient temperature and stirred for one hour and then concentrated under reduced pressure. The residue was dissolved in dichloromethane (50 mL), and morpholine (2.41 mL, 27.6 mmol) was added. The reaction was stirred overnight, washed sequentially with saturated aqueous sodium bicarbonate and brine, dried over magnesium sulfate, filtered, and concentrated under reduced pressure to provide 3.6 g of 1-(6-morpholin-4-yl-6-oxohexyl)-2-propyl-1H-imidazo[4,5-c]quinoline.

Part G

Under a nitrogen atmosphere, a solution of 1-(6-morpholin-4-yl-6-oxohexyl)-2-propyl-1H-imidazo[4,5-c]quinoline (3.6 g, 9.1 mmol) in chloroform (100 mL) was treated with mCPBA (6.29 g, 36.5 mmol). The reaction was stirred for two hours, washed sequentially with saturated aqueous sodium bicarbonate (3×) and brine, dried over magnesium sulfate, and filtered. Concentrated ammonium hydroxide (40 mL) and p-toluenesulfonyl chloride (2.60 g, 13.7 mmol) were added sequentially to the filtrate. The reaction was stirred vigorously for two hours, and then the organic layer was separated and washed sequentially with saturated aqueous sodium bicarbonate and brine, dried over magnesium sulfate, filtered, and concentrated under reduced pressure. The crude product was purified by column chromatography on silica gel (eluting with 95:5 dichloromethane:methanol) followed by recrystallization from ethyl acetate:hexane to provide 0.84 g of 1-(6-morpholin-4-yl-6-oxohexyl)-2-propyl-1H-imidazo[4,5-c]quinolin-4-amine as brown needles, mp 149-151° C.

Anal. Calcd for $C_{23}H_{31}N_5O_2$: C, 67.46; H, 7.63; N, 17.12. Found: C, 67.28; H, 7.56; N, 16.75.

Example 7

6-(4-Amino-2-propyl-1H-imidazo[4,5-c]quinolin-1-yl)-N-propylhexanamide

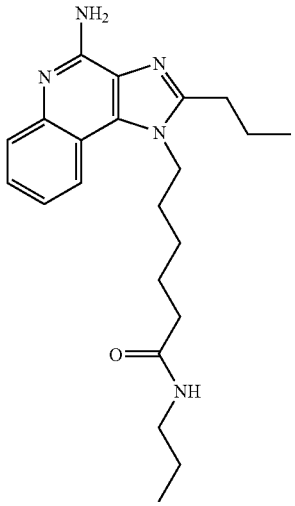 [SMILES: CCCNC(=O)CCCCCn1c(CCC)nc2c(N)nc3ccccc3c21]

Part A 6-(2-Propyl-1H-imidazo[4,5-c]quinolin-1-yl)hexanoic acid (3.0 g, 9.2 mmol, prepared in Parts A through E of Example 6) was treated with oxalyl chloride (1.45 mL, 16.6 mmol) and n-propylamine (2.27 mL, 27.6 mmol) according to the method described in Part F of Example 6 to provide 3.4 g of N-propyl-6-(2-propyl-1H-imidazo[4,5-c]quinolin-1-yl) hexanamide. The acid chloride solution was cooled to 0° C. before the addition of n-propylamine.

Part B mCPBA (6.4 g, 37.1 mmol) was added to a solution of the material from Part A in chloroform (75 mL). The reaction was stirred for two hours, washed sequentially with saturated aqueous sodium bicarbonate (2 x) and brine, dried over magnesium sulfate, and filtered. Concentrated ammonium hydroxide (40 mL) was added to the filtrate. The mixture was stirred for ten minutes before the addition of p-toluenesulfonyl chloride (2.65 g, 13.9 mmol). The reaction was stirred vigorously for two hours, and then the organic layer was separated and washed sequentially with 10% sodium hydroxide (2×) and brine, dried over magnesium sulfate, filtered, and concentrated under reduced pressure. The crude product was purified by column chromatography on silica gel (eluting with dichloromethane:methanol in a gradient from 97:3 to 95:5) followed by recrystallization from methanol:water to provide 0.45 g of 6-(4-amino-2-propyl-1H-imidazo[4,5-c] quinolin-1-yl)-N-propylhexanamide as brown needles, mp 139-141° C.

Anal. Calcd for $C_{22}H_{31}N_5O \cdot 0.44H_2O$: C, 67.85; H, 8.25; N, 17.98. Found: C, 67.80; H, 8.22; N, 17.82.

Example 8

6-(4-Amino-2-propyl-1H-imidazo[4,5-c]quinolin-1-yl)-N-methylhexanamide

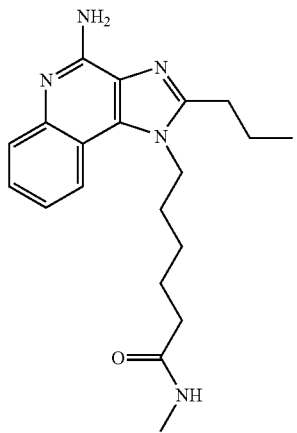 [SMILES: CCCc1nc2c(N)nc3ccccc3c2n1CCCCCC(=O)NC]

Part A

A solution of sodium hydrosulfite (73.55 g, 422.4 mmol) and potassium carbonate (65.9 g, 476 mmol) in water (200 mL) was stirred for 15 minutes. A mixture of ethyl 6-(3-nitroquinolin-4-ylamino)hexanoate (40.0 g, 121 mmol, prepared as described in Parts A and B of Example 6), 1,1'-di-n-octyl-4,4'-bipyridinium dibromide (0.65 g, 1.2 mmol), dichloromethane (200 mL), and water (40 mL) was added over a period of five minutes, and the reaction was stirred overnight at ambient temperature. Water (100 mL) was added; the organic layer was separated and washed with water (3×150 mL), dried over potassium carbonate, filtered, and concentrated under reduced pressure to provide 25.15 g of ethyl 6-[(3-aminoquinolin-4-yl)amino]hexanoate. The product was mixed with material from another run.

Part B

A solution of ethyl 6-[(3-aminoquinolin-4-yl)amino]hexanoate (44.0 g, 146 mmol) in toluene (500 mL) was heated at reflux under a Dean-Stark trap for 1.5 hours and then allowed to cool to ambient temperature. Trimethyl orthobutyrate (29.2 mL, 182.5 mmol) and pyridinium p-toluenesulfonate (0.300 g, 1.20 mmol) were sequentially added, and the reaction was heated at reflux for three hours, allowed to cool to ambient temperature, and concentrated under reduced pressure. The residue was dissolved in dichloromethane, and the resulting solution was washed sequentially with saturated aqueous sodium bicarbonate and brine, dried over magnesium sulfate, filtered, and concentrated under reduced pressure. The crude product was purified by column chromatography on silica gel (eluting with 97:3 dichloromethane:methanol) to provide 38 g of ethyl 6-(2-propyl-1H-imidazo[4,5-c]quinolin-1-yl)hexanoate.

Part C

The method described in Part D of Example 3 was used to treat ethyl 6-(2-propyl-1H-imidazo[4,5-c]quinolin-1-yl)hexanoate (5.0 g, 14 mmol) with methylamine (8 mL of a 40% solution). The reaction was complete after being stirred overnight at 70° C. Following the work-up procedure, 3.42 g of N-methyl-6-(2-propyl-1H-imidazo[4,5-c]quinolin-1-yl)hexanamide were obtained.

Part D mCPBA (5.0 g, 29.03 mmol) was added to a solution of N-methyl-6-(2-propyl-1H-imidazo[4,5-c]quinolin-1-yl)hexanamide (3.42 g, 9.67 mmol) in chloroform (100 mL). The reaction was stirred for two hours at ambient temperature and then washed with 10% aqueous sodium hydroxide. Ammonium hydroxide (40 mL) and p-toluenesulfonyl chloride (2.39 g, 12.6 mmol) were sequentially added, and the reaction was stirred vigorously for two hours. The organic layer was separated and washed sequentially with 10% sodium hydroxide, saturated aqueous sodium bicarbonate, and brine; dried over magnesium sulfate; filtered; and concentrated under reduced pressure. The crude product was purified by column chromatography on silica gel (eluting with 95:5 dichloromethane:methanol) followed by recrystallization from methanol:water to provide 1.055 g of 6-(4-amino-2-propyl-1H-imidazo[4,5-c]quinolin-1-yl)-N-methylhexanamide as beige needles, mp 158-159° C.

Anal. Calcd for $C_{20}H_{27}N_5O$: C, 67.96; H, 7.70; N, 19.81. Found: C, 67.65; H, 7.45; N, 19.74.

Example 9

6-(4-Amino-2-propyl-1H-imidazo[4,5-c]quinolin-1-yl)hexanamide

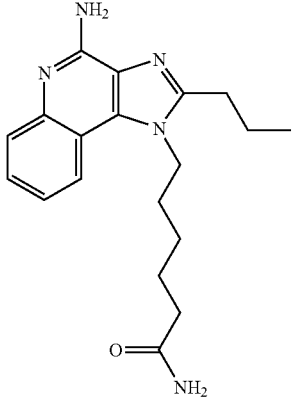 [SMILES: CCCc1nc2c(N)nc3ccccc3c2n1CCCCCC(N)=O]

Part A

A solution ethyl 6-[(3-aminoquinolin-4-yl)amino]hexanoate (25.15 g, 83.4 mmol, prepared in Part A of Example 8) in toluene (400 mL) was treated with trimethyl orthobutyrate (15.4 mL, 96.2 mmol) and pyridinium p-toluenesulfonate (0.20 g, 0.80 mmol) according to, a modification of the method described in Part D of Example 6. The reaction was not complete after five hours and was allowed to cool to ambient temperature overnight. Additional pyridinium p-toluenesulfonate (0.20 g, 0.80 mmol) and trimethyl orthobutyrate (2.0 mL, 12 mmol) were added. The reaction was heated at reflux for two hours and then subjected to the work-up procedure to provide 25.0 g of ethyl 6-(2-propyl-1H-imidazo[4,5-c]quinolin-1-yl)hexanoate.

Part B

Ammonium acetate (20 g) and ethyl 6-(2-propyl-1H-imidazo[4,5-c]quinolin-1-yl)hexanoate (4.11 g, 11.6 mmol) were heated overnight at 140° C. in a sealed vessel. The reaction was allowed to cool to ambient temperature, and saturated aqueous sodium bicarbonate was added. The mixture was extracted with chloroform (3×), and the extracts were combined and concentrated under reduced pressure. The crude product was purified by column chromatography on silica gel (eluting with 95:5 dichloromethane:methanol) to provide 1.7 g of 6-(2-propyl-1H-imidazo[4,5-c]quinolin-1-yl)hexanamide.

Part C 6-(2-Propyl-1H-imidazo[4,5-c]quinolin-1-yl)hexanamide (1.7 g, 5.2 mmol) was treated with mCPBA (3.61 g, 15.7 mmol) followed by ammonium hydroxide (40 mL) and p-toluenesulfonyl chloride (1.49 g, 7.84 mmol) according to the method described in Part D of Example 8. The crude product was purified as described in Part D of Example 8 to provide 0.137 g of 6-(4-amino-2-propyl-1H-imidazo[4,5-c]quinolin-1-yl)hexanamide as tan needles, mp 210-211° C.

Anal. Calcd for $C_{19}H_{25}N_5O$: C, 67.23; H, 7.42; N, 20.63. Found: C, 66.95; H, 7.76; N, 20.43.

Example 10

6-(4-Amino-1H-imidazo[4,5-c]quinolin-1-yl)-N-propylhexanamide

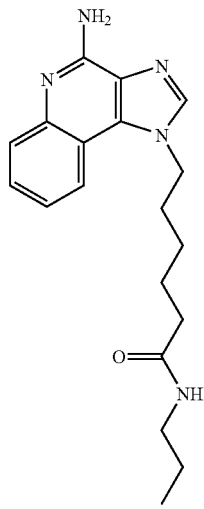 [SMILES: CCCNC(=O)CCCCCn1cnc2c(N)nc3ccccc3c21]

Part A

Triethyl orthoformate (12.74 mL, 76.64 mmol) and pyridinium p-toluenesulfonate (0.200 g) were sequentially added to a solution of ethyl 6-[(3-aminoquinolin-4-yl)amino]hexanoate (16.5 g, 54.7 mmol, prepared as described in Part A of Example 8) in toluene (200 mL), and the reaction was heated at reflux under a Dean-Stark trap for four hours, allowed to cool to ambient temperature, and concentrated under reduced pressure. The residue was dissolved in dichloromethane, and the resulting solution was washed sequentially with saturated aqueous sodium bicarbonate and brine, dried over magnesium sulfate, filtered, and concentrated under reduced pressure to provide 16.4 g of ethyl 6-(1H-imidazo[4,5-c]quinolin-1-yl)hexanoate.

Part B

A solution of ethyl 6-(1H-imidazo[4,5-c]quinolin-1-yl)hexanoate (7.0 g, 22.5 mmol) and n-propylamine (11.1 mL, 135 mmol) in THF (10 mL) was heated at 100° C. for ten days in a sealed high-pressure vessel. Additional n-propylamine (20 mL) was added after three days and again after seven days. After ten days, the reaction was concentrated under reduced pressure to provide 7.0 g of 6-(1H-imidazo[4,5-c]quinolin-1-yl)-N-propylhexanamide.

Part C 6-(1H-Imidazo[4,5-c]quinolin-1-yl)-N-propylhexanamide (7.0 g, 26 mmol) was treated with mCPBA (8.68 g, 37.7 mmol) followed by ammonium hydroxide (40 mL) and p-toluenesulfonyl chloride (8.01 g, 42.1 mmol) according to the method described in Part D of Example 8. The crude product was triturated with ethyl acetate and recrystallized twice from methanol:water to provide 2.00 g of 6-(4-amino-1H-imidazo[4,5-c]quinolin-1-yl)-N-propylhexanamide as brown needles, mp 128-130° C.

Anal. Calcd for $C_{19}H_{25}N_5O \cdot 0.20H_2O$: C, 66.52; H, 7.46; N, 20.42. Found: C, 66.12; H, 7.38; N, 20.10.

Example 11

1-(6-Morpholin-4-yl-6-oxohexyl)-1H-imidazo[4,5-c]quinolin-4-amine

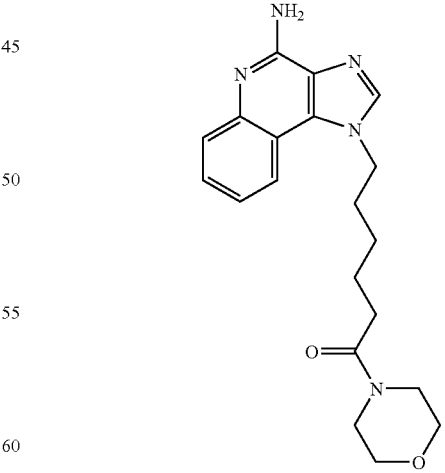

Part A

A solution of sodium hydroxide (1.66 g, 41.7 mmol) in water (15 mL) was added to a solution of ethyl 6-(1H-imidazo[4,5-c]quinolin-1-yl)hexanoate (10.0 g, 32.1 mmol, prepared in Part A of Example 10) in ethanol (75 mL), and the reaction was stirred at ambient temperature for two hours and then concentrated under reduced pressure. The residue was diluted with water and adjusted to pH 5 with the addition of 10% hydrochloric acid. The mixture was extracted with dichloromethane, and the combined extracts were dried over magnesium sulfate, filtered, and concentrated under reduced pressure to provide 2.5 g of 6-(1H-imidazo[4,5-c]quinolin-1-yl)hexanoic acid.

Part B 6-(1H-Imidazo[4,5-c]quinolin-1-yl)hexanoic acid (2.5 g, 8.8 mmol) was treated with oxalyl chloride (1.39 mL, 15.9 mmol) and morpholine (2.31 mL, 26.5 mmol) according to a modification of the method described in Part F of Example 6. The reaction with oxalyl chloride was carried out at ambient temperature, and the reaction with morpholine was complete after one hour. Following the work-up procedure, 3.1 g of 1-(6-morpholin-4-yl-6-oxohexyl)-1H-imidazo[4,5-c]quinoline were obtained.

Part C 1-(6-Morpholin-4-yl-6-oxohexyl)-1H-imidazo[4,5-c]quinoline (3.09 g, 8.79 mmol) was treated with mCPBA (3.54 g, 15.4 mmol) followed by ammonium hydroxide (50 mL) and p-toluenesulfonyl chloride (3.26 g, 17.4 mmol) according to the method described in Part D of Example 8. The crude product was purified as described in Part C of Example 10 to provide 0.422 g of 1-(6-morpholin-4-yl-6-oxohexyl)-1H-imidazo[4,5-c]quinolin-4-amine as brown needles, mp 166-168° C.

Anal. Calcd for $C_{20}H_{25}N_5O_2$: C, 65.37; H, 6.86; N, 19.06. Found: C, 65.09; H, 6.75; N, 18.87.

Example 12

2-(2-Methoxyethyl)-1-(6-morpholin-4-yl-6-oxohexyl)-1H-imidazo[4,5-c]quinolin-4-amine

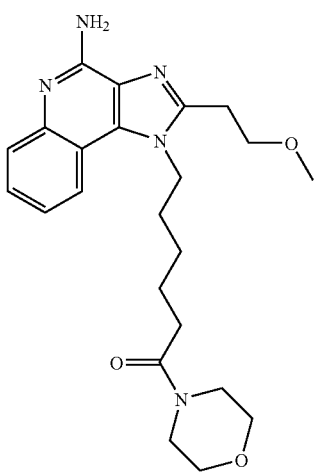 [SMILES: COCCc1nc2c(N)nc3ccccc3c2n1CCCCCC(=O)N1CCOCC1]

Part A

Methoxypropionyl chloride (4.85 g, 39.8 mmol) was added dropwise over a period of ten minutes to a solution of ethyl 6-(3-aminoquinolin-4-ylamino)hexanoate (10.0 g, 33.2 mmol, prepared as described in Part A of Example 8) in dichloromethane (200 mL). The reaction was stirred for one hour at ambient temperature and then concentrated under reduced pressure. Triethylamine (18.49 g, 132.7 mmol) and ethanol (200 mL) were added, and the resulting solution was heated at reflux for three hours. The solvent was removed under reduced pressure. Dichloromethane (75 mL) was added, and the resulting solution was washed with saturated aqueous sodium bicarbonate, dried over magnesium sulfate, filtered, and concentrated under reduced pressure to provide 12.05 g of ethyl 6-[2-(2-methoxyethyl)-1H-imidazo[4,5-c]quinolin-1-yl]hexanoate as a dark oil.

Part B

Ethyl 6-[2-(2-methoxyethyl)-1H-imidazo[4,5-c]quinolin-1-yl]hexanoate (12.05 g, 32.61 mmol) was treated with sodium hydroxide (1.70 g, 42.4 mmol) according to a modification of the method described in Part A of Example 11. The reaction was stirred overnight at ambient temperature to provide 8.35 g of 6-[2-(2-methoxyethyl)-1H-imidazo[4,5-c]quinolin-1-yl]hexanoic acid after the aqueous work-up procedure.

Part C

6-[2-(2-Methoxyethyl)-1H-imidazo[4,5-c]quinolin-1-yl]hexanoic acid (4.1 g, 12 mmol) was treated with oxalyl chloride (1.89 mL, 21.6 mmol) and morpholine (3.15 mL, 36.0 mmol) according to a modification of the method described in Part F of Example 6. The reaction with oxalyl chloride was carried out at ambient temperature, and the reaction with morpholine was complete after two hours. Following the work-up procedure, 4.55 g of 2-(2-methoxyethyl)-1-(6-morpholin-4-yl-6-oxohexyl)-1H-imidazo[4,5-c]quinoline were obtained.

Part D 2-(2-Methoxyethyl)-1-(6-morpholin-4-yl-6-oxohexyl)-1H-imidazo[4,5-c]quinoline (4.55 g, 11.1 mmol) was treated with mCPBA (4.97 g, 21.6 mmol) followed by ammonium hydroxide (40 mL) and p-toluenesulfonyl chloride (3.69 g, 19.4 mmol) according to the method described in Part D of Example 8. The crude product was recrystallized twice from ethyl acetate to provide 1.17 g of 2-(2-methoxyethyl)-1-(6-morpholin-4-yl-6-oxohexyl)-1H-imidazo[4,5-c]quinolin-4-amine as brown needles, mp 131-132° C.

Anal. Calcd for $C_{23}H_{31}N_5O_3 \cdot 0.14H_2O$: C, 64.54; H, 7.37; N, 16.36. Found: C, 64.14; H, 7.43; N, 16.40.

Example 13

2-(Ethoxymethyl)-1-(6-morpholin-4-yl-6-oxohexyl)-1H-imidazo[4,5-c]quinolin-4-amine

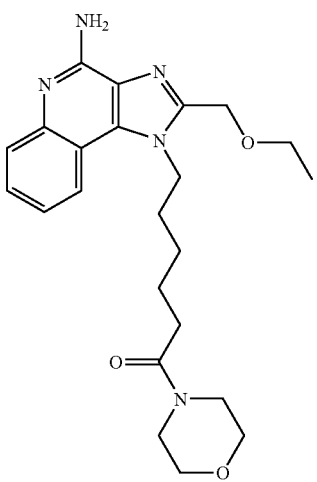 [SMILES: CCOCc1nc2c(N)nc3ccccc3c2n1CCCCCC(=O)N1CCOCC1]

Part A

Ethyl 6-(3-nitroquinolin-4-ylamino)hexanoate (27.1 g, 81.8 mmol, prepared as described in Parts A and B of Example 6) was treated with sodium hydrosulfite (49.8 g, 286 mmol), potassium carbonate (44.6 g, 323 mmol), and ethyl viologen dibromide (0.306 g, 0.818 mmol) according to a modification of the method described in Part A of Example 8. After the reaction was stirred overnight, additional sodium hydrosulfite (5.0 g, 29 mmol) was added, and the reaction was stirred for one additional hour. The organic layer was separated, washed three times with water, and concentrated under reduced pressure to provide 24 g of ethyl 6-(3-aminoquinolin-4-ylamino)hexanoate.

Part B

A solution of ethyl 6-(3-aminoquinolin-4-ylamino)hexanoate (9.25 g, 30.7 mmol) in chloroform (100 mL) was cooled to 0° C.; triethylamine (5.13 mL, 36.8 mmol) was added. Ethoxyacetyl chloride (4.51 g, 36.8 mmol) was then added dropwise over a period of five minutes. The reaction was allowed to warm to ambient temperature, heated at reflux overnight, and concentrated under reduced pressure. The crude product was purified by column chromatography on silica gel (eluting with 93:7 dichloromethane:methanol) to provide 7.73 g of ethyl 6-(2-ethoxymethyl-1H-imidazo[4,5-c]quinolin-1-yl)hexanoate.

Part C

A solution of ethyl 6-(2-ethoxymethyl-1H-imidazo[4,5-c]quinolin-1-yl)hexanoate (4.0 g, 11 mmol) in morpholine (7 mL) was heated at reflux for three days, allowed to cool to ambient temperature, and concentrated under reduced pressure. The residue was dissolved in dichloromethane; the resulting solution was washed sequentially with saturated aqueous sodium bicarbonate and brine, dried over magnesium sulfate, and concentrated under reduced pressure to provide 4.4 g of 2-(ethoxymethyl)-1-(6-morpholin-4-yl-6-oxohexyl)-1H-imidazo[4,5-c]quinoline.

Part D 2-(Ethoxymethyl)-1-(6-morpholin-4-yl-6-oxohexyl)-1H-imidazo[4,5-c]quinoline (4.4 g, 11 mmol) was treated with mCPBA (5.54 g, 32.1 mmol) followed by ammonium hydroxide (40 mL) and p-toluenesulfonyl chloride (2.74 g, 14.4 mmol) according to the method described in Part D of Example 8. The crude product was purified as described in Part D of Example 8 and then dried for two days at 60° C. to provide 1.061 g of 2-(ethoxymethyl)-1-(6-morpholin-4-yl-6-oxohexyl)-1H-imidazo[4,5-c]quinolin-4-amine as a beige powder, mp 160-162° C.

Anal. Calcd for $C_{23}H_{31}N_5O_3 \cdot 0.47H_2O$: C, 63.65; H, 7.42; N, 16.14. Found: C, 63.64; H, 7.42; N, 16.05.

Example 14

6-[4-Amino-2-(ethoxymethyl)-1H-imidazo[4,5-c]quinolin-1-yl]-N-propylhexanamide

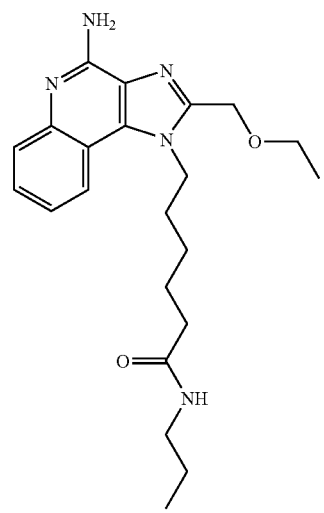 [SMILES: CCCNC(=O)CCCCCn1c(COCC)nc2c(N)nc3ccccc3c21]

Part A

A solution of ethyl 6-(2-ethoxymethyl-1H-imidazo[4,5-c]quinolin-1-yl)hexanoate (3.73 g, 10.1 mmol, prepared in Parts A and B of Example 13), n-propylamine (5 mL), and THF (5 mL) was heated at 80° C. for three days in a high-pressure vessel, allowed to cool to ambient temperature, and concentrated under reduced pressure. The work-up procedure described in Part C of Example 13 was followed to provide 4.1 g of 6-[2-(ethoxymethyl)-1H-imidazo[4,5-c]quinolin-1-yl]-N-propylhexanamide.

Part B

6-[2-(Ethoxymethyl)-1H-imidazo[4,5-c]quinolin-1-yl]-N-propylhexanamide (4.1 g, 11 mmol) was treated with mCPBA (5.74 g, 33.3 mmol) followed by ammonium hydroxide (50 mL) and p-toluenesulfonyl chloride (2.85 g, 14.9 mmol) according to the method described in Part D of Example 8. The crude product was purified by column chromatography on silica gel (eluting with 97:3 dichloromethane:methanol) followed by recrystallization from methanol:water to provide 0.548 g of 6-[4-amino-2-(ethoxymethyl)-1H-imi

Example 15

3-(4-Amino-2-propyl-1H-imidazo[4,5-c]quinolin-1-yl)-N-propylpropanamide

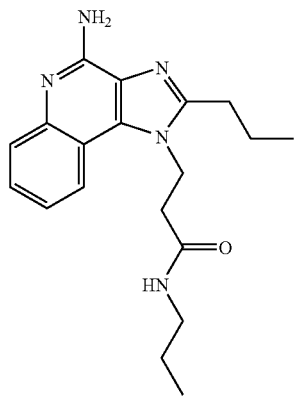 [SMILES: CCCNC(=O)CCn1c(CCC)nc2c(N)nc3ccccc3c21]

Part A

Potassium carbonate (19.87 g, 143.8 mmol) and triethylamine (50.1 mL, 359 mmol) were sequentially added with stirring to a solution of 4-chloro-3-nitroquinoline (30.0 g, 144 mmol) in chloroform (200 mL). After 15 minutes, β-alanine ethyl ester hydrochloride (26.5 g, 173 mmol) was slowly added, and the reaction was stirred overnight at ambient temperature. Water (100 mL) was added, and the mixture was stirred for 15 minutes. The organic layer was separated, washed sequentially with saturated aqueous sodium bicarbonate and brine, dried over magnesium sulfate, filtered, and concentrated under reduced pressure to provide 27.4 g of ethyl N-(3-nitroquinolin-4-yl)-β-alaninate as a yellow solid, which was used without purification.

Part B

Ethyl N-(3-nitroquinolin-4-yl)-β-alaninate (28.2 g, 97.5 mmol) was treated with sodium hydrosulfite (50.9 g, 292 mmol), potassium carbonate (53.2 g, 385 mmol), and ethyl viologen dibromide (0.364 g, 0.973 mmol) according to a modification of the method described in Part A of Example 8. After the reaction was stirred overnight, additional sodium hydrosulfite (5.0 g, 29 mmol) was added, and the reaction was stirred for two additional hours. Additional sodium hydrosulfite (2.0 g, 5.3 mmol) was added, and the reaction was stirred for one additional hour. An analysis by TLC indicated the reaction was complete. The organic layer was separated, washed three times with water, and concentrated under reduced pressure to provide 20.7 g of ethyl N-(3-aminoquinolin-4-yl)-β-alaninate.

Part C

Ethyl N-(3-aminoquinolin-4-yl)-β-alaninate (10.0 g, 38.6 mmol) was treated according to a modification of the method described in Part B of Example 8. After the addition of trimethyl orthobutyrate (7.71 mL, 48.2 mmol) and pyridinium p-toluenesulfonate (0.200 g, 0.796 mmol), the reaction was heated at reflux for one hour and subjected to the work-up procedure to provide 12.3 g of ethyl 3-(2-propyl-1H-imidazo[4,5-c]quinolin-1-yl)propanoate, which was used without purification.

Part D

A solution of ethyl 3-(2-propyl-1H-imidazo[4,5-c]quinolin-1-yl)propanoate (3.45 g, 11.1 mmol), n-propylamine (9.1 mL, 110 mmol), and THF (5 mL) was heated at 80° C. for two days in a high-pressure vessel, allowed to cool to ambient temperature, and concentrated under reduced pressure to provide 3.5 g of 3-(2-propyl-1H-imidazo[4,5-c]quinolin-1-yl)-N-propylpropanamide.

Part E

3-(2-Propyl-1H-imidazo[4,5-c]quinolin-1-yl)-N-propylpropanamide (3.5 g, 11 mmol) was treated with mCPBA (5.85 g, 32.4 mmol) followed by ammonium hydroxide (40 mL) and p-toluenesulfonyl chloride (2.76 g, 14.6 mmol) according to a modification of the method described in Part D of Example 8. When the reaction was complete, the organic layer was separated, washed with 10% aqueous sodium bicarbonate, and concentrated under reduced pressure. The crude product was purified as described in Part D of Example 8 to provide 1.026 g of 3-(4-amino-2-propyl-1H-imidazo[4,5-c]quinolin-1-yl)-N-propylpropanamide as beige needles, mp 157-158° C.

Anal. Calcd for $C_{19}H_{25}N_5O \cdot 0.97H_2O$: C, 63.94; H, 7.61; N, 19.62. Found: C, 63.95; H, 7.69; N, 19.55.

Example 16

1-(3-Morpholin-4-yl-3-oxopropyl)-2-propyl-1H-imidazo[4,5-c]quinolin-4-amine

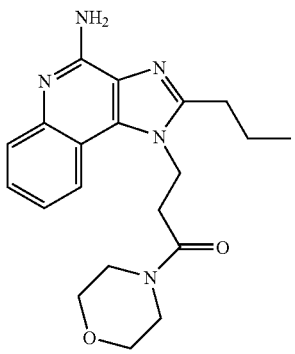 [SMILES: CCCc1nc2c(N)nc3ccccc3c2n1CCC(=O)N1CCOCC1]

Part A

Ethyl N-(3-nitroquinolin-4-yl)-β-alaninate (41.6 g, 144 mmol, prepared as described in Part A of Example 15) was treated with sodium hydrosulfite (87.62 g, 503.3 mmol), potassium carbonate (78.5 g, 568 mmol), and ethyl viologen dibromide (0.54 g, 1.4 mmol) according to a modification of the method described in Part A of Example 8. After the reaction was stirred overnight, additional sodium hydrosulfite (5.0 g, 29 mmol) was added, and the reaction was stirred for one additional hour. The organic layer was separated, washed with water (5×200 mL), dried over magnesium sulfate, filtered, and concentrated under reduced pressure to provide 33.3 g of ethyl N-(3-aminoquinolin-4-yl)-β-alaninate.

Part B

Ethyl N-(3-aminoquinolin-4-yl)-β-alaninate (33.3 g, 128 mmol) was treated according to a modification of the method described in Part B of Example 8. After the addition of trimethyl orthobutyrate (25.6 mL, 161 mmol) and pyridinium p-toluenesulfonate (0.200 g, 0.796 mmol), the reaction was heated at reflux for two hours and subjected to the work-up procedure to provide 37.1 g of ethyl 3-(2-propyl-1H-imidazo[4,5-c]quinolin-1-yl)propanoate, which was used without purification.

Part C

A solution of ethyl 3-(2-propyl-1H-imidazo[4,5-c]quinolin-1-yl)propanoate (4.0 g, 15 mmol) in morpholine (20 mL, 0.2 mol) was heated at reflux for two days, allowed to cool to ambient temperature, and concentrated under reduced pressure to provide 5.2 g of 1-(3-morpholin-4-yl-3-oxopropyl)-2-propyl-1H-imidazo[4,5-c]quinoline.

Part D 1-(3-Morpholin-4-yl-3-oxopropyl)-2-propyl-1H-imidazo[4,5-c]quinoline (5.2 g, 15 mmol) was treated with mCPBA (7.64 g, 44.3 mmol) followed by ammonium hydroxide (40 mL) and p-toluenesulfonyl chloride (3.79 g, 19.9 mmol) according to the method described in Part D of Example 8. The crude product was purified by column chromatography on silica gel (eluting with 95:5 dichloromethane:methanol) followed by recrystallization from methanol:dichloromethane to provide 0.358 g of 1-(3-morpholin-4-yl-3-oxopropyl)-2-propyl-1H-imidazo[4,5-c]quinolin-4-amine as yellow needles, mp 172-173° C.

Anal. Calcd for $C_{20}H_{25}N_5O_2 \cdot 0.2\ CH_3OH \cdot 0.2H_2O$: C, 64.27; H, 6.99; N, 18.55. Found: C, 64.20; H, 6.92; N, 18.67.

Example 17

3-(4-Amino-2-propyl-1H-imidazo[4,5-c]quinolin-1-yl)-N-methylpropanamide

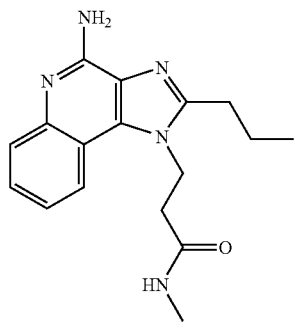 [SMILES: CCCc1nc2c(N)nc3ccccc3c2n1CCC(=O)NC]

Part A

A mixture of ethyl 3-(2-propyl-1H-imidazo[4,5-c]quinolin-1-yl)propanoate (4.24 g, 16.5 mmol, prepared in Parts A and B of Example 16), THF (15 mL), and methylamine (available as a 40% solution in water, 8 mL) was sealed in a high-pressure vessel, heated at 80° C. overnight, and concentrated under reduced pressure to provide 4.7 g of N-methyl-3-(2-propyl-1H-imidazo[4,5-c]quinolin-1-yl)propanamide.

Part B

N-Methyl-3-(2-propyl-1H-imidazo[4,5-c]quinolin-1-yl)propanamide (4.7 g, 13 mmol) was treated with mCPBA (6.58 g, 38.2 mmol) followed by ammonium hydroxide (40 mL) and p-toluenesulfonyl chloride (3.27 g, 17.2 mmol) according to the method described in Part D of Example 8. The crude product was purified as described in Part D of Example 8 to provide 0.674 g of 3-(4-amino-2-propyl-1H-imidazo[4,5-c]quinolin-1-yl)-N-methylpropanamide as a tan powder, mp 177-178° C.

Anal. Calcd for $C_{17}H_{21}N_5O \cdot 0.22H_2O$: C, 64.75; H, 6.85; N, 22.21. Found: C, 65.01; H, 6.97; N, 22.20.

Example 18

3-(4-Amino-2-propyl-1H-imidazo[4,5-c]quinolin-1-yl)propanamide hydrochloride

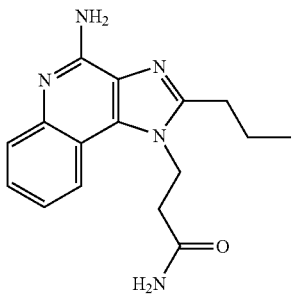 [SMILES: CCCc1nc2c(N)nc3ccccc3c2n1CCC(N)=O]

Part A

Ethyl N-(3-nitroquinolin-4-yl)-β-alaninate (62.0 g, 214 mmol, prepared as described in Part A of Example 15) was treated with sodium hydrosulfite (130.6 g, 750.1 mmol), potassium carbonate (117 g, 847 mmol), and ethyl viologen dibromide (0.802 g, 2.14 mmol) according to a modification of the method described in Part A of Example 8. After the reaction was stirred overnight, additional water (100 mL), dichloromethane, and sodium hydrosulfite (20.0 g, 115 mmol) were added, and the reaction was stirred for three additional hours. The organic layer was separated; washed with water (6×), saturated aqueous sodium bicarbonate, and brine; dried over magnesium sulfate; filtered; and concentrated under reduced pressure to provide 40.2 g of ethyl N-(3-aminoquinolin-4-yl)-β-alaninate.

Part B

Ethyl N-(3-aminoquinolin-4-yl)-β-alaninate (11.0 g, 42.4 mmol) was treated according to a modification of the method described in Part B of Example 8. After the addition of trimethyl orthobutyrate (7.8 mL, 49 mmol) and pyridinium p-toluenesulfonate (0.200 g, 0.796 mmol), the reaction was heated at reflux for one hour and subjected to the work-up procedure to provide 10.6 g of ethyl 3-(2-propyl-1H-imidazo[4,5-c]quinolin-1-yl)propanoate, which was used without purification.

Part C

Ethyl 3-(2-propyl-1H-imidazo[4,5-c]quinolin-1-yl)propanoate (5.0 g, 16 mmol) was treated with ammonium acetate (25.0 g) according to the method described in Part B of Example 9 to provide 3.9 g of 3-(2-propyl-1H-imidazo[4,5-c]quinolin-1-yl)propanamide, which was used without purification.

Part D 3-(2-Propyl-1H-imidazo[4,5-c]quinolin-1-yl)propanamide (3.9 g, 14 mmol) was treated with mCPBA (6.19 g, 26.9 mmol) followed by ammonium hydroxide (50 mL) and p-toluenesulfonyl chloride (4.6 g, 24 mmol) according to the method described in Part D of Example 8. The crude product was dissolved in methanol, and hydrogen chloride (1.25 mL of a 1 M solution in diethyl ether) was added. The resulting solid was isolated by filtration and dried overnight under high vacuum to provide 0.477 g of 3-(4-amino-2-propyl-1H-imidazo[4,5-c]quinolin-1-yl)propanamide hydrochloride as tan needles, mp 242-243° C.

Anal. Calcd for $C_{16}H_{19}N_5O \cdot 1.0\ HCl \cdot 0.04H_2O$: C, 54.82; H, 6.29; N, 19.98. Found: C, 54.81; H, 6.66; N, 19.81.

Example 19

2-(2-Methoxyethyl)-1-(3-morpholin-4-yl-3-oxopropyl)-1H-imidazo[4,5-c]quinolin-4-amine

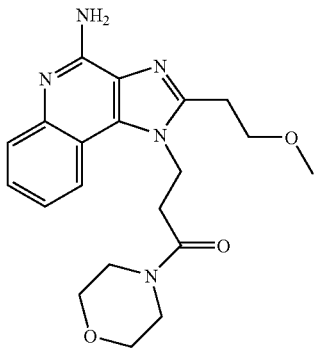 [SMILES: COCCc1nc2c(N)nc3ccccc3c2n1CCC(=O)N1CCOCC1]

Part A

The method described in Part A of Example 12 was used to treat ethyl N-(3-aminoquinolin-4-yl)-β-alaninate (9.82 g, 37.9 mmol, prepared in Part A of Example 18) with methoxypropionyl chloride (5.54 g, 45.4 mmol). The reaction with triethylamine (21.1 mL, 151 mmol) was heated at reflux for six hours and then subjected to the work-up procedure to provide 10.3 g of ethyl 3-[2-(2-methoxyethyl)-1H-imidazo[4,5-c]quinolin-1-yl]propanoate.

Part B

A solution of ethyl 3-[2-(2-methoxyethyl)-1H-imidazo[4,5-c]quinolin-1-yl]propanoate (4.0 g, 15 mmol), morpholine (13.49 mL, 154.3 mmol), and 2-methyltetrahydrofuran (10 mL) was heated for three days in a high-pressure vessel at 120° C., allowed to cool to ambient temperature, and concentrated under reduced pressure to provide 5.6 g of 2-(2-methoxyethyl)-1-(3-morpholin-4-yl-3-oxopropyl)-1H-imidazo[4,5-c]quinoline.

Part C 2-(2-Methoxyethyl)-1-(3-morpholin-4-yl-3-oxopropyl)-1H-imidazo[4,5-c]quinoline (4.7 g, 13 mmol) was treated with mCPBA (5.73 g, 24.9 mmol) followed by ammonium hydroxide (40 mL) and p-toluenesulfonyl chloride (4.23 g, 22.2 mmol) according to the method described in Part D of Example 8. The crude product was recrystallized twice from ethyl acetate to provide 0.233 g of 2-(2-methoxyethyl)-1-(3-morpholin-4-yl-3-oxopropyl)-1H-imidazo[4,5-c]quinolin-4-amine as beige needles, mp 125-126° C.

Anal. Calcd for $C_{20}H_{25}N_5O_3 \cdot 0.29H_2O$: C, 61.81; H, 6.63; N, 18.02. Found: C, 61.57; H, 6.45; N, 17.76.

Example 20

3-(4-Amino-1H-imidazo[4,5-c]quinolin-1-yl)-N-methylpropanamide

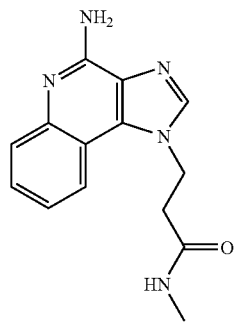 [SMILES: CNC(=O)CCn1cnc2c(N)nc3ccccc3c21]

Part A

The method described in Part A of Example 10 was used to treat ethyl N-(3-aminoquinolin-4-yl)-β-alaninate (10.0 g, 38.6 mmol, prepared in Part A of Example 18) with triethyl orthoformate (8.98 mL, 54.0 mmol). The reaction was complete in three hours. The reaction mixture was filtered to remove a precipitate and then subjected to the work-up procedure to provide 9.7 g of ethyl 3-(1H-imidazo[4,5-c]quinolin-1-yl)propanoate.

Part B

A mixture of ethyl 3-(1H-imidazo[4,5-c]quinolin-1-yl)propanoate (4.70 g, 17.5 mmol), THF (5 mL), and methylamine (available as a 40% solution in water, 10 mL) was sealed in a high-pressure vessel, stirred at 100° C. overnight, and concentrated under reduced pressure to provide 4.4 g of 3-(1H-imidazo[4,5-c]quinolin-1-yl)-N-methylpropanamide.

Part C mCPBA (8.95 g, 38.9 mmol) was added to a solution of 3-(1H-imidazo[4,5-c]quinolin-1-yl)-N-methylpropanamide (4.4 g, 15.6 mmol) in chloroform (100 mL); the reaction was stirred for one hour at ambient temperature. Ammonium hydroxide (40 mL) was added, and the mixture was stirred vigorously for 15 minutes. p-Toluenesulfonyl chloride (5.94 g, 31.2 mmol) was added over a period of ten minutes, and the reaction was stirred for two hours. The reaction mixture was filtered to remove a precipitate, and the organic layer was separated and washed with saturated aqueous sodium bicarbonate, dried over magnesium sulfate, filtered, and concentrated under reduced pressure. The crude product was recrystallized from methanol to provide 0.535 g of 3-(4-amino-1H-imidazo[4,5-c]quinolin-1-yl)-N-methylpropanamide as off-white needles, mp>260° C.

Anal. Calcd for $C_{14}H_{15}N_5O \cdot 0.13H_2O$: C, 61.90; H, 5.66; N, 25.78. Found: C, 61.51; H, 5.39; N, 25.41.

Example 21

3-(4-Amino-1H-imidazo[4,5-c]quinolin-1-yl)-N-propylpropanamide

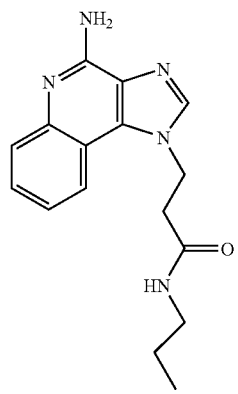 [SMILES: CCCNC(=O)CCn1cnc2c(N)nc3ccccc3c21]

Part A

Ethyl 3-(1H-imidazo[4,5-c]quinolin-1-yl)propanoate (3.75 g, 13.9 mmol, prepared as described in Part A of Example 20) was treated with n-propylamine (11.4 mL, 139 mmol) according to the method described in Part B of Example 20 to provide 3.9 g of 3-(1H-imidazo[4,5-c]quinolin-1-yl)-N-propylpropanamide.

Part B mCPBA (5.6 g, 24 mmol) was added to a solution of 3-(1H-imidazo[4,5-c]quinolin-1-yl)-N-propylpropanamide (3.9 g, 14 mmol) in chloroform (100 mL). The reaction was stirred for two hours and washed with saturated aqueous sodium bicarbonate. Concentrated ammonium hydroxide (40 mL) was added. The mixture was stirred vigorously for five minutes before the addition of p-toluenesulfonyl chloride (5.13 g, 26.9 mmol). The reaction was stirred vigorously for two hours, and then the organic layer was separated and washed sequentially with saturated aqueous sodium bicarbonate (2×) and brine, dried over magnesium sulfate, filtered, and concentrated under reduced pressure. The crude product was recrystallized three times from ethyl acetate to provide 0.496 g of 3-(4-amino-1H-imidazo[4,5-c]quinolin-1-yl)-N-propylpropanamide as a brown powder, mp 212-214° C.

Anal. Calcd for $C_{16}H_{19}N_5O\cdot0.04H_2O$: C, 64.47; H, 6.45; N, 23.49. Found: C, 64.09; H, 6.64; N, 23.52.

Example 22

2-Methyl-1-(3-morpholin-4-yl-3-oxopropyl)-1H-imidazo[4,5-c]quinolin-4-amine

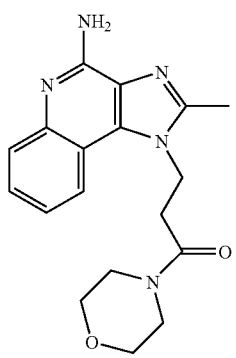 [SMILES: Cc1nc2c(N)nc3ccccc3c2n1CCC(=O)N1CCOCC1]

Part A

4-Chloro-3-nitroquinoline (76.1 g, 365 mmol) was treated with β-alanine ethyl ester hydrochloride (50.0 g, 326 mmol) in the presence of triethylamine (94.5 mL, 678 mmol) and potassium carbonate (37.45 g, 271.2 mmol) according to a modification of the method described in Part A of Example 15. Before the addition of β-alanine ethyl ester hydrochloride, the reaction was cooled to 0° C. After this addition, the reaction was stirred for four hours at ambient temperature and subjected to the work-up procedure to provide 105 g of ethyl N-(3-nitroquinolin-4-yl)-β-alaninate.

Part B

Ethyl N-(3-nitroquinolin-4-yl)-β-alaninate (50.0 g, 173 mmol) was hydrogenated in the presence of 5% platinum on carbon (1.0 g) according to the method described in Part C of Example 1. The reaction was allowed to proceed overnight under hydrogen pressure (40 psi, $2.8\times10^5$ Pa) and then subjected to the work-up procedure to provide 42.3 g of ethyl N-(3-aminoquinolin-4-yl)-β-alaninate.

Part C

Ethyl N-(3-aminoquinolin-4-yl)-β-alaninate (15.0 g, 57.8 mmol) was treated with trimethyl orthoacetate (10.3 mL, 81.0 mmol) and pyridinium p-toluenesulfonate (0.200 g) according to the method described in Part A of Example 10 to provide 14.0 g of ethyl 3-(2-methyl-1H-imidazo[4,5-c]quinolin-1-yl)propanoate as a brown solid.

Part D

A solution of ethyl 3-(2-methyl-1H-imidazo[4,5-c]quinolin-1-yl)propanoate (4.0 g, 15 mmol) and morpholine (10 mL, 100 mmol) was heated for three days in a high-pressure vessel at 100° C., allowed to cool to ambient temperature, and concentrated under reduced pressure. The residue was dissolved in dichloromethane, and the resulting solution was washed with saturated aqueous sodium bicarbonate, dried over magnesium sulfate, filtered, and concentrated under reduced pressure to provide 4.8 g of 2-methyl-1-(3-morpholin-4-yl-3-oxopropyl)-1H-imidazo[4,5-c]quinoline.

Part E

2-Methyl-1-(3-morpholin-4-yl-3-oxopropyl)-1H-imidazo[4,5-c]quinoline (4.8 g, 15 mmol) was treated with mCPBA (5.95 g, 25.9 mmol) followed by ammonium hydroxide (50 mL) and p-toluenesulfonyl chloride (5.49 g, 28.8 mmol) according to a modification of the method described in Part D of Example 8. The reaction was not washed with 10% aqueous sodium hydroxide prior to the addition of ammonium hydroxide. After the amination reaction was stirred for two hours, water was added. Following the work-up procedure, the chromatographic purification was carried out eluting with 90:10 dichloromethane:methanol. The resulting product was triturated with ethyl acetate and isolated by filtration to provide 2-methyl-1-(3-morpholin-4-yl-3-oxopropyl)-1H-imidazo[4,5-c]quinolin-4-amine as brown needles, mp 166-169° C.

Anal. Calcd for $C_{18}H_{21}N_5O_2\cdot0.50H_2O$: C, 62.05; H, 6.36; N, 20.10. Found: C, 61.67; H, 6.63; N, 19.93.

Example 23

2-(Ethoxymethyl)-1-(3-morpholin-4-yl-3-oxopropyl)-1H-imidazo[4,5-c]quinolin-4-amine

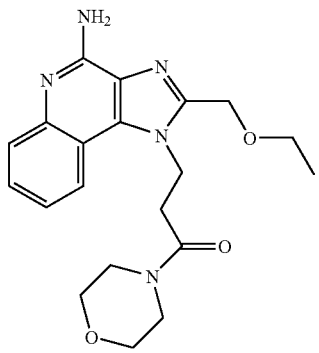 [SMILES: CCOCc1nc2c(N)nc3ccccc3c2n1CCC(=O)N1CCOCC1]

Part A

Ethyl N-(3-aminoquinolin-4-yl)-β-alaninate (20.0 g, 77.3 mmol, prepared in Parts A and B of Example 22) was treated with ethoxyacetyl chloride (11.29 g, 92.5 mmol) according to a modification the method described in Part A of Example 12. The reaction in dichloromethane (300 mL) was stirred for 1.5 hours, and after the addition of triethylamine (43.08 mL, 309.1 mmol) and ethanol (300 mL), the reaction was heated at reflux for four hours and then subjected to the work-up procedure to provide 25.0 g of ethyl 3-(2-ethoxymethyl-1H-imidazo[4,5-c]quinolin-1-yl)propanoate.

Part B

A solution of ethyl 3-(2-ethoxymethyl-1H-imidazo[4,5-c]quinolin-1-yl)propanoate (5.0 g, 15 mmol) and morpholine (10 mL, 100 mmol) was heated overnight in a high-pressure vessel at 90° C. An analysis by HPLC indicated the reaction was incomplete. The reaction was then heated overnight in a high-pressure vessel at 110° C., allowed to cool to ambient temperature, and concentrated under reduced pressure to provide 5.1 g of 2-(ethoxymethyl)-1-(3-morpholin-4-yl-3-oxopropyl)-1H-imidazo[4,5-c]quinoline.

Part C 2-(Ethoxymethyl)-1-(3-morpholin-4-yl-3-oxopropyl)-1H-imidazo[4,5-c]quinoline (5.1 g, 14 mmol) was treated with mCPBA (5.57 g, 24.2 mmol) followed by ammonium hydroxide (40 mL) and p-toluenesulfonyl chloride (5.14 g, 26.9 mmol) according to a modification of the method described in Part D of Example 8. The reaction was not washed with 10% aqueous sodium hydroxide prior to the addition of ammonium hydroxide. The crude product was purified by column chromatography on silica gel (eluting with 90:10 dichloromethane:methanol) and then triturated with ethyl acetate and isolated by filtration to provide 0.843 g of 2-(ethoxymethyl)-1-(3-morpholin-4-yl-3-oxopropyl)-1H-imidazo[4,5-c]quinolin-4-amine as off-white needles, mp 187-189° C.

Anal. Calcd for $C_{20}H_{25}N_5O_3$: C, 62.65; H, 6.57; N, 18.26. Found: C, 62.28; H, 6.83; N, 18.19.

Example 24

3-[4-Amino-2-(ethoxymethyl)-1H-imidazo[4,5-c]quinolin-1-yl]propanamide

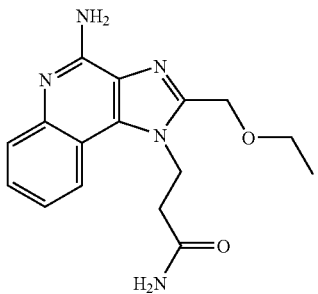 [SMILES: CCOCc1nc2c(N)nc3ccccc3c2n1CCC(N)=O]

Part A

Ammonium acetate (7 g) and ethyl 3-(2-ethoxymethyl-1H-imidazo[4,5-c]quinolin-1-yl)propanoate (5.0 g, 15 mmol, prepared in Part A of Example 23) were stirred overnight at 125° C. in a sealed vessel. The reaction was allowed to cool to ambient temperature, and water (20 mL) was added. A precipitate formed and was isolated by filtration, washed with saturated aqueous sodium bicarbonate, and dried to provide 2.4 g of 3-[2-(ethoxymethyl)-1H-imidazo[4,5-c]quinolin-1-yl]propanamide as a tan powder.

Part B

3-[2-(Ethoxymethyl)-1H-imidazo[4,5-c]quinolin-1-yl]propanamide (2.4 g, 8.1 mmol) was treated with mCPBA (3.24 g, 14.1 mmol) followed by ammonium hydroxide (40 mL) and p-toluenesulfonyl chloride (2.99 g, 15.7 mmol) according to a modification of the method described in Part D of Example 8. The reaction was not washed with 10% aqueous sodium hydroxide prior to the addition of ammonium hydroxide. After the amination reaction was stirred for two hours, 10% aqueous sodium hydroxide (25 mL) and saturated aqueous sodium bicarbonate (25 mL) were sequentially added with stirring. A precipitate formed and was isolated by filtration. The solid was triturated twice with 25% aqueous sodium hydroxide, isolated by filtration, washed with water, and dried in a vacuum oven for three days to provide 0.685 g of 3-[4-amino-2-(ethoxymethyl)-1H-imidazo[4,5-c]quinolin-1-yl]propanamide as tan needles, mp>250° C.

Anal. Calcd for $C_{16}H_{19}N_5O_2$: C, 61.33; H, 6.11; N, 22.35. Found: C, 61.03; H, 6.11; N, 22.24.

Example 25

12-(4-Amino-2-propyl-1H-imidazo[4,5-c]quinolin-1-yl)-N-methyldodecanamide

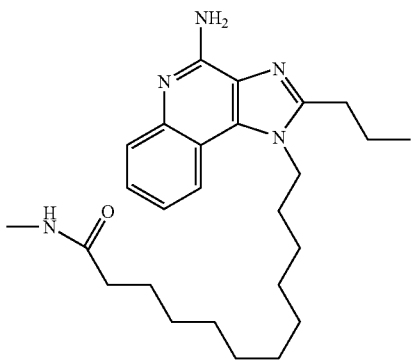 [SMILES: CCCc1nc2c(N)nc3ccccc3c2n1CCCCCCCCCCCC(=O)NC]

Part A

Ethanol (150 mL) was cooled to 0° C., and thionyl chloride (16.57 mL, 139.3 mmol) was added over a period of ten minutes. The reaction was stirred for ten minutes at 0° C., and 12-aminododecanoic acid (25.0 g, 116 mol) was then added. The reaction was allowed to warm to ambient temperature, stirred at a slightly elevated temperature for one hour, and stirred at ambient temperature for two hours. The Ethanol was removed under reduced pressure, and the solid residue was recrystallized from ethyl acetate. The crystals were isolated by filtration, washed with diethyl ether, and dried under vacuum to provide 37.4 g of ethyl 12-aminododecanoate hydrochloride as a white solid.

Part B

4-Chloro-3-nitroquinoline (15.52 g, 74.40 mmol) was treated with ethyl 12-aminododecanoate hydrochloride (25.0 g, 89.3 mmol) in the presence of potassium carbonate (10.28 g, 74.38 mmol) and triethylamine (25.9 mL, 186 mmol) according to a modification of the method described in Part A of Example 15. After the reaction was stirred for six hours, an analysis by TLC indicated the presence of starting material, and additional ethyl 12-aminododecanate hydrochloride (1.0 g, 3.6 mmol) was added. The reaction was stirred overnight and subjected to the work-up procedure to provide 31.0 g of ethyl 12-(3-nitroquinolin-4-ylamino)dodecanoate.

Part C

Water (25 mL) and ethyl viologen dibromide (0.279 g, 0.746 mmol) were added to a solution of the material from Part B. Sodium hydrosulfite (45.4 g, 261 mmol) and a solution of potassium carbonate (40.7 g, 295 mmol) in water (200 mL) were added, and the reaction was stirred overnight. An analysis by TLC indicated that the reaction was incomplete.

Additional sodium hydrosulfite (5.0 g, 29 mmol) was added, and the reaction was stirred for 0.5 additional hour. The organic layer was separated, washed three times with water, dried over magnesium sulfate, filtered, and concentrated under reduced pressure to provide ethyl 12-(3-aminoquinolin-4-ylamino)dodecanoate.

Part D

Ethyl 12-(3-aminoquinolin-4-ylamino)dodecanoate (20.0 g, 51.8 mmol) was treated according to a modification of the method described in Part B of Example 8. Prior to the addition of trimethyl orthobutyrate (9.53 mL, 59.6 mmol) and pyridinium p-toluenesulfonate (0.500 g, 1.99 mmol), the reaction was heated at reflux for ten minutes. After the reaction was heated at reflux, it was allowed to cool to ambient temperature, washed sequentially with saturated aqueous sodium bicarbonate and brine, dried over magnesium sulfate, and concentrated under reduced pressure to provide 22.3 g of ethyl 12-(2-propyl-1H-imidazo[4,5-c]quinolin-1-yl)dodecanoate, which was used without purification.

Part E

A mixture of ethyl 12-(2-propyl-1H-imidazo[4,5-c]quinolin-1-yl)dodecanoate (4.0 g, 9.1 mmol), THF (5 mL), and methylamine (available as a 40% solution in water, 8 mL) was sealed in a high-pressure vessel and heated at 80° C. overnight. The solvent was removed under reduced pressure, and the residue was dissolved in dichloromethane. The resulting solution was washed sequentially with saturated aqueous sodium bicarbonate and brine, dried over magnesium sulfate, filtered, and concentrated under reduced pressure to provide 3.8 g of N-methyl-12-(2-propyl-1H-imidazo[4,5-c]quinolin-1-yl)dodecanamide.

Part F

N-Methyl-12-(2-propyl-1H-imidazo[4,5-c]quinolin-1-yl)dodecanamide (3.8 g, 9.0 mmol) was treated with mCPBA (4.65 g, 26.9 mmol) followed by ammonium hydroxide (40 mL) and p-toluenesulfonyl chloride (2.31 g, 12.1 mmol) according to the method described in Part D of Example 8. The crude product was purified as described in Part D of Example 8 to provide 1.036 g of 12-(4-amino-2-propyl-1H-imidazo[4,5-c]quinolin-1-yl)-N-methyldodecanamide as a brown crystalline solid, mp 135-137° C.

Anal. Calcd for $C_{26}H_{39}N_5O$: C, 71.36; H, 8.98; N, 16.0. Found: C, 71.12; H, 9.18; N, 15.90.

Example 26

3-(4-Amino-2-propyl-1H-imidazo[4,5-c]quinolin-1-yl)-2,2-dimethylpropanamide

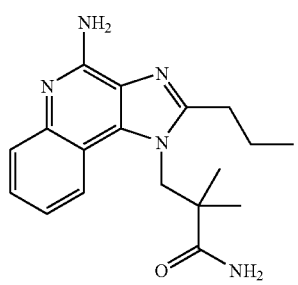 [SMILES: CCCc1nc2c(N)nc3ccccc3c2n1CC(C)(C)C(N)=O]

Part A

Concentrated ammonium hydroxide (150 mL of 29%) was cooled to 0° C. in a high-pressure vessel; bromopivalic acid (30.0 g, 359 mmol) was added with stirring over a period of ten minutes. The reaction was stirred for 30 minutes, sealed, heated at 55° C. for three days, and allowed to cool to ambient temperature. The solution was concentrated under reduced pressure, and the residue was dissolved in ethanol (150 mL). The resulting solution was concentrated under reduced pressure; the residue was dissolved in toluene, which was removed under reduced pressure to provide a white solid.

Part B

The material from Part A was suspended in ethanol (300 mL) and cooled to 0° C. Thionyl chloride (45.0 mL, 617 mmol) was added dropwise. The reaction was allowed to warm to ambient temperature, stirred overnight, heated at reflux for one hour, and allowed to cool to ambient temperature. The volatiles were removed under reduced pressure, and the residue was mixed with ethyl acetate. The resulting mixture was filtered, and the filtrate was concentrated under reduced pressure to provide ethyl 3-amino-2,2-dimethylpropanoate as a yellow oil, which was used without purification.

Part C

A suspension of 4-chloro-3-nitroquinoline (35.0 g, 168 mmol) and triethylamine (84 mL, 0.60 mol) in dichloromethane (400 mL) was cooled to 0° C.; a solution of ethyl 3-amino-2,2-dimethylpropanoate (40.0 g, 0.220 mol) in dichloromethane (50 mL) was added dropwise. The reaction was stirred at 0° C. for 30 minutes and then at ambient temperature for four hours. The reaction was incomplete as determined by a TLC analysis, and additional ethyl 3-amino-2,2-dimethylpropionate (10.0 g, 55.0 mmol) was added. The reaction was stirred overnight; another analysis by TLC indicated the reaction was incomplete. Additional ethyl 3-amino-2,2-dimethylpropionate (5.0 g, 28 mmol) was added, and the reaction was heated at reflux for three hours. Potassium carbonate (10 g) was added, and the reaction was heated at reflux for two hours and stirred overnight at ambient temperature. Saturated aqueous sodium bicarbonate (50 mL) was added, and the reaction was stirred for three days. The organic layer was separated, washed with water (3×100 mL), dried over potassium carbonate, filtered, and concentrated under reduced pressure to provide ethyl 2,2-dimethyl-3-[(3-nitroquinolin-4-yl)amino]propanoate as an orange oil, which was mixed with material from another run and used without purification.

Part D A mixture of ethyl 2,2-dimethyl-3-[(3-nitroquinolin-4-yl)amino]propanoate (59 g), sodium hydrosulfite (109 g, 532 mmol), potassium carbonate (103 g, 744 mmol), and ethyl viologen dibromide (0.50 g, 1.3 mmol), dichloromethane (350 mL), and water (350 mL) was stirred overnight at ambient temperature. The aqueous layer was separated and extracted with dichloromethane (100 mL). The combined organic fractions were washes with water (4×75 mL), dried over potassium carbonate, filtered, and concentrated under reduced pressure to provide 46.1 g of ethyl 3-[(3-aminoquinolin-4-yl)amino]-2,2-dimethylpropanoate as a dark oil.

Part E

Ethyl 3-[(3-aminoquinolin-4-yl)amino]-2,2-dimethylpropanoate (8.2 g, 29 mmol) was treated according to a modification of the method described in Part B of Example 8. Prior to the addition of trimethyl orthobutyrate (5.3 g, 36 mmol) and pyridinium p-toluenesulfonate (0.10 g, 0.40 mmol), the reaction was heated at reflux for ten minutes. During the work-up procedure, the solution was dried over potassium carbonate. The crude product was purified by column chromatography on silica gel (eluting with 93:7 dichloromethane: methanol containing 3 mL concentrated ammonium hydroxide per liter of eluent) to provide 2.1 g of ethyl 2,2-dimethyl-3-(2-propyl-1H-imidazo[4,5-c]quinolin-1-yl)propanoate as an orange oil.

Part F

Aqueous sodium hydroxide (1 mL of 50%) was added to a mixture of ethyl 2,2-dimethyl-3-(2-propyl-1H-imidazo[4,5-c]quinolin-1-yl)propanoate (2.1 g, 6.2 mmol), ethanol (50 mL), and water (5 mL). The reaction was stirred for one hour at ambient temperature and concentrated under reduced pressure. The residue was extracted with dichloromethane (2×50 mL); the combined extracts were diluted with dichloromethane (100 mL). The resulting solution was treated with water (10 mL) and adjusted to pH 6 with the addition of concentrated hydrochloric acid (<1 mL). The aqueous layer was separated and extracted with dichloromethane (25 mL). The combined organic fractions were dried over sodium sulfate, filtered, and concentrated under reduced pressure to provide 0.45 g of 2,2-dimethyl-3-(2-propyl-1H-imidazo[4,5-c]quinolin-1-yl)propionic acid hydrochloride as a yellow oil. The acidic aqueous layer was concentrated under reduced pressure and dried for one hour under vacuum at 55° C. to provide 1.5 g of 2,2-dimethyl-3-(2-propyl-1H-imidazo[4,5-c]quinolin-1-yl)propanoic acid hydrochloride as a yellow solid.

Part G

A suspension of the oil and the solid from Part F in dichloromethane (100 mL) was cooled to 0° C., and a solution of oxalyl chloride (1.1 mL, 11 mmol) in dichloromethane (4 mL) was added. After the addition, the reaction was stirred for 30 minutes at ambient temperature and concentrated under reduced pressure. A second treatment with oxalyl chloride was carried out as described above. The residue was suspended in dichloromethane (75 mL) and cooled to 0° C. A solution of ammonia (10 mL of 2 M in isopropanol) was then added over a period of two minutes. The reaction was stirred for 30 minutes and then concentrated under reduced pressure. The residue was mixed with dichloromethane (100 mL) and saturated aqueous sodium bicarbonate (25 mL). The aqueous layer was separated and extracted with dichloromethane (50 mL). The combined organic fractions were dried over potassium carbonate, filtered, and concentrated under reduced pressure to provide 1.0 g of 2,2-dimethyl-3-(2-propyl-1H-imidazo[4,5-c]quinolin-1-yl)propanamide as a yellow solid, which was combined with material from another run.

Part H 2,2-Dimethyl-3-(2-propyl-1H-imidazo[4,5-c]quinolin-1-yl)propanamide was treated with mCPBA (3.24 g, 14.4 mmol) followed by ammonium hydroxide (75 mL) and p-toluenesulfonyl chloride (2.5 g, 13 mmol) according to a modification of the method described in Part F of Example 1. The reaction was cooled to 0° C. before the addition of mCPBA. After the addition, the reaction was stirred for 15 minutes at 0° C. and 1.75 hours at ambient temperature. The reaction was not washed prior to the addition of ammonium hydroxide. The amination reaction was stirred for one hour. The crude product was purified by column chromatography on silica gel (eluting with 90:10 dichloromethane:methanol), recrystallized from toluene:methanol, dried overnight in a vacuum oven at 80° C., recrystallized from acetonitrile:water, and dried overnight in a vacuum oven at 80° C. to provide 0.553 g of 3-(4-amino-2-propyl-1H-imidazo[4,5-c]quinolin-1-yl)-2,2-dimethylpropanamide as a yellow solid, mp 219-221° C.

Anal. Calcd for $C_{18}H_{23}N_5O$: C, 66.44; H, 7.12; N, 21.52. Found: C, 66.14; H, 7.04; N, 21.41.

Example 27

1-(2,2-Dimethyl-3-morpholin-4-yl-3-oxopropyl)-2-propyl-1H-imidazo[4,5-c]quinolin-4-amine

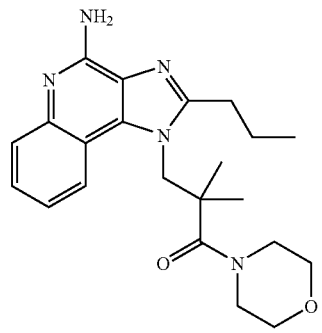 [SMILES: CCCc1nc2c(N)nc3ccccc3c2n1CC(C)(C)C(=O)N1CCOCC1]

Part A

Ethyl 3-[(3-aminoquinolin-4-yl)amino]-2,2-dimethylpropanoate (7.1 g, 25 mmol) was prepared according to the methods described in Parts A through D of Example 26 and treated according to a modification of the method described in Part B of Example 8. Prior to the addition of trimethyl orthobutyrate (4.0 g, 27 mmol) and pyridinium p-toluenesulfonate (0.10 g, 0.40 mmol), the reaction was heated at reflux for ten minutes. After the addition, the reaction was heated at reflux for four hours and allowed to stand at ambient temperature overnight. An analysis by TLC indicated the reaction was incomplete, and it was heated at reflux for an additional eight hours and allowed to stand for three days at ambient temperature. Additional pyridinium p-toluenesulfonate (0.10 g, 0.40 mmol) was added, and the reaction was heated at reflux for eleven hours and then allowed to cool to ambient temperature. Ethyl acetate (100 mL) was added, and the resulting solution was washed with saturated aqueous sodium bicarbonate (3×50 mL), dried over potassium carbonate, filtered, and concentrated under reduced pressure to 8 g of ethyl 2,2-dimethyl-3-(2-propyl-1H-imidazo[4,5-c]quinolin-1-yl)propanoate as a dark oil, which was used without purification.

Part B

A solution of ethyl 2,2-dimethyl-3-(2-propyl-1H-imidazo[4,5-c]quinolin-1-yl)propanoate (5.1 g, 15 mmol) and morpholine (5 mL, 60 mmol) was heated at reflux overnight. An analysis by LC/MS indicated the reaction was incomplete. The solution was then heated overnight in a high-pressure vessel at 165° C. Again, an analysis by LC/MS indicated the reaction was incomplete. The volatiles were removed under reduced pressure, and the residue was dissolved in ethanol (30 mL). Aqueous sodium hydroxide (1.35 mL of 50%, 20.0 mmol) was added, and the reaction was stirred for 1.5 hours. The solution was adjusted to pH 7 with the addition of concentrated hydrochloric acid (~1 mL) and then concentrated under reduced pressure. The residue was dissolved in dichloromethane (75 mL); a solution of oxalyl chloride (2.5 mL, 28 mmol) in dichloromethane (5 mL) was added dropwise over a period of two minutes. The reaction was stirred for 30 minutes, and additional oxalyl chloride (0.5 mL, 6 mmol) was added. The reaction was stirred for 30 minutes and diluted with dichloromethane (75 mL). A solution of morpholine (4.0 mL, 41 mmol) in dichloromethane (10 mL) was then added dropwise, and the reaction was stirred for two hours. The reaction was diluted with dichloromethane (45 mL), washed with saturated aqueous sodium bicarbonate (3×50 mL), dried over potassium carbonate, filtered, and concentrated under reduced pressure. The resulting dark oil was purified by column chromatography on silica gel (eluting with 93:7 dichloromethane:methanol) to provide 5.8 g of 1-(2,2-dimethyl-3-morpholin-4-yl-3-oxopropyl)-2-propyl-1H-imidazo[4,5-c]quinoline as a semi-solid.

Part C mCPBA (8.7 g, 39 mmol) was added to a solution of the material from Part B in chloroform (150 mL). The reaction was stirred for 1.75 hours at ambient temperature and then washed with 5% aqueous sodium hydroxide (2×50 mL). Ammonium hydroxide (150 mL) and p-toluenesulfonyl chloride (4.4 g, 23 mmol) were sequentially added, and the reaction was stirred vigorously for two hours. The aqueous layer was separated and extracted with dichloromethane (50 mL). The combined organic fractions were washed with 5% sodium hydroxide (2×50 mL), dried over potassium carbonate, decanted, and concentrated under reduced pressure. The crude product was recrystallized several times from methanol:water to provide 1.84 g of 1-(2,2-dimethyl-3-morpholin-4-yl-3-oxopropyl)-2-propyl-1H-imidazo[4,5-c]quinolin-4-amine as a yellow solid, mp 212-214° C.

Anal. Calcd for $C_{22}H_{29}N_5O_2 \cdot 0.15H_2O$: C, 66.35; H, 7.42; N, 17.59. Found: C, 66.15; H, 7.25; N, 17.82.

Example 28

3-[4-Amino-2-(ethoxymethyl)-1H-imidazo[4,5-c]quinolin-1-yl]-2,2-dimethylpropanamide

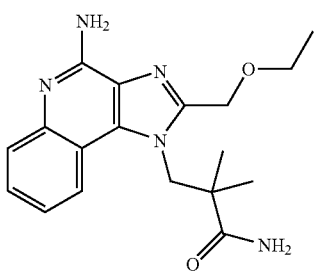 [SMILES: CCOCc1nc2c(N)nc3ccccc3c2n1CC(C)(C)C(N)=O]

Part A

A modification of the method described in Part C of Example 5 was used to treat ethyl 3-[(3-aminoquinolin-4-yl)amino]-2,2-dimethylpropanoate (15.5 g, 60.2 mmol, prepared in Parts A through D of Example 26) with ethoxyacetyl chloride (8.7 g, 71 mmol) followed by triethylamine (24.4 mL, 175 mmol). The reaction with ethoxyacetyl chloride was stirred overnight, and the reaction with triethylamine was heated at reflux in ethanol (125 mL) for four days. Following the work-up procedure, the crude product was purified by column chromatography on silica gel (eluting with dichloromethane:methanol in a gradient from 100:0 to 95:5) to provide 7.9 g of ethyl 3-[2-(ethoxymethyl)-1H-imidazo[4,5-c]quinolin-1-yl]-2,2-dimethylpropanoate as an oil.

Part B

Aqueous sodium hydroxide (1.5 mL of 50%, 19 mmol) was added to a mixture of ethyl 3-[2-(ethoxymethyl)-1H-imidazo[4,5-c]quinolin-1-yl]-2,2-dimethylpropanoate (5.0 g, 14 mmol), ethanol (50 mL), and water (5 mL). The reaction was stirred for two hours at ambient temperature; an analysis by TLC indicated that starting material was present. Additional aqueous sodium hydroxide (0.5 mL of 50%) was added, and the reaction was heated at reflux for two hours and concentrated under reduced pressure. Ethanol (100 mL) was added to the residue and then removed under reduced pressure to provide 3-[2-(ethoxymethyl)-1H-imidazo[4,5-c]quinolin-1-yl]-2,2-dimethylpropanoic acid, which was dried overnight under vacuum.

Part C

A modification of the method described in Part G of Example 26 was used to treat the material from Part B with oxalyl chloride (2×2.6 mL, 59.6 mmol) followed by ammonia (5 mL of a 7 M solution in methanol). The reactions were carried out at ambient temperature, and the reaction with ammonia was stirred for two hours. Aqueous sodium hydroxide (5 mL of 50%) and water (45 mL) were added, and the mixture was stirred. The organic layer was separated, although not completely, and stirred with aqueous sodium hydroxide (10 mL of 25%). The organic fraction was separated and concentrated under reduced pressure to provide 3-[2-(ethoxymethyl)-1H-imidazo[4,5-c]quinolin-1-yl]-2,2-dimethylpropanamide as a light-brown solid.

Part D

The material from Part C was treated with mCPBA (5.4 g, 24 mmol) followed by ammonium hydroxide (75 mL) and p-toluenesulfonyl chloride (4.1 g, 22 mmol) according to a modification of the method described in Part F of Example 1. The reaction was cooled to 0° C. before the addition of mCPBA. After the addition, the reaction was allowed to warm to ambient temperature and stirred for 2.25 hours. Additional mCPBA (1.5 g, 6.1 mmol) was added, and the reaction was stirred overnight. The reaction was not washed prior to the addition of ammonium hydroxide. The amination reaction was stirred for two hours. The extraction was carried out with dichloromethane (10×50 mL). The crude product was purified by column chromatography on silica gel (eluting with dichloromethane:methanol in a gradient from 95:5 to 80:20), recrystallized from ethanol:water, and dried overnight in a vacuum oven at 70° C. to provide 0.417 g of 3-[4-amino-2-(ethoxymethyl)-1H-imidazo[4,5-c]quinolin-1-yl]-2,2-dimethylpropanamide as tan crystals, mp 241-243° C.

Anal. Calcd for $C_{18}H_{23}N_5O_2$: C, 63.32; H, 6.79; N, 20.51. Found: C, 63.21; H, 7.08; N 20.62.

Example 29

1-(4-Morpholin-4-yl-4-oxobutyl)-2-propyl-6,7,8,9-tetrahydro-1H-imidazo[4,5-c]quinolin-4-amine

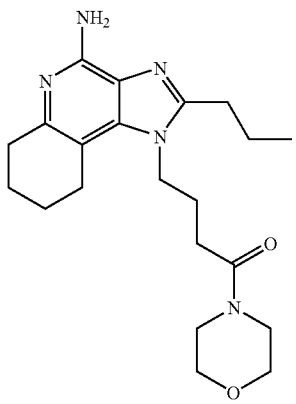 [SMILES: CCCc1nc2c(N)nc3c(c2n1CCCC(=O)N1CCOCC1)CCCC3]

A mixture of 1-(4-morpholin-4-yl-4-oxobutyl)-2-propyl-1H-imidazo[4,5-c]quinolin-4-amine (0.62 g, 1.6 mmol, prepared as described in Example 1), platinum (IV) oxide (0.25 g, 1.1 mmol), and trifluoroacetic acid (25 mL) was placed in a Parr vessel and shaken under hydrogen pressure (50 psi, $3.5 \times 10^5$ Pa) for two hours. An analysis by LC/MS indicated the reaction was incomplete. Additional platinum (IV) oxide (0.5 g) was added, and the reaction was continued overnight. The trifluoroacetic acid was removed under reduced pressure, and the residue was dissolved in methanol (35 mL). Aqueous sodium hydroxide (10 mL of 25%) was added to the solution, and the mixture was stirred for 15 minutes and then diluted with dichloromethane (100 mL). The mixture was filtered through a layer of CELITE filter aid, and the filtrate was concentrated under reduced pressure. The residue was dissolved in dichloromethane, washed with 5% aqueous sodium hydroxide (2×25 mL), dried over potassium carbonate, filtered, and concentrated under reduced pressure. The resulting solid was recrystallized from water:acetonitrile; the crystals were triturated with 25% aqueous sodium hydroxide for one hour, diluted with water, isolated by filtration, and recrystallized from water:ethanol. The resulting crystals were dried overnight in a vacuum oven at 70° C. to provide 0.5706 g of 1-(4-morpholin-4-yl-4-oxobutyl)-2-propyl-6,7,8,9-tetrahydro-1H-imidazo[4,5-c]quinolin-4-amine as white crystals, mp 181-183° C.

Anal. Calcd for $C_{21}H_{31}N_5O_2$: C, 65.43; H, 8.11; N, 18.17. Found: C, 65.36; H, 8.40; N, 18.11.

Example 30

1-(6-Morpholin-4-yl-6-oxohexyl)-2-propyl-6,7,8,9-tetrahydro-1H-imidazo[4,5-c]quinolin-4-amine

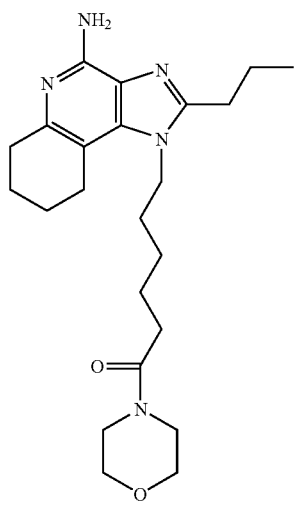 [SMILES: CCCc1nc2c(N)nc3c(c2n1CCCCCC(=O)N1CCOCC1)CCCC3]

A second batch of 1-(6-morpholin-4-yl-6-oxohexyl)-2-propyl-1H-imidazo[4,5-c]quinolin-4-amine was prepared according to the methods described in Example 6 with the following modifications. In Part C, a solution of ethyl 6-(3-nitroquinolin-4-ylamino)hexanoate (122.94 g, 371.6 mmol) in dichloromethane (800 mL) was added to a solution of sodium hydrosulfite (226.44 g, 1.30 mol), potassium carbonate (202.86 g, 1.47 mol), and ethyl viologen diiodide (1.737 g, 3.71 mmol) in water (800 mL), and the reaction was stirred overnight at ambient temperature. The organic layer was separated, washed with water (4×), dried over magnesium sulfate, filtered, and concentrated under reduced pressure to provide 106.7 g of ethyl 6-(3-aminoquinolin-4-ylamino)hexanoate. The crude product from Part G was recrystallized from methanol, triturated with hot ethyl acetate twice, triturated with hexanes, and isolated by filtration to provide 20.9 g of 1-(6-morpholin-4-yl-6-oxohexyl)-2-propyl-1H-imidazo[4,5-c]quinolin-4-amine as a light tan powder, mp 156-158° C.

A mixture of 1-(6-morpholin-4-yl-6-oxohexyl)-2-propyl-1H-imidazo[4,5-c]quinolin-4-amine (2.0 g, 4.9 mmol), platinum (IV) oxide (1.5 g, 6.6 mmol), and trifluoroacetic acid (50 mL) was placed in a Parr vessel and shaken under hydrogen pressure (50 psi, $3.5 \times 10^5$ Pa) for 24 hours. The trifluoroacetic acid was removed under reduced pressure, and the residue was sonicated with 10% aqueous sodium hydroxide. The resulting solid was mixed with material from another run and recrystallized from water. The crystals were isolated by filtration and dried overnight at 80° C. to provide 0.978 g of 1-(6-morpholin-4-yl-6-oxohexyl)-2-propyl-6,7,8,9-tetrahydro-1H-imidazo[4,5-c]quinolin-4-amine as a white crystalline powder, mp 162-163° C.

Anal. Calcd for $C_{23}H_{35}N_5O_2$: C, 66.80; H, 8.53; N, 16.93. Found: C, 66.54; H, 8.85; N, 16.87

Example 31

3-(4-Amino-2-methyl-1H-imidazo[4,5-c]quinolin-1-yl)propanamide

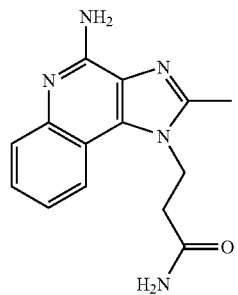 [SMILES: Cc1nc2c(N)nc3ccccc3c2n1CCC(N)=O]

Part A

Ammonium acetate (4.0 g) and ethyl 3-(2-methyl-1H-imidazo[4,5-c]quinolin-1-yl)propanoate (4.5 g, 17 mmol, prepared as described in Parts A through C of Example 22) were heated for three days at 130° C. in a sealed vessel. The reaction was allowed to cool to ambient temperature, and water was added. The mixture was concentrated under reduced pressure, and the residue was purified by column chromatography on silica gel (eluting with dichloromethane:methanol in a gradient from 90:10 to 85:15) to provide 2.20 g of 3-(2-methyl-1H-imidazo[4,5-c]quinolin-1-yl)propanamide as a tan solid.

Part B mCPBA (3.48 g, 15.1 mmol) was added to a solution of 3-(2-methyl-1H-imidazo[4,5-c]quinolin-1-yl)propanamide (2.20 g, 8.65 mmol) in chloroform (100 mL). The reaction was stirred for two hours at ambient temperature and cooled to 0° C. Ammonium hydroxide (40 mL) was added followed by p-toluenesulfonyl chloride (3.21 g, 16.9 mmol), which was added over a period of five minutes. The reaction was stirred for two hours at ambient temperature and then concentrated under reduced pressure. The crude product was purified by column chromatography on silica gel (eluting with dichloromethane:methanol in a gradient from 90:10 to 80:20). The resulting solid was triturated with 10% aqueous sodium hydroxide, isolated by filtration, washed with water, and dried overnight in a vacuum oven at 60° C. to provide 0.145 g of 3-(4-amino-2-methyl-1H-imidazo[4,5-c]quinolin-1-yl)propanamide as a off-white powder, mp 237-239° C.

Anal. Calcd for $C_{14}H_{15}N_5O$: C, 57.78; H, 6.03; N, 24.06. Found: C, 57.38; H, 5.82; N, 24.29.

Example 32

3-(4-Amino-2-methyl-1H-imidazo[4,5-c]quinolin-1-yl)-N-propylpropanamide

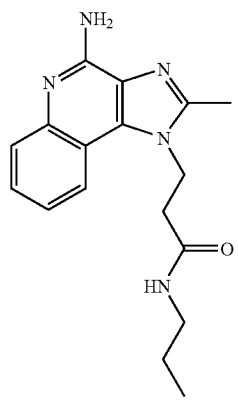 [SMILES: CCCNC(=O)CCn1c(C)nc2c(N)nc3ccccc3c21]

Part A

Ethyl N-(3-nitroquinolin-4-yl)-β-alaninate (62.0 g, 214 mmol, prepared as described in Part A of Example 22) was treated with sodium hydrosulfite (130.59 g, 750.04 mmol), potassium carbonate (117 g, 847 mmol), and ethyl viologen dibromide (0.802 g, 2.14 mmol) according to a modification of the method described in Part A of Example 8. After the reaction was stirred overnight, additional water (100 mL), dichloromethane (100 mL) and sodium hydrosulfite (20.0 g, 11.5 mmol) were added, and the reaction was stirred for three additional hours. The organic layer was separated; washed sequentially with water, saturated aqueous sodium bicarbonate, and brine; dried over magnesium sulfate; filtered; and concentrated under reduced pressure to provide 40.2 g of ethyl N-(3-aminoquinolin-4-yl)-β-alaninate.

Part B

Ethyl N-(3-aminoquinolin-4-yl)-β-alaninate (9.0 g, 35 mmol) was treated with triethyl orthoacetate (8.91 mL, 48.6 mmol) and pyridinium p-toluenesulfonate (0.200 g) according to the method described in Part A of Example 10 to provide 6.10 g of ethyl 3-(2-methyl-1H-imidazo[4,5-c]quinolin-1-yl)propanoate. The reaction was complete in two hours, and a precipitate was removed by filtration from the organic layer during the work-up procedure.

Part C

Propylamine (20 mL) and ethyl 3-(2-methyl-1H-imidazo[4,5-c]quinolin-1-yl)propanoate (5.77 g, 20.4 mmol) were heated overnight at 100° C. in a sealed vessel. The reaction was allowed to cool to ambient temperature and concentrated under reduced pressure to provide 6.0 g of 3-(2-methyl-1H-imidazo[4,5-c]quinolin-1-yl)-N-propylpropanamide.

Part D 3-(2-Methyl-1H-imidazo[4,5-c]quinolin-1-yl)-N-propylpropanamide (610 g, 20.2 mmol) was treated with mCPBA (8.15 g, 35.4 mmol) followed by ammonium hydroxide (40 mL) and p-toluenesulfonyl chloride (7.52 g, 39.5 mmol) according to a modification of the method described in Part D of Example 8. The reaction was not washed with 10% aqueous sodium hydroxide prior to the addition of ammonium hydroxide. The crude product was twice triturated with ethyl acetate and isolated by filtration. The solid was then purified by column chromatography on silica gel (eluting with 90:10 dichloromethane:methanol). The product was then triturated sequentially with 10% aqueous sodium hydroxide and acetone (2×). The solid was then purified again by column chromatography on silica gel (eluting with dichloromethane:methanol in a gradient from 95:5 to 90:10). The resulting solid was triturated with 10% aqueous sodium hydroxide, isolated by filtration, washed with water, and dried overnight to provide 0.477 g of 3-(4-amino-2-methyl-1H-imidazo[4,5-c]quinolin-1-yl)-N-propylpropanamide as an off-white powder, mp 188-189° C.

Anal. Calcd for $C_{17}H_{21}N_5O$: C, 65.57; H, 6.80; N, 22.49. Found: C, 65.24; H, 6.67; N, 22.44.

Example 33

4-[4-Amino-2-(ethoxymethyl)-1H-imidazo[4,5-c]quinolin-1-yl]butanamide

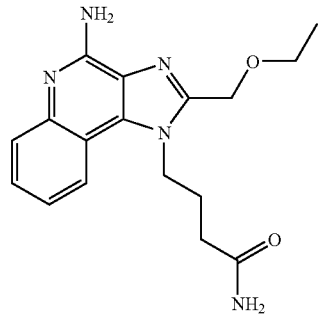 [SMILES: CCOCc1nc2c(N)nc3ccccc3c2n1CCCC(N)=O]

Part A

Ethyl 4-[2-(ethoxymethyl)-1H-imidazo[4,5-c]quinolin-1-yl]butanoate (15.9 g, 46.6 mmol, prepared as described in Parts A through C of Example 5) and ammonium acetate (35.0 g, 455 mmol) were sealed and heated in a high-pressure vessel at 130° C. for two days. An analysis by LC/NS indicated the presence of starting material, and additional ammonium acetate (15 g, 190 mmol) was added. The reaction was heated to 130° C. for several hours, allowed to cool to ambient temperature, stirred for three days, and poured into water (200 mL). Solid sodium bicarbonate was added until the solution was basic. The solution was extracted with dichloromethane (3×100 mL, 5×75 mL, and then in a continuous extractor for about 20 hours). The extracts were dried over potassium carbonate, filtered, and concentrated under reduced pressure to provide 10.3 g of 4-[2-(ethoxymethyl)-1H-imidazo[4,5-c]quinolin-1-yl]butanamide as a light yellow solid.

Part B

4-[2-(Ethoxymethyl)-1H-imidazo[4,5-c]quinolin-1-yl]butanamide (4.3 g, 14 mmol) was treated with mCPBA (6.1 g, 27 mmol), concentrated ammonium hydroxide (50 mL of 29%), and p-toluenesulfonyl chloride (4.6 g, 24 mmol) according to a modification of the method described in Part E of Example 3. The mCPBA addition was carried out at 0° C., and the reaction was carried out in dichloromethane (150 mL). At the end of the reaction the layers were separated, and saturated aqueous sodium bicarbonate (100 mL) and 5% aqueous sodium hydroxide (10 mL) were added to the organic layer. The aqueous layer was extracted with dichloromethane (1.3 L), and the combined extracts were dried over potassium carbonate, filtered, and concentrated under reduced pressure. The crude product was purified by column chromatography on silica gel (eluting with 90:10 dichloromethane:methanol containing 4 mL/L of ammonium hydroxide) followed by recrystallization five times from ethanol containing a small amount of water. The resulting solid was recrystallized from water:acetonitrile (5:L), dried overnight in a vacuum oven at 70° C., triturated with 25% aqueous ammonium hydroxide, diluted with water, isolated by filtration, recrystallized from ethanol:water, and dried overnight in a vacuum oven at 70° C. to provide 0.4704 g of 4-[4-amino-2-(ethoxymethyl)-1H-imidazo[4,5-c]quinolin-1-yl]butanamide as tan crystals, mp 233-235° C.

Anal. Calcd for $C_{17}H_{21}N_5O_2 \cdot 0.07H_2O$: C, 62.12; H, 6.48; N, 21.31. Found: C, 61.77; H, 6.83; N, 21.22.

Example 34

1-(5-Morpholin-4-yl-5-oxopentyl)-2-propyl-1H-imidazo[4,5-c]quinolin-4-amine

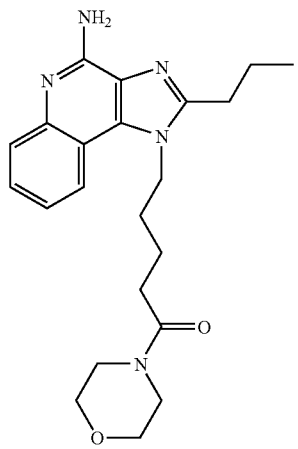 [SMILES: CCCc1nc2c(N)nc3ccccc3c2n1CCCCC(=O)N1CCOCC1]

Part A

Potassium carbonate (66.23 g, 479.3 mmol), triethylamine (167 mL, 1.20 mol), and ethyl 5-aminovalerate hydrochloride (104.4 g, 575.2 mmol) were added to a solution of 4-chloro-3-nitroquinoline (100.0 g, 479.3 mmol) in chloroform (1000 mL) according to the method described in Part B of Example 6. The reaction was run for four hours and provided 151 g of ethyl 5-(3-nitroquinolin-4-ylamino)pentanoate.

Part B

A solution of ethyl 5-(3-nitroquinolin-4-ylamino)pentanoate (151 g, 476 mmol) in dichloromethane (1 L) was added to a solution of sodium hydrosulfite (248.5 g, 1.427 mol), potassium carbonate (259.3 g, 1.876 mol), and ethyl viologen dibromide (1.78 g, 4.75 mmol) in water (1 L), and the reaction was stirred overnight at ambient temperature. An analysis by TLC indicated the presence of starting material; additional sodium hydrosulfite (5.0 g, 29 mmol) was added to the reaction, which was stirred for one additional hour. The organic layer was separated, washed with water (3×), dried over magnesium sulfate, filtered, and concentrated under reduced pressure to provide 131.51 g of ethyl 5-(3-aminoquinolin-4-ylamino)pentanoate.

Part C

The method described in Part A of Example 10 was used to treat ethyl 5-(3-aminoquinolin-4-ylamino)pentanoate (26.3 g, 91.5 mmol) with trimethyl orthobutyrate (18.3 mL, 114 mmol) and pyridinium p-toluenesulfonate (0.5 g). The reaction was complete in three hours to provide 28 g of ethyl 5-(2-propyl-1H-imidazo[4,5-c]quinolin-1-yl)pentanoate as a brown oil.

Part D

A solution of sodium hydroxide (2.23 g, 55.9 mmol) in water (100 mL) was added to a solution of ethyl 5-(2-propyl-1H-imidazo[4,5-c]quinolin-1-yl)pentanoate (14.6 g, 43.0 mmol) in ethanol (100 mL), and the reaction was stirred at ambient temperature overnight, concentrated to remove ethanol, and washed with dichloromethane. The resulting solution was adjusted to pH 5 with the addition of 10% hydrochloric acid. The mixture was extracted twice with chloroform, and the combined extracts were dried over magnesium sulfate, filtered, and concentrated under reduced pressure to provide 11.5 g of 5-(2-propyl-1H-imidazo[4,5-c]quinolin-1-yl)pentanoic acid.

Part E

A modification of the method described in Part F of Example 6 was used to treat 5-(2-propyl-1H-imidazo[4,5-c]quinolin-1-yl)pentanoic acid (5.14 g, 16.5 mmol) with oxalyl chloride (2.59 mL, 29.7 mmol) and morpholine (4.33 mL, 49.5 mmol). The oxalyl chloride addition was carried out at ambient temperature, and the reaction with morpholine was complete in three hours. Following the work-up procedure, 6.2 g of 1-(5-morpholin-4-yl-5-oxopentyl)-2-propyl-1H-imidazo[4,5-c]quinoline were obtained.

Part F mCPBA (6.56 g, 28.5 mmol) was added to a solution of 1-(5-morpholin-4-yl-5-oxopentyl)-2-propyl-1H-imidazo[4,5-c]quinoline (6.2 g, 16 mmol) in chloroform (100 mL); the reaction was stirred for three hours at ambient temperature. Ammonium hydroxide (50 mL) was added. p-Toluenesulfonyl chloride (6.056 g, 31.76 mmol) was added over a period of five minutes, and the reaction was stirred for one hour. The work-up procedure and chromatographic purification was carried out as described in Part D of Example 8. The resulting oil was triturated with acetone, isolated by filtration, and dried to provide 1-(5-morpholin-4-yl-5-oxopentyl)-2-propyl-1H-imidazo[4,5-c]quinolin-4-amine as a tan powder, mp 178-179° C.

Anal. Calcd for $C_{22}H_{29}N_5O_2$: C, 66.81; H, 7.391; N, 17.71. Found: C, 66.50; H, 7.38; N, 17.41.

Example 35

5-(4-Amino-2-propyl-1H-imidazo[4,5-c]quinolin-1-yl)pentanamide

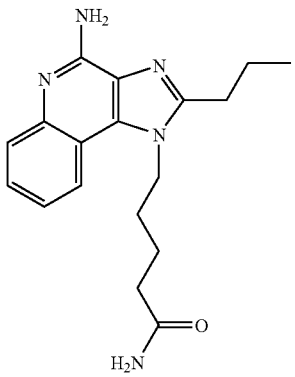 [SMILES: CCCc1nc2c(N)nc3ccccc3c2n1CCCCC(N)=O]

Part A

Ethyl 5-(2-propyl-1H-imidazo[4,5-c]quinolin-1-yl)pentanoate (5.4 g, 15.9 mmol), prepared as described in Parts A through C of Example 34) and ammonium acetate (11.0 g, 143 mmol) were sealed in a high-pressure vessel and heated for two days at 130° C. and then allowed to cool to ambient temperature. Ammonium hydroxide was added to adjust the mixture to a neutral pH. The mixture was then extracted with dichloromethane, and the combined extracts were washed with saturated aqueous sodium bicarbonate, dried over magnesium sulfate, filtered, and concentrated under reduced pressure to provide 2.8 g of 5-(2-propyl-1H-imidazo[4,5-c]quinolin-1-yl)pentanamide, which was combined with material from another run.

Part B 5-(2-Propyl-1H-imidazo[4,5-c]quinolin-1-yl)pentanamide (4.4 g, 14 mmol) was treated with mCPBA (4.28 g, 24.8 mmol), ammonium hydroxide (40 mL), and p-toluenesulfonyl chloride (5.24 g, 27.4 mmol) according to a modification of the method described in Part F of Example 34. At the completion of the amination reaction, a precipitate was present and was isolated by filtration. The precipitate was triturated and sonicated with acetone, isolated by filtration, and dried in a vacuum oven at 80° C. to provide 1.28 g of 5-(4-amino-2-propyl-1H-imidazo[4,5-c]quinolin-1-yl)pentanamide as a tan powder, mp 202-203° C.

Anal. Calcd for $C_{18}H_{23}N_5O \cdot 0.09H_2O$: C, 66.09; H, 7.15; N, 21.41. Found: C, 65.69; H, 7.46; N, 21.22.

Example 36

2-(2-Methoxyethyl)-1-(5-morpholin-4-yl-5-oxopentyl)-1H-imidazo[4,5-c]quinolin-4-amine

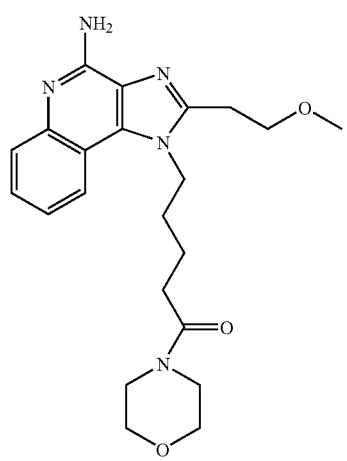 [SMILES: COCCc1nc2c(N)nc3ccccc3c2n1CCCCC(=O)N1CCOCC1]

Part A

Ethyl 5-(3-aminoquinolin-4-ylamino)pentanoate (23.0 g, 88.6 mmol, prepared in Parts A and B of Example 34) was treated according to the method described in Part A of Example 12. The addition of methoxypropionyl chloride (12.97 g, 106.3 mmol) was carried out at 0° C., and the reaction was stirred at ambient temperature for two hours. The reaction with triethylamine (49.4 g, 354 mmol) was heated at reflux for four hours. After the work-up procedure, 28.6 g of ethyl 5-[2-(2-methoxyethyl)-1H-imidazo[4,5-c]quinolin-1-yl]pentanoate were obtained as a brown oil.

Part B

Ethyl 5-[2-(2-methoxyethyl)-1H-imidazo[4,5-c]quinolin-1-yl]pentanoate (15.1 g, 42.4 mmol) was treated with sodium hydroxide (2.20 g, 55.2 mmol) according to the method described in Part A of Example 11. The reaction was stirred overnight at ambient temperature to provide 10.2 g of 5-[2-(2-methoxyethyl)-1H-imidazo[4,5-c]quinolin-1-yl]pentanoic acid after the aqueous work-up procedure.

Part C

5-[2-(2-Methoxyethyl)-1H-imidazo[4,5-c]quinolin-1-yl]pentanoic acid (5.5 g, 17 mmol) was treated according to a modification of the method described in Part F of Example 6. The reaction with oxalyl chloride (2.63 mL, 30.2 mmol) was carried out at ambient temperature and was complete in 30 minutes. The reaction with morpholine (4.40 mL, 50.4 mmol) was complete after 30 minutes. Following the work-up procedure, 6.5 g of 2-(2-methoxyethyl)-1-(5-morpholin-4-yl-5-oxopentyl)-1H-imidazo[4,5-c]quinoline were obtained.

Part D mCPBA (6.60 g, 28.7 mmol) was added to a solution of 2-(2-methoxyethyl)-1-(5-morpholin-4-yl-5-oxopentyl)-1H-imidazo[4,5-c]quinoline (6.5 g, 17 mmol) in chloroform (100 mL); the reaction was stirred for two hours at ambient temperature. The reaction was cooled to 0° C., and ammonium hydroxide (50 mL) was added. A solution of benzenesulfonyl chloride (4.11 mL, 33.0 mmol) in chloroform (20 mL) was added over a period of 20 minutes, and the reaction was allowed to warm to ambient temperature and stirred for two hours. The work-up procedure and chromatographic purification was carried out as described in Part D of Example 8. The resulting product was triturated with 10% aqueous sodium hydroxide, isolated by filtration, washed with water, and dried overnight in a vacuum oven to provide 2-(2-methoxyethyl)-1-(5-morpholin-4-yl-5-oxopentyl)-1H-imidazo[4,5-c]quinolin-4-amine as an off-white powder, mp 128-129° C.

Anal. Calcd for $C_{22}H_{29}N_5O_3 \cdot 0.17H_2O$: C, 63.74; H, 7.13; N, 16.89. Found: C, 63.33; H, 7.34; N, 16.73.

Example 37

1-(4-Morpholin-4-yl-4-oxobutyl)-2-propyl-1H-imidazo[4,5-c][1,5]naphthyridin-4-amine

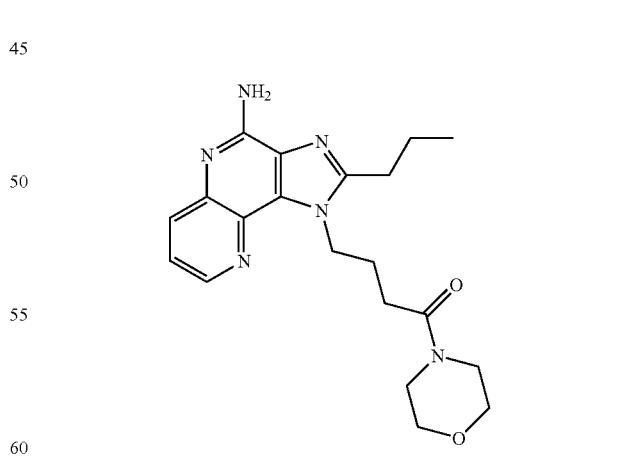

Part A

A suspension of 4-chloro-3-nitro[1,5]naphthyridine (10.0 g, 47.7 mmol) and ethyl 4-aminobutyrate hydrochloride (9.6 g, 57 mmol) in dichloromethane (200 mL) was cooled to 5° C. Triethylamine (16.6 mL, 119 mmol) was added, and the reaction was allowed to warm to ambient temperature and stirred for two hours. The mixture was diluted with dichloromethane (200 mL) and washed with saturated aqueous sodium bicarbonate (2×150 mL). The combined aqueous fractions were extracted with dichloromethane (100 mL), and the combined organic fractions were dried over magnesium sulfate, filtered, and concentrated under reduced pressure to provide 14.5 g of ethyl 4-(3-nitro[1,5]naphthyridin-4-ylamino)butanoate as a yellow solid.

Part B

A mixture of ethyl 4-(3-nitro[1,5]naphthyridin-4-ylamino) butanoate (5.0 g, 16 mmol), 5% platinum on carbon (0.50 g), and ethyl acetate (80 mL) was added to a Parr vessel, and the reaction was placed under hydrogen pressure (30 psi, $2.1 \times 10^5$ Pa) for 2.5 hours. The reaction mixture was filtered through a layer of CELITE filter agent, and the filter cake was washed with ethyl acetate (50 mL). The filtrate was concentrated under reduced pressure to provide ethyl 4-(3-amino[1,5] naphthyridin-4-ylamino)butanoate as a yellow oil.

Part C

A solution of ethyl 4-(3-amino[1,5]naphthyridin-4-ylamino)butanoate (2.0 g, 7.3 mmol) in dichloromethane (35 mL) was cooled to 0° C. Butyryl chloride (0.68 mL, 8.0 mmol) was added dropwise over a period of ten minutes, and the reaction was allowed to warm to ambient temperature, stirred for 90 minutes, and concentrated under reduced pressure. Triethylamine (3.0 mL, 22 mmol) and ethanol (35 mL) were added, and the resulting solution was heated at reflux for two days. Pyridine hydrochloride (0.1 equivalents) was added, and the reaction was heated at reflux overnight. The solvent was removed under reduced pressure, and the residue was partitioned between dichloromethane (70 mL) and saturated aqueous sodium bicarbonate (50 mL). The aqueous layer was separated and extracted with dichloromethane (2×25 mL), and the combined organic fractions were dried over magnesium sulfate, filtered, and concentrated under reduced pressure to provide 2.43 g of ethyl 4-(2-propyl-1H-imidazo[4,5-c][1,5]naphthyridin-1-yl]butanoate as a brown oil.

Part D

Aqueous sodium hydroxide (2.4 mL of 6 M) was added to a solution of ethyl 4-(2-propyl-1H-imidazo[4,5-c][1,5]naphthyridin-1-yl]butanoate (2.37 g, 7.26 mmol) in ethanol (25 mL); the reaction was stirred at ambient temperature for two hours and concentrated under reduced pressure. The residue was dissolved in water (15 mL) and adjusted to pH 4 with the addition of 2 M hydrochloric acid. A precipitate formed, was isolated by filtration, and was mixed with toluene, which was removed under reduced pressure to provide 1.78 g of 4-(2-propyl-1H-imidazo[4,5-c][1,5]naphthyridin-1-yl]butanoic acid as a tan powder.

Part E 4-(2-Propyl-1H-imidazo[4,5-c][1,5]naphthyridin-1-yl] butanoic acid (prepared in a separate run, 5.34 mmol) was treated according to a modification of Part F of Example 6. One drop of N,N-dimethylformamide (DMF) was added to the reaction mixture. The addition of oxalyl chloride (1.4 mL, 16 mmol) was carried out at ambient temperature, and the reaction was stirred for two hours. Additional oxalyl chloride (0.5 mL) was added, and the reaction was stirred for an additional hour. The reaction with morpholine (1.17 mL, 13.3 mmol) was stirred for one hour. Following the work-up procedure 1.80 g of 1-(4-morpholin-4-yl-4-oxobutyl)-2-propyl-1H-imidazo[4,5-c][1,5]naphthyridine were obtained as a yellow solid.

Part F mCPBA (1.18 g, 6.86 mmol) was added to a solution of 1-(4-morpholin-4-yl-4-oxobutyl)-2-propyl-1H-imidazo[4,5-c][1,5]naphthyridine (1.80 g, 4.90 mmol) in chloroform (25 mL); the reaction was stirred for two hours at ambient temperature. Ammonium hydroxide (10 mL) was added followed by p-toluenesulfonyl chloride (1.03 g, 5.39 mmol). The reaction was stirred for one hour and partitioned between saturated aqueous sodium bicarbonate (75 mL) and dichloromethane (70 mL). The aqueous layer was extracted with dichloromethane (2×25 mL), and the combined organic fractions were dried over magnesium sulfate, filtered, and concentrated under reduced pressure. The resulting brown solid was triturated twice with acetonitrile and then purified by column chromatography using a HORIZON HPFC system (an automated, modular high-performance flash purification product available from Biotage, Inc.; Charlottesville, Va., USA) using a FLASH 40+M cartridge (also available from Biotage, Inc.). The polar component of the eluent was chloroform:methanol:ammonium hydroxide 80:18:2 (CMA). The purification was carried out eluting with chloroform:CMA in a gradient from 100:0 to 75:25. The resulting solid was dried under high vacuum at 80° C. to provide 0.583 g of 1-(4-morpholin-4-yl-4-oxobutyl)-2-propyl-1H-imidazo[4,5-c][1,5]naphthyridin-4-amine as an off-white powder, mp 196-197° C.

Anal. Calcd for $C_{20}H_{26}N_6O_2$: C, 62.81; H, 6.85; N, 21.97. Found: C, 62.60; H, 7.06; N, 22.00.

Example 38

2-(Ethoxymethyl)-1-(4-morpholin-4-yl-4-oxobutyl)-1H-imidazo[4,5-c][1,5]naphthyridin-4-amine

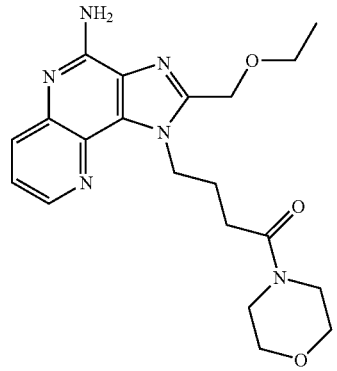 [SMILES: CCOCc1nc2c(N)nc3cccnc3c2n1CCCC(=O)N1CCOCC1]

Part A

Ethyl 4-(3-amino[1,5]naphthyridin-4-ylamino)butanoate (2.5 g, 9.1 mmol, prepared in Parts A and B of Example 37) was treated with ethoxyacetyl chloride (1.02 mL, 10.0 mmol) and cyclized according to a modification of the method described in Part C of Example 37. The reaction with triethylamine (3.8 mL, 27 mmol) was heated at reflux overnight and was complete. Following the work-up procedure, 3.11 g of ethyl 4-(2-ethoxymethyl-1H-imidazo[4,5-c][1,5]naphthyridin-1-yl]butanoate were obtained as a brown oil.

Part B

The methods of Parts D and E of Example 37 were used to treat ethyl 4-(2-ethoxymethyl-1H-imidazo[4,5-c][1,5]naphthyridin-1-yl]butanoate (1.0 g, 2.9 mmol) with aqueous sodium hydroxide (2.9 mL of 2 M), oxalyl chloride (0.42 mL, 4.8 mmol), and morpholine (0.35 mL, 4.0 mmol). The reaction with oxalyl chloride was complete within two hours, and no additional reagent was added. Following the work-up procedure 0.64 g of 2-(ethoxymethyl)-1-(4-morpholin-4-yl-4-oxobutyl)-1H-imidazo[4,5-c][1,5]naphthyridine was obtained as a yellow solid, which was combined with material from another run.

Part C

The method described in Part F of Example 37 was used to treat 2-(ethoxymethyl)-1-(4-morpholin-4-yl-4-oxobutyl)-1H-imidazo[4,5-c][1,5]naphthyridine (1.42 g, 3.70 mmol) with mCPBA (0.958 g, 5.55 mmol), ammonium hydroxide (4 mL), and p-toluenesulfonyl chloride (0.776 g, 4.07 mmol). Following the chromatographic purification, the resulting solid was dried for 48 hours under high vacuum at 120° C. to provide 0.614 g of 2-(ethoxymethyl)-1-(4-morpholin-4-yl-4-oxobutyl)-1H-imidazo[4,5-c][1,5]naphthyridin-4-amine as a tan powder, mp 156-157° C.

Anal. Calcd for $C_{20}H_{26}N_6O_3 \cdot 0.3H_2O$: C, 59.48; H, 6.64; N, 20.81. Found: C, 59.55; H, 6.63; N, 20.70.

Example 39

4-[4-Amino-2-(ethoxymethyl)-1H-imidazo[4,5-c][1,5]naphthyridin-1-yl]butanamide

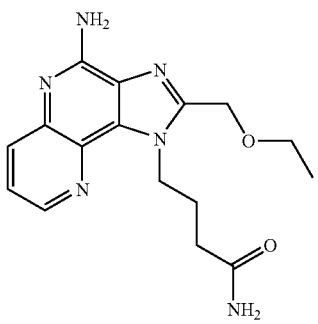 [SMILES: CCOCc1nc2c(N)nc3cccnc3c2n1CCCC(N)=O]

Part A

A solution of ammonia in dioxane (33 mL of 0.5 M) was added to a solution of 4-[2-(ethoxymethyl)-1H-imidazo[4,5-c][1,5]naphthyridin-1-yl]butanoyl chloride (4.64 mmol, prepared as described in Parts A and B of Example 38) in dichloromethane (20 mL), and the reaction was stirred overnight at ambient temperature. An analysis by HPLC indicated the reaction was incomplete; ammonia gas was bubbled through the solution for 10 minutes. The reaction was then stirred for one hour and concentrated under reduced pressure. The residue was triturated with water and isolated by filtration to provide 1.02 g of 4-[2-(ethoxymethyl)-1H-imidazo[4,5-c][1,5]naphthyridin-1-yl]butanamide. The filtrate was extracted with dichloromethane (3×20 mL), and the combined extracts were dried over magnesium sulfate, filtered, and concentrated under reduced pressure to provide an additional 0.39 g of product. The combined solids were mixed with material from another run.

Part B mCPBA (1.80 g, 7.28 mmol) was added to a solution of 4-[2-(ethoxymethyl)-1H-imidazo[4,5-c][1,5]naphthyridin-1-yl]butanamide (1.63 g, 5.20 mmol) in chloroform (50 mL); the reaction was stirred for three hours at ambient temperature. An analysis by LC/MS indicated the reaction was incomplete; therefore, additional mCPBA (1.2 equivalents) was added. The reaction was stirred for two hours and then diluted with saturated aqueous sodium bicarbonate (75 mL) and chloroform (75 mL). The aqueous layer was extracted with dichloromethane (2×30 mL) and chloroform (12×20 mL), and the combined organic fractions were dried over magnesium sulfate, filtered, and concentrated under reduced pressure to provide 2.34 g of 4-[2-(ethoxymethyl)-5-oxido-1H-imidazo[4,5-c][1,5]naphthyridin-1-yl]butanamide as an orange solid.

Part C

A solution of the material from Part B in methanol (25 mL) was cooled to 0° C.; ammonium hydroxide (1.8 mL, 26 mmol) was added. Benzenesulfonyl chloride (1.3 mL, 10.4 mmol) was added dropwise, and the reaction was stirred for one hour at 0° C. and concentrated under reduced pressure. The residue was triturated with methanol, isolated by filtration, and dissolved in aqueous sodium hydroxide (20 mL of 2 M). The solution was sonicated to form a precipitate, which was isolated by filtration, washed with cold water, and dried overnight in a vacuum oven at 80° C. to provide 0.432 g of 4-[4-amino-2-(ethoxymethyl)-1H-imidazo[4,5-c][1,5]naphthyridin-1-yl]butanamide as a pale yellow powder, mp 231-232° C.

Anal. Calcd for $C_{16}H_{20}N_6O_2 \cdot 0.3H_2O$: C, 57.58; H, 6.22; N, 25.18. Found: C, 57.76; H, 6.39; N, 25.12.

Examples 40-45

Part A

Under a nitrogen atmosphere, triethylamine (47 mL, 340 mmol) was added to a solution of 2,4-dichloro-5,6-dimethyl-3-nitropyridine (30.0 g, 136 mmol) and ethyl 4-aminobutyrate hydrochloride (32 g, 190 mmol) in DMF (500 mL), and the reaction was stirred overnight. The solvent was removed under reduced pressure, and the residue was partitioned between chloroform (500 mL), water (25 mL), and brine (25 mL). The organic layer was separated and washed with water:brine (1:1, 3×50 mL), dried over magnesium sulfate, filtered, and concentrated under reduced pressure. The resulting orange solid was recrystallized from ethyl acetate:hexanes and dried under high vacuum to provide 21.5 g of ethyl 4-[(2-chloro-5,6-dimethyl-3-nitropyridin-4-yl)amino]butanoate.

Part B

Under a nitrogen atmosphere, a mixture of ethyl 4-[(2-chloro-5,6-dimethyl-3-nitropyridin-4-yl)amino]butanoate (21.5 g, 68 mmol), sodium azide (8.90 g, 136 mmol), cerium (III) chloride heptahydrate (12.7 g, 34 mmol), and 9:1 acetonitrile:water (250 mL) was heated overnight at reflux. The hot reaction mixture was filtered, and the filter cake was washed with acetonitrile. The filtrate was concentrated under reduced pressure, and the residue was triturated with ethyl acetate:hexanes and isolated by filtration to provide 21.5 g of ethyl 4-[(5,6-dimethyl-8-nitrotetraazolo[1,5-a]pyridin-7-yl)amino]butanoate.

Part C

A mixture of ethyl 4-[(5,6-dimethyl-8-nitrotetraazolo[1,5-a]pyridin-7-yl)amino]butanoate (10.0 g, 31.0 mmol), 10% palladium on carbon (1.0 g), and acetonitrile (310 mL) was added to a pressure vessel, and the reaction was placed under hydrogen pressure (30 psi, $2.1 \times 10^5$ Pa) overnight. The reaction mixture was filtered through a layer of CELITE filter agent, and the filter cake was washed with methanol (50 mL). The filtrate was concentrated under reduced pressure to provide ethyl 4-[(8-amino-5,6-dimethyltetraazolo[1,5-a]pyridin-7-yl)amino]butanoate as a solid. This reaction was repeated a second time.

Part D

For Examples 40 and 41, pyridine hydrochloride (1.34 g, 11.6 mmol) and trimethyl orthobutyrate (5.42 mL, 34.1 mmol) were sequentially added with stirring to a solution of ethyl 4-[(8-amino-5,6-dimethyltetraazolo[1,5-a]pyridin-7-yl)amino]butanoate (9.1 g, 31 mmol) in toluene (310 mL) under a nitrogen atmosphere. The reaction was heated at reflux for 1.5 hours, allowed to cool to ambient temperature overnight, and concentrated under reduced pressure. The residue was partitioned between chloroform (300 mL) and saturated aqueous sodium bicarbonate (75 mL). The aqueous layer was extracted with chloroform (2×100 mL), and the combined organic fractions were washed with saturated aqueous sodium bicarbonate (2×75 mL), dried over magnesium sulfate, filtered, and concentrated under reduced pressure. The resulting solid was triturated with ethyl acetate and isolated by filtration to provide 6.0 g of ethyl 4-(5,6-dimethyl-8-propyl-7H-imidazo[4,5-c]tetraazolo[1,5-a]pyridin-7-yl) butanoate as a white solid.

For Examples 42 and 43, pyridine hydrochloride (668 mg, 5.78 mmol) and triethyl orthopropionate (3.4 mL, 17 mmol) were added to a solution of ethyl 4-[(8-amino-5,6-dimethyltetraazolo[1,5-a]pyridin-7-yl)amino]butanoate (4.5 g, 15 mmol) in toluene (100 mL). The reaction and work-up procedure were as described for Examples 40 and 41. The crude product was recrystallized from ethyl acetate:hexane, isolated by filtration, washed with ethyl acetate:hexane, and dried under high vacuum to provide 4.7 g of ethyl 4-(8-ethyl-5,6-dimethyl-7H-imidazo[4,5-c]tetraazolo[1,5-a]pyridin-7-yl)butanoate as off-white crystals.

For Examples 44 and 45, a solution of ethyl 4-[(8-amino-5,6-dimethyltetraazolo[1,5-a]pyridin-7-yl)amino]butanoate (4.5 g, 15 mmol) in dichloromethane (150 mL) was cooled to 0° C. under a nitrogen atmosphere. Ethoxyacetyl chloride (2.46 g, 18.5 mmol) was added dropwise, and the reaction was allowed to warm to ambient temperature and stirred for four hours. Additional ethoxyacetyl chloride (0.5 g) was added, and the reaction was stirred for three days. Additional ethoxyacetyl chloride (1.0 g) was again added, and the reaction was stirred for two hours and concentrated under reduced pressure.

Part E

For Examples 40-43, aqueous sodium hydroxide (2.0 equivalents of 2 M or 6 M) was added dropwise to a suspension of the material from Part D in ethanol (0.2 M) under a nitrogen atmosphere. The reaction was stirred for one hour and concentrated under reduced pressure. The residue was dissolved in a small amount of water (5-8 mL), and the resulting solution was adjusted to pH 4 with the addition of 2 M hydrochloric acid. A precipitate formed and was isolated by filtration, washed with water, and optionally mixed with toluene, which was removed under reduced pressure. The resulting solid was dried under vacuum for two to several hours, optionally at 60-70° C.

For Examples 44 and 45, aqueous sodium hydroxide (39 mL of 2 M) was added dropwise to a suspension of the material from Part D in ethanol (154 mL), and the reaction was heated at 60° C. under nitrogen for two hours. The reaction was allowed to cool to ambient temperature, adjusted to pH 7 with the addition of 1 N hydrochloric acid, and allowed to stand overnight. The solvent was removed under reduced pressure. Toluene (50 mL) and methanol (10 mL) were twice added and removed under reduced pressure. The residue was dried under high vacuum, mixed with methanol (200 mL), and filtered to remove sodium chloride. The filter cake was washed with methanol, and the filtrate was concentrated under reduced pressure to provide a solid.

Part F

Under a nitrogen atmosphere, oxalyl chloride (3.0 equivalents) was added dropwise over a period of five minutes to a suspension of the butanoic acid from Part E in dichloromethane (0.1 M) and four drops of DMF. The reaction was stirred for one hour, and additional oxalyl chloride (0.5 mL) was added in Examples 40, 41, 44, and 45. The solvent was removed under reduced pressure.

Part G

For Examples 40, 42, and 44, a suspension of the acid chloride from Part F in dichloromethane (0.1 M) was cooled to 0° C. under a nitrogen atmosphere. Ammonia (1.5 equivalents of a 0.5 M solution in dioxane) was added dropwise over a period of five minutes. The reaction was stirred for ten minutes, and then ammonia gas was bubbled through the solution for ten minutes. The reaction was stirred overnight at ambient temperature and concentrated under reduced pressure. The residue was triturated with water (Example 40 and 44) or water:ethyl acetate (Example 42), isolated by filtration, washed with water or water:ethyl acetate, and dried under vacuum for two to three hours optionally at 70° C. to provide the amide product as a solid.

For Examples 41, 43, and 45, a suspension of the acid chloride from Part F in dichloromethane (0.1 M) was cooled to 0° C. under a nitrogen atmosphere. Morpholine (6.0 equivalents) was added dropwise over a period of five minutes, and the reaction was stirred overnight at ambient temperature. The solvent was removed under reduced pressure. For Example 41, the residue was triturated with ethyl acetate (30 mL) and methanol (5 mL), and the resulting solid was isolated by filtration, washed with ethyl acetate, and partitioned between chloroform (100 mL) and saturated aqueous sodium bicarbonate (40 mL). The aqueous layer was separated and extracted with chloroform (2×50 mL), and the combined organic fractions were washed with saturated aqueous sodium bicarbonate (2×30 mL), dried over magnesium sulfate, filtered, and concentrated under reduced pressure to provide a white solid. For Example 43, the residue was triturated with ethyl acetate:water, and the resulting solid was isolated by filtration, washed with ethyl acetate and water, and dried in a vacuum oven for one hour at 70° C. For Example 45, the residue was subjected to the aqueous work-up procedure described for Example 41. The resulting solid was triturated with ethyl acetate, isolated by filtration, washed with ethyl acetate, and dried under high vacuum to provide a white solid.

Part H

A pressure vessel was charged with the material from Part G, platinum (IV) oxide (20 wt. %), and trifluoroacetic acid (0.1 M), and the mixture was placed under hydrogen pressure (50 psi, $3.4 \times 10^5$ Pa) and shaken over three days. The reaction mixture was filtered, optionally through a pad of CELITE filter agent (Example 40), and the filter cake was washed with methanol. The filtrate was concentrated under reduced pressure, and the residue was mixed with 1 N hydrochloric acid (5-10 mL), stirred for between 1.5 and three hours, cooled to 0 IC, and optionally diluted with chloroform (20-30 mL). The resulting mixture was made basic with the addition of 6 N sodium hydroxide (Examples 40, 42, and 43), 6 N aqueous potassium carbonate (Examples 44 and 45), or saturated aqueous sodium bicarbonate (Example 41). For Examples 40 and 42, a precipitate formed, was isolated by filtration, dissolved in methanol, and concentrated under reduced pressure. For Examples 41 and 43-45, the aqueous layer was separated and extracted with chloroform (3×50 mL). The combined organic fractions were washed with saturated aqueous sodium bicarbonate, dried over sodium sulfate, filtered, and concentrated under reduced pressure. The purification and characterization is given below for each product.

Example 40

4-(4-Amino-6,7-dimethyl-2-propyl-1H-imidazo[4,5-c]pyridin-1-yl)butanamide

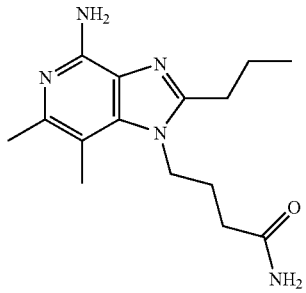 [SMILES: CCCc1nc2c(N)nc(C)c(C)c2n1CCCC(N)=O]

The product was triturated with ethyl acetate, isolated by filtration, triturated with methanol, isolated by filtration, washed with methanol and acetonitrile, and dried overnight under high vacuum at 80 IC to provide 4-(4-amino-6,7-dimethyl-2-propyl-1H-imidazo[4,5-c]pyridin-1-yl)butanamide as a white powder, mp 226.0-228.0° C.

Anal. Calcd for $C_{15}H_{23}N_5O$: C, 62.26; H, 8.01; N, 24.20. Found: C, 61.99; H, 8.07; N, 24.36.

Example 41

6,7-Dimethyl-1-(4-morpholin-4-yl-4-oxobutyl)-2-propyl-1H-imidazo[4,5-c]pyridin-4-amine

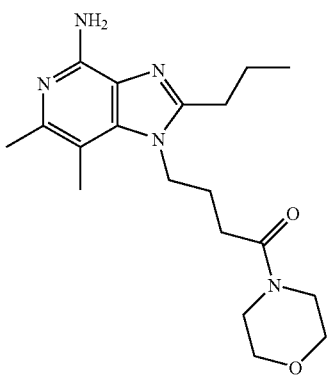 [SMILES: CCCc1nc2c(N)nc(C)c(C)c2n1CCCC(=O)N1CCOCC1]

The product was purified by chromatography using a HORIZON HPFC system (eluting with chloroform:CMA in a gradient from 95:5 to 60:40) followed by recrystallization from ethyl acetate. The crystals were dried under high vacuum to provide 6,7-dimethyl-1-(4-morpholin-4-yl-4-oxobutyl)-2-propyl-1H-imidazo[4,5-c]pyridin-4-amine as a white powder, mp 164.0-165.0° C.

Anal. Calcd for $C_{19}H_{29}N_5O_2$: C, 63.48; H, 8.13; N, 19.48. Found: C, 63.30; H, 8.33; N, 19.49.

Example 42

4-(4-Amino-2-ethyl-6,7-dimethyl-1H-imidazo[4,5-c]pyridin-1-yl)butanamide

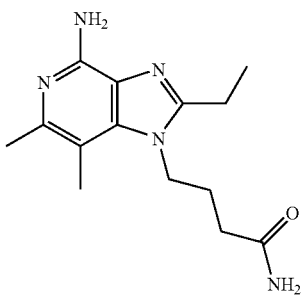 [SMILES: CCc1nc2c(N)nc(C)c(C)c2n1CCCC(N)=O]

The product was triturated with acetonitrile, isolated by filtration, triturated with 1 N sodium hydroxide, isolated by filtration, washed with water, triturated with ethyl acetate, and dried under high vacuum with stirring at 100° C. for three hours to provide 4-(4-amino-2-ethyl-6,7-dimethyl-1H-imidazo[4,5-c]pyridin-1-yl)butanamide as a white powder, mp 228.0-230.0° C.

Anal. Calcd for $C_{14}H_{21}N_5O.0.09H_2O$: C, 60.71; H, 7.71; N, 25.29. Found: C, 60.45; H, 8.07; N, 25.56.

Example 43

2-Ethyl-6,7-dimethyl-1-(4-morpholin-4-yl-4-oxobutyl)-1H-imidazo[4,5-c]pyridin-4-amine

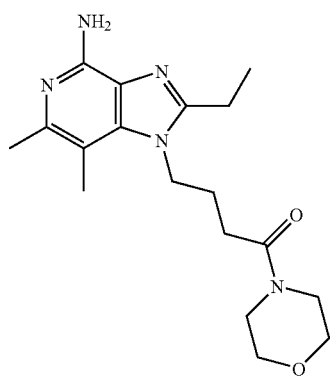 [SMILES: CCc1nc2c(N)nc(C)c(C)c2n1CCCC(=O)N1CCOCC1]

The product was triturated with ethyl acetate, dried under high vacuum, recrystallized twice from acetonitrile, isolated by filtration, washed with acetonitrile, and dried under high vacuum with stirring at 100° C. for three hours to provide 2-ethyl-6,7-dimethyl-1-(4-morpholin-4-yl-4-oxobutyl)-1H- imidazo[4,5-c]pyridin-4-amine as a white powder, mp 209.0-210.0° C.

Anal. Calcd for $C_{18}H_{27}N_5O_2$: C, 62.59; H, 7.88; N, 20.27. Found: C, 62.49; H, 8.09; N, 20.34.

Example 44

4-[4-Amino-2-(ethoxymethyl)-6,7-dimethyl-1H-imidazo[4,5-c]pyridin-1-yl]butanamide

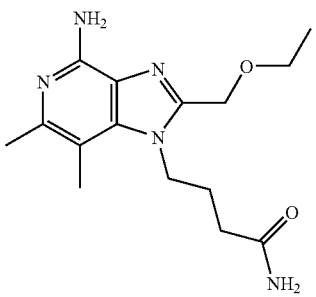 [SMILES: CCOCc1nc2c(N)nc(C)c(C)c2n1CCCC(N)=O]

The product was triturated with ethyl acetate, isolated by filtration, washed with ethyl acetate, sonicated with 1 N sodium hydroxide for one minute, isolated by filtration, washed with Water, and dried under high vacuum overnight to provide 4-[4-amino-2-(ethoxymethyl)-6,7-dimethyl-1H-imidazo[4,5-c]pyridin-1-yl]butanamide as a white powder, mp 199.0-200.0° C.

Anal. Calcd for $C_{15}H_{23}N_5O_2$: C, 59.00; H, 7.59; N, 22.93. Found: C, 58.72; H, 7.53; N, 22.76.

Example 45

2-(Ethoxymethyl)-6,7-dimethyl-1-(4-morpholin-4-yl-4-oxobutyl)-1H-imidazo[4,5-c]pyridin-4-amine

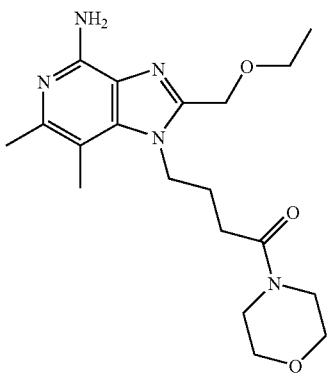 [SMILES: CCOCc1nc2c(N)nc(C)c(C)c2n1CCCC(=O)N1CCOCC1]

The product was triturated with ethyl acetate, isolated by filtration, washed with ethyl acetate, sonicated with 1 N sodium hydroxide (5 mL) for 30 seconds, and diluted with water (20 mL) and chloroform (50 mL). The aqueous layer was separated and extracted with chloroform (3×20 mL). The combined organic fractions were washed with 1 N sodium hydroxide (10 mL), dried over sodium sulfate, filtered, and concentrated under reduced pressure. The residue was triturated with ethyl acetate, isolated by filtration, and dried under high vacuum for two hours at 70° C. to provide 2-(ethoxymethyl)-6,7-dimethyl-1-(4-morpholin-4-yl-4-oxobutyl)-1H-imidazo[4,5-c]pyridin-4-amine as a white powder, mp 156.0-158.0° C.

Anal. Calcd for $C_{19}H_{29}N_5O_3$: C, 60.78; H, 7.785; N, 18.65. Found: C, 60.44; H, 8.07; N, 18.32.

Example 46

2-Butyl-1-(5-morpholin-4-yl-5-oxopentyl)-1H-imidazo[4,5-c]quinolin-4-amine

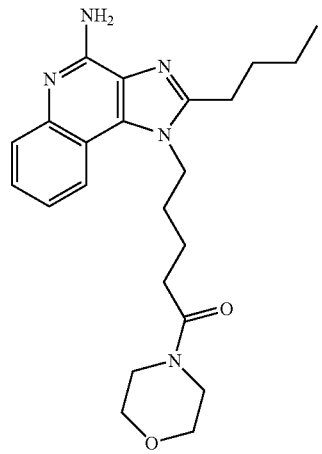 [SMILES: CCCCc1nc2c(N)nc3ccccc3c2n1CCCCC(=O)N1CCOCC1]

The methods described in Parts C, D, E, and F of Example 34 were used to treat ethyl 5-(3-aminoquinolin-4-ylamino) pentanoate, prepared in Parts A and B of Example 34. Trimethyl orthovalerate was used instead of trimethyl orthobutyrate in Part C. Following chromatographic purification of the product from Part F (eluting with 95:5 dichloromethane: methanol), 2-butyl-1-(5-morpholin-4-yl-5-oxopentyl)-1H-imidazo[4,5-c]quinolin-4-amine was obtained as an off-white powder, mp 141-143° C.

Anal. Calcd for $C_{23}H_{31}N_5O_2$: C, 67.46; H, 7.63; N, 17.10. Found: C, 67.37; H, 7.66; N, 16.90.

Example 47

2-Methyl-1-(5-morpholin-4-yl-5-oxopentyl)-1H-imidazo[4,5-c]quinolin-4-amine

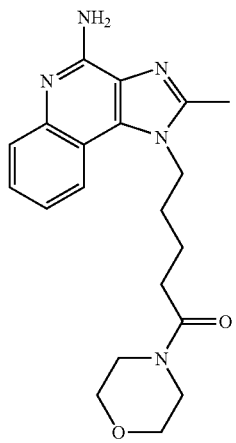 [SMILES: Cc1nc2c(N)nc3ccccc3c2n1CCCCC(=O)N1CCOCC1]

Part A

The methods described in Parts C, D, and E of Example 34 were used to convert 5 ethyl 5-(3-aminoquinolin-4-ylamino) pentanoate, prepared in Parts A and B of Example 34, to 2-methyl-1-(5-morpholin-4-yl-5-oxopentyl)-1H-imidazo[4,5-c]quinoline. Trimethyl orthoacetate was used instead of trimethyl orthobutyrate in Part C, and the reaction was heated for four hours. In Part E, the treatment with oxalyl chloride (1.8 equivalents) was carried out three times for 15 minutes each time. DMF (5 mL) was added to the reaction before the first addition.

Part B

2-Methyl-1-(5-morpholin-4-yl-5-oxopentyl)-1H-imidazo[4,5-c]quinoline (8.4 g, 24 mmol) was treated with mCPBA (7.19 g, 41.7 mmol), ammonium hydroxide (40 mL), and benzenesulfonyl chloride (5.93 mL, 46.5 mmol) according to the method described in Part D of Example 36. The crude product was purified by column chromatography on silica gel (eluting with 90:10 dichloromethane:methanol). The resulting product was triturated with 10% aqueous sodium hydroxide, isolated by filtration, washed with water, and dried overnight in a vacuum oven to provide 0.487 g of 2-methyl-1-(5-morpholin-4-yl-5-oxopentyl)-1H-imidazo[4,5-c]quinolin-4-amine as an off-white powder, mp 218-219° C.

Anal. Calcd for $C_{20}H_{25}N_5O_2$: C, 65.37; H, 6.86; N, 19.06. Found: C, 65.20; H, 7.03; N, 18.98.

Example 48

2-(Ethoxymethyl)-1-(5-morpholin-4-yl-5-oxopentyl)-1H-imidazo[4,5-c]quinolin-4-amine

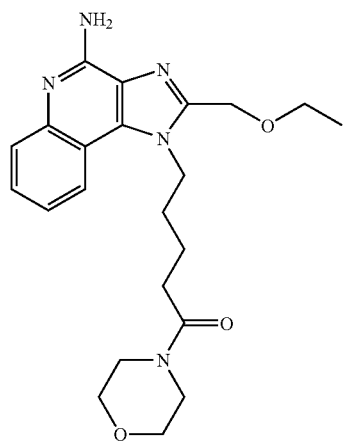 [SMILES: CCOCc1nc2c(N)nc3ccccc3c2n1CCCCC(=O)N1CCOCC1]

The methods described in Parts A through D of Example 36 were used to treat ethyl 5-(3-aminoquinolin-4-ylamino)pentanoate, prepared in Parts A and B of Example 34. Ethoxyacetyl chloride was used instead of methoxypropionyl chloride in Part A. Following chromatographic purification of the product from Part D (eluting with 95:5 dichloromethane:methanol), the product was triturated with 10% sodium hydroxide, isolated by filtration, washed with water, and dried overnight in a vacuum oven to provide 2-(ethoxymethyl)-1-(5-morpholin-4-yl-5-oxopentyl)-1H-imidazo[4,5-c]quinolin-4-amine as a tan solid, mp 128-129° C.

Anal. Calcd for $C_{22}H_{29}N_5O_3 \cdot 0.54H_2O$: C, 62.72; H, 7.20; N, 16.62. Found: C, 62.72; H, 7.16; N, 16.60.

Example 49

5-[4-Amino-2-(ethoxymethyl)-1H-imidazo[4,5-c]quinolin-1-yl]pentanamide

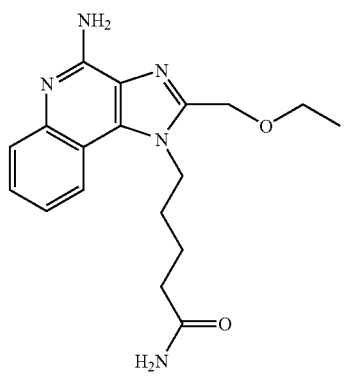

Part A

Ethyl 5-(3-aminoquinolin-4-ylamino)pentanoate, prepared in Parts A and B of Example 34, was treated as described in Part A of Example 36. Ethoxyacetyl chloride was used instead of methoxypropionyl chloride. Ethyl 5-(2-ethoxymethyl-1H-imidazo[4,5-c]quinolin-1-yl)pentanoate (6.0 g, 17 mmol) and ammonium acetate (15 g) were sealed in a high-pressure vessel and heated for four days at 110° C. and then allowed to cool to ambient temperature. Aqueous sodium hydroxide (10%) was added, and the mixture was then extracted with dichloromethane (3×). The product crystallized from the dichloromethane and was collected in two crops to provide 2.64 g of 5-[2-(ethoxymethyl)-1H-imidazo[4,5-c]quinolin-1-yl]pentanamide as an off-white solid, mp 157-158° C.

Anal. Calcd for $C_{18}H_{22}N_4O_2$: C, 66.24; H, 6.79; N, 17.17. Found: C, 65.99; H, 6.67; N, 17.08.

Part B

5-[2-(Ethoxymethyl)-1H-imidazo[4,5-c]quinolin-1-yl]pentanamide (2.25 g, 6.89 mmol) was treated with mCPBA (2.77 g, 12.0 mmol), ammonium hydroxide (40 mL), and benzenesulfonyl chloride (1.71 mL, 13.4 mmol) according to the method described in Part D of Example 36. The crude product was purified by column chromatography on silica gel (eluting with dichloromethane:methanol in a gradient from 90:10 to 85:15). The resulting product was triturated with 10% aqueous sodium hydroxide, isolated by filtration, washed with water, and dried overnight in a vacuum oven to provide 0.752 g of 5-[4-amino-2-(ethoxymethyl)-1H-imidazo[4,5-c]quinolin-1-yl]pentanamide as a tan solid, mp 198-200° C.

Anal. Calcd for $C_{18}H_{23}N_5O_2 \cdot 0.21H_2O$: C, 62.64; H, 6.84; N, 20.29. Found: C, 62.26; H, 6.80; N, 19.96.

Example 50

1-(5-Morpholin-4-yl-5-oxopentyl)-2-propyl-6,7,8,9-tetrahydro-1H-imidazo[4,5-c]quinolin-4-amine

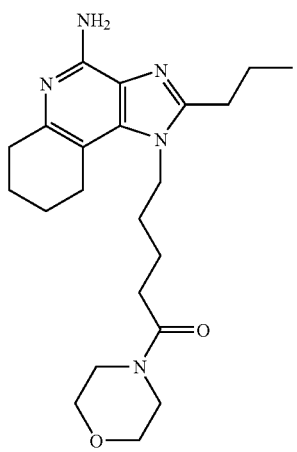 [SMILES: CCCc1nc2c(N)nc3c(c2n1CCCCC(=O)N1CCOCC1)CCCC3]

A mixture of 1-(5-morpholin-4-yl-5-oxopentyl)-2-propyl-1H-imidazo[4,5-c]quinolin-4-amine (1.66 g, 4.19 mmol, prepared in Example 34), platinum (IV) oxide (1.5 g, 6.6 mmol), and trifluoroacetic acid (25 mL) was placed in a Parr vessel and shaken under hydrogen pressure (40 psi, $2.8 \times 10^5$ Pa) overnight. The reaction mixture was filtered through a layer of CELITE filter agent, and the filter cake was washed with ethanol. The filtrate was concentrated under reduced pressure, and the residue was purified by flash column chromatography on silica gel (eluting with 95:5 dichloromethane: methanol). The resulting solid was triturated three times with 10% aqueous sodium hydroxide, isolated by filtration, and washed with water to provide 0.468 g of 1-(5-morpholin-4-yl-5-oxopentyl)-2-propyl-6,7,8,9-tetrahydro-1H-imidazo[4,5-c]quinolin-4-amine as a white solid, mp 158-160° C.

Anal. Calcd for $C_{22}H_{33}N_5O_2 \cdot 0.05H_2O$: C, 65.99; H, 8.33; N, 17.49. Found: C, 65.59; H, 8.60; N, 17.76.

Example 51

3-(4-Amino-2-propyl-1H-imidazo[4,5-c]quinolin-1-yl)-N,N-dimethylpropanamide

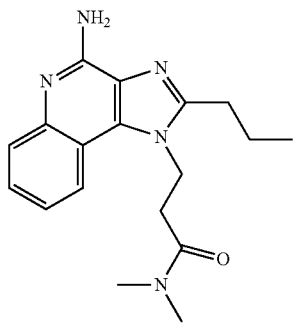 [SMILES: CCCc1nc2c(N)nc3ccccc3c2n1CCC(=O)N(C)C]

Part A

Dimethylamine (15 mL of a 40% aqueous solution) was added to a solution of ethyl 3-(2-propyl-1H-imidazo[4,5-c]quinolin-1-yl)propanoate (4.02 g, 12.9 mmol, prepared in Part B of Example 18) in THF (7 mL), and the reaction mixture was heated at 110° C. overnight in a pressure vessel. The reaction was allowed to cool to ambient temperature and concentrated under reduced pressure to provide 4.1 g of N,N-dimethyl-3-(2-propyl-1H-imidazo[4,5-c]quinolin-1-yl)propanamide as a dark brown solid.

Part B

N,N-Dimethyl-3-(2-propyl-1H-imidazo[4,5-c]quinolin-1-yl)propanamide (2.40 g, 7.73 mmol) was treated with mCPBA (3.11 g, 13.5 mmol), ammonium hydroxide (40 mL), and benzenesulfonyl chloride (1.92 mL, 15.1 mmol) according to the method described in Part D of Example 36. The crude product was purified by column chromatography on silica gel (eluting with 93:7 dichloromethane:methanol) to provide 0.097 g of 3-(4-amino-2-propyl-1H-imidazo[4,5-c]quinolin-1-yl)-N,N-dimethylpropanamide as a tan powder, mp 207-209° C.

Anal. Calcd for $C_{18}H_{23}N_5O \cdot 0.19H_2O$: C, 65.75; H, 7.07; N, 21.3. Found: C, 65.71; H, 7.38; N, 20.9.

Example 52

5-(4-Amino-2-butyl-1H-imidazo[4,5-c]quinolin-1-yl)pentanamide

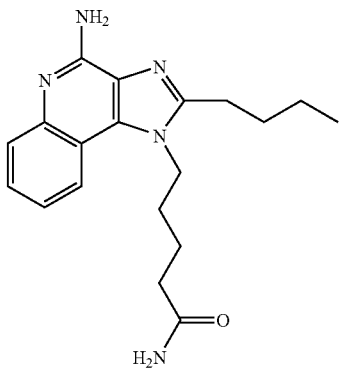 [SMILES: CCCCc1nc2c(N)nc3ccccc3c2n1CCCCC(N)=O]

Part A

Ethyl 5-(2-butyl-1H-imidazo[4,5-c]quinolin-1-yl)pentanoate (10.0 g, 28.2 mmol, prepared in Example 46) and ammonium acetate (10 g) were sealed in a high-pressure vessel, heated for two days at 130° C., and then allowed to cool to ambient temperature. Saturated aqueous sodium bicarbonate was added, and the mixture was then extracted with dichloromethane. The combined organic fractions were washed sequentially with saturated aqueous sodium bicarbonate and brine, dried over magnesium sulfate, filtered, and concentrated under reduced pressure to provide 8.6 g of 5-(2-butyl-1H-imidazo[4,5-c]quinolin-1-yl)pentanamide.

Part B 5-(2-Butyl-1H-imidazo[4,5-c]quinolin-1-yl)pentanamide (8.6 g, 26.5 mmol) was treated with mCPBA (10.7 g, 46.4 mmol), ammonium hydroxide (40 mL), and benzenesulfonyl chloride (6.59 mL, 51.6 mmol) according to the method described in Part D of Example 36. The crude product was purified by column chromatography on silica gel (eluting with dichloromethane:methanol in a gradient from 90:10 to 80:20). The resulting product was sonicated three times with 10% aqueous sodium hydroxide and once with 30% aqueous sodium hydroxide, isolated by filtration, washed with water, and dried overnight in a vacuum oven to provide 0.367 g of 5-(4-amino-2-butyl-1H-imidazo[4,5-c]quinolin-1-yl)pentanamide as a tan solid, mp 219-221° C.

Anal. Calcd for $C_{19}H_{25}N_5O \cdot 0.21H_2O$: C, 66.50; H, 7.46; N, 20.41. Found: C, 66.34; H, 7.81; N, 20.01.

Example 53

1-(6-Morpholin-4-yl-6-oxohexyl)-2-propyl-1H-imidazo[4,5-c][1,5]naphthyridin-4-amine

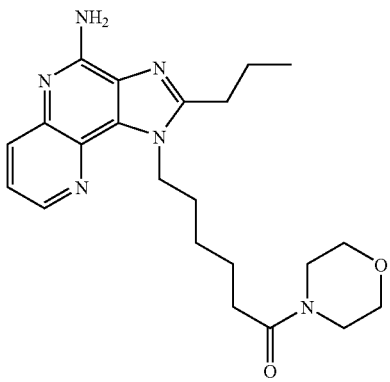 [SMILES: CCCc1nc2c(N)nc3cccnc3c2n1CCCCCC(=O)N1CCOCC1]

Part A

A suspension of 4-chloro-3-nitro[1,5]naphthyridine (9.0 g, 42.9 mmol) in chloroform (180 mL) was cooled to approximately 0° C. Ethyl 6-aminohexanoate hydrochloride (12.6 g, 64.4 mmol) and triethylamine (16.6 mL, 119 mmol) were sequentially added with stirring, and the reaction was stirred for 15 minutes. The mixture was diluted with chloroform (180 mL), washed with 1% aqueous sodium carbonate (3×125 mL), dried over sodium sulfate, filtered, and concentrated under reduced pressure to provide ethyl 6-(3-nitro[1,5]naphthyridin-4-ylamino)hexanoate as a yellow oil.

Part B

The method described in Part B of Example 37 was used to hydrogenate the material from Part A to provide 6-(3-amino[1,5]naphthyridin-4-ylamino) ethyl hexanoate, which was dissolved in chloroform (650 mL) and divided into three portions (300 mL, 175 mL, and 175 mL).

Part C

Butyryl chloride (3.61 mL, 34.7 mmol) was added in four portions over the course of 105 minutes to a 175 mL portion from Part B. After a total reaction time of two hours, the solvent was removed under reduced pressure. The residue was triturated with acetone (2 mL/g) while cooling to approximately 0° C., and the resulting solid was isolated by filtration, air-dried, and suspended in ethanol (33 mL). A mixture of 50% (w/w) aqueous sodium hydroxide (2.78 g, 34.7 mmol) and 11.4 mL water was added with stirring, and the resulting mixture was stirred at ambient temperature for ten minutes, heated at 85° C. for one hour, and allowed to cool to ambient temperature. The solvents were removed under reduced pressure, and the residue was partitioned between chloroform (90 mL) and deionized water (15 mL) and stirred for ten minutes. The aqueous phase was adjusted to pH 5 with the addition of 1 N hydrochloric acid, and then the organic phase was separated, dried over sodium sulfate, and concentrated under reduced pressure to provide 3.8 g of 6-(2-propyl-1H-imidazo[4,5-c][1,5]naphthyridin-1-yl)hexanoic acid.

Part D

A solution of oxalyl chloride (2.04 mL, 23.4 mmol) in dichloromethane (15 mL) was added dropwise to a suspension of 6-(2-propyl-1H-imidazo[4,5-c][1,5]naphthyridin-1-yl]hexanoic acid (2.56 g, 7.8 mmol) in dichloromethane (38 mL) containing one drop of DMF. The reaction mixture was stirred at ambient temperature for 1.75 hours, and then additional oxalyl chloride (0.35 mL, 4.1 mmol) was added. The reaction was stirred for an additional 45 minutes and then concentrated under reduced pressure to provide 6-(2-propyl-1H-imidazo[4,5-c][1,5]naphthyridin-1-yl)hexanoyl chloride.

Part E

Morpholine (1.72 mL, 19.6 mmol) was added to a solution of the material from Part D in dichloromethane (20 mL/g), and the reaction was stirred for 30 minutes at ambient temperature and then diluted with dichloromethane (20 mL/g) and saturated aqueous sodium bicarbonate (20 mL/g). The organic fraction was separated and concentrated under reduced pressure to provide 1-(6-morpholin-4-yl-6-oxohexyl)-2-propyl-1H-imidazo[4,5-c][1,5]naphthyridine.

Part F mCPBA (70-77% purity, 4.52 g) was added to a solution of the material from Part E in chloroform (40 mL), and the reaction was stirred for 3.25 hours before the addition of more mCPBA (2.26 g). The stirring was continued for an additional 45 minutes, and then the reaction was diluted with chloroform (30 mL/g), washed twice with 1% aqueous sodium carbonate, and concentrated under reduced pressure. The residue was dissolved in dichloromethane (25 mL), and ammonium hydroxide (13 mL of 28%) and p-toluenesulfonyl chloride (1.93 g, 10.1 mmol) were sequentially added. The reaction mixture was stirred for 15 minutes, and additional dichloromethane (75 mL) was added. The organic layer was separated, dried over sodium sulfate, and concentrated under reduced pressure. The crude product (5.06 g) was purified by column chromatography on silica gel (eluting with 2.5% methanol in chloroform) followed by recrystallization from acetonitrile/water. The crystals were dried in a vacuum oven for three days at 90° C. and for four hours at 112° C. to provide 1.25 g of 1-(6-morpholin-4-yl-6-oxohexyl)-2-propyl-1H-imidazo[4,5-c][1,5]naphthyridin-4-amine as a light yellow solid, mp 148-150° C.

Anal. calcd for $C_{22}H_{30}N_6O_2$: C, 64.37; H, 7.37; N, 20.47. Found: C, 64.19; H, 7.58; N, 20.70.

Example 54

6-(4-Amino-2-propyl-1H-imidazo[4,5-c][1,5]naphthyridin-1-yl)hexanamide

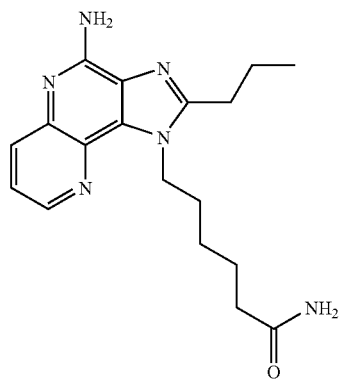 [SMILES: CCCc1nc2c(N)nc3cccnc3c2n1CCCCCC(N)=O]

Part A

A solution of 6-(2-propyl-1H-imidazo[4,5-c][1,5]naphthyridin-1-yl]hexanoyl chloride, prepared according to the methods described in Parts A through D of Example 53, (4.8 mmol) in dichloromethane (20 mL/g) was cooled to approximately 0° C., and anhydrous ammonia was bubbled through the solution for ten minutes. The reaction was warmed to ambient temperature and stirred for an additional 30 minutes. Chloroform (20 mL/g) and water (15 mL/g) were added to the reaction. The aqueous layer was separated and extracted with dichloromethane (20 mL). The combined organic fractions were concentrated under reduced pressure. The crude product was recrystallized from acetonitrile (19 mL/g) to provide 1.20 g of 6-(2-propyl-1H-imidazo[4,5-c][1,5]naphthyridin-1-yl) hexanamide.

Part B

A modification of the method described in Part F of Example 53 was used to treat 6-(2-propyl-1H-imidazo[4,5-c][1,5]naphthyridin-1-yl)hexanamide (1.20 g, 3.7 mmol) with mCPBA (2.47 g of 70-77% purity) followed by ammonium hydroxide (4 mL), and p-toluenesulfonyl chloride (0.70 g). After the amination reaction was stirred for one hour, a precipitate was present and was isolated by filtration and washed with chloroform and water. The precipitate was ground up and dried for three days at 70° C. and then overnight at 95° C. to provide 0.46 g of 6-(4-amino-2-propyl-1H-imidazo[4,5-c][1,5]naphthyridin-1-yl)hexanamide as a white solid, mp 216.5-217.5° C.

Anal. calcd for $C_{18}H_{24}N_6O$: C, 63.51; H, 7.11; N, 24.69. Found: C, 63.29; H, 7.10; N, 24.68.

Part D

The method described in Part D of Example 53 was used to treat 6-(2-ethyl-1H-imidazo[4,5-c][1,5]naphthyridin-1-yl] hexanoic acid (3.46 g, 11.1 mmol) with oxalyl chloride (3.87 mL, 44.0 mmol) to obtain 6-[2-(ethoxymethyl)-1H-imidazo [4,5-c][1,5]naphthyridin-1-yl]hexanoyl chloride, which was dissolved in dichloromethane (20 mL/g) and divided into two equal portions.

Part E

Morpholine (1.21 mL, 13.8 mmol) was added to one portion from Part D, and the reaction was stirred for 15 minutes at ambient temperature and then diluted with dichloromethane (20 mL/g) and saturated aqueous sodium bicarbonate (20 mL/g). The organic fraction was separated, dried over sodium sulfate, filtered, and concentrated under reduced pressure to provide 2-ethyl-1-(6-morpholin-4-yl-6-oxohexyl)-1H-imidazo[4,5-c][1,5]naphthyridine.

Part F

The method described in Part F of Example 53 was used to treat the material from Part E with mCPBA (4.92 g of 70-77% purity) followed by ammonium hydroxide (9 mL) and p-toluenesulfonyl chloride (1.40 g, 7.34 mmol). The crude product (3.22 g) was purified by column chromatography on silica gel (eluting with 2.5% methanol in chloroform) followed by recrystallization from acetonitrile. The crystals were dried in a vacuum oven for three days at 90° C. and for four hours at 112° C. to provide 0.79 g of 2-ethyl-1-(6-morpholin-4-yl-6-oxohexyl)-1H-imidazo[4,5-c][1,5]naphthyridin-4-amine as a light yellow solid, mp 163-165° C.

Anal. calcd for $C_{21}H_{28}N_6O_2$: C, 63.61; H, 7.12; N, 21.20. Found: C, 63.52; H, 7.29; N, 21.47.

Example 55

2-Ethyl-1-(6-morpholin-4-yl-6-oxohexyl)-1H-imidazo[4,5-c][1,5]naphthyridin-4-amine Example 56

6-(4-Amino-2-ethyl-1H-imidazo[4,5-c][1,5]naphthyridin-1-yl)hexanamide

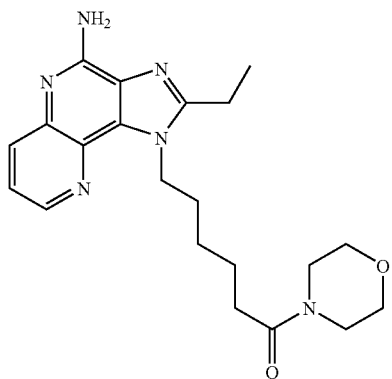 [SMILES: CCc1nc2c(N)nc3cccnc3c2n1CCCCCC(=O)N1CCOCC1]

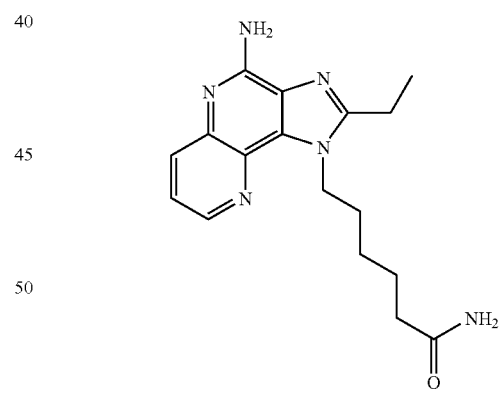

Part A

Propionyl chloride (5.17 mL, 59.5 mmol) was added in three portions (19.8 mmol each) 45 to 60 minutes apart to the 300 mL portion from Part B of Example 53. After a total reaction time of three hours, the solvent was removed under reduced pressure. The residue was purified, isolated, and treated with a mixture of 50% (w/w) aqueous sodium hydroxide (4.76 g, 59.6 mmol) and 18.8 mL water according to the methods described in Part C of Example 53. The methods of Part C of Example 53 were then used to isolate 3.56 g of 6-(2-ethyl-1H-imidazo[4,5-c][1,5]naphthyridin-1-yl]hexanoic acid.

Part A

The second portion of the solution from Part D of Example 55 was cooled to approximately 0° C., and anhydrous ammonia was bubbled through the solution for ten minutes. The reaction was warmed to ambient temperature and stirred for an additional 30 minutes. Chloroform (30 mL/g) and water (15 mL/g) were added to the reaction, and the mixture was stirred for 30 minutes. The organic fraction was separated, dried over sodium sulfate, filtered, and concentrated under reduced pressure. The crude product was recrystallized from acetonitrile (10 mL/g) to provide 1.18 g of 6-(2-ethyl-1H-imidazo[4,5-c][1,5]naphthyridin-1-yl)hexanamide.

Part B

A modification of the method described in Part F of Example 53 was used to treat 6-(2-ethyl-1H-imidazo[4,5-c][1,5]naphthyridin-1-yl)hexanamide (1.18 g, 3.8 mmol) with mCPBA (2.54 g of 70-77% purity) followed by ammonium hydroxide (4 mL), and p-toluenesulfonyl chloride (0.72 g). After the amination reaction was stirred for 15 minutes, a precipitate was present and was isolated by filtration. The precipitate was purified by chromatography using a HORIZON HPFC system (silica cartridge, eluting with 0-55% CMA in chloroform) and dried for three days at 90° C. to provide 0.34 g of 6-(4-amino-2-ethyl-1H-imidazo[4,5-c][1,5]naphthyridin-1-yl)hexanamide as a light yellow solid, mp 220-221° C.

Anal. calcd for $C_{17}H_{24}N_6O_2 \cdot 0.1H_2O$: C, 62.21; H, 6.82; N, 25.61. Found: C, 61.69; H, 6.89; N, 25.54.

Example 57

2-(Ethoxymethyl)-1-(6-morpholin-4-yl-6-oxohexyl)-1H-imidazo[4,5-c][1,5]naphthyridin-4-amine

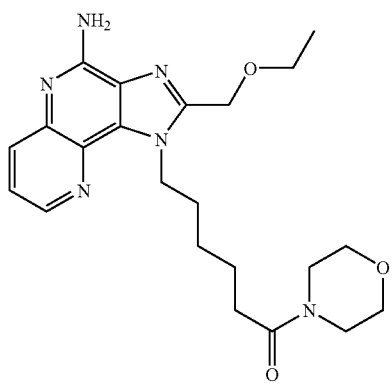 [SMILES: CCOCc1nc2c(N)nc3cccnc3c2n1CCCCCC(=O)N1CCOCC1]

Part A

Ethoxyacetyl chloride (1.55 g, 12.2 mmol) was added to a 175 mL portion of the solution from Part B of Example 53. After a total reaction time of one hour, the solvent was removed under reduced pressure. The residue was triturated with ethyl acetate (2 mL/g) while cooling to approximately 0° C., and the resulting solid was isolated by filtration, air-dried, and treated with a mixture of 50% (w/w) aqueous sodium hydroxide (2.78 g, 34.7 mmol) and 11.8 mL water according to the method described in Part C of Example 53. A solid was present during the work-up between the organic and acidic aqueous phases. The solid was isolated by filtration, triturated with methanol, isolated by filtration, dried under reduced pressure, and combined with the material isolated from the organic phase to provide 3.25 g of 6-[2-(ethoxymethyl)-1H-imidazo[4,5-c][1,5]naphthyridin-1-yl]hexanoic acid.

Part B

The method described in Part D of Example 53 was used to treat 6-[2-(ethoxymethyl)-1H-imidazo[4,5-c][1,5]naphthyridin-1-yl]hexanoic acid (3.23 g, 9.4 mmol) with oxalyl chloride (3.29 mL, 37.7 mmol) to obtain 6-[2-(ethoxymethyl)-1H-imidazo[4,5-c][1,5]naphthyridin-1-yl]hexanoyl chloride. The reaction was complete in two hours.

Part C

The method described in Part E of Example 53 was used to treat the material from Part B with morpholine (2.06 mL, 23.6 mmol) to provide 2-(ethoxymethyl)-1-(6-morpholin-4-yl-6-oxohexyl)-1H-imidazo[4,5-c][1,5]naphthyridine.

Part D

The method described in Part F of Example 53 was used to treat the material from Part C with mCPBA (8.15 g of 70-77% purity) followed by ammonium hydroxide (15 mL) and p-toluenesulfonyl chloride (2.32 g). The crude product (5.91 g) was purified by column chromatography on silica gel (eluting with 2% methanol in chloroform) followed by recrystallization from acetonitrile/water. The crystals were dried in a vacuum oven for three days at 90° C. and for four hours at 112° C. to provide 0.63 g of 2-(ethoxymethyl)-1-(6-morpholin-4-yl-6-oxohexyl)-1H-imidazo[4,5-c][1,5]naphthyridin-4-amine as a light yellow solid, mp 168-170° C.

Anal. calcd for $C_{22}H_{30}N_6O_3$: C, 61.95; H, 7.09; N, 19.70. Found: C, 61.80; H, 7.13; N, 19.96.

Example 58

6-[4-Amino-2-(ethoxymethyl)-1H-imidazo[4,5-c][1,5]naphthyridin-1-yl]hexanamide

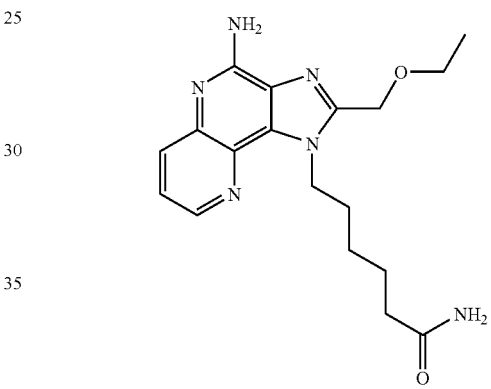

Part A

A solution of 6-[2-(ethoxymethyl)-1H-imidazo[4,5-c][1,5]naphthyridin-1-yl]hexanoyl chloride, prepared according to the methods described in Parts A and B of Example 57, (5.8 mmol) in dichloromethane (20 mL/g) was cooled to approximately 0° C., and anhydrous ammonia was bubbled through the solution for ten minutes. The reaction was warmed to ambient temperature and stirred for an additional 30 minutes. Chloroform (20 mL/g) and water (15 mL/g) were added to the reaction. A solid was present and was isolated by filtration to provide 0.96 g of 6-[2-(ethoxymethyl)-1H-imidazo[4,5-c][1,5]naphthyridin-1-yl]hexanamide. The filtrate was concentrated under reduced pressure, and the residue was partitioned between chloroform (75 mL) and 1% aqueous sodium carbonate (20 ml). The organic fraction was concentrated under reduced pressure, and the residue was triturated with acetonitrile and isolated by filtration to provide an additional 0.74 g of product. The two solids were combined and used in the next step.

Part B

A modification of the methods described in Part F of Example 53 was used to treat 6-[2-(ethoxymethyl)-1H-imidazo[4,5-c][1,5]naphthyridin-1-yl]hexanamide (1.70 g, 5.0 mmol) with mCPBA (3.34 g of 70-77% purity) followed by ammonium hydroxide (5.5 mL), and p-toluenesulfonyl chloride (0.95 g). After the amination reaction was stirred for one hour, a precipitate was present and was isolated by filtration and washed with chloroform and water. The precipitate was triturated with 2-propanol (7.5 mL/g at 97° C.), and the mixture was filtered hot. The isolated solid was dried overnight under vacuum and then in a vacuum oven for six days at 65° C. The product was then sonicated in 1 M aqueous sodium hydroxide for 15 minutes, isolated by filtration, washed with deionized water, and dried in a vacuum oven for three days at 90° C. to provide 0.32 g of 6-[4-amino-2-(ethoxymethyl)-1H-imidazo[4,5-c][1,5]naphthyridin-1-yl]hexanamide as a yellow solid, mp 215-217° C.

Anal. calcd for $C_{18}H_{24}N_6O_2 \cdot 0.37H_2O$: C, 59.54; H, 6.87; N, 23.15. Found: C, 59.66; H, 7.00; N, 23.44.

Example 59

2-(4-Amino-2-propyl-1H-imidazo[4,5-c]quinolin-1-yl)acetamide

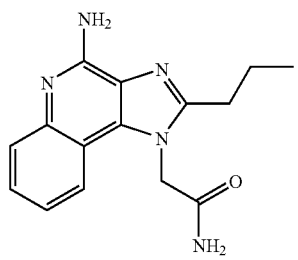 [SMILES: CCCc1nc2c(N)nc3ccccc3c2n1CC(N)=O]

Part A

Triethylamine (22.3 mL, 0.160 mmol) was added with stirring to a solution of 3-amino-4-chloroquinoline, see Surrey et al., *Journal of the American Chemical Society*, 73, pp. 2413-2416 (1951), (13.2 g, 74.0 mmol) in anhydrous dichloromethane (100 mL). A solution of butyryl chloride (13 mL, 125 mmol) in dichloromethane (50 mL) was then added dropwise, and the reaction mixture was stirred at ambient temperature overnight. Methanol (25 mL) was added, and the reaction mixture was stirred for one hour at ambient temperature. Saturated aqueous sodium bicarbonate (50 mL) was added, and the resulting mixture was stirred at ambient temperature for 30 minutes and then allowed to stand. The aqueous layer was separated and extracted with dichloromethane (75 mL), and the combined organic fractions were then washed with saturated aqueous sodium bicarbonate (2×50 mL), dried over potassium carbonate, filtered, and concentrated under reduced pressure. The crude product (22.8 g) was recrystallized from a mixture of toluene (45 mL) and hexane (15 mL) to provide 9.2 of N-(4-chloroquinolin-3-yl)butanamide as brown needles.

Part B

A neat mixture of N-(4-chloroquinolin-3-yl)butanamide (5.0 g, 20 mmol) and glycine ethyl ester hydrochloride (10.0 g, 72 mmol) was heated gently with a heat gun until the solids melted. The reaction was followed by LC/MS, and heat was applied briefly twice more until no starting material remained. Dichloromethane (100 mL) and saturated aqueous sodium bicarbonate (50 mL) were added, and the resulting mixture was stirred until all solids were dissolved. The aqueous layer was separated and extracted with dichloromethane (2×50 mL), and the combined organic fractions were washed sequentially with saturated aqueous sodium bicarbonate (50 mL) and water, dried over potassium carbonate, filtered, and concentrated under reduced pressure. The residue was (3.6 g) was dissolved in hot toluene (150 mL), and pyridinium tosylate (100 mg) was added. The reaction was heated at reflux under a Dean-Stark trap for one hour, allowed to stand at ambient temperature for three days, heated at reflux for two hours, cooled to ambient temperature, and diluted with dichloromethane (150 mL). The resulting solution was washed with saturated aqueous sodium bicarbonate (2×35 mL), dried over potassium carbonate, filtered, and concentrated under reduced pressure to provide 3.2 g of ethyl (2-propyl-1H-imidazo[4,5-c]quinolin-1-yl)acetate as a light brown solid.

Part C mCPBA (4.70 g of 75%, 27.3 mmol) was added over a period of five minutes to a solution of ethyl (2-propyl-1H-imidazo[4,5-c]quinolin-1-yl)acetate (3.2 g, 11 mmol) in dichloromethane (100 mL), which had been cooled to approximately 0° C. The reaction mixture was stirred cold for ten minutes and then for one hour at room temperature at which time analysis by LC/MS indicated that the reaction was not complete. The reaction mixture was stirred for one hour and was still incomplete; additional mCPBA (1.0 g) was added. The reaction was stirred for an additional 30 minutes, and then the aqueous layer was separated and extracted with dichloromethane (2×35 mL). The combined organics were washed twice with a mixture of saturated aqueous sodium bicarbonate (33 mL) and 25% aqueous sodium hydroxide (2 mL) and then cooled to 0° C. With vigorous stirring, ammonium hydroxide (50 mL) was added, and a solution of benzenesulfonyl chloride (2.4 mL, 19 mmol) in dichloromethane (15 mL) was then added dropwise. The reaction mixture was stirred for 15 minutes, warmed to ambient temperature, and then stirred for two hours. The aqueous layer was separated and extracted with dichloromethane (2×35 mL). The combined organics were washed twice with a mixture of saturated aqueous sodium bicarbonate (33 mL) and 25% aqueous sodium hydroxide (2 mL), dried over potassium carbonate, filtered, and concentrated under reduced pressure. The residue was purified by column chromatography (silica gel, eluting with 5% methanol in dichloromethane containing 3 mL of ammonium hydroxide per liter of eluent) followed by recrystallization three times from ethanol/water. The crystals were dried in a vacuum oven overnight at 70° C. to provide ethyl (4-amino-2-propyl-1H-imidazo[4,5-c]quinolin-1-yl)acetate as tan needles, mp 170-172° C. Anal. calcd for $C_{17}H_{20}N_4O_2 \cdot 0.27H_2O \cdot 0.14 \, C_2H_5OH$: C, 64.17; H, 6.61; N, 17.33. Found: C, 63.93; H, 6.60; N, 17.10.

Part D

Ethyl (4-amino-2-propyl-1H-imidazo[4,5-c]quinolin-1-yl)acetate (0.80 g), a solution of ammonia in methanol (35 mL of 7 N), and ammonium chloride (0.50 g) were heated in a sealed pressure vessel at 150° C. for 20 hours. The volatiles were removed under reduced pressure, and the solid residue was triturated with saturated aqueous sodium bicarbonate for one hour, isolated by filtration, and washed with water. The solid was recrystallized from methanol/water, and the crystals were washed sequentially with 25% aqueous sodium hydroxide (2×25 mL) and water (2×25 mL) and dried overnight in a vacuum oven at 70° C. to provide 0.120 g of 2-(4-amino-2-propyl-1H-imidazo[4,5-c]quinolin-1-yl)acetamide as light tan crystals, mp>300° C.

MS (APCI) m/z 284 (M+H$^+$);

Anal. calcd for $C_{15}H_{17}N_5O$: C, 63.59; H, 6.05; N, 24.72. Found: C, 63.29; H, 5.88; N, 25.07.

Example 60

3-(4-Amino-2-ethyl-1H-imidazo[4,5-c]quinolin-1-yl)-2,2-dimethylpropanamide

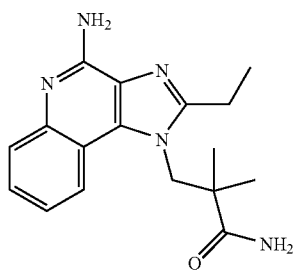 [SMILES: CCc1nc2c(N)nc3ccccc3c2n1CC(C)(C)C(N)=O]

Part A

Ethyl 3-[(3-aminoquinolin-4-yl)amino]-2,2-dimethylpropanoate (see Example 26 Parts A through D, 3.6 g, 12 mmol) was treated according to a modification of the method described in Part B of Example 8 using triethyl orthopropionate in lieu of trimethyl orthobutyrate. Prior to the addition of triethyl orthopropionate (4.0 mL, 20 mmol) and pyridinium p-toluenesulfonate (0.030 g), the reaction was heated at reflux for 15 minutes. After the reaction was heated at reflux for three hours, it was concentrated under reduced pressure and found to be incomplete by $^1$H NMR. The oil was dissolved in toluene (100 mL), and concentrated sulfuric acid (one drop) was added. The reaction was heated at reflux for two hours and allowed to cool. Triethylamine (5 mL) was added, and the reaction was heated at reflux for two hours, allowed to cool to ambient temperature, washed with saturated aqueous sodium bicarbonate (2×35 mL), dried over potassium carbonate, filtered, and concentrated to provide 3.6 g of ethyl 3-(2-ethyl-1H-imidazo[4,5-c]quinolin-1-yl)-2,2-dimethylpropanoate as an oil.

Part B mCPBA (4.8 g of 75%, 22 mmol) was added over a period of several minutes to a solution of ethyl 3-(2-ethyl-1H-imidazo[4,5-c]quinolin-1-yl)-2,2-dimethylpropanoate (3.6 g, 11 mmol) in dichloromethane (100 mL), which had been cooled to approximately 0° C. The reaction mixture was stirred cold for ten minutes and then for three hours at ambient temperature. The reaction mixture was then washed twice with a mixture of saturated aqueous sodium bicarbonate (34 mL) and 25% aqueous sodium hydroxide (1 mL), dried over potassium carbonate, filtered, and then cooled to 0° C. Trichloroacetyl isocyanate (1.7 mL, 14 mmol) was added, and the reaction was stirred cold for 15 minutes, warmed to ambient temperature, and stirred for one hour. The solvent was removed under reduced pressure, and the residue was dissolved in methanol (50 mL). Sodium methoxide (6.5 mL of a 25% solution in methanol, 30 mmol) was added to the resulting solution, and the reaction was stirred at ambient temperature overnight and cooled to approximately 0° C. for 30 minutes. A precipitate formed and was isolated by filtration to provide 1.2 g of methyl 3-(4-amino-2-ethyl-1H-imidazo[4,5-c]quinolin-1-yl)-2,2-dimethylpropanoate.

Part C

A solution of potassium hydroxide (16 mL of a 0.5 M solution in methanol) was added to methyl 3-(4-amino-2-ethyl-1H-imidazo[4,5-c]quinolin-1-yl)-2,2-dimethylpropanoate (1.2 g, 3.7 mmol), and the resulting solution was heated at reflux for five days and allowed to cool to ambient temperature. Hydrogen chloride (8.5 mL of a 1 N solution in diethyl ether) was added, and the reaction was stirred for 30 minutes. The solvents were removed under reduced pressure, and the residue was dissolved in dichloromethane (50 mL). A solution of oxalyl chloride (0.70 mL, 8.0 mmol) in dichloromethane (5 mL) was added, and the solution was stirred overnight at ambient temperature and then concentrated under reduced pressure. The residue was dissolved in dichloromethane (50 mL), and ammonia (10 mL of a 0.5 M solution in 1,4-dioxane) was added. The reaction was stirred for 15 minutes, and then additional ammonia (10 mL of a 7 N solution in methanol) was added. The reaction was stirred for two hours and concentrated under reduced pressure. The residue was stirred with dichloromethane for five minutes, isolated by filtration, and recrystallized from methanol/water. The resulting needles were dried overnight in a vacuum oven at 80° C. to provide 3-(4-amino-2-ethyl-1H-imidazo[4,5-c]quinolin-1-yl)-2,2-dimethylpropanamide as light yellow needles, mp 279-281° C.

MS (APCI) m/z 312 (M+H$^+$);

Anal. calcd for $C_{17}H_{21}N_5O$: C, 64.35; H, 6.88; N, 22.07. Found: C, 64.14; H, 7.22; N, 22.46.

Example 61

3-(4-Amino-2-methyl-1H-imidazo[4,5-c]quinolin-1-yl)-2,2-dimethylpropanamide

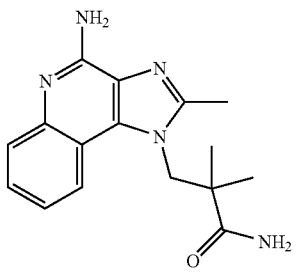 [SMILES: Cc1nc2c(N)nc3ccccc3c2n1CC(C)(C)C(N)=O]

Part A

Ethyl 3-[(3-aminoquinolin-4-yl)amino]-2,2-dimethylpropanoate (see Example 26 Parts A through D, 6.3 g, 2 mmol) was treated according to a modification of the method described in Part B of Example 8 using trimethyl orthoacetate in lieu of trimethyl orthobutyrate. Prior to the addition of trimethyl orthoacetate (3.8 mL, 30 mmol) and pyridinium p-toluenesulfonate (0.050 g), the reaction was heated at reflux for 15 minutes. During the work-up procedure, the solution was washed with saturated aqueous sodium bicarbonate (2×35 mL) and dried over potassium carbonate. The product, ethyl 2,2-dimethyl-3-(2-methyl-1H-imidazo[4,5-c]quinolin-1-yl)propanoate (7.3 g), was used without purification.

Part B

The methods described in Part B of Example 60 were used to treat ethyl 2,2-dimethyl-3-(2-methyl-1H-imidazo[4,5-c]quinolin-1-yl)propanoate (7.2 g, 22 mmol) with mCPBA (9.6 g of 77% pure material), followed by trichloroacetyl isocyanate (3.1 mL, 26 mmol), followed by sodium methoxide (20 mL of 25% in methanol). After the collection of the precipitate, the filtrate was concentrated under reduced pressure, and the residue was mixed with methanol (50 mL). The resulting solid was isolated by filtration, and the isolated solids were combined to provide 2.3 g of methyl 3-(4-amino-2-methyl-1H-imidazo[4,5-c]quinolin-1-yl)-2,2-dimethylpropanoate.

Part C

A solution of potassium hydroxide (20 mL of a 0.5 M solution in methanol) was added to a mixture of methyl 3-(4-amino-2-methyl-1H-imidazo[4,5-c]quinolin-1-yl)-2,2-dimethylpropanoate (1.7 g, 5.4 mmol) and methanol (50 mL), and the resulting solution was heated at reflux for one day, allowed to cool, stirred for three days and ambient temperature, heated at reflux for one day, and allowed to cool. Hydrogen chloride (11 mL of a 1 N solution in diethyl ether) was added, and the reaction was stirred for 15 minutes. The solvents were removed under reduced pressure, and the residue was dissolved in dichloromethane (50 mL) and three drops of DMF. A solution of oxalyl chloride (0.96 mL, 11 mmol) in dichloromethane (10 mL) was added rapidly, and the solution was stirred for three days at ambient temperature and then concentrated under reduced pressure. The residue was dissolved in dichloromethane (50 mL), and ammonia (15 mL of a 0.5 M solution in 1,4-dioxane) was added. The reaction was stirred for 30 minutes, and then additional ammonia (10 mL of a 7 N solution in methanol) was added. The reaction was stirred overnight at ambient temperature and concentrated under reduced pressure. The solid residue was stirred with saturated aqueous sodium bicarbonate (50 mL) for 15 minutes, isolated by filtration, washed with saturated aqueous sodium bicarbonate (50 mL), and recrystallized from methanol/water containing a few mL of 0.5 M potassium hydroxide in methanol. The resulting crystals were mixed with material from a separate run, and the combined solids were dried overnight in a vacuum oven at 80° C., washed with water (3×15 mL), and recrystallized from a mixture of methanol (20 mL), water (7 mL), and 0.5 N potassium hydroxide in methanol (3 mL). The crystals were dried overnight in a vacuum oven at 80° C. to provide 3-(4-amino-2-methyl-1H-imidazo[4,5-c]quinolin-1-yl)-2,2-dimethylpropanamide as light yellow crystals, mp 284-287° C.

MS (APCI) m/z 298 (M+H$^+$);

Anal. calcd for $C_{16}H_{19}N_5O$: C, 64.63; H, 6.44; N, 23.55. Found: C, 64.37; H, 6.37; N, 23.54.

Example 62

3-(4-Amino-1H-imidazo[4,5-c]quinolin-1-yl)-2,2-dimethylpropanamide

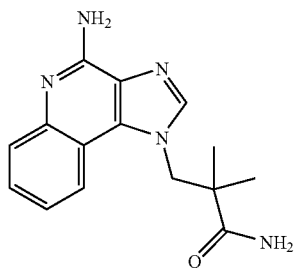 [SMILES: CC(C)(Cn1cnc2c(N)nc3ccccc3c21)C(N)=O]

Part A

Ethyl 3-(3-aminoquinolin-4-ylamino)-2,2-dimethylpropanoate (see Example 26 Parts A through D, 5.3 g, 18 mmol) was treated according to a modification of the method described in Part B of Example 8 using trimethyl orthoformate in lieu of trimethyl orthobutyrate. Prior to the addition of trimethyl orthoformate (3.0 mL, 27 mmol) and pyridinium p-toluenesulfonate (0.050 g), the reaction was heated at reflux for 15 minutes. The reaction was heated at reflux overnight, allowed to cool to ambient temperature, washed with saturated aqueous sodium bicarbonate (2×35 mL), and extracted with water (45 mL) containing 10% hydrochloric acid (5 mL). The acidic extract was made basic with the addition of potassium carbonate and then extracted with dichloromethane (3×50 mL). The combined organic extracts were dried over potassium carbonate, filtered, and concentrated under reduced pressure to provide 4.3 g of ethyl 3-(1H-imidazo[4,5-c]quinolin-1-yl)-2,2-dimethylpropanoate as an oil.

Part B

A modification of the methods described in Part B of Example 60 was used to treat ethyl 3-(1H-imidazo[4,5-c]quinolin-1-yl)-2,2-dimethylpropanoate (4.3 g, 14 mmol) with mCPBA (6.3 g of 77% pure material), followed by trichloroacetyl isocyanate (2.0 mL, 17 mmol). The reaction with the isocyanate was stirred for two hours before the addition of additional trichloroacetyl isocyanate (1.0 mL) and stirring for an additional two hours. After the reaction with sodium methoxide (11 mL of 25% in methanol), the solvent was removed under reduced pressure. The residue was mixed with methanol (25 mL), and the mixture was cooled to 0° C. and filtered to isolate 1.61 g of methyl 3-(4-amino-1H-imidazo[4,5-c]quinolin-1-yl)-2,2-dimethylpropanoate as a solid. The filtrate was concentrated under reduced pressure, and the residue was mixed with saturated aqueous sodium bicarbonate (100 mL). A precipitate formed, was isolated by filtration, and was mixed with concentrated hydrochloric acid to adjust to pH 7. The precipitate was again isolated by filtration and dissolved in dichloromethane. The resulting solution was dried over potassium carbonate, filtered, and concentrated under reduced pressure to provide an additional 1.51 g of methyl 3-(4-amino-1H-imidazo[4,5-c]quinolin-1-yl)-2,2-dimethylpropanoate as an oil.

Part C

A modification of the methods described in Part C of Example 61 was used to treat methyl 3-(4-amino-1H-imidazo[4,5-c]quinolin-1-yl)-2,2-dimethylpropanoate (1.61 g, 5.4 mmol) with potassium hydroxide (22 mL of 0.5 M); the reaction was heated at reflux overnight. The reaction with oxalyl chloride (0.96 mL) in dichloromethane (55 mL total) was stirred for one hour before more oxalyl chloride (1.0 mL) and DMF (three drops) were added, and then the reaction was stirred overnight. The precipitate isolated after the reaction with ammonia and treatment with sodium bicarbonate was combined with material from another run and recrystallized from methanol/water. The resulting solid was isolated by filtration and heated gently in a mixture of methanol (35 mL), water (10 mL), and concentrated hydrochloric acid (0.83 mL). The mixture was filtered to remove a small amount of insoluble material, and a precipitate formed in the filtrate. The precipitate was isolated by filtration, recrystallized twice from methanol/water, dried overnight in a vacuum oven at 70° C., and recrystallized four times from ethyl acetate/methanol/water with a filtration through a 20 micron filter prior to the last two crystallizations. The resulting crystals were dried overnight in a vacuum oven at 70° C. to provide 3-(4-amino-1H-imidazo[4,5-c]quinolin-1-yl)-2,2-dimethylpropanamide as white crystals, mp 287-289° C.

MS (APCI) m/z 284 (M+H$^+$);

Anal. calcd for $C_{15}H_{17}N_5O$·1.0 HCl·1.0H$_2$O: C, 53.33; H, 5.97; N, 20.73. Found: C, 53.25; H, 5.85; N, 20.60.

Example 63

3-(4-Amino-2-butyl-1H-imidazo[4,5-c]quinolin-1-yl)-2,2-dimethylpropanamide

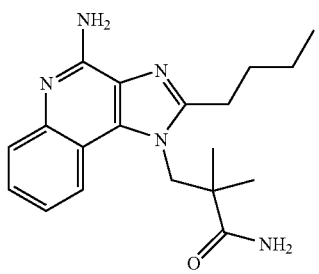 [SMILES: CCCCc1nc2c(N)nc3ccccc3c2n1CC(C)(C)C(N)=O]

Part A

Ethyl 3-(3-aminoquinolin-4-ylamino)-2,2-dimethylpropanoate (see Example 26 Parts A through D, 9.0 g, 31.3 mmol) was treated according to a modification of the method described in Part B of Example 8 using trimethyl orthovalerate in lieu of trimethyl orthobutyrate. Prior to the addition of trimethyl orthovalerate (6.1 mL, 35 mmol) and pyridinium p-toluenesulfonate (0.050 g), the reaction was heated at reflux for 15 minutes and then cooled slightly. The reaction was heated at reflux for five hours, allowed to cool to ambient temperature, stirred overnight, and concentrated under reduced pressure to provide 11.2 g of ethyl 3-(2-butyl-1H-imidazo[4,5-c]quinolin-1-yl)-2,2-dimethylpropanoate.

Part B

A modification of the methods described in Part B of Example 60 was used to treat ethyl 3-(2-butyl-1H-imidazo[4,5-c]quinolin-1-yl)-2,2-dimethylpropanoate (11.0 g, 31 mmol) with mCPBA (13.6 g of 77% pure material), followed by trichloroacetyl isocyanate (4.4 mL, 37 mmol). The reaction with the isocyanate was stirred for 1.5 hours before the addition of additional trichloroacetyl isocyanate (4.4 mL) and stirring for three days. Additional trichloroacetyl isocyanate (0.5 mL) was added, and the reaction was stirred for four hours. After the addition of methanol (50 mL), the solution was stirred overnight, and then the solvent was removed under reduced pressure. The residue was dissolved in dichloromethane (150 mL), and the solution was washed with saturated aqueous sodium bicarbonate (2×35 mL), dried over potassium carbonate, filtered, and concentrated under reduced pressure. The crude product was purified by column chromatography on silica gel (eluting with 5% methanol in dichloromethane containing 2 mL ammonium hydroxide per liter of eluent) to provide 11.4 g of methyl 3-(4-amino-2-butyl-1H-imidazo[4,5-c]quinolin-1-yl)-2,2-dimethylpropanoate as a semi-solid.

Part C

A modification of the methods described in Part C of Example 60 was used to treat methyl 3-(4-amino-2-butyl-1H-imidazo[4,5-c]quinolin-1-yl)-2,2-dimethylpropanoate (7.6 g, 21 mmol) with potassium hydroxide (44 mL of 0.5 M); additional potassium hydroxide (22 mL) was added after refluxing for four hours. After the reaction was heated at reflux for five days, additional potassium hydroxide (11 mL) was added, and the reaction was heated for four more hours. After the reaction with oxalyl chloride (3.7 mL, 42 mmol) was stirred overnight, additional oxalyl chloride (1.0 mL) was added, and then the reaction was stirred for two hours. After the addition of ammonia in methanol (35 mL), the reaction was stirred for one hour and then concentrated. The residue was stirred with saturated aqueous sodium bicarbonate for 30 minutes, isolated by filtration, and recrystallized three times from methanol/water. During the first recrystallization, a solution in methanol was filtered through a 20 micron filter prior to the addition of water. The resulting crystals were dried overnight in a vacuum oven at 70° C. to provide 1.60 g of 3-(4-amino-2-butyl-1H-imidazo[4,5-c]quinolin-1-yl)-2,2-dimethylpropanamide as light tan crystals, mp 231-233° C.

MS (APCI) m/z 340 (M+H$^+$);

Anal. calcd for $C_{19}H_{25}N_5O$: C, 67.23; H, 7.42; N, 20.63. Found: C, 66.85; H, 7.56; N, 20.67.

Example 64

1-{[4-Amino-2-(ethoxymethyl)-1H-imidazo[4,5-c]quinolin-1-yl]methyl}cyclopropanecarboxamide

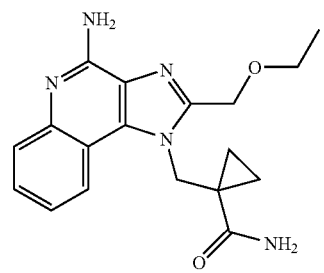 [SMILES: CCOCc1nc2c(N)nc3ccccc3c2n1CC1(C(N)=O)CC1]

Part A

Ethylcyanoacetate (15.0 mL, 141 mmol) was added to a mixture of potassium carbonate (48.7 g, 353 mmol) and acetone (200 mL), and 1,2-dibromoethane (13.4 mL, 155 mmol) was added dropwise to the resulting mixture over a period of eight minutes. The reaction was heated at reflux overnight. An analysis by TLC indicated the presence of ethylcyanoacetate, and additional 1,2-dibromoethane (1.8 mL, 0.15 equivalent) was added. The reaction mixture was heated at reflux for an additional four hours and filtered through a layer of CELITE filter agent. The filter cake was washed with acetone (200 mL), and the combined filtrates were concentrated under reduced pressure to provide ethyl 1-cyanocyclopropanecarboxylate as an orange oil containing about 10 mole % 1,2-dibromoethane.

Part B

Platinum (IV) oxide (0.98 g) and concentrated hydrochloric acid (25 mL) were added to a solution of the material from Part A in ethanol (225 mL), and the mixture was placed under hydrogen pressure (40 psi, 2.8×10$^5$ Pa) on a Parr apparatus and shaken for 20 hours and then filtered through a layer of CELITE filter agent. The filter cake was washed with methanol (200 mL), and the combined filtrates were concentrated under reduced pressure. The residue was three times dissolved in methanol and concentrated and then twice dissolved in toluene and concentrated to afford ethyl 1-(aminomethyl)cyclopropanecarboxylate hydrochloride as a thick, pale yellow oil.

Part C

A suspension of 4-chloro-3-nitroquinoline (24.5 g, 118 mmol) and triethylamine (41 mL, 294 mmol) in dichloromethane (450 mL) was cooled to 5° C., and a solution of the material from Part B in dichloromethane (200 mL) was added over a period of 15 minutes. The reaction was stirred at 5° C. for one hour, allowed to warm to ambient temperature, stirred overnight, and washed with saturated aqueous sodium bicarbonate (250 mL). The aqueous layer was extracted with dichloromethane (2×50 mL), and the combined organic fractions were dried over magnesium sulfate, filtered, and concentrated under reduced pressure. The resulting orange oil was recrystallized from acetonitrile to provide 21.47 g of ethyl 1-{[(3-nitroquinolin-4-yl)amino]methyl}cyclopropanecarboxylate as a bright yellow solid.
Part D A suspension of 5% platinum on carbon (0.80 g) and ethyl 1-{[(3-nitroquinolin-4-yl)amino]methyl}cyclopropanecarboxylate (8.0 g, 25 mmol) in ethyl acetate was placed under hydrogen pressure (30 psi, $2.1 \times 10^5$ Pa) on a Parr apparatus for three hours and filtered through a layer of CELITE filter agent. The filter cake was washed with ethyl acetate (50 mL), and the combined filtrates were concentrated under reduced pressure to provide ethyl 1-{[(3-aminoquinolin-4-yl)amino]methyl}cyclopropanecarboxylate as a yellow solid.
Part E A solution of the material from Part D in dichloromethane (100 mL) was cooled to 0° C., and ethoxyacetyl chloride (2.9 mL, 28 mmol) was added dropwise over a period of five minutes. The reaction was allowed to slowly warm to ambient temperature, stirred overnight, and concentrated under reduced pressure to provide ethyl 1-[({3-[(ethoxyacetyl)amino]quinolin-4-yl}amino)methyl]cyclopropanecarboxylate hydrochloride.
Part F Triethylamine (10.6 mL, 76.2 mmol) was added to a solution from Part E in ethanol (100 mL), and the reaction was heated at 60° C. overnight. The solvent was removed under reduced pressure, and the residue was dissolved in dichloromethane (100 mL). The resulting solution was washed with saturated aqueous sodium bicarbonate (75 mL). The aqueous fraction was extracted with dichloromethane (2×35 mL), and the combined organic fractions were dried over magnesium sulfate, filtered, and concentrated under reduced pressure to provide ethyl 1-{[2-(ethoxymethyl)-1H-imidazo[4,5-c]quinolin-1-yl]methyl}cyclopropanecarboxylate as a brown semi-solid.
Part G Aqueous sodium hydroxide (8.5 mL of 6 M) was added to a solution of the material from Part F in ethanol (80 mL); the reaction was stirred at ambient temperature for three hours and concentrated under reduced pressure. The residue was mixed with water (60 mL) and adjusted to pH 5 with the addition of 2 M hydrochloric acid. No precipitate formed, and the mixture was adjusted to pH 12 and washed with diethyl ether (3×20 mL). The solution was adjusted to pH 4, and a precipitate formed and was isolated by filtration and dried to provide 4.36 g of 1-{[2-(ethoxymethyl)-1H-imidazo[4,5-c]quinolin-1-yl]methyl}cyclopropanecarboxylic acid. The filtrate was adjusted to pH 7 and extracted with chloroform (3×20 mL), and the combined extracts were dried over magnesium sulfate, filtered, and concentrated under reduced pressure to provide an orange solid. The solid was triturated with acetonitrile and isolated by filtration to provide an additional 1.76 g of 1-{[2-(ethoxymethyl)-1H-imidazo[4,5-c]quinolin-1-yl]methyl}cyclopropanecarboxylic acid.
Part H Oxalyl chloride (1.6 mL, 18 mmol) was added dropwise over a period of 5 minutes to a suspension of 1-{[2-(ethoxymethyl)-1H-imidazo[4,5-C]quinolin-1-yl]methyl}cyclopropanecarboxylic acid (2.0 g, 6.2 mmol) in dichloromethane (50 mL) containing one drop of DMF. The reaction mixture was stirred for two hours and then concentrated under reduced pressure to provide 1-{[2-(ethoxymethyl)-1H-imidazo[4,5-c]quinolin-1-yl]methyl}cyclopropanecarbonyl chloride.
Part I A solution of the material from Part H in dichloromethane (35 mL) was cooled to 0° C., and a solution of ammonia in 1,4-dioxane (18.5 mL of 0.5 M) was added. The reaction was stirred for ten minutes, and then ammonia gas was bubbled through the solution for ten minutes. The reaction was then sealed, allowed to warm to ambient temperature slowly, and stirred overnight. The solvent was removed under reduced pressure, and the residue was triturated with 1 M-aqueous sodium hydroxide and isolated by filtration to provide 1.70 g of 1-{[2-(ethoxymethyl)-1H-imidazo[4,5-c]quinolin-1-yl]methyl}cyclopropanecarboxamide as an off-white solid.
Part J mCPBA (1.68 g, 6.81 mmol) was added to a suspension of 1-{[2-(ethoxymethyl)-1H-imidazo[4,5-c]quinolin-1-yl]methyl}cyclopropanecarboxamide (1.70 g, 5.24 mmol) in chloroform (25 mL); the reaction was stirred for two hours at ambient temperature and then cooled to 0° C. Ammonium hydroxide (5 mL) and p-toluenesulfonyl chloride (1.10 g, 5.76 mmol) were added. The reaction was stirred for one hour at 5° C. and then filtered to isolate a precipitate. The precipitate was triturated with 2 M aqueous sodium hydroxide, isolated by filtration, triturated with hot acetonitrile, isolated by filtration, and recrystallized from ethanol. The crystals were dried overnight at 85° C. in a vacuum oven to provide 0.78 g of 1-{[4-amino-2-(ethoxymethyl)-1H-imidazo[4,5-c]quinolin-1-yl]methyl}cyclopropanecarboxamide as tan needles, mp 230.5-232.5° C.

MS (ESI) m/z 340 (M+H)$^+$;

Anal. calcd for $C_{18}H_{21}N_5O_2$: C, 63.70; H, 6.24; N, 20.63. Found: C, 63.65; H, 6.31; N, 20.57.

Example 65

1-[(4-Amino-2-propyl-1H-imidazo[4,5-c]quinolin-1-yl)methyl]cyclobutanecarboxamide

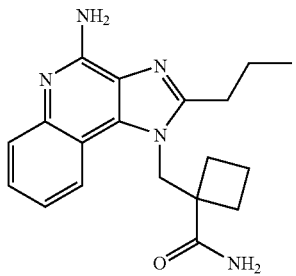 [SMILES: CCCc1nc2c(N)nc3ccccc3c2n1CC1(C(N)=O)CCC1]

Part A

The method described in Part A of Example 64 was used to treat ethylcyanoacetate (45 mL, 420 mmol) with 1,3-dibromopropane (51 mL, 510 mmol) and potassium carbonate (146 g, 1.06 mol) to provide ethyl 1-cyanocyclobutanecarboxylate as an orange oil containing about 15 mole % 1,2-dibromopropane.
Part B The method described in Part B of Example 64 was used to hydrogenate (30 psi, $2.1 \times 10^5$ Pa) the material from Part A for 28 hours in the presence of platinum (IV) oxide (2.0 g) and concentrated hydrochloric acid (70 mL) to provide ethyl 1-(aminomethyl)cyclobutanecarboxylate hydrochloride as a thick, pale yellow oil.
Part C A modification of the method described in Part C of Example 64 was used to treat the material from Part B with 4-chloro-3-nitroquinoline (73.6 g, 353 mmol) and triethylamine (147 mL, 1.06 mol). The crude product was divided into three portions, and each portion was purified by chromatography on 175 g of silica gel (eluting with 25-40% ethyl acetate in hexane). The resulting yellow-orange solid was triturated with acetonitrile and isolated by filtration to provide 27.56 g of ethyl 1-{[(3-nitroquinolin-4-yl)amino]methyl}cyclobutanecarboxylate as a bright yellow solid.
Part D The method described in Part D of Example 64 was used to hydrogenate (35 psi, $2.4 \times 10^5$ Pa) ethyl 1-{[(3-nitroquinolin-4-yl)amino]methyl}cyclobutanecarboxylate (10.0 g, 30.4 mmol) in the presence of 5% platinum on carbon (1.0 g) to provide ethyl 1-{[(3-aminoquinolin-4-yl)amino]methyl}cyclobutanecarboxylate as a yellow solid.
Part E Trimethyl orthobutyrate (5.0 mL, 32 mmol) and pyridine hydrochloride (0.14 g, 1.2 mmol) were added to a suspension of the material from Part D in toluene (100 mL), and the reaction was heated at reflux for two hours, allowed to cool to ambient temperature, and concentrated under reduced pressure. The crude product was triturated with acetonitrile and isolated by filtration to provide 7.55 g of ethyl 1-[(2-propyl-1H-imidazo[4,5-c]quinolin-1-yl)methyl]cyclobutanecarboxylate as a white solid
Part F Aqueous sodium hydroxide (7 mL of 6 M) was added to a solution of ethyl 1-[(2-propyl-1H-imidazo[4,5-c]quinolin-1-yl)methyl]cyclobutanecarboxylate (7.55 g, 21.5 mmol) in ethanol (60 mL); the reaction was stirred at ambient temperature for one hour and concentrated under reduced pressure. The residue was dissolved in water (40 mL) and adjusted to pH 7 with the addition of 2 M hydrochloric acid. A precipitate formed, was isolated by filtration, and dried in a vacuum oven at 70° C. for two hours to provide 6.76 g of 1-[(2-propyl-1H-imidazo[4,5-c]quinolin-1-yl)methyl]cyclobutanecarboxylic acid as a tan solid.
Part G The methods described in Parts H and I of Example 64 were used to treat 1-[2-propyl-1H-imidazo[4,5-c]quinolin-1-yl)methyl]cyclobutanecarboxylic acid (1.75 g, 5.41 mmol) with oxalyl chloride (1.4 mL, 16 mmol) followed by ammonia and to isolate the final product, 1-[(2-propyl-1H-imidazo[4,5-c]quinolin-1-yl)methyl]cyclobutanecarboxamide as an off-white solid (1.81 g).
Part H The method described in Part J of Example 64 was used to treat the material from Part G with mCPBA (1.73 g, 7.03 mmol) followed by ammonium hydroxide (6 mL) and p-toluenesulfonyl chloride (1.13 g, 5.95 mmol). At the completion of the reaction, the mixture was filtered to remove a solid impurity. The filtrate was diluted with chloroform (20 mL) and washed with saturated aqueous sodium bicarbonate (40 mL). The aqueous fraction was extracted with chloroform (2×15 mL), and the combined organic fractions were dried over magnesium sulfate, filtered, and concentrated under reduced pressure. The residue was triturated with acetonitrile and isolated by filtration. The resulting solid was dissolved in 10% methanol in chloroform and treated with activated charcoal. After filtration, the solution was purified by chromatography on a HORIZON HPFC system (40+M cartridge, eluting with 0 to 55% CMA in chloroform), and the resulting white solid was triturated with acetonitrile, isolated by filtration, and dried in a vacuum oven at 85° C. to provide 0.859 g of 1-[(4-amino-2-propyl-1H-imidazo[4,5-c]quinolin-1-yl)methyl]cyclobutanecarboxamide as a white powder, mp 234-237° C.

MS (ESI) m/z 338 (M+H)$^+$;

Anal. calcd for $C_{19}H_{23}N_5O$: C, 67.63; H, 6.87; N, 20.76. Found: C, 67.43; H, 7.12; N, 21.00.

Example 66

1-[(4-Amino-2-ethyl-1H-imidazo[4,5-c]quinolin-1-yl)methyl]cyclobutanecarboxamide

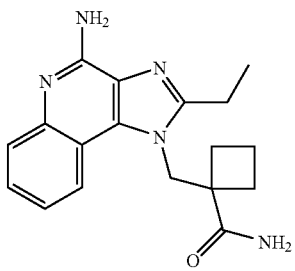 [SMILES: CCc1nc2c(N)nc3ccccc3c2n1CC1(C(N)=O)CCC1]

Part A

The method described in Part E of Example 65 was used to treat ethyl 1-{[(3-aminoquinolin-4-yl)amino]methyl}cyclobutanecarboxylate (6 mmol) with triethyl orthopropionate (1.6 mL, 7.9 mmol) and pyridine hydrochloride (35 mg) and isolate the final product, ethyl 1-[(2-ethyl-1H-imidazo[4,5-c]quinolin-1-yl)methyl]cyclobutanecarboxylate (1.86 g, 5.51 mmol), as a white solid, which was treated with sodium hydroxide (1.8 mL of 6 M) according to the method of Part F of Example 65. The product, 1-[(2-ethyl-1H-imidazo[4,5-c]quinolin-1-yl)methyl]cyclobutanecarboxylic acid, was isolated as a tan solid (1.49 g) according to the methods of Part F of Example 65.
Part B A modification of the method described in Parts H of Example 64 was used to treat 1-[2-ethyl-1H-imidazo[4,5-c]quinolin-1-yl)methyl]cyclobutanecarboxylic acid (1.49 g, 4.61 mmol) with oxalyl chloride (1.2 mL, 14 mmol) in dichloromethane (30 mL). After the reaction was stirred for 1.5 hours, additional oxalyl chloride (0.6 mL) was added. The product was carried on as a mixture of the carboxylic acid and the acid chloride, which was treated according to the method of Part I of Example 64 to provide 0.66 g of 1-[(2-ethyl-1H-imidazo[4,5-c]quinolin-1-yl)methyl]cyclobutanecarboxamide as an off-white solid.
Part C The method described in Part J of Example 64 was used to treat the material from Part B with mCPBA (0.69 g, 2.8 mmol) followed by ammonium hydroxide (3 mL) and p-toluenesulfonyl chloride (0.45 g, 2.35 mmol). At the completion of the reaction, the precipitated product was isolated by filtration, triturated with 1 M aqueous sodium hydroxide, and isolated by filtration. The resulting tan solid was purified by chromatography on a HORIZON HPFC system (40+M cartridge, eluting with 0 to 65% CMA in chloroform), and the resulting white solid was triturated with hot acetonitrile, isolated by filtration, and dried in a vacuum oven at 85° C. to provide 0.218 g of 1-[(4-amino-2-ethyl-1H-imidazo[4,5-c]quinolin-1-yl)methyl]cyclobutanecarboxamide as a white powder, mp 227-230° C.

MS (ESI) m/z 324 (M+H)$^+$;

Anal. calcd for $C_{18}H_{21}N_5O$: C, 66.85; H, 6.55; N, 21.66. Found: C, 66.92; H, 6.72; N, 21.83.

Example 67

1-{[4-Amino-2-(ethoxymethyl)-1H-imidazo[4,5-c]quinolin-1-yl]methyl}cyclohexanecarboxamide

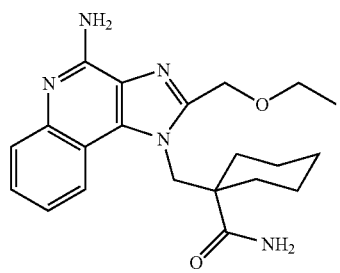 [SMILES: CCOCc1nc2c(N)nc3ccccc3c2n1CC1(C(N)=O)CCCCC1]

Part A

Potassium carbonate (30.4 g, 0.220 mol) and 1,5-dibromopentane (13.6 mL, 0.100 mol) were sequentially added to a solution of ethylcyanoacetate (10.6 mL, 0.100 mol) in DMF (100 mL), and the reaction was stirred overnight at ambient temperature. The reaction mixture was partitioned between water and ethyl acetate, and the organic fraction was separated, washed with water, dried over magnesium sulfate, filtered, and concentrated under reduced pressure to provide ethyl 1-cyanocyclohexanecarboxylate.

Part B

Platinum (IV) oxide (1.72 g) was added to a solution of ethyl 1-cyanocyclohexanecarboxylate (17.15 g, 94.6 mmol) in concentrated hydrochloric acid (20 mL) and ethanol (200 mL), and the mixture was placed under hydrogen pressure on a Parr apparatus and shaken for 20 hours. The solvent was removed under reduced pressure, and the residue was diluted with water. The resulting mixture was adjusted to pH 7 with the addition of solid sodium carbonate and then extracted several times with dichloromethane. The combined extracts were dried over magnesium sulfate, filtered, and concentrated under reduced pressure to provide 5.67 g of ethyl 1-(aminomethyl)cyclohexanecarboxylate as a colorless oil. A portion of the water was removed from the aqueous layer, and dichloromethane was added. The mixture was stirred overnight at ambient temperature, and the organic fraction was separated, dried over magnesium sulfate, filtered, and concentrated under reduced pressure to provide 11.69 g of ethyl 1-(aminomethyl)cyclohexanecarboxylate hydrochloride as a white solid.

Part C

A solution of 4-chloro-3-nitroquinoline (10.96 g, 52.5 mmol) in dichloromethane (200 mL) was cooled to approximately 0° C., and triethylamine (22.0 mL, 158 mmol) and a solution of ethyl 1-(aminomethyl)cyclohexanecarboxylate hydrochloride (11.65 g, 52.5 mmol) in dichloromethane (30 mL) were sequentially added. The reaction was stirred for four hours, and the solvent was removed under reduced pressure. The residue was stirred in deionized water (50 mL) for one hour, and the mixture was extracted several times with dichloromethane. The combined extracts were dried over magnesium sulfate, filtered, and concentrated under reduced pressure. The resulting orange oil was purified by chromatography on silica gel (eluting with 3-5% methanol in dichloromethane) to provide 11.72 g of ethyl 1-{[(3-nitroquinolin-4-yl)amino]methyl}cyclohexanecarboxylate as an orange oil that solidified upon standing.

Part D

A suspension of 5% platinum on carbon (1.2 g) and ethyl 1-{[(3-nitroquinolin-4-yl)amino]methyl}cyclohexanecarboxylate (11.7 g, 32.7 mmol) in acetonitrile (100 mL) was placed under hydrogen pressure (3 atm, $2.1 \times 10^5$ Pa) on a Parr apparatus for five hours and filtered through a layer of CELITE filter agent. The filtrate was concentrated under reduced pressure to provide 9.60 g of ethyl 1-{[(3-aminoquinolin-4-yl)amino]methyl}cyclohexanecarboxylate as an orange oil that solidified upon standing.

Part E

A solution of ethoxyacetyl chloride (3.95 g, 32.3 mmol) in acetonitrile (10 mL) was added to a solution of ethyl 1-{[(3-aminoquinolin-4-yl)amino]methyl}cyclohexanecarboxylate (9.60 g, 29.3 mmol) in acetonitrile (200 mL), and the resulting mixture was stirred for five hours at ambient temperature. A precipitate was present and was isolated by filtration, washed with cold acetonitrile, and dried overnight under vacuum to provide 10.18 g of ethyl 1-[({3-[(ethoxyacetyl)amino]quinolin-4-yl}amino)methyl]cyclohexanecarboxylate hydrochloride.

Part F

Sodium hydroxide (2.71 g, 67.7 mmol) was added to a solution of ethyl 1-[({3-[(ethoxyacetyl)amino]quinolin-4-yl}amino)methyl]cyclohexanecarboxylate hydrochloride (10.15 g, 22.6 mmol) in 9:1 ethanol/water (30 mL), and the solution was heated at reflux for several hours. The ethanol was removed under reduced pressure, and the resulting solution was diluted with water and adjusted to pH 4 to 5 with the addition of 3 M hydrochloric acid. The mixture was then extracted several times with dichloromethane The aqueous fraction was adjusted to pH 7 and extracted several more times with dichloromethane. The combined extracts were dried over magnesium sulfate, filtered, and concentrated under reduced pressure to provide 5.73 g of 1-{[2-(ethoxymethyl)-1H-imidazo[4,5-c]quinolin-1-yl]methyl}cyclohexanecarboxylic acid.

Part G

Excess oxalyl chloride was added to a suspension of 1-{[2-(ethoxymethyl)-1H-imidazo[4,5-c]quinolin-1-yl]methyl}cyclohexanecarboxylic acid (1.30 g, 3.54 mmol) in chloroform, and the reaction mixture was heated at 60° C. overnight under an argon atmosphere. The volatiles were removed under reduced pressure, and chloroform was added to the residue. An excess of ammonia (0.5 M in 1,4-dioxane) was added, and the reaction mixture was stirred for two hours. The volatiles were removed under reduced pressure, and the residue was purified by column chromatography on silica gel to provide 1.30 g of 1-{[2-(ethoxymethyl)-1H-imidazo[4,5-c]quinolin-1-yl]methyl}cyclohexanecarboxamide.

Part H mCPBA (953 mg of 77% pure material, 4.25 mmol) was added to a solution of 1-{[2-(ethoxymethyl)-1H-imidazo[4,5-c]quinolin-1-yl]methyl}cyclohexanecarboxamide (1.30 g, 3.54 mmol) in chloroform (15 mL); the reaction was stirred for one hour at ambient temperature. Ammonium hydroxide (15 mL) and p-toluenesulfonyl chloride (742 mg, 3.89 mmol) were added, and the mixture was stirred vigorously for two hours. The aqueous fraction was separated and extracted several times with chloroform. The combined organic fractions were dried over magnesium sulfate, filtered, and concentrated under reduced pressure. The residue was purified by flash column chromatography on silica gel (eluting with 2-7% methanol in dichloromethane) followed by recrystallization from acetonitrile to provide 1-{[4-amino-2-(ethoxymethyl)-1H-imidazo[4,5-c]quinolin-1-yl]methyl}cyclohexanecarboxamide as a tan crystalline solid, mp 221-223° C.

MS (APCI) m/z 382 (M+H$^+$);

Anal. calcd for $C_{20}H_{25}N_5O_3$ (with 0.25 eq. $NH_4$): C, 65.35; H, 7.31; N, 19.05. Found: C, 64.87; H, 6.85; N, 18.95.

Example 68

3-[4-Amino-2-(hydroxymethyl)-1H-imidazo[4,5-c]quinolin-1-yl)-2,2-dimethylpropanamide

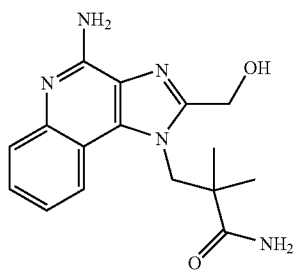 [SMILES: CC(C)(Cn1c(CO)nc2c(N)nc3ccccc3c21)C(N)=O]

Boron tribromide (15 mL of a 1 N solution in dichloromethane) was added to a solution of 3-[4-amino-2-(ethoxymethyl)-1H-imidazo[4,5-c]quinolin-1-yl)-2,2-dimethylpropanamide (1.1 g, 3.2 mmol, Example 28) in 1,2-dichloroethane (35 mL). The reaction was heated at reflux for 35 minutes, cooled to approximately 0° C., and adjusted to pH 8 with the addition of a solution of potassium hydroxide (90 mL of a 0.5 N solution in methanol). The volatiles were removed under reduced pressure, and the residue was mixed with methanol (50 mL) and isolated by filtration. The filtrate was concentrated under reduced pressure, and the residue was stirred overnight with saturated aqueous sodium bicarbonate (35 mL). The resulting solid was isolated by filtration, combined with material from another run, and purified by column chromatography on silica gel (eluting with 20% methanol in dichloromethane containing 1% ammonium hydroxide) and dried in a vacuum oven for three hours at 60° C. to provide 3-[4-amino-2-(hydroxymethyl)-1H-imidazo[4,5-c]quinolin-1-yl)-2,2-dimethylpropanamide as white crystals, mp 201-203° C.

MS (APCI) m/z 314 (M+H$^+$);

Anal. calcd for $C_{16}H_{19}N_5O\cdot0.47H_2O\cdot0.24$ $CH_3OH$: C, 59.22; H, 6.33; N, 21.26. Found: C, 59.37; H, 6.35; N, 21.26.

Exemplary Compounds

Certain exemplary compounds, including some of those described above in the Examples, have the following Formulas (IIIa, IVd, Vc, or VIb) and the following $R_1'$, $R_1''$, $X_a$, and $R_2$ substituents, wherein each line of the table is matched with Formula IIIa, IVd, Vc, or VIb to represent a specific embodiment of the invention.

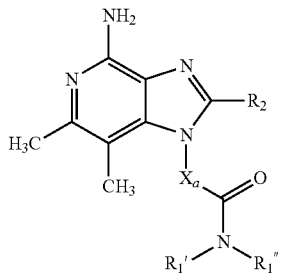

IIIa

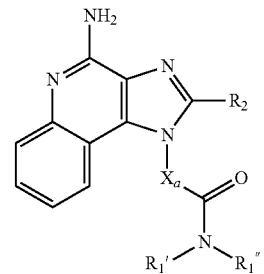

IVd

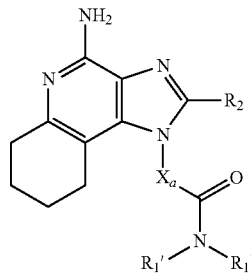

Vc

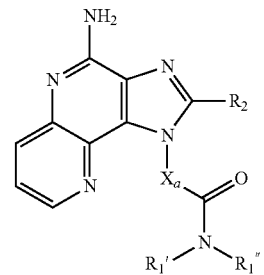

VIb

| $R_1'$ | $R_1''$ | $X_a$ | $R_2$ |
|---|---|---|---|
| hydrogen | hydrogen | —(CH$_2$)— | methyl |
| hydrogen | hydrogen | —(CH$_2$)— | ethyl |
| hydrogen | hydrogen | —(CH$_2$)— | n-propyl |
| hydrogen | hydrogen | —(CH$_2$)— | n-butyl |
| hydrogen | hydrogen | —(CH$_2$)— | ethoxymethyl |
| hydrogen | hydrogen | —(CH$_2$)— | 2-methoxyethyl |
| hydrogen | hydrogen | —(CH$_2$)$_2$— | methyl |

-continued

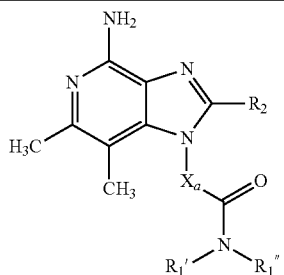

IIIa

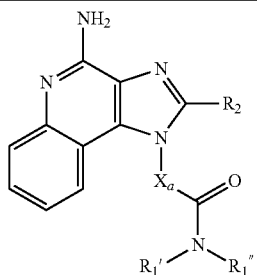

IVd

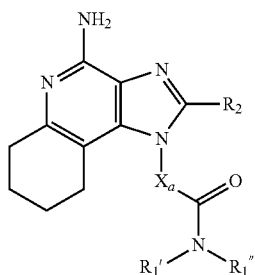

Vc

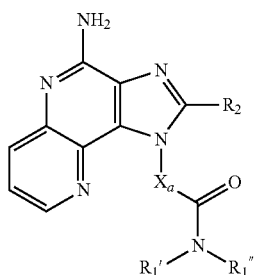

VIb

| $R_1'$ | $R_1''$ | $X_a$ | $R_2$ |
|---|---|---|---|
| hydrogen | hydrogen | —(CH$_2$)$_2$— | ethyl |
| hydrogen | hydrogen | —(CH$_2$)$_2$— | n-propyl |
| hydrogen | hydrogen | —(CH$_2$)$_2$— | n-butyl |
| hydrogen | hydrogen | —(CH$_2$)$_2$— | ethoxymethyl |
| hydrogen | hydrogen | —(CH$_2$)$_2$— | 2-methoxyethyl |
| hydrogen | hydrogen | —(CH$_2$)$_3$— | methyl |
| hydrogen | hydrogen | —(CH$_2$)$_3$— | ethyl |
| hydrogen | hydrogen | —(CH$_2$)$_3$— | n-propyl |
| hydrogen | hydrogen | —(CH$_2$)$_3$— | n-butyl |
| hydrogen | hydrogen | —(CH$_2$)$_3$— | ethoxymethyl |
| hydrogen | hydrogen | —(CH$_2$)$_3$— | 2-methoxyethyl |
| hydrogen | hydrogen | —CH$_2$C(CH$_3$)$_2$— | methyl |
| hydrogen | hydrogen | —CH$_2$C(CH$_3$)$_2$— | ethyl |
| hydrogen | hydrogen | —CH$_2$C(CH$_3$)$_2$— | n-propyl |
| hydrogen | hydrogen | —CH$_2$C(CH$_3$)$_2$— | n-butyl |
| hydrogen | hydrogen | —CH$_2$C(CH$_3$)$_2$— | ethoxymethyl |
| hydrogen | hydrogen | —CH$_2$C(CH$_3$)$_2$— | 2-methoxyethyl |
| hydrogen | hydrogen | —CH$_2$C(CH$_3$)$_2$CH$_2$— | methyl |
| hydrogen | hydrogen | —CH$_2$C(CH$_3$)$_2$CH$_2$— | ethyl |
| hydrogen | hydrogen | —CH$_2$C(CH$_3$)$_2$CH$_2$— | n-propyl |
| hydrogen | hydrogen | —CH$_2$C(CH$_3$)$_2$CH$_2$— | n-butyl |
| hydrogen | hydrogen | —CH$_2$C(CH$_3$)$_2$CH$_2$— | ethoxymethyl |
| hydrogen | hydrogen | —CH$_2$C(CH$_3$)$_2$CH$_2$— | 2-methoxyethyl |
| hydrogen | methyl | —(CH$_2$)— | methyl |
| hydrogen | methyl | —(CH$_2$)— | ethyl |
| hydrogen | methyl | —(CH$_2$)— | n-propyl |
| hydrogen | methyl | —(CH$_2$)— | n-butyl |
| hydrogen | methyl | —(CH$_2$)— | ethoxymethyl |
| hydrogen | methyl | —(CH$_2$)— | 2-methoxyethyl |
| hydrogen | methyl | —(CH$_2$)$_2$— | methyl |
| hydrogen | methyl | —(CH$_2$)$_2$— | ethyl |
| hydrogen | methyl | —(CH$_2$)$_2$— | n-propyl |
| hydrogen | methyl | —(CH$_2$)$_2$— | n-butyl |
| hydrogen | methyl | —(CH$_2$)$_2$— | ethoxymethyl |
| hydrogen | methyl | —(CH$_2$)$_2$— | 2-methoxyethyl |
| hydrogen | methyl | —(CH$_2$)$_3$— | methyl |
| hydrogen | methyl | —(CH$_2$)$_3$— | ethyl |
| hydrogen | methyl | —(CH$_2$)$_3$— | n-propyl |
| hydrogen | methyl | —(CH$_2$)$_3$— | n-butyl |
| hydrogen | methyl | —(CH$_2$)$_3$— | ethoxymethyl |
| hydrogen | methyl | —(CH$_2$)$_3$— | 2-methoxyethyl |
| hydrogen | methyl | —CH$_2$C(CH$_3$)$_2$— | methyl |
| hydrogen | methyl | —CH$_2$C(CH$_3$)$_2$— | ethyl |
| hydrogen | methyl | —CH$_2$C(CH$_3$)$_2$— | n-propyl |
| hydrogen | methyl | —CH$_2$C(CH$_3$)$_2$— | n-butyl |
| hydrogen | methyl | —CH$_2$C(CH$_3$)$_2$— | ethoxymethyl |

-continued

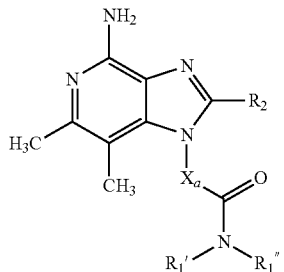

IIIa

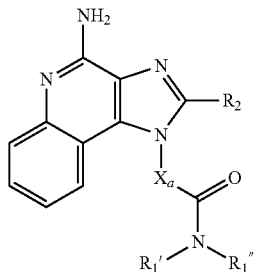

IVd

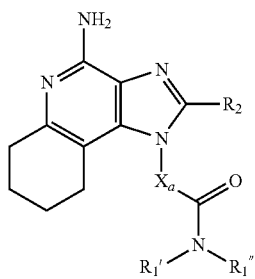

Vc

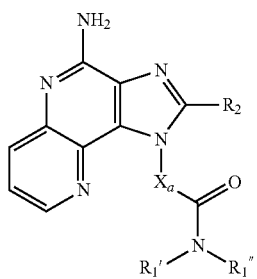

VIb

| R₁' | R₁" | X$_a$ | R₂ |
|---|---|---|---|
| hydrogen | methyl | —CH₂C(CH₃)₂— | 2-methoxyethyl |
| hydrogen | methyl | —CH₂C(CH₃)₂CH₂— | methyl |
| hydrogen | methyl | —CH₂C(CH₃)₂CH₂— | ethyl |
| hydrogen | methyl | —CH₂C(CH₃)₂CH₂— | n-propyl |
| hydrogen | methyl | —CH₂C(CH₃)₂CH₂— | n-butyl |
| hydrogen | methyl | —CH₂C(CH₃)₂CH₂— | ethoxymethyl |
| hydrogen | methyl | —CH₂C(CH₃)₂CH₂— | 2-methoxyethyl |
| methyl | methyl | —(CH₂)— | methyl |
| methyl | methyl | —(CH₂)— | ethyl |
| methyl | methyl | —(CH₂)— | n-propyl |
| methyl | methyl | —(CH₂)— | n-butyl |
| methyl | methyl | —(CH₂)— | ethoxymethyl |
| methyl | methyl | —(CH₂)— | 2-methoxyethyl |
| methyl | methyl | —(CH₂)₂— | methyl |
| methyl | methyl | —(CH₂)₂— | ethyl |
| methyl | methyl | —(CH₂)₂— | n-propyl |
| methyl | methyl | —(CH₂)₂— | n-butyl |
| methyl | methyl | —(CH₂)₂— | ethoxymethyl |
| methyl | methyl | —(CH₂)₂— | 2-methoxyethyl |
| methyl | methyl | —(CH₂)₃— | methyl |
| methyl | methyl | —(CH₂)₃— | ethyl |
| methyl | methyl | —(CH₂)₃— | n-propyl |
| methyl | methyl | —(CH₂)₃— | n-butyl |
| methyl | methyl | —(CH₂)₃— | ethoxymethyl |
| methyl | methyl | —(CH₂)₃— | 2-methoxyethyl |
| methyl | methyl | —CH₂C(CH₃)₂— | methyl |
| methyl | methyl | —CH₂C(CH₃)₂— | ethyl |
| methyl | methyl | —CH₂C(CH₃)₂— | n-propyl |
| methyl | methyl | —CH₂C(CH₃)₂— | n-butyl |
| methyl | methyl | —CH₂C(CH₃)₂— | ethoxymethyl |
| methyl | methyl | —CH₂C(CH₃)₂— | 2-methoxyethyl |
| methyl | methyl | —CH₂C(CH₃)₂CH₂— | methyl |
| methyl | methyl | —CH₂C(CH₃)₂CH₂— | ethyl |
| methyl | methyl | —CH₂C(CH₃)₂CH₂— | n-propyl |
| methyl | methyl | —CH₂C(CH₃)₂CH₂— | n-butyl |
| methyl | methyl | —CH₂C(CH₃)₂CH₂— | ethoxymethyl |
| methyl | methyl | —CH₂C(CH₃)₂CH₂— | 2-methoxyethyl |
| ethyl | hydrogen | —(CH₂)— | methyl |
| ethyl | hydrogen | —(CH₂)— | ethyl |
| ethyl | hydrogen | —(CH₂)— | n-propyl |
| ethyl | hydrogen | —(CH₂)— | n-butyl |
| ethyl | hydrogen | —(CH₂)— | ethoxymethyl |
| ethyl | hydrogen | —(CH₂)— | 2-methoxyethyl |
| ethyl | hydrogen | —(CH₂)₂— | methyl |
| ethyl | hydrogen | —(CH₂)₂— | ethyl |
| ethyl | hydrogen | —(CH₂)₂— | n-propyl |

-continued

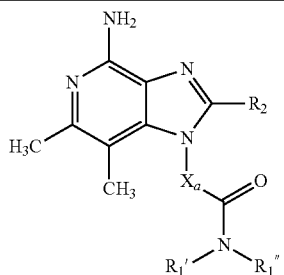

IIIa

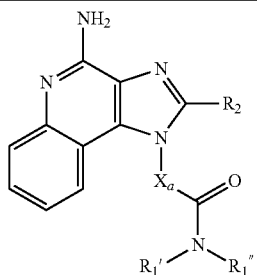

IVd

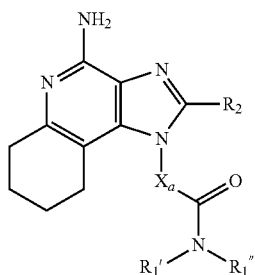

Vc

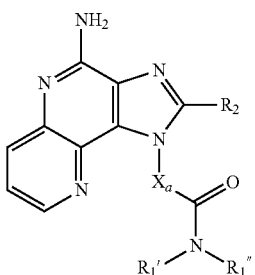

VIb

| R$_1$' | R$_1$" | X$_a$ | R$_2$ |
|---|---|---|---|
| ethyl | hydrogen | —(CH$_2$)$_2$— | n-butyl |
| ethyl | hydrogen | —(CH$_2$)$_2$— | ethoxymethyl |
| ethyl | hydrogen | —(CH$_2$)$_2$— | 2-methoxyethyl |
| ethyl | hydrogen | —(CH$_2$)$_3$— | methyl |
| ethyl | hydrogen | —(CH$_2$)$_3$— | ethyl |
| ethyl | hydrogen | —(CH$_2$)$_3$— | n-propyl |
| ethyl | hydrogen | —(CH$_2$)$_3$— | n-butyl |
| ethyl | hydrogen | —(CH$_2$)$_3$— | ethoxymethyl |
| ethyl | hydrogen | —(CH$_2$)$_3$— | 2-methoxyethyl |
| ethyl | hydrogen | —CH$_2$C(CH$_3$)$_2$— | methyl |
| ethyl | hydrogen | —CH$_2$C(CH$_3$)$_2$— | ethyl |
| ethyl | hydrogen | —CH$_2$C(CH$_3$)$_2$— | n-propyl |
| ethyl | hydrogen | —CH$_2$C(CH$_3$)$_2$— | n-butyl |
| ethyl | hydrogen | —CH$_2$C(CH$_3$)$_2$— | ethoxymethyl |
| ethyl | hydrogen | —CH$_2$C(CH$_3$)$_2$— | 2-methoxyethyl |
| ethyl | hydrogen | —CH$_2$C(CH$_3$)$_2$CH$_2$— | methyl |
| ethyl | hydrogen | —CH$_2$C(CH$_3$)$_2$CH$_2$— | ethyl |
| ethyl | hydrogen | —CH$_2$C(CH$_3$)$_2$CH$_2$— | n-propyl |
| ethyl | hydrogen | —CH$_2$C(CH$_3$)$_2$CH$_2$— | n-butyl |
| ethyl | hydrogen | —CH$_2$C(CH$_3$)$_2$CH$_2$— | ethoxymethyl |
| ethyl | hydrogen | —CH$_2$C(CH$_3$)$_2$CH$_2$— | 2-methoxyethyl |
| ethyl | methyl | —(CH$_2$)— | methyl |
| ethyl | methyl | —(CH$_2$)— | ethyl |
| ethyl | methyl | —(CH$_2$)— | n-propyl |
| ethyl | methyl | —(CH$_2$)— | n-butyl |
| ethyl | methyl | —(CH$_2$)— | ethoxymethyl |
| ethyl | methyl | —(CH$_2$)— | 2-methoxyethyl |
| ethyl | methyl | —(CH$_2$)$_2$— | methyl |
| ethyl | methyl | —(CH$_2$)$_2$— | ethyl |
| ethyl | methyl | —(CH$_2$)$_2$— | n-propyl |
| ethyl | methyl | —(CH$_2$)$_2$— | n-butyl |
| ethyl | methyl | —(CH$_2$)$_2$— | ethoxymethyl |
| ethyl | methyl | —(CH$_2$)$_2$— | 2-methoxyethyl |
| ethyl | methyl | —(CH$_2$)$_3$— | methyl |
| ethyl | methyl | —(CH$_2$)$_3$— | ethyl |
| ethyl | methyl | —(CH$_2$)$_3$— | n-propyl |
| ethyl | methyl | —(CH$_2$)$_3$— | n-butyl |
| ethyl | methyl | —(CH$_2$)$_3$— | ethoxymethyl |
| ethyl | methyl | —(CH$_2$)$_3$— | 2-methoxyethyl |
| ethyl | methyl | —CH$_2$C(CH$_3$)$_2$— | methyl |
| ethyl | methyl | —CH$_2$C(CH$_3$)$_2$— | ethyl |
| ethyl | methyl | —CH$_2$C(CH$_3$)$_2$— | n-propyl |
| ethyl | methyl | —CH$_2$C(CH$_3$)$_2$— | n-butyl |
| ethyl | methyl | —CH$_2$C(CH$_3$)$_2$— | ethoxymethyl |
| ethyl | methyl | —CH$_2$C(CH$_3$)$_2$— | 2-methoxyethyl |
| ethyl | methyl | —CH$_2$C(CH$_3$)$_2$CH$_2$— | methyl |

-continued

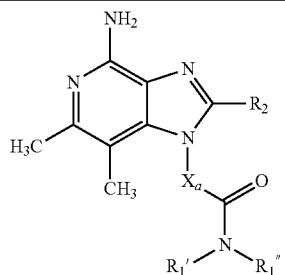

IIIa

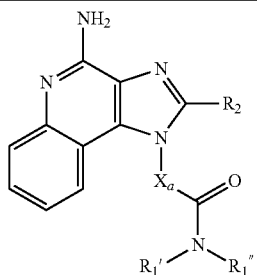

IVd

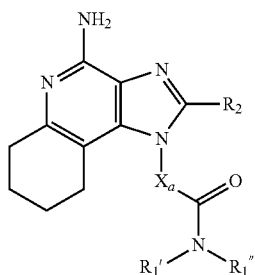

Vc

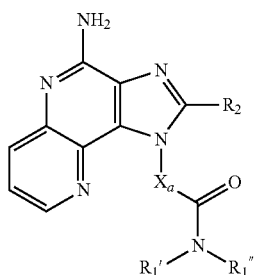

VIb

| $R_1'$ | $R_1''$ | $X_a$ | $R_2$ |
|---|---|---|---|
| ethyl | methyl | —CH$_2$C(CH$_3$)$_2$CH$_2$— | ethyl |
| ethyl | methyl | —CH$_2$C(CH$_3$)$_2$CH$_2$— | n-propyl |
| ethyl | methyl | —CH$_2$C(CH$_3$)$_2$CH$_2$— | n-butyl |
| ethyl | methyl | —CH$_2$C(CH$_3$)$_2$CH$_2$— | ethoxymethyl |
| ethyl | methyl | —CH$_2$C(CH$_3$)$_2$CH$_2$— | 2-methoxyethyl |
| n-propyl | hydrogen | —(CH$_2$)— | methyl |
| n-propyl | hydrogen | —(CH$_2$)— | ethyl |
| n-propyl | hydrogen | —(CH$_2$)— | n-propyl |
| n-propyl | hydrogen | —(CH$_2$)— | n-butyl |
| n-propyl | hydrogen | —(CH$_2$)— | ethoxymethyl |
| n-propyl | hydrogen | —(CH$_2$)— | 2-methoxyethyl |
| n-propyl | hydrogen | —(CH$_2$)$_2$— | methyl |
| n-propyl | hydrogen | —(CH$_2$)$_2$— | ethyl |
| n-propyl | hydrogen | —(CH$_2$)$_2$— | n-propyl |
| n-propyl | hydrogen | —(CH$_2$)$_2$— | n-butyl |
| n-propyl | hydrogen | —(CH$_2$)$_2$— | ethoxymethyl |
| n-propyl | hydrogen | —(CH$_2$)$_2$— | 2-methoxyethyl |
| n-propyl | hydrogen | —(CH$_2$)$_3$— | methyl |
| n-propyl | hydrogen | —(CH$_2$)$_3$— | ethyl |
| n-propyl | hydrogen | —(CH$_2$)$_3$— | n-propyl |
| n-propyl | hydrogen | —(CH$_2$)$_3$— | n-butyl |
| n-propyl | hydrogen | —(CH$_2$)$_3$— | ethoxymethyl |
| n-propyl | hydrogen | —(CH$_2$)$_3$— | 2-methoxyethyl |
| n-propyl | hydrogen | —CH$_2$C(CH$_3$)$_2$— | methyl |
| n-propyl | hydrogen | —CH$_2$C(CH$_3$)$_2$— | ethyl |
| n-propyl | hydrogen | —CH$_2$C(CH$_3$)$_2$— | n-propyl |
| n-propyl | hydrogen | —CH$_2$C(CH$_3$)$_2$— | n-butyl |
| n-propyl | hydrogen | —CH$_2$C(CH$_3$)$_2$— | ethoxymethyl |
| n-propyl | hydrogen | —CH$_2$C(CH$_3$)$_2$— | 2-methoxyethyl |
| n-propyl | hydrogen | —CH$_2$C(CH$_3$)$_2$CH$_2$— | methyl |
| n-propyl | hydrogen | —CH$_2$C(CH$_3$)$_2$CH$_2$— | ethyl |
| n-propyl | hydrogen | —CH$_2$C(CH$_3$)$_2$CH$_2$— | n-propyl |
| n-propyl | hydrogen | —CH$_2$C(CH$_3$)$_2$CH$_2$— | n-butyl |
| n-propyl | hydrogen | —CH$_2$C(CH$_3$)$_2$CH$_2$— | ethoxymethyl |
| n-propyl | hydrogen | —CH$_2$C(CH$_3$)$_2$CH$_2$— | 2-methoxyethyl |
| n-propyl | methyl | —(CH$_2$)— | methyl |
| n-propyl | methyl | —(CH$_2$)— | ethyl |
| n-propyl | methyl | —(CH$_2$)— | n-propyl |
| n-propyl | methyl | —(CH$_2$)— | n-butyl |
| n-propyl | methyl | —(CH$_2$)— | ethoxymethyl |
| n-propyl | methyl | —(CH$_2$)— | 2-methoxyethyl |
| n-propyl | methyl | —(CH$_2$)$_2$— | methyl |
| n-propyl | methyl | —(CH$_2$)$_2$— | ethyl |
| n-propyl | methyl | —(CH$_2$)$_2$— | n-propyl |
| n-propyl | methyl | —(CH$_2$)$_2$— | n-butyl |
| n-propyl | methyl | —(CH$_2$)$_2$— | ethoxymethyl |

-continued

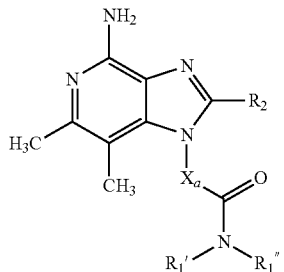
IIIa

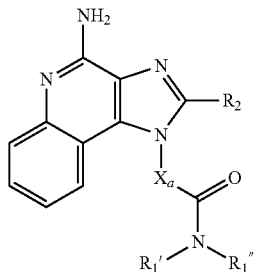
IVd

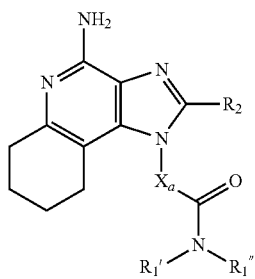
Vc

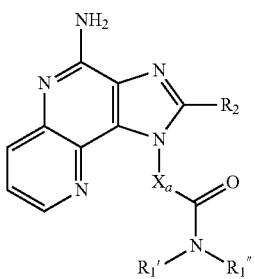
VIb

| R₁' | R₁" | Xₐ | R₂ |
|---|---|---|---|
| n-propyl | methyl | —(CH₂)₂— | 2-methoxyethyl |
| n-propyl | methyl | —(CH₂)₃— | methyl |
| n-propyl | methyl | —(CH₂)₃— | ethyl |
| n-propyl | methyl | —(CH₂)₃— | n-propyl |
| n-propyl | methyl | —(CH₂)₃— | n-butyl |
| n-propyl | methyl | —(CH₂)₃— | ethoxymethyl |
| n-propyl | methyl | —(CH₂)₃— | 2-methoxyethyl |
| n-propyl | methyl | —CH₂C(CH₃)₂— | methyl |
| n-propyl | methyl | —CH₂C(CH₃)₂— | ethyl |
| n-propyl | methyl | —CH₂C(CH₃)₂— | n-propyl |
| n-propyl | methyl | —CH₂C(CH₃)₂— | n-butyl |
| n-propyl | methyl | —CH₂C(CH₃)₂— | ethoxymethyl |
| n-propyl | methyl | —CH₂C(CH₃)₂— | 2-methoxyethyl |
| n-propyl | methyl | —CH₂C(CH₃)₂CH₂— | methyl |
| n-propyl | methyl | —CH₂C(CH₃)₂CH₂— | ethyl |
| n-propyl | methyl | —CH₂C(CH₃)₂CH₂— | n-propyl |
| n-propyl | methyl | —CH₂C(CH₃)₂CH₂— | n-butyl |
| n-propyl | methyl | —CH₂C(CH₃)₂CH₂— | ethoxymethyl |
| n-propyl | methyl | —CH₂C(CH₃)₂CH₂— | 2-methoxyethyl |
| n-butyl | hydrogen | —(CH₂)— | methyl |
| n-butyl | hydrogen | —(CH₂)— | ethyl |
| n-butyl | hydrogen | —(CH₂)— | n-propyl |
| n-butyl | hydrogen | —(CH₂)— | n-butyl |
| n-butyl | hydrogen | —(CH₂)— | ethoxymethyl |
| n-butyl | hydrogen | —(CH₂)— | 2-methoxyethyl |
| n-butyl | hydrogen | —(CH₂)₂— | methyl |
| n-butyl | hydrogen | —(CH₂)₂— | ethyl |
| n-butyl | hydrogen | —(CH₂)₂— | n-propyl |
| n-butyl | hydrogen | —(CH₂)₂— | n-butyl |
| n-butyl | hydrogen | —(CH₂)₂— | ethoxymethyl |
| n-butyl | hydrogen | —(CH₂)₂— | 2-methoxyethyl |
| n-butyl | hydrogen | —(CH₂)₃— | methyl |
| n-butyl | hydrogen | —(CH₂)₃— | ethyl |
| n-butyl | hydrogen | —(CH₂)₃— | n-propyl |
| n-butyl | hydrogen | —(CH₂)₃— | n-butyl |
| n-butyl | hydrogen | —(CH₂)₃— | ethoxymethyl |
| n-butyl | hydrogen | —(CH₂)₃— | 2-methoxyethyl |
| n-butyl | hydrogen | —CH₂C(CH₃)₂— | methyl |
| n-butyl | hydrogen | —CH₂C(CH₃)₂— | ethyl |
| n-butyl | hydrogen | —CH₂C(CH₃)₂— | n-propyl |
| n-butyl | hydrogen | —CH₂C(CH₃)₂— | n-butyl |
| n-butyl | hydrogen | —CH₂C(CH₃)₂— | ethoxymethyl |
| n-butyl | hydrogen | —CH₂C(CH₃)₂— | 2-methoxyethyl |
| n-butyl | hydrogen | —CH₂C(CH₃)₂CH₂— | methyl |
| n-butyl | hydrogen | —CH₂C(CH₃)₂CH₂— | ethyl |
| n-butyl | hydrogen | —CH₂C(CH₃)₂CH₂— | n-propyl |

-continued

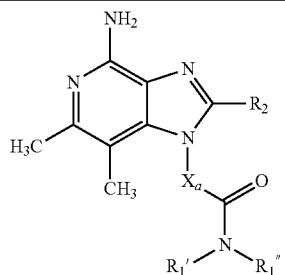

IIIa

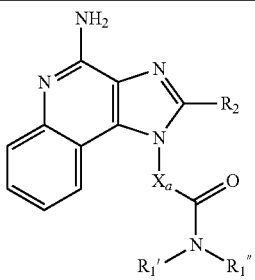

IVd

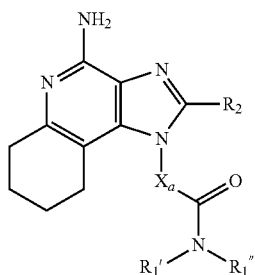

Vc

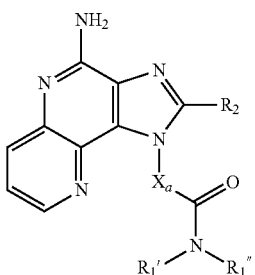

VIb

| $R_1'$ | $R_1''$ | $X_a$ | $R_2$ |
|---|---|---|---|
| n-butyl | hydrogen | —CH$_2$C(CH$_3$)$_2$CH$_2$— | n-butyl |
| n-butyl | hydrogen | —CH$_2$C(CH$_3$)$_2$CH$_2$— | ethoxymethyl |
| n-butyl | hydrogen | —CH$_2$C(CH$_3$)$_2$CH$_2$— | 2-methoxyethyl |
| n-butyl | methyl | —(CH$_2$)— | methyl |
| n-butyl | methyl | —(CH$_2$)— | ethyl |
| n-butyl | methyl | —(CH$_2$)— | n-propyl |
| n-butyl | methyl | —(CH$_2$)— | n-butyl |
| n-butyl | methyl | —(CH$_2$)— | ethoxymethyl |
| n-butyl | methyl | —(CH$_2$)— | 2-methoxyethyl |
| n-butyl | methyl | —(CH$_2$)$_2$— | methyl |
| n-butyl | methyl | —(CH$_2$)$_2$— | ethyl |
| n-butyl | methyl | —(CH$_2$)$_2$— | n-propyl |
| n-butyl | methyl | —(CH$_2$)$_2$— | n-butyl |
| n-butyl | methyl | —(CH$_2$)$_2$— | ethoxymethyl |
| n-butyl | methyl | —(CH$_2$)$_2$— | 2-methoxyethyl |
| n-butyl | methyl | —(CH$_2$)$_3$— | methyl |
| n-butyl | methyl | —(CH$_2$)$_3$— | ethyl |
| n-butyl | methyl | —(CH$_2$)$_3$— | n-propyl |
| n-butyl | methyl | —(CH$_2$)$_3$— | n-butyl |
| n-butyl | methyl | —(CH$_2$)$_3$— | ethoxymethyl |
| n-butyl | methyl | —(CH$_2$)$_3$— | 2-methoxyethyl |
| n-butyl | methyl | —CH$_2$C(CH$_3$)$_2$— | methyl |
| n-butyl | methyl | —CH$_2$C(CH$_3$)$_2$— | ethyl |
| n-butyl | methyl | —CH$_2$C(CH$_3$)$_2$— | n-propyl |
| n-butyl | methyl | —CH$_2$C(CH$_3$)$_2$— | n-butyl |
| n-butyl | methyl | —CH$_2$C(CH$_3$)$_2$— | ethoxymethyl |
| n-butyl | methyl | —CH$_2$C(CH$_3$)$_2$— | 2-methoxyethyl |
| n-butyl | methyl | —CH$_2$C(CH$_3$)$_2$CH$_2$— | methyl |
| n-butyl | methyl | —CH$_2$C(CH$_3$)$_2$CH$_2$— | ethyl |
| n-butyl | methyl | —CH$_2$C(CH$_3$)$_2$CH$_2$— | n-propyl |
| n-butyl | methyl | —CH$_2$C(CH$_3$)$_2$CH$_2$— | n-butyl |
| n-butyl | methyl | —CH$_2$C(CH$_3$)$_2$CH$_2$— | ethoxymethyl |
| n-butyl | methyl | —CH$_2$C(CH$_3$)$_2$CH$_2$— | 2-methoxyethyl |
| phenyl | hydrogen | —(CH$_2$)— | methyl |
| phenyl | hydrogen | —(CH$_2$)— | ethyl |
| phenyl | hydrogen | —(CH$_2$)— | n-propyl |
| phenyl | hydrogen | —(CH$_2$)— | n-butyl |
| phenyl | hydrogen | —(CH$_2$)— | ethoxymethyl |
| phenyl | hydrogen | —(CH$_2$)— | 2-methoxyethyl |
| phenyl | hydrogen | —(CH$_2$)$_2$— | methyl |
| phenyl | hydrogen | —(CH$_2$)$_2$— | ethyl |
| phenyl | hydrogen | —(CH$_2$)$_2$— | n-propyl |
| phenyl | hydrogen | —(CH$_2$)$_2$— | n-butyl |
| phenyl | hydrogen | —(CH$_2$)$_2$— | ethoxymethyl |
| phenyl | hydrogen | —(CH$_2$)$_2$— | 2-methoxyethyl |
| phenyl | hydrogen | —(CH$_2$)$_3$— | methyl |

-continued

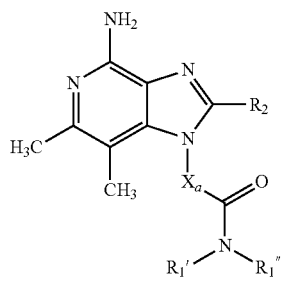

IIIa

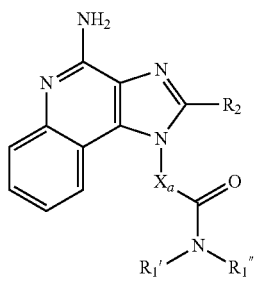

IVd

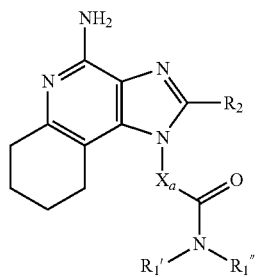

Vc

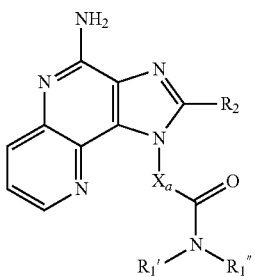

VIb

| R₁' | R₁" | Xₐ | R₂ |
|---|---|---|---|
| phenyl | hydrogen | —(CH₂)₃— | ethyl |
| phenyl | hydrogen | —(CH₂)₃— | n-propyl |
| phenyl | hydrogen | —(CH₂)₃— | n-butyl |
| phenyl | hydrogen | —(CH₂)₃— | ethoxymethyl |
| phenyl | hydrogen | —(CH₂)₃— | 2-methoxyethyl |
| phenyl | hydrogen | —CH₂C(CH₃)₂— | methyl |
| phenyl | hydrogen | —CH₂C(CH₃)₂— | ethyl |
| phenyl | hydrogen | —CH₂C(CH₃)₂— | n-propyl |
| phenyl | hydrogen | —CH₂C(CH₃)₂— | n-butyl |
| phenyl | hydrogen | —CH₂C(CH₃)₂— | ethoxymethyl |
| phenyl | hydrogen | —CH₂C(CH₃)₂— | 2-methoxyethyl |
| phenyl | hydrogen | —CH₂C(CH₃)₂CH₂— | methyl |
| phenyl | hydrogen | —CH₂C(CH₃)₂CH₂— | ethyl |
| phenyl | hydrogen | —CH₂C(CH₃)₂CH₂— | n-propyl |
| phenyl | hydrogen | —CH₂C(CH₃)₂CH₂— | n-butyl |
| phenyl | hydrogen | —CH₂C(CH₃)₂CH₂— | ethoxymethyl |
| phenyl | hydrogen | —CH₂C(CH₃)₂CH₂— | 2-methoxyethyl |
| phenyl | methyl | —(CH₂)— | methyl |
| phenyl | methyl | —(CH₂)— | ethyl |
| phenyl | methyl | —(CH₂)— | n-propyl |
| phenyl | methyl | —(CH₂)— | n-butyl |
| phenyl | methyl | —(CH₂)— | ethoxymethyl |
| phenyl | methyl | —(CH₂)— | 2-methoxyethyl |
| phenyl | methyl | —(CH₂)₂— | methyl |
| phenyl | methyl | —(CH₂)₂— | ethyl |
| phenyl | methyl | —(CH₂)₂— | n-propyl |
| phenyl | methyl | —(CH₂)₂— | n-butyl |
| phenyl | methyl | —(CH₂)₂— | ethoxymethyl |
| phenyl | methyl | —(CH₂)₂— | 2-methoxyethyl |
| phenyl | methyl | —(CH₂)₃— | methyl |
| phenyl | methyl | —(CH₂)₃— | ethyl |
| phenyl | methyl | —(CH₂)₃— | n-propyl |
| phenyl | methyl | —(CH₂)₃— | n-butyl |
| phenyl | methyl | —(CH₂)₃— | ethoxymethyl |
| phenyl | methyl | —(CH₂)₃— | 2-methoxyethyl |
| phenyl | methyl | —CH₂C(CH₃)₂— | methyl |
| phenyl | methyl | —CH₂C(CH₃)₂— | ethyl |

-continued

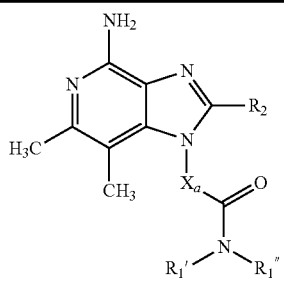
IIIa

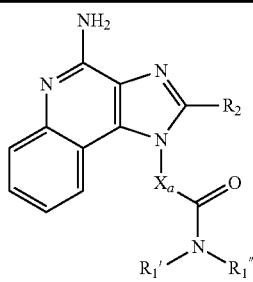
IVd

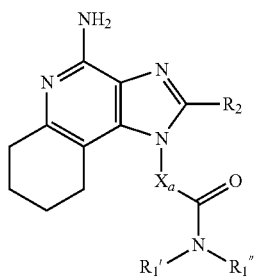
Vc

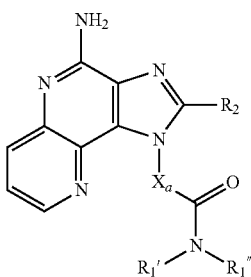
VIb

| $R_1'$ | $R_1''$ | $X_a$ | $R_2$ |
|---|---|---|---|
| phenyl | methyl | —CH$_2$C(CH$_3$)$_2$— | n-propyl |
| phenyl | methyl | —CH$_2$C(CH$_3$)$_2$— | n-butyl |
| phenyl | methyl | —CH$_2$C(CH$_3$)$_2$— | ethoxymethyl |
| phenyl | methyl | —CH$_2$C(CH$_3$)$_2$— | 2-methoxyethyl |
| phenyl | methyl | —CH$_2$C(CH$_3$)$_2$CH$_2$— | methyl |
| phenyl | methyl | —CH$_2$C(CH$_3$)$_2$CH$_2$— | ethyl |
| phenyl | methyl | —CH$_2$C(CH$_3$)$_2$CH$_2$— | n-propyl |
| phenyl | methyl | —CH$_2$C(CH$_3$)$_2$CH$_2$— | n-butyl |
| phenyl | methyl | —CH$_2$C(CH$_3$)$_2$CH$_2$— | ethoxymethyl |
| phenyl | methyl | —CH$_2$C(CH$_3$)$_2$CH$_2$— | 2-methoxyethyl |

Certain exemplary compounds, including some of those described above in the Examples, have the following Formulas (IIIb, IVe, Vd, or VIc) and the following

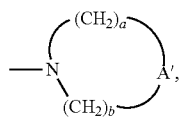

X'', and R$_2$ substituents, wherein each line of the table is matched with Formula IIIb, IVe, Vd, or VIc to represent a specific embodiment of the invention.

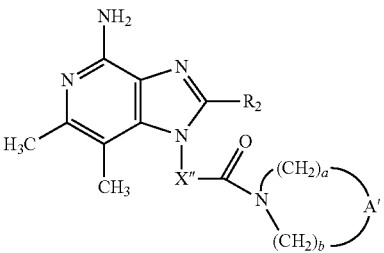

IIIb

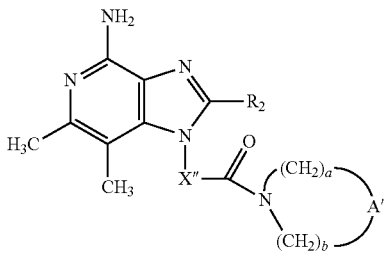

IIIb

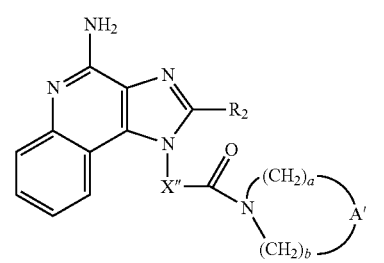

IVe

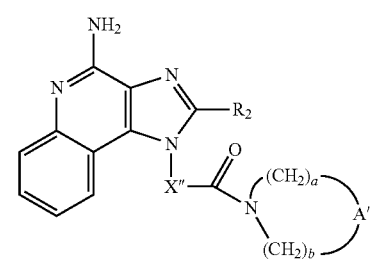

IVe

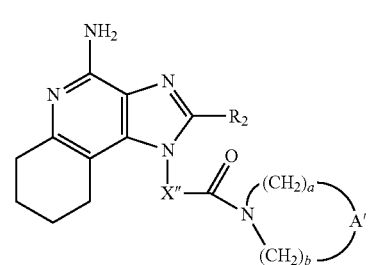

Vd

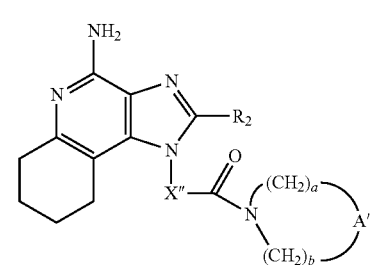

Vd

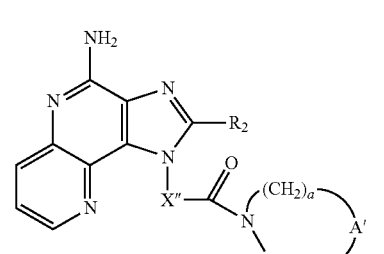

VIc

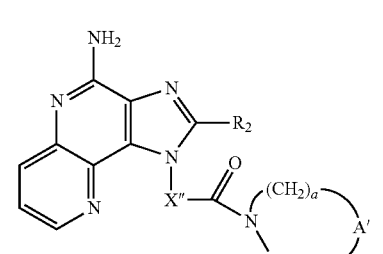

VIc

| | X″ | $R_2$ |
|---|---|---|
| pyrrolidin-1-yl | —(CH$_2$)— | methyl |
| pyrrolidin-1-yl | —(CH$_2$)— | ethyl |
| pyrrolidin-1-yl | —(CH$_2$)— | n-propyl |
| pyrrolidin-1-yl | —(CH$_2$)— | n-butyl |
| pyrrolidin-1-yl | —(CH$_2$)— | ethoxymethyl |
| pyrrolidin-1-yl | —(CH$_2$)— | 2-methoxyethyl |
| pyrrolidin-1-yl | —(CH$_2$)$_2$— | methyl |
| pyrrolidin-1-yl | —(CH$_2$)$_2$— | ethyl |
| pyrrolidin-1-yl | —(CH$_2$)$_2$— | n-propyl |
| pyrrolidin-1-yl | —(CH$_2$)$_2$— | n-butyl |
| pyrrolidin-1-yl | —(CH$_2$)$_2$— | ethoxymethyl |
| pyrrolidin-1-yl | —(CH$_2$)$_2$— | 2-methoxyethyl |
| pyrrolidin-1-yl | —(CH$_2$)$_3$— | methyl |
| pyrrolidin-1-yl | —(CH$_2$)$_3$— | ethyl |

| | X″ | $R_2$ |
|---|---|---|
| pyrrolidin-1-yl | —(CH$_2$)$_3$— | n-propyl |
| pyrrolidin-1-yl | —(CH$_2$)$_3$— | n-butyl |
| pyrrolidin-1-yl | —(CH$_2$)$_3$— | ethoxymethyl |
| pyrrolidin-1-yl | —(CH$_2$)$_3$— | 2-methoxyethyl |
| pyrrolidin-1-yl | —CH$_2$C(CH$_3$)$_2$— | methyl |
| pyrrolidin-1-yl | —CH$_2$C(CH$_3$)$_2$— | ethyl |
| pyrrolidin-1-yl | —CH$_2$C(CH$_3$)$_2$— | n-propyl |
| pyrrolidin-1-yl | —CH$_2$C(CH$_3$)$_2$— | n-butyl |
| pyrrolidin-1-yl | —CH$_2$C(CH$_3$)$_2$— | ethoxymethyl |
| pyrrolidin-1-yl | —CH$_2$C(CH$_3$)$_2$— | 2-methoxyethyl |
| pyrrolidin-1-yl | —CH$_2$C(CH$_3$)$_2$CH$_2$— | methyl |
| pyrrolidin-1-yl | —CH$_2$C(CH$_3$)$_2$CH$_2$— | ethyl |
| pyrrolidin-1-yl | —CH$_2$C(CH$_3$)$_2$CH$_2$— | n-propyl |
| pyrrolidin-1-yl | —CH$_2$C(CH$_3$)$_2$CH$_2$— | n-butyl |

-continued

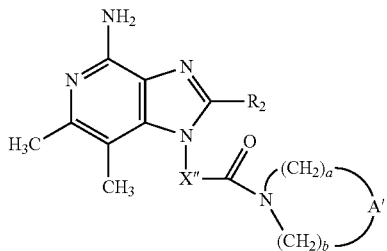

IIIb

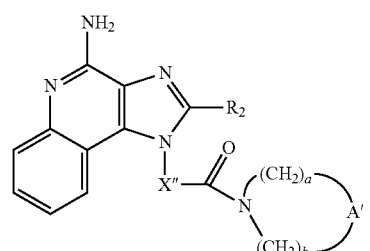

IVe

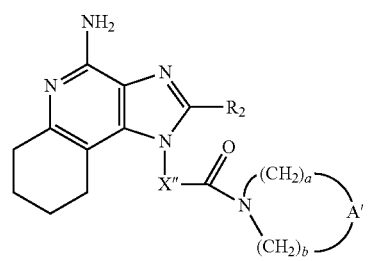

Vd

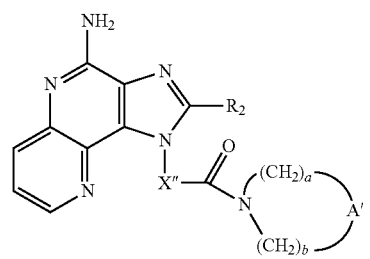

VIc

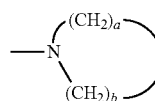

| | X″ | R₂ |
|---|---|---|
| pyrrolidin-1-yl | —CH₂C(CH₃)₂CH₂— | ethoxymethyl |
| pyrrolidin-1-yl | —CH₂C(CH₃)₂CH₂— | 2-methoxyethyl |
| piperidin-1-yl | —(CH₂)— | methyl |
| piperidin-1-yl | —(CH₂)— | ethyl |
| piperidin-1-yl | —(CH₂)— | n-propyl |
| piperidin-1-yl | —(CH₂)— | n-butyl |
| piperidin-1-yl | —(CH₂)— | ethoxymethyl |
| piperidin-1-yl | —(CH₂)— | 2-methoxyethyl |
| piperidin-1-yl | —(CH₂)₂— | methyl |
| piperidin-1-yl | —(CH₂)₂— | ethyl |
| piperidin-1-yl | —(CH₂)₂— | n-propyl |
| piperidin-1-yl | —(CH₂)₂— | n-butyl |
| piperidin-1-yl | —(CH₂)₂— | ethoxymethyl |
| piperidin-1-yl | —(CH₂)₂— | 2-methoxyethyl |

-continued

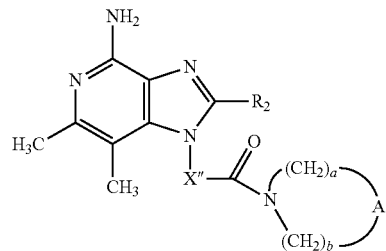

IIIb

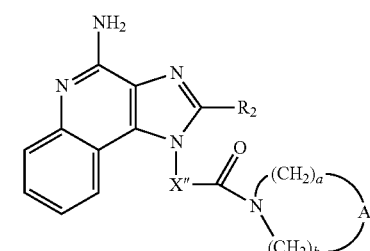

IVe

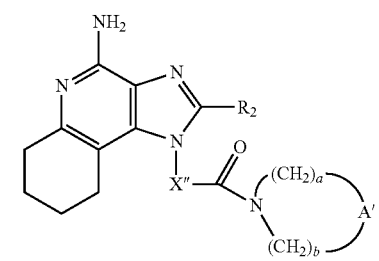

Vd

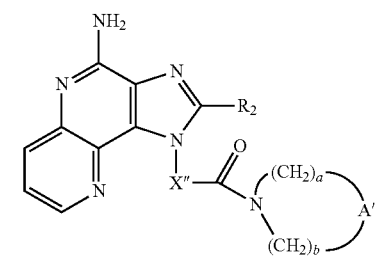

VIc

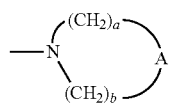

| | X″ | R₂ |
|---|---|---|
| piperidin-1-yl | —(CH₂)₃— | methyl |
| piperidin-1-yl | —(CH₂)₃— | ethyl |
| piperidin-1-yl | —(CH₂)₃— | n-propyl |
| piperidin-1-yl | —(CH₂)₃— | n-butyl |
| piperidin-1-yl | —(CH₂)₃— | ethoxymethyl |
| piperidin-1-yl | —(CH₂)₃— | 2-methoxyethyl |
| piperidin-1-yl | —CH₂C(CH₃)₂— | methyl |
| piperidin-1-yl | —CH₂C(CH₃)₂— | ethyl |
| piperidin-1-yl | —CH₂C(CH₃)₂— | n-propyl |
| piperidin-1-yl | —CH₂C(CH₃)₂— | n-butyl |
| piperidin-1-yl | —CH₂C(CH₃)₂— | ethoxymethyl |
| piperidin-1-yl | —CH₂C(CH₃)₂— | 2-methoxyethyl |
| piperidin-1-yl | —CH₂C(CH₃)₂CH₂— | methyl |
| piperidin-1-yl | —CH₂C(CH₃)₂CH₂— | ethyl |

161
-continued

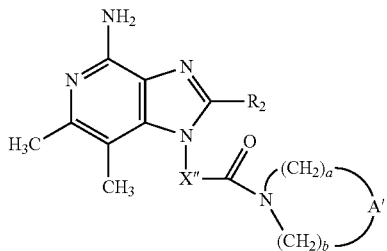

IIIb

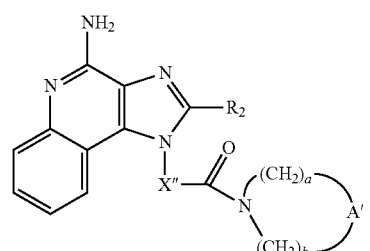

IVe

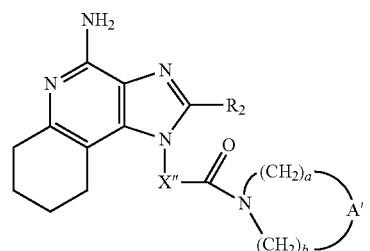

Vd

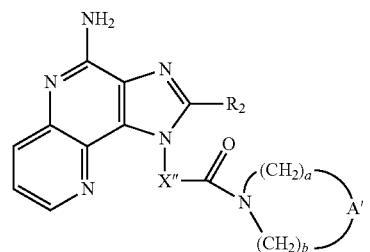

VIc

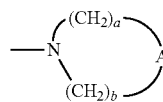

| | X″ | R₂ |
|---|---|---|
| piperidin-1-yl | —CH₂C(CH₃)₂CH₂— | n-propyl |
| piperidin-1-yl | —CH₂C(CH₃)₂CH₂— | n-butyl |
| piperidin-1-yl | —CH₂C(CH₃)₂CH₂— | ethoxymethyl |
| piperidin-1-yl | —CH₂C(CH₃)₂CH₂— | 2-methoxyethyl |
| 4-acetylpiperazin-1-yl | —(CH₂)— | methyl |
| 4-acetylpiperazin-1-yl | —(CH₂)— | ethyl |
| 4-acetylpiperazin-1-yl | —(CH₂)— | n-propyl |
| 4-acetylpiperazin-1-yl | —(CH₂)— | n-butyl |
| 4-acetylpiperazin-1-yl | —(CH₂)— | ethoxymethyl |
| 4-acetylpiperazin-1-yl | —(CH₂)— | 2-methoxyethyl |
| 4-acetylpiperazin-1-yl | —(CH₂)₂— | methyl |
| 4-acetylpiperazin-1-yl | —(CH₂)₂— | ethyl |
| 4-acetylpiperazin-1-yl | —(CH₂)₂— | n-propyl |
| 4-acetylpiperazin-1-yl | —(CH₂)₂— | n-butyl |

162
-continued

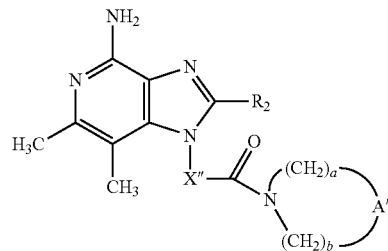

IIIb

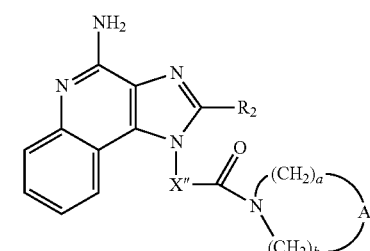

IVe

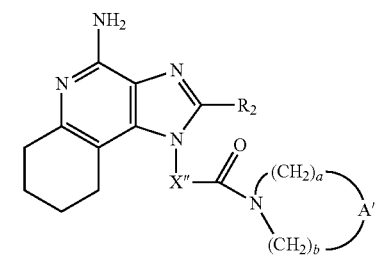

Vd

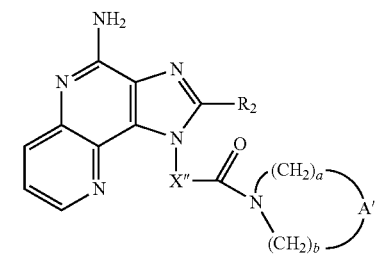

VIc

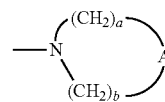

| | X″ | R₂ |
|---|---|---|
| 4-acetylpiperazin-1-yl | —(CH₂)₂— | ethoxymethyl |
| 4-acetylpiperazin-1-yl | —(CH₂)₂— | 2-methoxyethyl |
| 4-acetylpiperazin-1-yl | —(CH₂)₃— | methyl |
| 4-acetylpiperazin-1-yl | —(CH₂)₃— | ethyl |
| 4-acetylpiperazin-1-yl | —(CH₂)₃— | n-propyl |
| 4-acetylpiperazin-1-yl | —(CH₂)₃— | n-butyl |
| 4-acetylpiperazin-1-yl | —(CH₂)₃— | ethoxymethyl |
| 4-acetylpiperazin-1-yl | —(CH₂)₃— | 2-methoxyethyl |
| 4-acetylpiperazin-1-yl | —CH₂C(CH₃)₂— | methyl |
| 4-acetylpiperazin-1-yl | —CH₂C(CH₃)₂— | ethyl |
| 4-acetylpiperazin-1-yl | —CH₂C(CH₃)₂— | n-propyl |
| 4-acetylpiperazin-1-yl | —CH₂C(CH₃)₂— | n-butyl |
| 4-acetylpiperazin-1-yl | —CH₂C(CH₃)₂— | ethoxymethyl |
| 4-acetylpiperazin-1-yl | —CH₂C(CH₃)₂— | 2-methoxyethyl |

163
-continued

[Structure IIIb: 4-amino-6,7-dimethyl-imidazo[4,5-c]pyridine with N-X''-C(O)-N((CH₂)ₐ)((CH₂)ᵦ)A' substituent, R₂ on imidazole]

IIIb

[Structure IVe: 4-amino-imidazo[4,5-c]quinoline with N-X''-C(O)-N((CH₂)ₐ)((CH₂)ᵦ)A' substituent, R₂ on imidazole]

IVe

[Structure Vd: 4-amino-tetrahydro-imidazo[4,5-c]quinoline with N-X''-C(O)-N((CH₂)ₐ)((CH₂)ᵦ)A' substituent, R₂ on imidazole]

Vd

[Structure VIc: 4-amino-imidazo[4,5-c]naphthyridine with N-X''-C(O)-N((CH₂)ₐ)((CH₂)ᵦ)A' substituent, R₂ on imidazole]

VIc

—N((CH₂)ₐ)((CH₂)ᵦ)A'

| —N((CH₂)ₐ)((CH₂)ᵦ)A' | X'' | R₂ |
|---|---|---|
| 4-acetylpiperazin-1-yl | —CH₂C(CH₃)₂CH₂— | methyl |
| 4-acetylpiperazin-1-yl | —CH₂C(CH₃)₂CH₂— | ethyl |
| 4-acetylpiperazin-1-yl | —CH₂C(CH₃)₂CH₂— | n-propyl |
| 4-acetylpiperazin-1-yl | —CH₂C(CH₃)₂CH₂— | n-butyl |
| 4-acetylpiperazin-1-yl | —CH₂C(CH₃)₂CH₂— | ethoxymethyl |
| 4-acetylpiperazin-1-yl | —CH₂C(CH₃)₂CH₂— | 2-methoxyethyl |
| morpholin-4-yl | —(CH₂)— | methyl |
| morpholin-4-yl | —(CH₂)— | ethyl |
| morpholin-4-yl | —(CH₂)— | n-propyl |
| morpholin-4-yl | —(CH₂)— | n-butyl |
| morpholin-4-yl | —(CH₂)— | ethoxymethyl |
| morpholin-4-yl | —(CH₂)— | 2-methoxyethyl |
| morpholin-4-yl | —(CH₂)₂— | methyl |
| morpholin-4-yl | —(CH₂)₂— | ethyl |

164
-continued

[Structure IIIb: 4-amino-6,7-dimethyl-imidazo[4,5-c]pyridine with N-X''-C(O)-N((CH₂)ₐ)((CH₂)ᵦ)A' substituent, R₂ on imidazole]

IIIb

[Structure IVe: 4-amino-imidazo[4,5-c]quinoline with N-X''-C(O)-N((CH₂)ₐ)((CH₂)ᵦ)A' substituent, R₂ on imidazole]

IVe

[Structure Vd: 4-amino-tetrahydro-imidazo[4,5-c]quinoline with N-X''-C(O)-N((CH₂)ₐ)((CH₂)ᵦ)A' substituent, R₂ on imidazole]

Vd

[Structure VIc: 4-amino-imidazo[4,5-c]naphthyridine with N-X''-C(O)-N((CH₂)ₐ)((CH₂)ᵦ)A' substituent, R₂ on imidazole]

VIc

—N((CH₂)ₐ)((CH₂)ᵦ)A'

| —N((CH₂)ₐ)((CH₂)ᵦ)A' | X'' | R₂ |
|---|---|---|
| morpholin-4-yl | —(CH₂)₂— | n-propyl |
| morpholin-4-yl | —(CH₂)₂— | n-butyl |
| morpholin-4-yl | —(CH₂)₂— | ethoxymethyl |
| morpholin-4-yl | —(CH₂)₂— | 2-methoxyethyl |
| morpholin-4-yl | —(CH₂)₃— | methyl |
| morpholin-4-yl | —(CH₂)₃— | ethyl |
| morpholin-4-yl | —(CH₂)₃— | n-propyl |
| morpholin-4-yl | —(CH₂)₃— | n-butyl |
| morpholin-4-yl | —(CH₂)₃— | ethoxymethyl |
| morpholin-4-yl | —(CH₂)₃— | 2-methoxyethyl |
| morpholin-4-yl | —CH₂C(CH₃)₂— | methyl |
| morpholin-4-yl | —CH₂C(CH₃)₂— | ethyl |
| morpholin-4-yl | —CH₂C(CH₃)₂— | n-propyl |
| morpholin-4-yl | —CH₂C(CH₃)₂— | n-butyl |

165
-continued

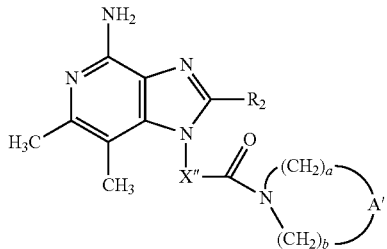

IIIb

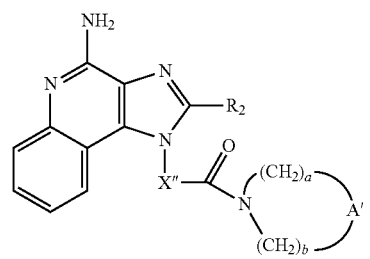

IVe

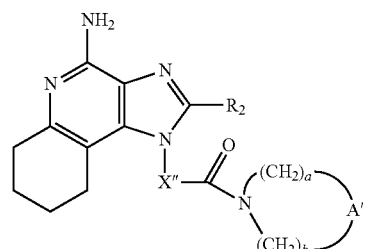

Vd

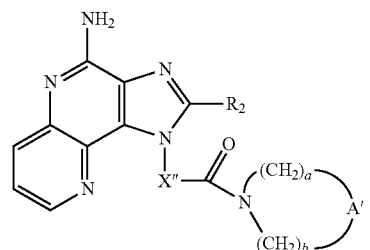

VIc

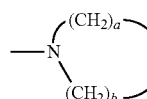

| | X" | R₂ |
|---|---|---|
| morpholin-4-yl | —CH₂C(CH₃)₂— | ethoxymethyl |
| morpholin-4-yl | —CH₂C(CH₃)₂— | 2-methoxyethyl |
| morpholin-4-yl | —CH₂C(CH₃)₂CH₂— | methyl |
| morpholin-4-yl | —CH₂C(CH₃)₂CH₂— | ethyl |
| morpholin-4-yl | —CH₂C(CH₃)₂CH₂— | n-propyl |
| morpholin-4-yl | —CH₂C(CH₃)₂CH₂— | n-butyl |
| morpholin-4-yl | —CH₂C(CH₃)₂CH₂— | ethoxymethyl |
| morpholin-4-yl | —CH₂C(CH₃)₂CH₂— | 2-methoxyethyl |
| 1,1-dioxothiomorpholin-4-yl | —(CH₂)— | methyl |
| 1,1-dioxothiomorpholin-4-yl | —(CH₂)— | ethyl |
| 1,1-dioxothiomorpholin-4-yl | —(CH₂)— | n-propyl |
| 1,1-dioxothiomorpholin-4-yl | —(CH₂)— | n-butyl |
| 1,1-dioxothiomorpholin-4-yl | —(CH₂)— | ethoxymethyl |
| 1,1-dioxothiomorpholin-4-yl | —(CH₂)— | 2-methoxyethyl |

166
-continued

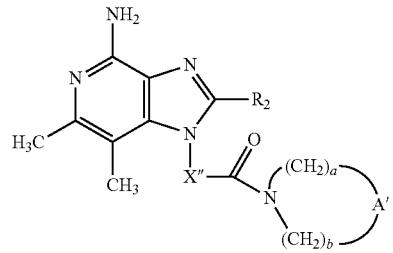

IIIb

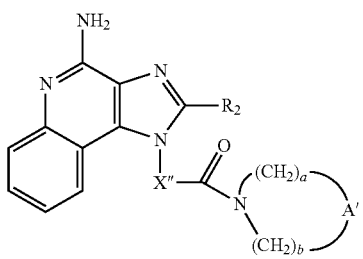

IVe

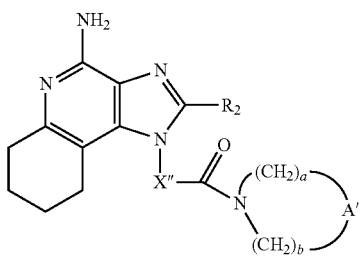

Vd

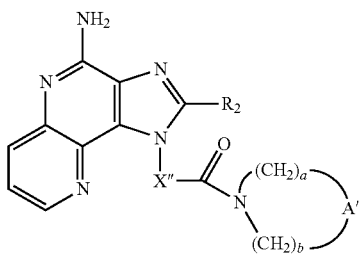

VIc

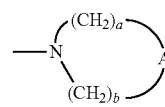

| | X" | R₂ |
|---|---|---|
| 1,1-dioxothiomorpholin-4-yl | —(CH₂)₂— | methyl |
| 1,1-dioxothiomorpholin-4-yl | —(CH₂)₂— | ethyl |
| 1,1-dioxothiomorpholin-4-yl | —(CH₂)₂— | n-propyl |
| 1,1-dioxothiomorpholin-4-yl | —(CH₂)₂— | n-butyl |
| 1,1-dioxothiomorpholin-4-yl | —(CH₂)₂— | ethoxymethyl |
| 1,1-dioxothiomorpholin-4-yl | —(CH₂)₂— | 2-methoxyethyl |
| 1,1-dioxothiomorpholin-4-yl | —(CH₂)₃— | methyl |
| 1,1-dioxothiomorpholin-4-yl | —(CH₂)₃— | ethyl |
| 1,1-dioxothiomorpholin-4-yl | —(CH₂)₃— | n-propyl |
| 1,1-dioxothiomorpholin-4-yl | —(CH₂)₃— | n-butyl |
| 1,1-dioxothiomorpholin-4-yl | —(CH₂)₃— | ethoxymethyl |
| 1,1-dioxothiomorpholin-4-yl | —(CH₂)₃— | 2-methoxyethyl |
| 1,1-dioxothiomorpholin-4-yl | —CH₂C(CH₃)₂— | methyl |
| 1,1-dioxothiomorpholin-4-yl | —CH₂C(CH₃)₂— | ethyl |

-continued

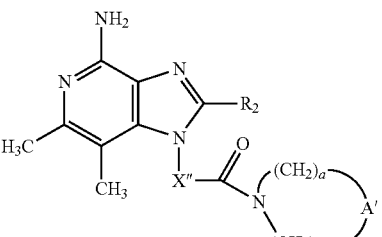

IIIb

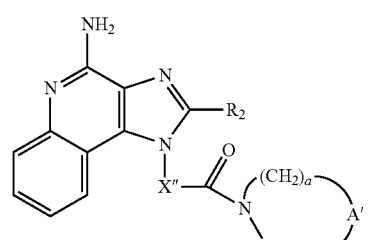

IVe

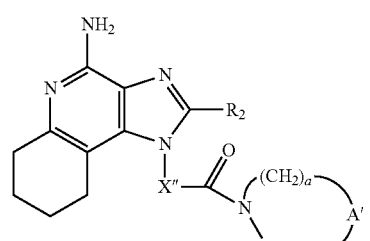

Vd

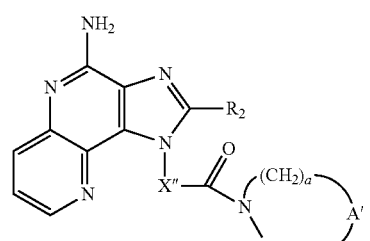

VIc

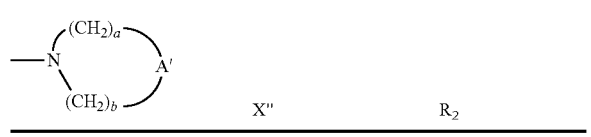

| —N(CH₂)ₐ/(CH₂)ᵦ—A' | X" | R₂ |
|---|---|---|
| 1,1-dioxothiomorpholin-4-yl | —CH₂C(CH₃)₂— | n-propyl |
| 1,1-dioxothiomorpholin-4-yl | —CH₂C(CH₃)₂— | n-butyl |
| 1,1-dioxothiomorpholin-4-yl | —CH₂C(CH₃)₂— | ethoxymethyl |
| 1,1-dioxothiomorpholin-4-yl | —CH₂C(CH₃)₂— | 2-methoxyethyl |
| 1,1-dioxothiomorpholin-4-yl | —CH₂C(CH₃)₂CH₂— | methyl |
| 1,1-dioxothiomorpholin-4-yl | —CH₂C(CH₃)₂CH₂— | ethyl |
| 1,1-dioxothiomorpholin-4-yl | —CH₂C(CH₃)₂CH₂— | n-propyl |
| 1,1-dioxothiomorpholin-4-yl | —CH₂C(CH₃)₂CH₂— | n-butyl |
| 1,1-dioxothiomorpholin-4-yl | —CH₂C(CH₃)₂CH₂— | ethoxymethyl |
| 1,1-dioxothiomorpholin-4-yl | —CH₂C(CH₃)₂CH₂— | 2-methoxyethyl |

Cytokine Induction in Human Cells

An in vitro human blood cell system is used to assess cytokine induction. Activity is based on the measurement of interferon (α) and tumor necrosis factor (α) (IFN-α and TNF-α, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM. Controls include cell samples with media only, cell samples with DMSO only (no compound), and cell samples with reference compound.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (usually 30-0.014 μM). The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype calorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (molar) is the lowest of the tested compound concentrations that induces a response over a fixed cytokine concentration for the tested cytokine (usually 20 pg/mL for IFN-α and 40 pg/mL for TNF-α). The maximal response (pg/mL) is the maximal response attained in the dose response curve.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the formula (II):

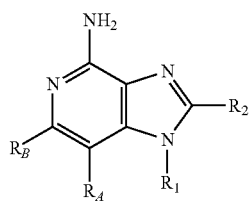

II wherein:
$R_1$ is selected from the group consisting of:

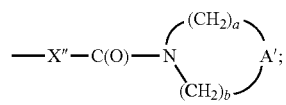

$X'$ is selected from the group consisting of —CH($R_9$)—, —CH($R_9$)-alkylene-, and —CH($R_9$)-alkenylene-;

$X''$ is selected from the group consisting of —CH($R_9$)—, —CH($R_9$)-alkylene-, and —CH($R_9$)— alkenylene-; wherein the alkylene and alkenylene are optionally interrupted with one or more —O— groups;

$R_1'$ and $R_1''$ are both hydrogen;

$A'$ is selected from the group consisting of —O—, —C(O)—, —CH$_2$—, —S(O)$_{0-2}$—, and —N(Q-$R_4$)—;

a and b are independently integers from 1 to 6 with the proviso that a+b is ≤7;

$R_A$ and $R_B$ are taken together to form either a fused aryl ring that is unsubstituted or substituted by one or more $R_a$ groups, or a fused 6-membered saturated ring that is unsubstituted or substituted by one or more $R_c$ groups;

$R_a$ is selected from the group consisting of:
halogen,
alkyl,
haloalkyl,
alkoxy, and
—N($R_9$)$_2$;

$R_c$ is selected from the group consisting of:
halogen,
hydroxy,
alkyl,
alkenyl,
haloalkyl,
alkoxy,
alkylthio, and
—N($R_9$)$_2$;

$R_2$ is selected from the group consisting of hydrogen, alkyl, alkoxyalkyl, and hydroxyalkyl;

$R_4$ is selected from the group consisting of hydrogen, alkyl, and aryl;

$R_6$ is selected from the group consisting of =O and =S;

$R_8$ is selected from the group consisting of hydrogen, alkyl, alkoxyalkylenyl, and arylalkylenyl;

$R_9$ is selected from the group consisting of hydrogen and alkyl;

Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—; and W is selected from the group consisting of a bond, —C(O)—, and —S(O)$_2$—;

or a pharmaceutically acceptable salt thereof.

2. A compound of the formula (IV):

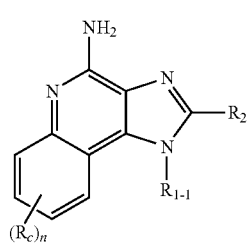

IV wherein:
R$_{1-1}$ is selected from the group consisting of:

—X"—C(O)—N(R$_1$')(R$_1$")    and $$-X''-C(O)-N\underset{(CH_2)_b}{\overset{(CH_2)_a}{\diagup\diagdown}}A';$$

X' is selected from the group consisting of —CH(R$_9$)—, —CH(R$_9$)-alkylene-, and —CH(R$_9$)— alkenylene-;
X" is selected from the group consisting of —CH(R$_9$)—, —CH(R$_9$)-alkylene-, and —CH(R$_9$)— alkenylene-; wherein the alkylene and alkenylene are optionally interrupted with one or more —O— groups;
R$_1$' and R$_1$" are both hydrogen;
A' is selected from the group consisting of —O—, —C(O)—, —CH$_2$—, —S(O)$_{0-2}$—, and —N(Q-R$_4$)—;
a and b are independently integers from 1 to 6 with the proviso that a+b is ≤7;
R$_a$ is selected from the group consisting of:
  halogen,
  alkyl,
  haloalkyl,
  alkoxy, and
  —N(R$_9$)$_2$
n is an integer from 0 to 4;
R$_2$ is selected from the group consisting of hydrogen, alkyl, alkoxyalkyl, and hydroxyalkyl;
R$_4$ is selected from the group consisting of hydrogen, alkyl, and aryl;
R$_6$ is selected from the group consisting of =O and =S;
R$_8$ is selected from the group consisting of hydrogen, alkyl, alkoxyalkylenyl, and arylalkylenyl;
R$_9$ is selected from the group consisting of hydrogen and alkyl;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—; and
W is selected from the group consisting of a bond, —C(O)—, and —S(O)$_2$—;
or a pharmaceutically acceptable salt thereof.

3. The compound or salt of claim 1 wherein the compound is of the following formula (V):

<chemical structure of formula V showing bicyclic system with NH$_2$, N, N, R$_2$, R$_{1-1}$, and (R$_c$)$_n$ substituents>

V wherein:
R$_{1-1}$ is selected from the group consisting of:

—X'—C(O)—N(R$_1$')(R$_1$")    and $$-X''-C(O)-N\underset{(CH_2)_b}{\overset{(CH_2)_a}{\diagup\diagdown}}A';$$

X' is selected from the group consisting of —CH(R$_9$)—, —CH(R$_9$)-alkylene-, and —CH(R$_9$)— alkenylene-;
X" is selected from the group consisting of —CH(R$_9$)—, —CH(R$_9$)-alkylene-, and —CH(R$_9$)— alkenylene-; wherein the alkylene and alkenylene are optionally interrupted with one or more —O-groups;
R$_1$' and R$_1$" are both hydrogen;
A' is selected from the group consisting of —O—, —C(O)—, —CH$_2$—, —S(O)$_{0-2}$—, and —N(Q-R$_4$)—;
a and b are independently integers from 1 to 6 with the proviso that a+b is ≤7;
R$_c$ is selected from the group consisting of:
  halogen,
  hydroxy,
  alkyl,
  alkenyl,
  haloalkyl,
  alkoxy,
  alkylthio, and
  —N(R$_9$)$_2$;
n is an integer from 0 to 4;
R$_2$ is selected from the group consisting of hydrogen, alkyl, alkoxyalkyl, and hydroxyalkyl;
R$_4$ is selected from the group consisting of hydrogen, alkyl, and aryl;
R$_6$ is selected from the group consisting of =O and =S;
R$_8$ is selected from the group consisting of hydrogen, alkyl, alkoxyalkylenyl, and arylalkylenyl;
R$_9$ is selected from the group consisting of hydrogen and alkyl;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—; and
W is selected from the group consisting of a bond, —C(O)—, and —S(O)$_2$;
or a pharmaceutically acceptable salt thereof.

4. The compound or salt of claim 2 wherein n is 0.

5. The compound or salt of claim 1 wherein X' is —CH$_2$—C$_{0-10}$ alkylene- or X" is —CH$_2$—C$_{0-10}$ alkylene- or —CH$_2$—C$_{1-4}$ alkylene-O—C$_{1-4}$ alkylene-.

6. The compound or salt of claim 5 wherein X' is —(CH$_2$)$_{1-5}$—, —CH$_2$C(CH$_3$)$_2$—, or —CH$_2$C(CH$_3$)$_2$CH$_2$—; or X" is —(CH$_2$)$_{1-5}$—, —CH$_2$C(CH$_3$)$_2$—, —CH$_2$C(CH$_3$)$_2$CH$_2$—, or —(CH$_2$)$_3$—O—CH$_2$—.

7. The compound or salt of claim 1 wherein R$_2$ is hydrogen, C$_{1-4}$ alkyl, hydroxy C$_{1-4}$ alkylenyl, or C$_{1-4}$ alkyl-O—C$_{14}$ alkylenyl.

8. A pharmaceutical composition comprising a therapeutically effective amount of a compound or salt of claim 1 and a pharmaceutically acceptable carrier.

9. The compound or salt of claim 2 wherein $R_{1-1}$ is

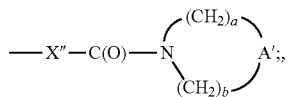

A' is —O—, and a and b are each 2.

10. The compound or salt of claim 2 wherein X' is —CH$_2$—C$_{0-10}$ alkylene- or X" is —CH$_2$—C$_{0-10}$ alkylene- or —CH$_2$—C$_{1-4}$-alkylene-O—C$_{1-4}$ alkylene-.

11. The compound or salt of claim 10 wherein X' is —(CH$_2$)$_{1-5}$—, —CH$_2$C(CH$_3$)$_2$—, or —CH$_2$C(CH$_3$)$_2$CH$_2$—; or X" is —(CH$_2$)$_{1-5}$—, —CH$_2$C(CH$_3$)$_2$—, —CH$_2$C(CH$_3$)$_2$CH$_2$—, or —(CH$_2$)$_3$—CH$_2$—.

12. The compound or salt of claim 2 wherein R$_2$ is hydrogen, C$_{1-4}$ alkyl, hydroxyC$_{1-4}$ alkylenyl, or C$_{1-4}$ alkyl-O—C$_{1-4}$ alkylenyl.

13. The compound or salt of claim 3 wherein $R_{1-1}$ is

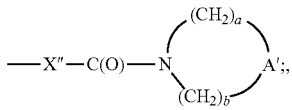

A' is —O—, and a and b are each 2.

14. The compound or salt of claim 3 wherein X is —CH$_2$—C$_{0-10}$ alkylene- or X" is —CH$_2$—C$_{0-10}$ alkylene- or —CH$_2$—C$_{1-4}$ alkylene-O—C$_{1-4}$ alkylene-.

15. The compound or salt of claim 3 wherein R$_2$ is hydrogen, C$_{1-4}$ alkyl, hydroxyC$_{1-4}$ alkylenyl, or C$_{1-4}$ alkyl-O—C$_{1-4}$ alkylenyl.

16. A pharmaceutical composition comprising a therapeutically effective amount of a compound or salt of claim 2 and a pharmaceutically acceptable carrier.

17. A pharmaceutical composition comprising a therapeutically effective amount of a compound or salt of claim 3 and a pharmaceutically acceptable carrier.

* * * * *

UNITED STATES PATENT AND TRADEMARK OFFICE
CERTIFICATE OF CORRECTION

PATENT NO.        : 8,697,873 B2
APPLICATION NO.   : 10/599159
DATED             : April 15, 2014
INVENTOR(S)       : Larry Krepski It is certified that error appears in the above-identified patent and that said Letters Patent is hereby corrected as shown below:

Title Page, item (56),

Page 6, Column 1 (Other Publications)
Line 40, Delete "acetyllactyl" and insert -- acetylacetyl --, therefor.
Line 56, Delete "Chmica" and insert -- Chimica --, therefor.

Page 7, Column 1 (Other Publications)
Line 31, Delete "hydocarbons" and insert -- hydrocarbons --, therefor.

Page 7, Column 2 (Other Publications)
Line 1, Delete "Napthyridines Hydroxynaphthyridies," and
insert -- Naphthyridines Hydroxynaphthyridines, --, therefor.
Line 17, Delete "Gessellschaft" and insert -- Gesellschaft --, therefor.

Page 8, Column 1 (Other Publications)
Line 34, Delete "yσ" and insert -- γσ --, therefor.

Page 8, Column 2 (Other Publications)
Line 67, Delete "Dermatologi;" and insert -- Dermatology; --, therefor.

Page 9, Column 1 (Other Publications)
Line 20, Delete "Activtiy" and insert -- Activity --, therefor.

Page 9, Column 2 (Other Publications)
Line 44, Delete "imizazo" and insert -- imidazo --, therefor.

Page 10, Column 1 (Other Publications)
Line 2-3, Delete "Assymmetry." and insert -- Asymmetry. --, therefor.

Signed and Sealed this
Sixth Day of January, 2015

Michelle K. Lee
*Deputy Director of the United States Patent and Trademark Office*

Page 10, Column 1 (Other Publications)
Line 9, Delete "Bacteroids" and insert -- Bacteroides --, therefor.
Line 68, Delete "2978:57-65." and insert -- 1978:57-65. --, therefor.

Page 10, Column 2 (Other Publications)
Line 39, Delete "Dekkar," and insert -- Dekker, --, therefor.

Page 11, Column 1 (Other Publications)
Line 5, Delete "Imiguimod." and insert -- Imiquimod. --, therefor.

Page 11, Column 2 (Other Publications)
Line 38, Delete "Heterocylic" and insert -- Heterocyclic --, therefor.

In the Specification,

Column 1
Line 51, Delete "imidazoquiniline," and insert -- imidazoquinoline, --, therefor.

Column 8
Line 23, Delete "allkynyl," and insert -- alkynyl, --, therefor.
Line 28, Delete "halo alkyl, halo alkoxy," and insert -- haloalkyl, haloalkoxy, --, therefor.

Column 11
Line 31, Delete "N((R1')" and insert -- N(R1') --, therefor.
Line 63, Delete "form" and insert -- from --, therefor.

Column 15
Line 46, Delete "halo alkyl, halo alkoxy," and insert -- haloalkyl, haloalkoxy, --, therefor.

Column 16
Line 10, Delete "$(R_9)$" and insert -- $(R_8)$ --, therefor.

Column 21
Line 9, Delete "$(R_9)$" and insert -- $(R_8)$ --, therefor.
Line 9, Delete "—$N(R_9)$—," and insert -- —$N(R_8)$—, --, therefor.
Line 12, Delete "—$N(R_9)$—" and insert -- —$N(R_8)$— --, therefor.

Column 22
Line 11, Delete "groups," and insert -- groups; --, therefor.

Column 23
Line 55, Delete "$(R_9)$" and insert -- $(R_8)$ --, therefor.
Line 55, Delete "—$N(R_9)$—," and insert -- —$N(R_8)$—, --, therefor.

Column 25
Line 50-59,

Delete " 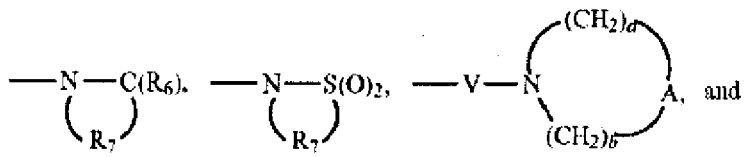 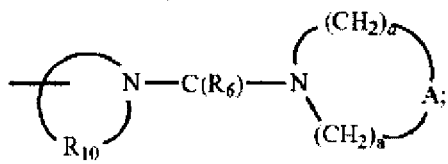 " and insert

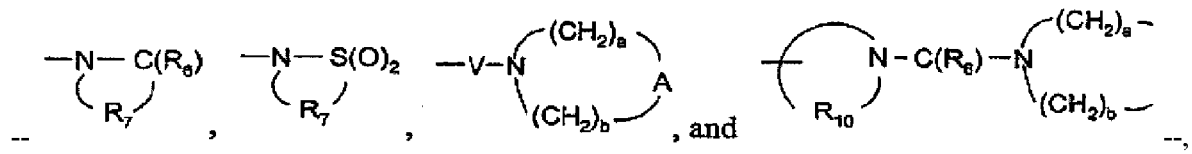

therefor.

Column 26
Line 5, Delete "($R_9$)" and insert -- ($R_8$) --, therefor.
Line 5, Delete "—C($R_4$)" and insert -- —C($R_6$) --, therefor.

Column 31
Line 47, Delete ""aryl,"" and insert -- "aryl," "heteroaryl," --, therefor.

Column 31
Line 56, Delete "substitutent." and insert -- substituent. --, therefor.

Column 33
Line 46, Delete "Re" and insert -- $R_B$ --, therefor.

Column 35
Line 47, Delete "—N($R_9$)—," and insert -- —N($R_8$)—, --, therefor.
Line 48, Delete "—O—," and insert -- —O—, and --, therefor.

Column 37
Line 15, Delete "($R_6$)—O—C(O)—O—," and insert -- ($R_6$), —O—C(O)—O—, --, therefor.
Line 35, Delete "—N($R_9$)—," and insert -- —N($R_8$)—, --, therefor.

Column 39
Line 5, Delete "—N($R_9$)—," and insert -- —N($R_8$)—, --, therefor.
Line 21, Delete "—N($R_9$)—," and insert -- —N($R_8$)—, --, therefor.

Column 48
Line 22, Delete "aid" and insert -- and --, therefor.
Line 62, Delete "am" and insert -- an --, therefor.

Column 52
Line 9, Delete "[4,6-c]" and insert -- [4,5-c] --, therefor.

Column 55
Line 63, Delete "$R_{21,}$" and insert -- $R_{2a}$, --, therefor.

Column 56
Line 24, Delete "formulating" and insert -- formylating --, therefor.

Column 62
Line 53, Delete "hemophilus" and insert -- haemophilus --, therefor.

Column 64
Line 45, Delete "ml)" and insert -- mL) --, therefor.
Line 62, Delete "2.08" and insert -- 20.8 --, therefor.

Column 65
Line 11, Delete "adder." and insert -- added. --, therefor.

Column 66
Line 31, Delete "even" and insert -- oven --, therefor.

Column 68
Line 20, Delete "hp" and insert -- mp --, therefor.

Column 71
Line 4, Delete "Pound:" and insert -- Found: --, therefor.

Column 83
Line 53, Delete "scaled" and insert -- sealed --, therefor.

Column 90
Line 43, Delete "Ethanol" and insert -- ethanol --, therefor.

Column 92
Line 45, Delete "A mixture . . . . . . . . oil." and insert the same on Col. 92, Line 46 as a new paragraph.
Line 52, Delete "washes" and insert -- washed --, therefor.

Column 97
Line 24, Delete "l-(4-morpholin" and insert -- 1-(4-morpholin --, therefor.

Column 99

Line 67, Delete "(610" and insert -- (6.0 --, therefor.

Column 100
Line 48, Delete "LC/NS" and insert -- LC/MS --, therefor.

Column 101
Line 13, Delete "(5:L)," and insert -- (5:1), --, therefor.

Column 110
Line 57, Delete "0IC," and insert -- 0 °C., --, therefor.

Column 111
Line 30, Delete "80 IC" and insert -- 80 °C. --, therefor.

Column 113
Line 29, Delete "Water," and insert -- water, --, therefor.

Column 115
Line 61, Delete "Pan t" and insert -- Part --, therefor.

Column 124
Line 12, Delete "over" and insert -- oven --, therefor.

Column 125
Line 33, Delete "mmol)" and insert -- mol) --, therefor.

Column 130
Line 66, Delete "N$_5$O1.0" and insert -- N$_5$O·1.0 --, therefor.

Column 133
Line 11, Delete "1-{[(3-" and insert -- 1-{[(3- --, therefor.
Line 64, Delete "5-C]" and insert -- 5-c] --, therefor.

Column 138
Line 5, Delete "art" and insert -- an --, therefor.
Line 38, Delete "dichloromethane" and insert -- dichloromethane. --, therefor.

Column 168
Line 54, Delete "calorimetric" and insert -- colorimetric --, therefor.

Column 169
Line 23, Delete "(molar)" and insert -- (μmolar) --, therefor.

In the Claims,

Column 170
Line 2, In Claim 1, delete "— alkenylene-;" and insert -- —alkenylene-; --, therefor.
Line 57-65, In Claim 2, delete " 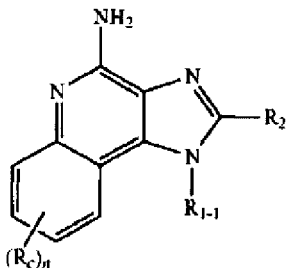 " and insert -- 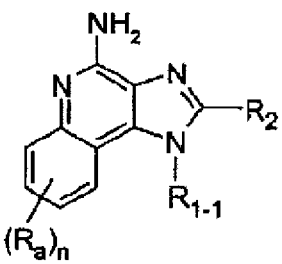 --, therefor.

Column 171
Line 12, In Claim 2, delete "— alkenylene-;" and insert -- —alkenylene-; --, therefor.
Line 15, In Claim 2, delete "— alkenylene-;" and insert -- —alkenylene-; --, therefor.

Column 172
Line 12, In Claim 3, delete "— alkenylene-;" and insert -- —alkenylene-; --, therefor.
Line 15, In Claim 3, delete "— alkenylene-;" and insert -- —alkenylene-; --, therefor.
Line 18, In Claim 3, delete "O-groups;" and insert -- O- groups; --, therefor.
Line 63, In Claim 7, delete "hydroxyl $C_{1-4}$" and insert -- hydroxy$C_{1-4}$ --, therefor.
Line 63, In Claim 7, delete "$C_{14}$" and insert -- $C_{1-4}$ --, therefor.

Column 173
Line 1-10,

In Claim 9, delete " 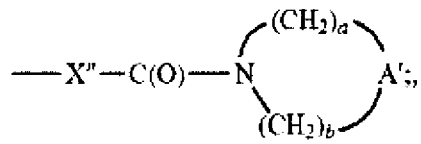 " and insert -- 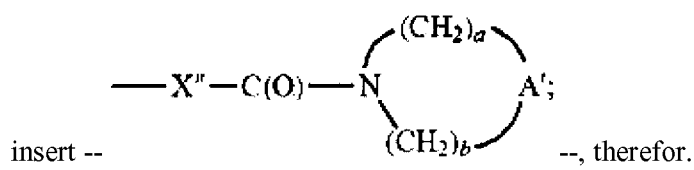 --, therefor.

Line 15, In Claim 10, delete "$C_{1-4}$-alkylene" and insert -- $C_{1-4}$ alkylene --, therefor.
Line 21, In Claim 12, delete "hydroxyl $C_{1-4}$" and insert -- hydroxy$C_{1-4}$ --, therefor.

Column 174

Line 2,
In Claim 13, delete " 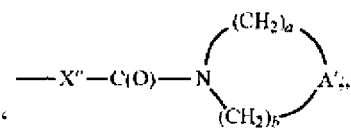 " and
insert -- 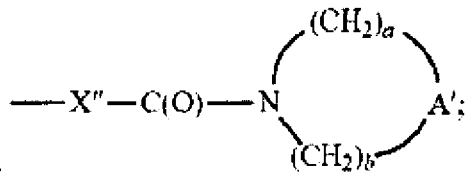 --, therefor.